United States Patent

Szczepanski et al.

[11] Patent Number: 4,997,947
[45] Date of Patent: Mar. 5, 1991

[54] PROCESS OF PREPARING 2-(IMIDAZOLIN-2-YL)-NICOTINIC ACID COMPOUNDS

[75] Inventors: Henry Szczepanski, Wallbach; Dieter Dürr, Bottmingen, both of Switzerland

[73] Assignee: Ciba-Geigy Corporation, Ardsley, N.Y.

[21] Appl. No.: 426,901

[22] Filed: Oct. 24, 1989

Related U.S. Application Data

[62] Division of Ser. No. 206,552, Jun. 14, 1988, abandoned.

[30] Foreign Application Priority Data

Jun. 18, 1987 [CH] Switzerland .................... 2301/87

[51] Int. Cl.$^5$ .......................................... C07D 401/04
[52] U.S. Cl. ................................ 546/278; 546/256; 544/180; 544/333
[58] Field of Search ............ 546/278, 256; 544/180, 544/333

[56] References Cited

U.S. PATENT DOCUMENTS

| | | | |
|---|---|---|---|
| 4,404,012 | 9/1983 | Orwick | 71/92 |
| 4,647,301 | 3/1987 | Los | 546/278 |
| 4,709,036 | 11/1987 | Los et al. | 546/167 |
| 4,721,522 | 1/1988 | Durr et al. | 71/92 |
| 4,726,838 | 2/1988 | Durr et al. | 71/94 |
| 4,743,296 | 10/1988 | Durr et al. | 71/94 |
| 4,758,667 | 7/1988 | Szczepanski | 546/167 |

FOREIGN PATENT DOCUMENTS

| | | | |
|---|---|---|---|
| 0041623 | 5/1981 | European Pat. Off. | 546/278 |
| 0216360 | 9/1986 | European Pat. Off. | 546/278 |

Primary Examiner—Robert W. Ramsuer
Assistant Examiner—Zinna Northington-Davis
Attorney, Agent, or Firm—Kevin T. Mansfield

[57] ABSTRACT

The invention relates to processes for the preparation of 6-substituted 2-(imidazolin-2-yl)-nicotinic acid derivatives that are distinguished by excellent herbicidal and plant growth-regulating properties, and to intermediates and processes for the preparation of the intermediates. The derivatives correspond to formula I

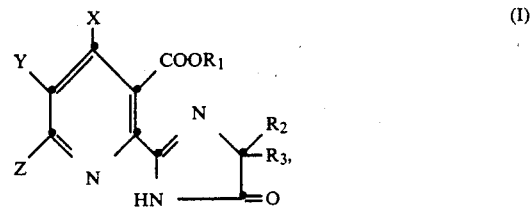

in which
$R_1$ represents hydrogen or a salt, ester or amide radical,
each of $R_2$ and $R_3$, independently of the other, represents $C_1$–$C_4$-alkyl or they together represent a $C_3$–$C_5$-alkylene radical,
X represents hydrogen or methyl,
Y represents hydrogen, halogen, alkyl, haloalkyl, hydroxyalkyl, alkoxy, alkylthio, phenoxy, nitro, cyano, alkylamino, phenyl, alkenyloxy or alkynyloxy, and
Z represents a $-CQ_1Q_2Q_3$ or $-CQ_1Q_4Q_5$ radical in which
$Q_1$ and $Q_2$ each represents hydrogen or $C_1$–$C_4$-alkyl,
$Q_3$ represents $C_1$–$C_6$-alkoxy or phenoxy that is unsubstituted or substituted, or $C_3$–$C_6$-alkenyloxy or $C_3$–$C_6$-alkynyloxy and
$Q_4$ and $Q_5$, together with the carbon atom to which they are bonded, represent a cycloalkyl, furyl, pyran, dioxan or dioxolan radical, or
Z represents a 5- or 6-membered heterocyclic radical.

2 Claims, No Drawings

PROCESS OF PREPARING 2-(IMIDAZOLIN-2-YL)-NICOTINIC ACID COMPOUNDS

This is a division of application Ser. No. 206,552, filed on June 14, 1988, now abandoned.

The present invention relates to processes for the preparation of 6-substituted 2-(imidazolin-2-yl)-nicotinic acid derivatives having herbicidal and plant growth-regulating activity, and to intermediates and processes for the preparation of the intermediates.

The derivatives to be prepared are 6-substituted 2-(imidazolin-2-yl)-nicotinic acid derivatives of formula I

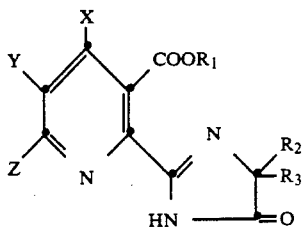

(I)

in which
R$_1$ represents hydrogen, the cation equivalent of an alkali metal, alkaline earth metal, magnesium, copper, iron, zinc, cobalt, lead, silver, nickel or quaternary ammonium or alkylammonium salt, C$_1$–C$_6$-alkyl unsubstituted or substituted by halogen, hydroxy, C$_1$–C$_3$-alkoxy, C$_3$–C$_6$-cycloalkyl, benzyloxy, furyl, phenyl, halophenyl, lower alkylphenyl, lower alkoxyphenyl, nitrophenyl, carboxy, C$_1$–C$_4$-alkoxycarbonyl or by cyano; C$_3$–C$_6$-cycloalkyl unsubstituted or mono- or di-substituted by C$_1$–C$_3$-alkyl; C$_3$–C$_6$-alkenyl unsubstituted or substituted by halogen, C$_1$–C$_3$-alkoxy, phenyl or by C$_1$–C$_4$-alkoxycarbonyl; or C$_3$–C$_6$-alkynyl unsubstituted or mono- or di-substituted by C$_1$–C$_3$-alkyl;

R$_2$ represents C$_1$–C$_4$-alkyl,

R$_3$ represents C$_1$–C$_4$-alkyl or C$_3$–C$_6$-cycloalkyl, or

R$_2$ and R$_3$, together with the carbon atom to which they are bonded, also represent a C$_3$–C$_6$-cycloalkyl radical which may be substituted by methyl radicals, X represents hydrogen or methyl, Y represents hydrogen, halogen, C$_1$–C$_6$-alkyl, C$_1$–C$_6$-haloalkyl, C$_1$–C$_6$-hydroxyalkyl, C$_1$–C$_6$-alkoxy, C$_1$–C$_6$-alkylthio, phenoxy, nitro, cyano, C$_1$–C$_4$-alkylamino, di-C$_1$–C$_4$-alkylamino, C$_1$–C$_4$-alkylsulphonyl, phenyl, halophenyl, lower alkylphenyl, lower alkoxyphenyl, C$_3$–C$_8$-alkenyloxy, C$_3$–C$_8$-haloalkenyloxy, C$_3$–C$_8$-alkynyloxy or C$_3$–C$_8$-haloalkynyloxy and Z represents a —CQ$_1$Q$_2$Q$_3$ or —CQ$_1$Q$_4$Q$_5$ radical in which Q$_1$ represents hydrogen or C$_1$–C$_4$-alkyl, Q$_2$ represents hydrogen or C$_1$–C$_4$-alkyl, Q$_3$ represents C$_1$–C$_6$-alkoxy that is unsubstituted or is substituted by C$_1$–C$_4$-alkyl, C$_1$–C$_4$-alkoxy, C$_4$–C$_9$-alkoxyalkoxy, cyano or by carbamoyl; phenoxy that is unsubstituted or is substituted by halogen, C$_1$–C$_4$-alkyl, C$_1$–C$_4$-alkoxy, C$_1$–C$_4$-haloalkyl or by nitro; or C$_3$–C$_6$-alkenyloxy or C$_3$–C$_6$-alkynyloxy, Q$_4$ and Q$_5$, together with the carbon atom to which they are bonded, represent C$_3$–C$_6$-cycloalkyl, or a 5- or 6-membered ring containing one oxygen atom or two oxygen atoms that are not vicinal, each of which radicals may be substituted by C$_1$–C$_4$-alkyl, or Z represents a 5- or 6-membered, saturated or unsaturated, heterocyclic radical that is bonded by way of carbon and is unsubstituted or is substituted by lower alkyl.

In these definitions, the alkyl and also the alkenyl and alkynyl radicals may be either straight-chain or branched.

The alkyl radicals may be methyl, ethyl, n-propyl, isopropyl, n-butyl, sec.-butyl, tert.-butyl, isobutyl, n-pentyl, isopentyl, neopentyl, tert.-pentyl, n-hexyl or isohexyl. Lower alkyl and lower alkoxy denote that the alkyl radicals contain from 1 to 4 carbon atoms.

"Lower alkyl" indicates an alkyl radical having from 1 to 4 carbon atoms.

The alkenyl and alkynyl radicals preferably have from 3 to 6 carbon atoms and may be represented by the following radicals: allyl, methallyl, propynyl, 2-butenyl, 1,3-butadienyl, 1-methylvinyl, pentenyl, butynyl, pentynyl.

Halogen indicates fluorine, chlorine, bromine and iodine. The 5- or 6-membered heterocyclic radicals include, for example, furan, tetrahydrofuran, thiophene, pyrrole, pyrrolidine, oxazole, oxazolidine, triazole, imidazole, oxadiazole, thiadiazole, triazole, pyran, pyridine, piperidine, dioxan, pyrimidine, morpholine, thiomorpholine and triazine.

Compounds of this kind, that is to say 2-(imidazolin-2-yl)-nicotinic acids and also 2-imidazolyl-3-quinonecarboxylic acids and their derivatives, are known; see, for example, EP-A No. 41 623, U.S. Pat. No. 4,518,780, EP-A No. 61 423 or U.S. Pat. No. 4,647,301.

2-(Imidazolin-2-yl)-nicotinic acid derivatives are known and some 6-substituted derivatives are known. They are, however, very difficult to produce, and substitution has involved only a lower alkyl or fused phenyl radical. The compounds with the defined substituents Z are prepared by first of all introducing the substituent Z into a pyridine-2,3-dicarboxylic acid diester in accordance with one of the processes described in EP-A No. 169 051, and producing the 2-(imidazolin-2-yl)-nicotinic acid derivatives therefrom in accordance, for example, with the process known from EP-A No. 41 623.

The introduction of substituents into the 6-position of 2-imidazolyl-nicotinic acid, and the preparation of such acids and esters, has hitherto not been successful, or has been successful only with difficulty.

Good activity is exhibited by those compounds of formula I

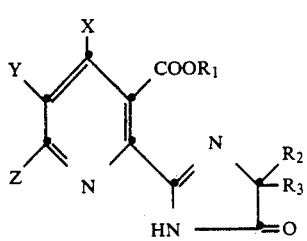

(I)

in which R$_1$ represents hydrogen or C$_1$–C$_6$-alkyl, R$_2$, R$_3$ and X are as defined for formula I, Y represents hydrogen, C$_1$–C$_6$-alkyl or halogen, Z is a heterocyclic radical or, if it represents —$CQ_1Q_2Q_3$, is a $C_1$-$C_6$-alkoxy-, $C_1$-$C_4$-alkyl-, phenoxy-$C_1$-$C_4$-alkyl or carbamoyl-$C_1$-$C_4$-alkoxyalkyl radical or, if it represents —$CQ_1Q_4Q_5$, is a $C_3$-$C_6$-cycloalkyl radical that may be substituted by $C_1$-$C_4$-alkyl.

Those compounds of formula I

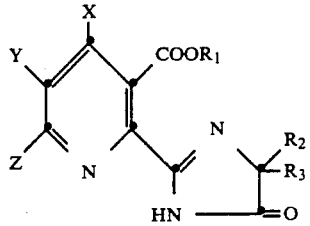

(I)

in which $R_1$ represents hydrogen or $C_1$-$C_6$-alkyl, $R_2$ represents methyl, $R_3$ represents isopropyl, X represents hydrogen or methyl, Y represents $C_1$-$C_6$-alkyl, chlorine or bromine and Z represents a $C_1$-$C_6$-alkoxyalkyl-, phenoxy-$C_1$-$C_4$-alkyl-carbamoyl-$C_1$-$C_4$-alkoxy-$C_1$-$C_4$-alkyl, an unsubstituted or $C_1$-$C_4$-alkyl-substituted $C_3$-$C_6$-cycloalkyl-, a thiophenyl-, pyridinyl-, methylpyrimidine-furanyl- or dioxanyl-radical, were especially active.

Even if such compounds have been described, scarcely any substituent other than a lower alkyl radical or a benzo-fused phenyl radical has been postulated for the 6-position.

It is therefore an object of the present invention to provide a process for the preparation of 2-(imidazolin-2-yl)-nicotinic acids of formula I that uses readily accessible and easily manipulable starting materials and makes it possible for these compounds to be produced in a simple manner and in a good yield.

According to a first process it is proposed that the 6-substituted 2-(imidazolin-2-yl)-nicotinic acid derivatives of formula I be prepared as follows: a 6-substituted pyridine-2,3-dicarboxylic acid diester of formula V

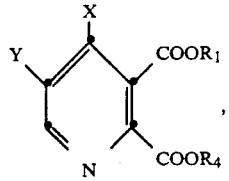

(V)

in which $R_1$, X and Y are as defined for formula I and $R_4$ represents a $C_1$-$C_8$-alkylphenyl radical or a phenyl-$C_1$-$C_4$-alkyl radical, is reacted in aqueous solution, in the presence of a catalytic amount of silver(II) ions and a peroxysulphate salt, with a carboxylic acid of formula XVII

Z—COOH (XVII), in which Z is as defined for formula I, to yield a 6-substituted pyridine-2,3-dicarboxylic acid diester of formula IV

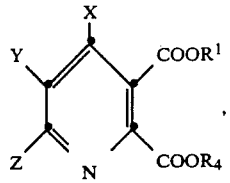

(IV)

in which $R_1$, $R_4$, X, Y and Z are as defined for formula I, and this ester is reacted in an inert organic solvent, in the presence of a strong base, with a 2-aminoalkanecarboxylic acid amide of formula XV

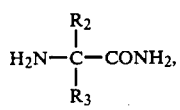

(XV)

in which $R_2$ and $R_3$ are as defined for formula I, the resulting salt of the 2-(imidazolin-2-yl)-nicotinic acid of formula III is taken up in aqueous acidic solution, the free 2-(imidazolin-2-yl)-nicotinic acid of formula III

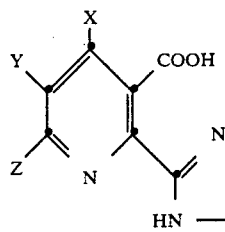

(III)

in which $R_2$, $R_3$, X, Y and Z are as defined for formula I, is isolated and then rearranged with a water-removing agent or reagent to form a tricyclic 2H-imidazo-[1',2':1,2]pyrrolo[3,4-b]pyridine-3,5-dione compound of formula II

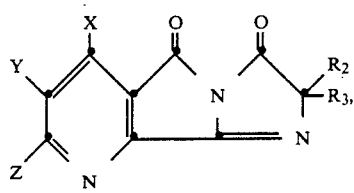

(II)

in which $R_2$, $R_3$, X, Y and Z are as defined for formula I, and this compound is then cleaved at elevated temperature with a hydroxide or alcohol of formula XVI $HOR_1$ (XVI), in which $R_1$ is as defined for formula I, to yield the 2-(imidazolin-2-yl)-nicotinic acid derivative of formula I.

The 2-(imidazolin-2-yl)-nicotinic acid of formula III and its salts fall within the scope of the general formula I. They, too, have extraordinary herbicidal and plant growth-regulating activity. These compounds and their preparation from the pyridine-2,3-dicarboxylic acid diesters of formula V in accordance with the above-described process also form part of this invention.

The 6-substituted pyridine-2,3-dicarboxylic acid diesters of formula IV are novel intermediates. These compounds and their preparation from the pyridine-2,3- dicarboxylic acid diesters of formula V by the addition of a carboxylic acid of formula XVII in the presence of silver ions and a peroxysulphate salt to a 6-unsubstituted pyridine-2,3-dicarboxylic acid diester of formula V also form a part of this invention.

The pyridine-2,3-dicarboxylic acid esters of formula V required as starting materials can be prepared in a simple manner by esterifying pyridine-2,3-dicarboxylic acid with corresponding alcohols. The pyridine-2,3-dicarboxylic acid can itself be prepared by the oxidation of quinoline (cf. DE-PS No. 1 010 524 and U.S. Pat. No. 2,512,482). The pyridine-2,3-dicarboxylic acid esters of formula V can also be prepared in accordance with the methods described in published European Patent Applications Nos. 0 161 221 and 0 172 140 starting from a hydrazone of an α,β-unsaturated carbonyl compound and a maleic acid derivative according to a Diels-Alder reaction scheme. Quinoline-2,3-dicarboxylic acid esters not substituted in the 6-position can be obtained, for example, by the method described in J. Org. Chem. 49, 4999–5000, 1984.

The majority of the 2-aminoalkanecarboxylic acid amides of formula X are known compounds which can be prepared in known manner by reacting corresponding ketones with ammonia and hydrocyanic acid.

The substituent Z is introduced into the 6-position of the pyridine ring by means of a carboxylic acid Z—COOH in which Z corresponds to the desired substitution radical. The addition reaction is carried out in accordance with a process described in EP-A No. 169 051 for pyridazine compounds, in the presence of one equivalent of peroxysulphate ion and a catalytic amount of silver ions in an aqueous solution of mineral acid at temperatures of from 40° to 80° C. Care must be taken that the mineral acid does not precipitate the silver ions. Suitable mineral acids are, for example, sulphuric acid, perchloric acid and trifluoroacetic acid. The silver ions may originate from a water-soluble silver salt, such as silver nitrate, silver fluoride, silver trifluoroacetate or silver perchlorate, but preferably originate from silver nitrate.

In the reaction, the carboxylic acid Z—COOH is oxidatively decarboxylated, the silver(I) ions originating from the silver salt being oxidised in the presence of the peroxydisulphate salt to silver(II) ions. The reaction proceeds selectively, so that only stoichiometric amounts of carboxylic acid and peroxysulphate salt should be employed. The reaction temperature is in the range of from 40° to 80° C., preferably 70° to 80° C. The preferred peroxydisulphate salts are ammonium, sodium and potassium salts.

If, in this reaction, X represents hydrogen, then there are also formed during the radical alkylation 4- and 4,6-substituted pyridine-2,3-dicarboxylic acid esters in accordance with the following equation:

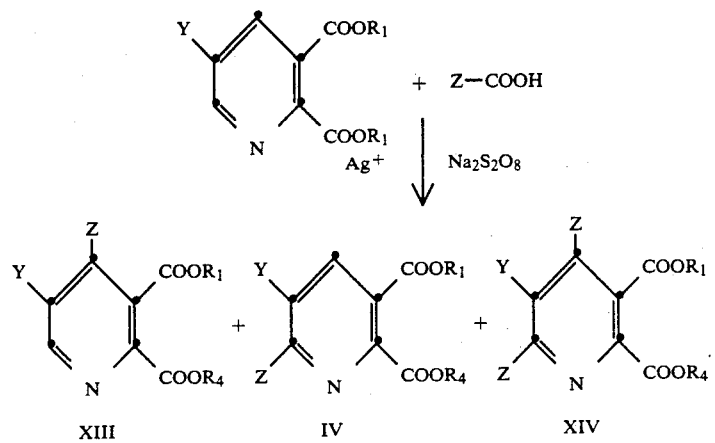

Such ester mixtures can be separated into their components by chromatography or fractional distillation.

Suitable carboxylic acids of formula XVIII are, for example, pivalic acid (trimethylacetic acid), butyric acid, isobutyric acid, propionic acid, acetic acid, cyclobutanecarboxylic acid, cyclopropanecarboxylic acid, cyclopentenecarboxylic acid, phenoxyacetic acid and glycolic acid.

The reaction of the 6-substituted pyridine-2,3-dicarboxylic acid ester of formula IV with a 2-aminoalkanecarboxylic acid amide of formula $H_2N—C(R_2)-R_3—CONH_2$ is effected in an inert organic solvent in the presence of a strong base in a temperature range of from room temperature to the reflux temperature of the reaction mixture.

Suitable inert solvents are, for example, liquid aromatic hydrocarbons and halogenated hydrocarbons, such as benzene, toluene, chlorobenzene and xylenes, $C_1$-$C_{10}$-alkanols, especially $C_1$-$C_4$-alkanols, such as methanol, ethanol, propanol, isopropanol, n-butanol, sec.-butanol, tert.-butanol and isobutanol, ethereal liquids, such as tetrahydrofuran and dioxan, and also strongly polar solvents, such as acetonitrile, N,N-dimethylformamide and dimethyl sulphoxide. Advantageously, water-immiscible solvents are used, such as benzene, toluene, chlorobenzene or xylenes.

Suitable strong bases in the presence of which the reaction of the pyridine-2,3-dicarboxylic acid ester of formula IV with a 2-aminoalkanecarboxylic acid amide of formula XV is carried out are alkali metal hydroxides and alkali metal alcoholates. Preferred bases are alkali metal alcoholates, especially those that are derived from $C_1$-$C_4$-alkanols, such as sodium methoxide, sodium ethoxide, sodium isopropoxide and potassium tert.-butoxide. Alkali metal hydroxides, such as sodium hydroxide and potassium hydroxide, are especially suitable when using alkanols as inert solvents. The reaction can furthermore be carried out in the presence of potash in ethanol. The strong base is normally used in at least an equimolar amount based on the pyridine-2,3-dicarboxylic acid ester of formula IV used. In carrying out the process of the invention, the use of from 1 to 3 mols of base per mol of pyridine-2,3-dicarboxylic acid ester of formula IV has proved suitable. Preferably, from 1.5 to 2.5 mol of base are used per mol of pyridine-2,3-dicarboxylic acid ester of formula IV.

Within the quoted temperature range of from room temperature to the reflux temperature of the reaction mixture, temperatures of from 50° to 90° C. are preferred for carrying out the process of the invention.

The condensation of the 2-(imidazolin-2-yl)-nicotinic acid of formula III to the tricyclic 2H-imidazo[1',2':1,2-]pyrrolo[3,4-b]pyridine-3,5-dione of formula II is effected by means of a water-removing agent or reagent.

Such a process comprises, for example, boiling the reaction mixture on a water separator with a water-immiscible organic solvent, such as benzene or toluene, or boiling the reaction mixture in an acid anhydride or with concentrated sulphuric acid or with an organic solvent that contains either an anhydride, for example acetic anhydride, or concentrated sulphuric acid. Other suitable water-removing agents are acid halides, such as phosgene, thionyl chloride, and also other reagents, such as dicyclohexyldiimide or alternatively phosphorus pentoxide. They are preferably dissolved in organic solvents and the reaction is carried out, while stirring, at temperatures in a range of from room temperature to the boiling point of the reaction mixture.

The nomenclature of compound II, 2H-imidazo[1',2':1,2]pyrrolo[3,4-b]-pyridine-3,5-dione has been taken from Chemical Abstracts. The basic three-ring structure is designated and numbered as follows:

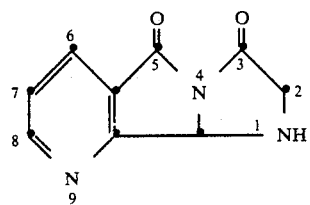

In accordance with a second process, the 6-substituted 2-(imidazolin-2-yl)-nicotinic acid derivatives of formula I are prepared as follows: a 6-substituted pyridine-2,3-dicarboxylic acid diester of formula IV

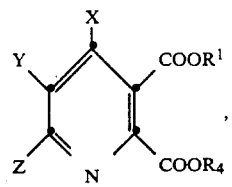

(IV)

in which $R_1$, $R_4$, X, Y and Z are as defined for formula I, is hydrolysed with a strong base in aqueous medium, and the resulting 6-substituted pyridine-2,3-dicarboxylic acid of formula VI

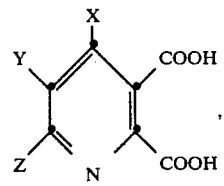

(VI)

in which X, Y and Z are as defined for formula I, is reacted in a water-removing environment to form the 6-substituted pyridine-2,3-dicarboxylic acid anhydride of formula VII

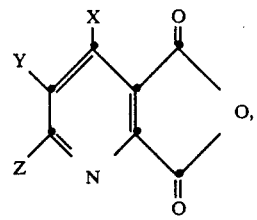

(VII)

in which X, Y and Z are as defined for formula I, and this anhydride is then condensed with a glycylamide of formula XVIII

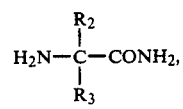

(XVIII)

in which $R_2$ and $R_3$ are as defined for formula I, and the 6-substituted 2-(N-carbamoylmethylcarbamoyl)-nicotinic acid of formula VIII

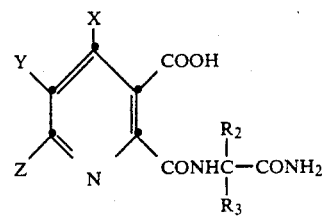

(VIII)

resulting therefrom, in which $R_2$, $R_3$, X, Y and Z are as defined for formula I, is cyclised in an inert dry solvent, yielding the 6-substituted 2-(imidazolin-2-yl)-nicotinic acid of formula III

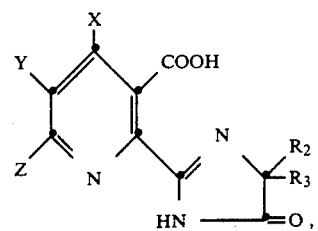

(III)

in which $R_2$, $R_3$, X, Y and Z are as defined for formula I, which is isolated and then rearranged with a water-removing agent or reagent to form a tricyclic 2H-imidazo-[1,2:1',2']pyrrolo[3,4-b]pyridine-3,5-dione compound of formula II

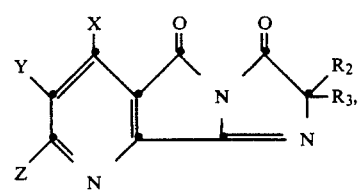

(II)

in which $R_2$, $R_3$, X, Y and Z are as defined for formula I, and this compound is then cleaved at elevated temperature with a hydroxide or alcohol of formula XVI

HOR₁ (XVI), in which R₁ is as defined for formula I, to yield the 2-(imidazolin-2-yl)-nicotinic acid derivative of formula I.

The hydrolysis of the pyridine-2,3-dicarboxylic acid diester of formula IV to the corresponding acid is a conventional hydrolysis, which is carried out with a strong base in aqueous medium at the boiling temperature of the reaction medium.

Alkali metal or alkaline earth metal hydroxides or carbonates are suitable bases, and water alone, or in admixture with an alcohol, a ketone or with dimethylformamide, is suitable as a solvent.

The reaction of the pyridine-2,3-dicarboxylic acid of formula VI to form the corresponding anhydride is carried out by boiling in a water-removing environment. Suitable water-removing media are, for example, acid anhydrides, such as, for example, acetic anhydride, and also concentrated sulphuric acid.

The addition of the glycylamide of formula XVIII to the acid anhydride of formula VII is carried out in an inert organic solvent at a temperature in the range of from room temperature to the boiling point of the solvent. The condensation of the 2-(N-carbamoylmethylcarbamoyl)nicotinic acid of formula VIII to the 2-(imidazolin-2-yl)-nicotinic acid of formula III is carried out by boiling in an inert organic solvent in the presence of a strong base under anhydrous conditions. For this preferably alkali metal alcoholates, for example potassium tert.-butoxide, are used in an alkanol as solvent.

The entire reaction, from the pyridinedicarboxylic acid diester of formula V to the 2-(imidazolin-2-yl)-nicotinic acid of formula III is preferably carried out in a one-pot process by boiling the ester, the glycylamide and the alcoholate in an inert organic solvent, such as, for example, benzene, toluene, xylene, cyclohexane, then evaporating the solvent and acidifying the residue. The nicotinic acids of formula III are obtained in pure form and free of isomers.

The process steps that lead from the 2-(imidazolin-2-yl)-nicotinic acid of formula III by way of the 2H-imidazo[1′,2′:1,2]pyrrolo[3,4-b]pyridine-3,5-dione of formula II to the 2-(imidazolin-2-yl)-nicotinic acid derivative of formula I are identical to the steps described in the first process.

According to a third process, the 6-substituted 2-(imidazolin-2-yl)-nicotinic acid derivatives of formula I are obtained as follows: a 6-substituted pyridine-2,3-dicarboxylic acid anhydride of formula VII

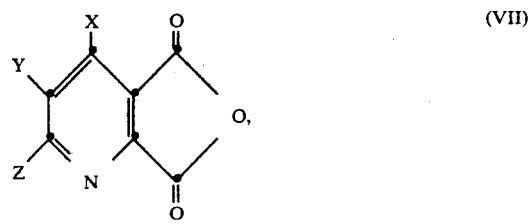

in which X, Y and Z are as defined for formula I, is reacted in an inert organic solvent with a glycylnitrile of formula XIX

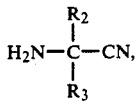

in which R₂ and R₃ are as defined for formula I, the resulting 6-substituted 2-(cyanomethylcarbamoyl)-nicotinic acid of formula IX

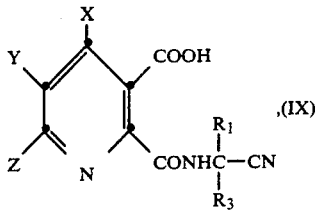

in which R₂, R₃, X, Y and Z are as defined for formula I, is then treated in a water-removing environment or a water-removing agent, so that an N-(cyanomethylcarbamoyl)-pyridine-2,3-dicarboxylic acid imide of formula X is obtained

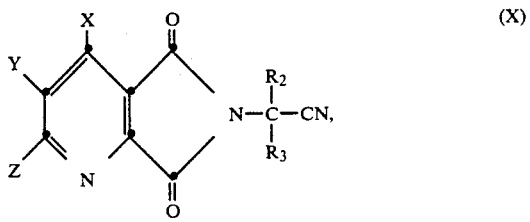

in which R₂, R₃, X, Y and Z are as defined for formula I, this imide is hydrolysed in aqueous-acidic medium, at elevated temperature, to the N-(carbamoylmethyl)-pyridine-2,3-dicarboxylic acid imide of formula XI

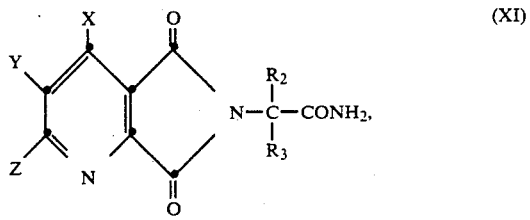

in which R₂, R₃, X, Y and Z are as defined for formula I, which compound is then converted, by heating in a basic medium, into the tricyclic 3H-imidazo[1,2:1′,2′-]pyrrolo[3,4-b]pyridine-2,5-dione compound of formula XII

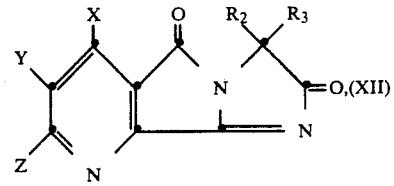

in which R₂, R₃, X, Y and Z are as defined for formula I, and this product is then cleaved at elevated temperature with a hydroxide or alcohol of formula XVI

HOR₁          (XVI), in which R₁ is as defined for formula I, to form the 2-(imidazolin-2-yl)-nicotinic acid derivative of formula I.

The condensation of the glycylnitrile of formula XIX with the pyridine-2,3-dicarboxylic acid anhydride of formula VII is carried out by stirring and heating in an inert organic solvent.

The subsequent condensation to the imide of formula X can be effected by boiling on a water separator or alternatively merely by concentrating the reaction medium by evaporation.

If the N-(glycylnitrile)-pyridine-2,3-dicarboxylic acid imide of formula X is then treated with concentrated sulphuric acid, the nitrile group is hydrolysed, yielding the N-(carbamoylmethyl)-pyridine-2,3-carboxylic acid imide of formula XI, which condenses under basic conditions to form the 3H-imidazo[1',2':1,2]pyrrolo[3,4-b]pyridine-2,5-dione of formula XII. This can then be converted in the presence of a hydroxide or alcohol into the 2-(imidazolin-2-yl)-nicotinic acid derivative of formula I. These reaction steps are described, for example, in European Published Application EP-A No. 41 623.

The nomenclature of compound XII, 3H-imidazo[1',2':1,2]pyrrolo[3,4-b]pyridine-2,5-dione has been taken from Chemical Abstracts. The basic three-ring structure is designated and numbered as follows:

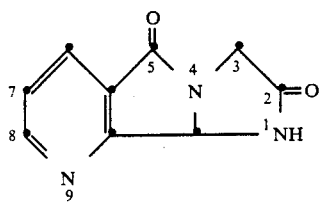

The 8-substituted 2H-imidazo[1',2':1,2]pyrrolo[3,4-b]pyridine-3,5-dione compounds of formula II and the 8-substituted 3H-imidazo[1',2':1,2]pyrrolo[3,4-b]pyridine-2,5-dione compounds of formula XII are novel. They are distinguished by excellent herbicidal and plant growth-regulating activity. The invention relates also to these compounds and their preparation.

Good activity was exhibited by those compounds of formulae

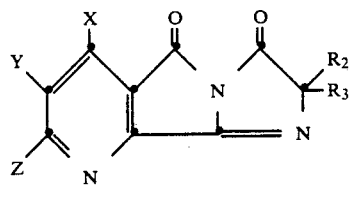

and

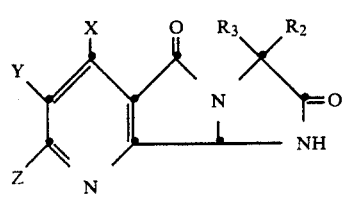

in which R₁ represents hydrogen or C₁-C₆-alkyl, R₂, R₃ and X are as defined for formula I, Y represents hydrogen, C₁-C₆-alkyl or halogen, Z is a heterocyclic radical or, if it represents —CQ₁Q₂Q₃, is a C₁-C₆-alkoxy-, C₁-C₄-alkyl-, phenoxy-C₁-C₄-alkyl or carbamoyl-C₁-C₄-alkoxyalkyl radical or, if it represents —CQ₁Q₄Q₅, is a C₃-C₆-cycloalkyl radical that may be substituted by C₁-C₄-alkyl.

Most especially active were those compounds of formulae

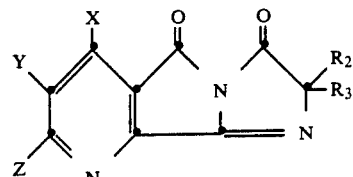

and

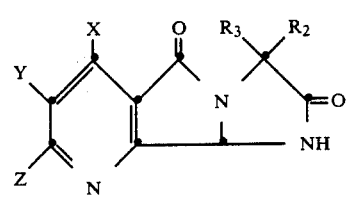

in which R₁ represents hydrogen or C₁-C₆-alkyl, R₂ represents methyl, R₃ represents isopropyl, hydrogen or methyl, Y represents C₁-C₆-alkyl, chlorine or bromine and Z represents a C₁-C₆-alkoxyalkyl-, phenoxy-C₁-C₄-alkyl-carbamoyl-C₁-C₄-alkoxy-C₁-C₄-alkyl, an unsubstituted or C₁-C₄-alkyl-substituted C₃-C₆-cycloalkyl-, a thiophenyl-, pyridinyl-, methylpyrimidine-furanyl- or dioxanyl-radical.

The 6-substituted 2-(cyanomethylcarbamoyl)-nicotinic acids of formula IX, the N-(cyanomethylcarbamoyl)-pyridine-2,3-dicarboxylic acid imides of formula X and the N-(carbamoylmethyl)-pyridinedicarboxylic acid imides of formula XI are novel intermediates. The invention also relates to these compounds and to the preparation thereof.

According to another process, the 6-substituted 2-(imidazolin-2-yl)-nicotinic acid derivatives of formula I are prepared as follows: a methyl ketone of formula XXIV

Z—COCH₃         (XXIV), in which Z is as defined for formula I, is reacted with a secondary amine of formula XX

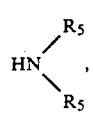         (XX)

in which R₅ represents C₁-C₄-alkyl or phenyl-C₁-C₄-alkyl, or the two R₅ radicals, together with the nitrogen atom to which they are bonded, form a 5- or 6-membered, saturated or unsaturated ring that may be interrupted by oxygen, the resulting methyleneamine of formula XXI

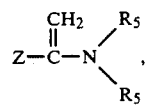         (XXI)

in which R₅ is as defined above, is then condensed with an alkoxymethyleneoxalacetic ester of formula XXII

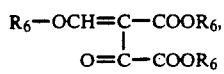  (XXII)

in which each of the R₆ radicals, independently of the others, represents a $C_1$–$C_6$-alkyl or phenyl-$C_1$–$C_6$-alkyl radical, resulting in a 6-amino-3-alkoxycarbonyl-hexane-3,5-dienecarboxylic acid ester of formula XXIII

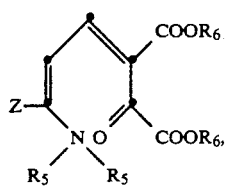  (XXIII)

in which R₅ and R₆ have the meanings given above and Z is as defined for formula I, this ester is then cyclised with ammonia in organic solution to yield the 6-substituted pyridine-2,3-dicarboxylic acid diester of formula IVa

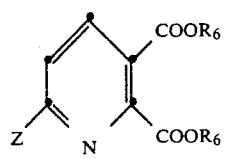  (IVa)

in which Z is as defined for formula I and R₆ represents a $C_1$–$C_6$-alkyl or phenyl-$C_1$–$C_6$-alkyl radical, which diester is then, in accordance with the process of claim 2, reacted in the presence of a strong base with the 2-glycylamide of formula XVIII

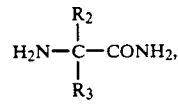  (XVIII)

in which R₂ and R₃ are as defined for formula I, the resulting salt of the 2-(imidazolin-2-yl)-nicotinic acid of formula III is taken up in aqueous acidic solution, the free 2-(imidazolin-2-yl)-nicotinic acid of formula III

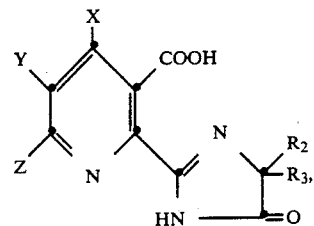  (III)

in which R₂, R₃, X, Y and Z are as defined for formula I, is isolated and then rearranged with a water-removing agent or reagent to form a tricyclic 2H-imidazo[1,2:1',2']pyrrolo[3,4-b]pyridine-3,5-dione compound of formula II

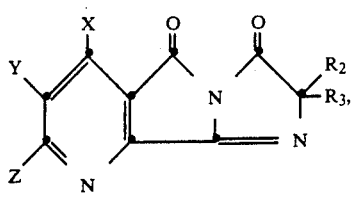  (II)

in which R₂, R₃,, X, Y and Z are as defined for formula I, and this compound is then cleaved at elevated temperature with a hydroxide or alcohol of formula XVI

HOR₁  (XVI), in which R₁ is as defined for formula I, to yield the 2-(imidazolin-2-yl)-nicotinic acid derivative of formula I.

If the reactions do not already proceed at room temperature then they are carried out at temperatures of from 0° C. to 200° C., that is to say if necessary the reaction mixture is heated up to boiling point or, if necessary, cooled with ice/water or ice/brine bath.

Suitable bases for these condensation and hydrolysis reactions are especially inorganic bases, such as sodium hydroxide, sodium carbonate, calcium hydroxide, calcium carbonate, potassium hydroxide, potassium carbonate, ammonia and also tertiary organic bases, such as triethylamine.

Suitable solvents are, for example, polar aprotic solvents, which can be used on their own or in mixtures consisting of at least two solvents. Examples are as follows: ether, such as dibutyl ether, tetrahydrofuran, dioxan, methylene glycol, dimethyl ethylene glycol, diethyl diethylene glycol, dimethyl triethylene glycol, halogenated hydrocarbons, such as methylene chloride, chloroform, 1,2-dichloroethane, 1,1,1-trichloroethane, 1,1,2,2-tetrachloroethane, carboxylic acid esters and lactones, such as ethyl acetate, methyl propionate, ethyl benzoate, 2-methoxyethyl acetate, γ-butyrolactone, o-valerolactone and pivalolactone, carboxylic acid amides and lactams, such as formamide, acetamide, N-methylformamide, N,N-dimethylformamide, N,N-diethylformamide, N,N-dimethylacetamide, N,N-diethylacetamide, γ-butyrolactam, ε-caprolactam, N-methylpyrrolidone, N-acetylpyrrolidone, N-methylcaprolactam, tetramethylurea, hexamethylphosphoric acid triamide, sulphoxides, such as dimethyl sulphoxide, sulphones, such as dimethyl sulphone, diethyl sulphone, trimethylene sulphone, tetramethylene sulphone, trimethylamine, triethylamine, N-methylpyrrolidine, N-methylpiperidine, N-methylmorpholine, substituted benzenes, such as chlorobenzene, nitrobenzene, and nitriles, such as, for example, acetonitrile.

Preferred as herbicides or for regulating plant growth are those derivatives of 2-(imidazolin-2-yl)-nicotinic acids and derivatives of formulae III and I and also 2H-imidazo[1',2':1,2]pyrrolo[3,4-b]pyridine-2,5-dione compounds of formulae II and XII, in which Z represents a $C_3$–$C_6$cycloalkyl, $C_2$–$C_8$-alkoxyalkyl, phenoxyalkyl, furanyl, dioxanyl or carbamoyloxymethoxymethyl radical.

The invention also relates to all diastereoisomeric and enantiomeric isomers of compounds of formula I.

The active ingredients of formula I are normally used successfully at application rates of from 0.05 to 4 kg/ha, especially from 0.1 to 1 kg/ha.

At lower rates of application the compounds of formula I are distinguished by good selective growth-inhibiting and selective herbicidal properties and are excellent for use in crops of useful plants, especially cereals, cotton, soybeans, maize and rice. There is also to some extent damage to weeds, hitherto to be approached only with total herbicides.

The nature of the action of these active ingredients is unusual. Many are translocatable, that is to say they are absorbed by the plant and transported to other parts of the plant where they are then active. For example, by surface-treating perennial weeds it is possible for damage to be caused right into the roots. In comparison with other herbicides and growth regulators the novel compounds of formula I are effective at very low rates of application.

The compounds of formula I in addition have pronounced plant growth-inhibiting properties. The growth of both monocotyledons and dicotyledons is impaired.

For example, leguminosae frequently planted in agriculture as cover crops in tropical areas can be selectively inhibited in their growth by the compounds of formula I, so that whilst soil erosion between the cultivated plants is prevented, the cover crops are not able to compete with the crop.

Inhibition of the vegetative growth enables denser planting of the crop in many cases, so that an increase in yield in relation to the soil area can be achieved.

Another mechanism of the yield increase using growth inhibitors is based on the fact that the nutrients are utilized to a greater extent in the flower and fruit formation whilst the vegetative growth is restricted.

At greater rates of application all plants tested are damaged in their development to such an extent that they die.

The invention relates also to herbicidal and plant growth-regulating compositions that contain a novel active ingredient of formula I, and to methods of controlling weeds pre- and post-emergence and of inhibiting the growth of monocotyledonous and dicotyledonous plants, especially grasses, tropical cover crops and tobacco suckers.

The compounds of formula I are used in unmodified form or, preferably, as compositions together with adjuvants customary in the art of formulation, and are therefore formulated in known manner, for example, into emulsifiable concentrates, directly sprayable or dilutable solutions, dilute emulsions, wettable powders, soluble powders, dusts, granulates, and encapsulations in, for example, polymeric substances. As with the nature of the compositions, the methods of application, such as spraying, atomising, dusting, scattering or pouring, are chosen in accordance with the intended objectives and the prevailing circumstances.

The formulations, that is to say the compositions, preparations or mixtures containing the active ingredient of formula I and, where appropriate, a solid or liquid adjuvant, are prepared in known manner, for example by homogeneous mixing and/or grinding of active ingredients with extenders, such as, for example, solvents, solid carriers and, where appropriate, surface-active substances (surfactants).

Suitable solvents are: aromatic hydrocarbons, preferably the fractions $C_8$–$C_{12}$, such as, for example, xylene mixtures or substituted naphthalenes, phthalic acid esters, such as dibutyl or dioctyl phthalate, aliphatic hydrocarbons, such as cyclohexane or paraffins, alcohols and glycols and ethers and esters thereof, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethylformamide, and also vegetable oils or epoxidised vegetable oils, such as epoxidised coconut oil or soybean oil; or water.

The solid carriers used, for example for dusts and dispersible powders, are normally powdered natural minerals, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, such as, for example, pumice, broken brick, sepiolite or bentonite, and suitable non-sorbent carrier materials are, for example, calcite or sand. Furthermore, a large number of pre-granulated materials of inorganic or organic nature can be used such as, especially, dolomite or pulverised plant residues.

Depending upon the nature of the active ingredient of formula I to be formulated, suitable surface-active substances are non-ionic, cationic and/or anionic surfactants having good emulsifying, dispersing and wetting properties. The term surfactants is also to include mixtures of surfactants.

Both so-called water-soluble soaps and also water-soluble synthetic surface-active compounds are suitable anionic surfactants.

As soaps there may be mentioned alkali metal, alkaline earth metal or substituted or unsubstituted ammonium salts of higher fatty acids ($C_{10}$–$C_{22}$) such as, for example, the sodium or potassium salts of oleic or stearic acid, or of mixtures of natural fatty acids that can be obtained, for example, from coconut oil or tallow oil. Fatty acid methyltaurin salts should also be mentioned.

More frequently, however, so-called synthetic surfactants are used, especially fatty sulphonates, fatty sulphates, sulphonated benzimidazole derivatives or alkylarylsulphonates.

The fatty sulphonates or sulphates are generally in the form of alkali metal, alkaline earth metal or substituted or unsubstituted ammonium salts and contain an alkyl radical having from 8 to 22 carbon atoms, which also includes the alkyl moiety of acyl radicals, for example the sodium or calcium salt of lignosulphonic acid, of dodecylsulphuric acid ester or of a mixture of fatty alcohol sulphates produced from natural fatty acids. Also included are the salts of sulphated and sulphonated fatty alcohol/ethylene oxide adducts. The sulphonated benzimidazole derivatives preferably contain 2 sulphonic acid groups and a fatty acid radical having from 8 to 22 carbon atoms. Examples of alkylarylsulphonates are the sodium, calcium or triethanolamine salts of dodecylbenzenesulphonic acid, of dibutylnaphthalenesulphonic acid or of a naphthalenesulphonic acid/formaldehyde condensation product.

There also come into consideration corresponding phosphates such as, for example, salts of the phosphoric acid ester of an adduct of p-nonylphenol with from 4 to 14 mols of ethylene oxide, or phospholipids.

Non-ionic surfactants are especially polyglycol ether derivatives of aliphatic or cycloaliphatic alcohols, of saturated or unsaturated fatty acids and alkylphenols, which derivatives may contain from 3 to 10 glycol ether groups and from 8 to 20 carbon atoms in the (aliphatic) hydrocarbon moiety and from 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The compounds mentioned usually contain from 1 to 5 ethylene glycol units per propylene glycol unit.

There may be mentioned as examples of non-ionic surfactants nonylphenolpolyethoxyethanols, castor oil polyglycol ethers, polypropylene/polyethylene oxide adducts, tributylphenoxypolyethanol, polyethylene glycol and octylphenoxypolyethoxyethanol.

Fatty acid esters of polyoxyethylene sorbitan, such as polyoxyethylene sorbitan trioleate, also come into consideration.

The cationic surfactants are especially quaternary ammonium salts that contain, as N-substituent, at least one alkyl radical having from 8 to 22 carbon atoms and, as further substituents, lower, optionally halogenated alkyl, benzyl or lower hydroxyalkyl radicals. The salts are preferably in the form of halides, methyl sulphates or ethyl sulphates, for example stearyltrimethylammonium chloride or benzyldi-(2-chloroethyl)-ethylammonium bromide.

The surfactants customary in the art of formulation are described, inter alia, in the following publications:
  "McCutcheon's Detergents and Emulsifiers Annual" MC Publishing Corp., Ridgewood, N.J., 1979.
  Dr. Helmut Stache "Tensid Taschenbuch" Carl Hanser Verlag, Munich/Vienna 1981.

The herbicidal and plant growth-regulating preparations usually contain from 0.1 to 95%, especially from 0.1 to 80%, of active ingredient of formula I, from 1 to 99.9% of a solid or liquid adjuvant and from 0 to 25%, especially from 0.1 to 25%, of a surfactant.

Preferred formulations are especially of the following composition: (% = percent by weight)

| Emulsifiable concentrates: | |
| --- | --- |
| active ingredient of formula I: | 1 to 20%, preferably 5 to 10% |
| surface-active agent: | 5 to 30%, preferably 10 to 20% |
| liquid carrier: | 50 to 94%, preferably 70 to 85%. |
| Dusts: | |
| active ingredient of formula I | 0.1 to 10%, preferably 0.1 to 1% |
| solid carrier: | 99.9 to 90%, preferably 99.9 to 99% |
| Suspension concentrates: | |
| active ingredient of formula I: | 5 to 75%, preferably 10 to 50% |
| water | 94 to 25%, preferably 90 to 30% |
| surface-active agent | 1 to 40%, preferably 2 to 30%. |
| Wettable powders: | |
| active ingredient of formula I: | 0.5 to 90%, preferably 1 to 80% |
| surface active agent: | 0.5 to 20%, preferably 1 to 15% |
| solid carrier: | 5 to 95%, preferably 15 to 90%. |
| Granulates: | |
| active ingredient of formula I: | 0.5 to 30%, preferably 3 to 15% |
| solid carrier: | 99.5 to 70%, preferably 97 to 85%. |

Whilst concentrated formulations are preferred as commercial products, the end user will normally use dilute formulations. The forms of application can be diluted down to 0.001% active ingredient. The rates of application are normally from 0.005 to 5 kg of active ingredient/hectare.

The compositions may also contain other adjuvants, such as stabilisers, antifoams, viscosity regulators, binders, tackifiers and also fertilizers or other active substances for achieving special effects.

EXAMPLE 1

Preparation of 6-cyclopropyl-pyridine-2,3-dicarboxylic acid diethyl ester

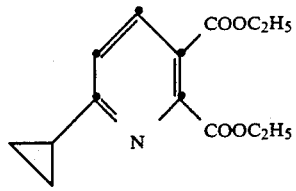

40 g of pyridine-2,3-dicarboxylic acid diethyl ester are dissolved in a mixture of 400 g of water and 36 g of concentrated sulphuric acid and 6.1 g of silver nitrate ($AgNO_3$). Subsequently, 32 g of cyclopropanecarboxylic acid are added and the reaction mixture is heated to 70°. A solution of 82.1 g of ammonium peroxydisulphate ($(NH_4)_2S_2O_8$ in 300 ml of water is added dropwise thereto while stirring vigorously. When the evolution of $CO_2$ has ceased, the reaction mixture is stirred for a further 20 minutes. It is then cooled to 15° and extracted twice with 200 ml of methylene chloride each time. The organic phase is collected, dried over magnesium sulphate, filtered and concentrated by evaporation. The residue is distilled at 13 millibars and the distillate is chromatographed over a column of silica gel with hexane/methylene chloride/ether. After the solvent has been evaporated 11.2 g of the above diester remain behind in the form of a colourless oil.

EXAMPLE 2

Preparation of 6-methoxymethylpyridine-2,3dicarboxylic acid diethyl ester

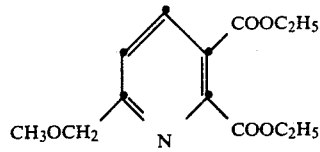

First of all 40 g of pyridine-2,3-dicarboxylic acid diethyl ester and then 33.3 g of methoxyacetic acid are added to a solution of 400 g of water, 36 g of concentrated sulphuric acid and 6.1 g of silver nitrate. The reaction mixture is then heated to 70° and a solution of 60.7 g of ammonium peroxydisulphate ($(NH_4)_2S_2O_8$) in 225 ml of water is added dropwise thereto while stirring vigorously. When the evolution of $CO_2$ has ceased, the reaction mixture is stirred for a further 20 minutes. It is then cooled to 15° and extracted twice with 200 ml of methylene chloride each time. The organic phases are collected, dried over magnesium sulphate, filtered and concentrated by evaporation. The oil that remains is chromatographed over a column of silica gel with ether/hexane 1:1, there being eluted from different fractions 9.1 g of 6-methoxymethylpyridine-2,3-dicarboxylic acid in the form of crystals having a melting point of 52°-54°, 12.9 g of 4,6-bis-methoxymethylpyridine-2,3-dicarboxylic acid diethyl ester in the form of an oil and 10.2 g of 4-methoxymethylpyridine-2,3-dicarboxylic acid diethyl ester also in the form of an oil.

EXAMPLE 3

Preparation of 5-ethyl-6-methoxymethyl-pyridine-2,3-dicarboxylic acid diethyl ester

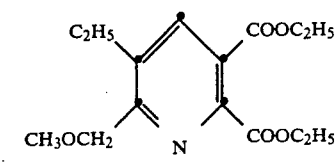

First of all 25.1 g of 5-ethylpyridine-2,3-dicarboxylic acid diethyl ester and then 13.5 g of methoxyacetic acid are added to a solution of 20 g of concentrated sulphuric acid and 3.4 g of silver nitrate (AgNO₃) in 200 ml of water. The reaction mixture is then heated to 70° and a solution of 34.2 g of ammonium peroxydisulphate $(NH_4)_2S_2O_8$ is added dropwise thereto while stirring vigorously. When the evolution of $CO_2$ has ceased, the reaction mixture is stirred for a further 20 minutes, then cooled to 15° and extracted twice with 200 ml of methylene chloride each time. The methylene chloride extracts are dried over magnesium sulphate, filtered and concentrated by evaporation. The oil that remains is purified by chromatography over a column of silica gel using ether/hexane 1:1. There are obtained from the eluate, in different fractions, 7.2 g of 5-ethyl-6-methoxymethylpyridine-2,3-dicarboxylic acid diethyl ester in the form of a light-yellow oil, 5.3 g of 4,6-bis-methoxymethyl-5-ethylpyridine-2,3-dicarboxylic acid diethyl ester in the form of a light-coloured oil and also 1 g of 5-ethyl-4-methoxymethylpyridine-2,3-dicarboxylic acid diethyl ester, also in the form of an oil.

EXAMPLE 4

Preparation of 5-ethyl-6-cyclopropyl-pyridine-2,3-dicarboxylic acid diethyl ester

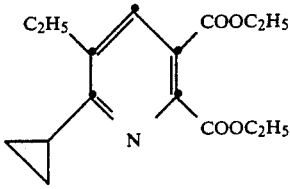

There is added to a solution of 32 ml of concentrated sulphuric acid and 6.8 g of silver nitrate (AgNO₃) in 400 ml of water first of all 50 g of 5-ethylpyridine-2,3-dicarboxylic acid diethyl ester and, when a homogeneous solution has been obtained, 25.8 g of cyclopropanecarboxylic acid. The solution is then heated to 70° and a solution of 68.2 g of ammonium peroxydisulphate $(NH_4)_2S_2O_8$ is added dropwise thereto while stirring vigorously. When the evolution of $CO_2$ has ceased, the reaction mixture is stirred for a further 20 minutes, then cooled to 15° and extracted twice with 200 ml of methylene chloride each time. The methylene chloride extract is dried over magnesium sulphate, filtered and concentrated. The oily residue is purified by chromatography over a column of silica gel using ether/hexane 1:1. Evaporation of the solvent yields 20 g of 5-ethyl-6-cyclopropyl-pyridine-2,3-dicarboxylic acid in the form of a yellow oil.

The following diesters of formula IV are prepared in a manner analogous to that described in Examples 1 to 4:

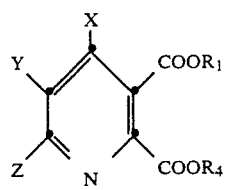

(IV)

TABLE 1.00

| No. | X | Y | R₁ | R₄ | Z | phys. data |
|---|---|---|---|---|---|---|
| 1.0001 | H | H | C₂H₅ | C₂H₅ | C₃H₅(cyclo) | m.p.155-163/0.13 mbar |
| 1.0002 | H | CH₃ | C₂H₅ | C₂H₅ | C₃H₅(cyclo) | oil |
| 1.0003 | H | C₂H₅ | C₂H₅ | C₂H₅ | C₃H₅(cyclo) | oil |
| 1.0004 | H | C₃H₇ | C₂H₅ | C₂H₅ | C₃H₅(cyclo) | |
| 1.0005 | H | OCH₃ | C₂H₅ | C₂H₅ | C₃H₅(cyclo) | |
| 1.0006 | H | OC₂H₅ | C₂H₅ | C₂H₅ | C₃H₅(cyclo) | |
| 1.0007 | H | OCH₂CH=CH₂ | C₂H₅ | C₂H₅ | C₃H₅(cyclo) | |
| 1.0008 | H | OCH₂CH=CHCH₃ | C₂H₅ | C₂H₅ | C₃H₅(cyclo) | |
| 1.0009 | H | OCH₂C(Cl)=CH₂ | C₂H₅ | C₂H₅ | C₃H₅(cyclo) | |
| 1.0010 | H | OCH₂CH=CHCl | C₂H₅ | C₂H₅ | C₃H₅(cyclo) | |
| 1.0011 | H | OCH₂C≡CH | C₂H₅ | C₂H₅ | C₃H₅(cyclo) | |
| 1.0012 | H | OCHF₂ | C₂H₅ | C₂H₅ | C₃H₅(cyclo) | |
| 1.0013 | H | OCF₃ | C₂H₅ | C₂H₅ | C₃H₅(cyclo) | |
| 1.0014 | H | OCF₂CHFCF₃ | C₂H₅ | C₂H₅ | C₃H₅(cyclo) | |
| 1.0015 | H | OC₆H₅ | C₂H₅ | C₂H₅ | C₃H₅(cyclo) | |
| 1.0016 | H | CF₃ | C₂H₅ | C₂H₅ | C₃H₅(cyclo) | |
| 1.0017 | H | Br | C₂H₅ | C₂H₅ | C₃H₅(cyclo) | oil |
| 1.0018 | H | Cl | C₂H₅ | C₂H₅ | C₃H₅(cyclo) | |
| 1.0019 | H | F | C₂H₅ | C₂H₅ | C₃H₅(cyclo) | |
| 1.0020 | H | SCH₃ | C₂H₅ | C₂H₅ | C₃H₅(cyclo) | |
| 1.0021 | H | SC₂H₅ | C₂H₅ | C₂H₅ | C₃H₅(cyclo) | |
| 1.0022 | H | SC₃H₇-n | C₂H₅ | C₂H₅ | C₃H₅(cyclo) | |
| 1.0023 | H | SO₂CH₃ | C₂H₅ | C₂H₅ | C₃H₅(cyclo) | |
| 1.0024 | H | SO₂C₂H₅ | C₂H₅ | C₂H₅ | C₃H₅(cyclo) | |
| 1.0025 | H | NO₂ | C₂H₅ | C₂H₅ | C₃H₅(cyclo) | |

TABLE 1.00-continued

| No. | X | Y | R₁ | R₄ | Z | phys. data |
|---|---|---|---|---|---|---|
| 1.0026 | H | CN | C₂H₅ | C₂H₅ | C₃H₅(cyclo) | |
| 1.0027 | H | CH₂OH | C₂H₅ | C₂H₅ | C₃H₅(cyclo) | |
| 1.0028 | H | CH₂CH₂OH | C₂H₅ | C₂H₅ | C₃H₅(cyclo) | |
| 1.0029 | H | CH₂CH₂CH₂OH | C₂H₅ | C₂H₅ | C₃H₅(cyclo) | |
| 1.0030 | H | C₆H₅ | C₂H₅ | C₂H₅ | C₃H₅(cyclo) | |
| 1.0031 | H | CH₂Cl | C₂H₅ | C₂H₅ | C₃H₅(cyclo) | |
| 1.0032 | H | CH₂CH₂Cl | C₂H₅ | C₂H₅ | C₃H₅(cyclo) | |
| 1.0033 | H | CH₂CH₂CH₂Cl | C₂H₅ | C₂H₅ | C₃H₅(cyclo) | |
| 1.0034 | H | H | C₂H₅ | C₃H₇-iso | C₃H₅(cyclo) | |
| 1.0035 | H | H | C₃H₇ | CH₂C₆H₅ | C₃H₅(cyclo) | |
| 1.0036 | H | H | CH₃ | CH₃ | C₃H₅(cyclo) | |
| 1.0037 | H | H | CH₂C₆H₅ | CH₂C₆H₅ | C₂H₅(cyclo) | |

TABLE 1.01

| No. | X | Y | R₁ | R₄ | Z | phys. data |
|---|---|---|---|---|---|---|
| 1.0101 | H | H | C₂H₅ | C₂H₅ | C₄H₇(cyclo) | |
| 1.0102 | H | CH₃ | C₂H₅ | C₂H₅ | C₄H₇(cyclo) | |
| 1.0103 | H | C₂H₅ | C₂H₅ | C₂H₅ | C₄H₇(cyclo) | |
| 1.0104 | H | C₃H₇ | C₂H₅ | C₂H₅ | C₄H₇(cyclo) | |
| 1.0105 | H | OCH₃ | C₂H₅ | C₂H₅ | C₄H₇(cyclo) | |
| 1.0106 | H | OC₂H₅ | C₂H₅ | C₂H₅ | C₄H₇(cyclo) | |
| 1.0107 | H | OCH₂CH=CH₂ | C₂H₅ | C₂H₅ | C₄H₇(cyclo) | |
| 1.0108 | H | OCH₂CH=CHCH₃ | C₂H₅ | C₂H₅ | C₄H₇(cyclo) | |
| 1.0109 | H | OCH₂C(Cl)=CH₂ | C₂H₅ | C₂H₅ | C₄H₇(cyclo) | |
| 1.0110 | H | OCH₂CH=CHCl | C₂H₅ | C₂H₅ | C₄H₇(cyclo) | |
| 1.0111 | H | OCH₂C≡CH | C₂H₅ | C₂H₅ | C₄H₇(cyclo) | |
| 1.0112 | H | OCHF₂ | C₂H₅ | C₂H₅ | C₄H₇(cyclo) | |
| 1.0113 | H | OCF₃ | C₂H₅ | C₂H₅ | C₄H₇(cyclo) | |
| 1.0114 | H | OCF₂CHFCF₃ | C₂H₅ | C₂H₅ | C₄H₇(cyclo) | |
| 1.0115 | H | OC₆H₅ | C₂H₅ | C₂H₅ | C₄H₇(cyclo) | |
| 1.0116 | H | CF₃ | C₂H₅ | C₂H₅ | C₄H₇(cyclo) | |
| 1.0117 | H | Br | C₂H₅ | C₂H₅ | C₄H₇(cyclo) | |
| 1.0118 | H | Cl | C₂H₅ | C₂H₅ | C₄H₇(cyclo) | |
| 1.0119 | H | F | C₂H₅ | C₂H₅ | C₄H₇(cyclo) | |
| 1.0120 | H | SCH₃ | C₂H₅ | C₂H₅ | C₄H₇(cyclo) | |
| 1.0121 | H | SC₂H₅ | C₂H₅ | C₂H₅ | C₄H₇(cyclo) | |
| 1.0122 | H | SC₃H₇-n | C₂H₅ | C₂H₅ | C₄H₇(cyclo) | |
| 1.0123 | H | SO₂CH₃ | C₂H₅ | C₂H₅ | C₄H₇(cyclo) | |
| 1.0124 | H | SO₂C₂H₅ | C₂H₅ | C₂H₅ | C₄H₇(cyclo) | |
| 1.0125 | H | NO₂ | C₂H₅ | C₂H₅ | C₄H₇(cyclo) | |
| 1.0126 | H | CN | C₂H₅ | C₂H₅ | C₄H₇(cyclo) | |
| 1.0127 | H | CH₂OH | C₂H₅ | C₂H₅ | C₄H₇(cyclo) | |
| 1.0128 | H | CH₂CH₂OH | C₂H₅ | C₂H₅ | C₄H₇(cyclo) | |
| 1.0129 | H | CH₂CH₂CH₂OH | C₂H₅ | C₂H₅ | C₄H₇(cyclo) | |
| 1.0130 | H | C₆H₅ | C₂H₅ | C₂H₅ | C₄H₇(cyclo) | |
| 1.0131 | H | CH₂Cl | C₂H₅ | C₂H₅ | C₄H₇(cyclo) | |
| 1.0132 | H | CH₂CH₂Cl | C₂H₅ | C₂H₅ | C₄H₇(cyclo) | |
| 1.0133 | H | CH₂CH₂CH₂Cl | C₂H₅ | C₂H₅ | C₄H₇(cyclo) | |

TABLE 1.02

| No. | X | Y | R₁ | R₄ | Z | phys. data |
|---|---|---|---|---|---|---|
| 1.0201 | H | H | C₂H₅ | C₂H₅ | C₅H₉(cyclo) | |
| 1.0202 | H | CH₃ | C₂H₅ | C₂H₅ | C₅H₉(cyclo) | |
| 1.0203 | H | C₂H₅ | C₂H₅ | C₂H₅ | C₅H₉(cyclo) | |
| 1.0204 | H | C₃H₇ | C₂H₅ | C₂H₅ | C₅H₉(cyclo) | |
| 1.0205 | H | OCH₃ | C₂H₅ | C₂H₅ | C₅H₉(cyclo) | |
| 1.0206 | H | OC₂H₅ | C₂H₅ | C₂H₅ | C₅H₉(cyclo) | |
| 1.0207 | H | OCH₂CH=CH₂ | C₂H₅ | C₂H₅ | C₅H₉(cyclo) | |
| 1.0208 | H | OCH₂CH=CHCH₃ | C₂H₅ | C₂H₅ | C₅H₉(cyclo) | |
| 1.0209 | H | OCH₂C(Cl)=CH₂ | C₂H₅ | C₂H₅ | C₅H₉(cyclo) | |
| 1.0210 | H | OCH₂CH=CHCl | C₂H₅ | C₂H₅ | C₅H₉(cyclo) | |
| 1.0211 | H | OCH₂C≡CH | C₂H₅ | C₂H₅ | C₅H₉(cyclo) | |
| 1.0212 | H | OCHF₂ | C₂H₅ | C₂H₅ | C₅H₉(cyclo) | |
| 1.0213 | H | OCF₃ | C₂H₅ | C₂H₅ | C₅H₉(cyclo) | |
| 1.0214 | H | OCF₂CHFCF₃ | C₂H₅ | C₂H₅ | C₅H₉(cyclo) | |
| 1.0215 | H | OC₆H₅ | C₂H₅ | C₂H₅ | C₅H₉(cyclo) | |
| 1.0216 | H | CF₃ | C₂H₅ | C₂H₅ | C₅H₉(cyclo) | |
| 1.0217 | H | Br | C₂H₅ | C₂H₅ | C₅H₉(cyclo) | |
| 1.0218 | H | Cl | C₂H₅ | C₂H₅ | C₅H₉(cyclo) | |
| 1.0219 | H | F | C₂H₅ | C₂H₅ | C₅H₉(cyclo) | |
| 1.0220 | H | SCH₃ | C₂H₅ | C₂H₅ | C₅H₉(cyclo) | |
| 1.0221 | H | SC₂H₅ | C₂H₅ | C₂H₅ | C₅H₉(cyclo) | |
| 1.0222 | H | SC₃H₇-n | C₂H₅ | C₂H₅ | C₅H₉(cyclo) | |
| 1.0223 | H | SO₂CH₃ | C₂H₅ | C₂H₅ | C₅H₉(cyclo) | |
| 1.0224 | H | SO₂C₂H₅ | C₂H₅ | C₂H₅ | C₅H₉(cyclo) | |
| 1.0225 | H | NO₂ | C₂H₅ | C₂H₅ | C₅H₉(cyclo) | |

TABLE 1.02-continued

| No. | X | Y | $R_1$ | $R_4$ | Z | phys. data |
|---|---|---|---|---|---|---|
| 1.0226 | H | CN | $C_2H_5$ | $C_2H_5$ | $C_5H_9$(cyclo) | |
| 1.0227 | H | $CH_2OH$ | $C_2H_5$ | $C_2H_5$ | $C_5H_9$(cyclo) | |
| 1.0228 | H | $CH_2CH_2OH$ | $C_2H_5$ | $C_2H_5$ | $C_5H_9$(cyclo) | |
| 1.0229 | H | $CH_2CH_2CH_2OH$ | $C_2H_5$ | $C_2H_5$ | $C_5H_9$(cyclo) | |
| 1.0230 | H | $C_6H_5$ | $C_2H_5$ | $C_2H_5$ | $C_5H_9$(cyclo) | |
| 1.0231 | H | $CH_2Cl$ | $C_2H_5$ | $C_2H_5$ | $C_5H_9$(cyclo) | |
| 1.0232 | H | $CH_2CH_2Cl$ | $C_2H_5$ | $C_2H_5$ | $C_5H_9$(cyclo) | |
| 1.0233 | H | $CH_2CH_2CH_2Cl$ | $C_2H_5$ | $C_2H_5$ | $C_5H_9$(cyclo) | |

TABLE 1.03

| No. | X | Y | $R_1$ | $R_4$ | Z | phys. data |
|---|---|---|---|---|---|---|
| 1.0301 | H | H | $C_2H_5$ | $C_2H_5$ | $C_6H_{11}$(cyclo) | oil |
| 1.0302 | H | $CH_3$ | $C_2H_5$ | $C_2H_5$ | $C_6H_{11}$(cyclo) | |
| 1.0303 | H | $C_2H_5$ | $C_2H_5$ | $C_2H_5$ | $C_6H_{11}$(cyclo) | |
| 1.0304 | H | $C_3H_7$ | $C_2H_5$ | $C_2H_5$ | $C_6H_{11}$(cyclo) | |
| 1.0305 | H | $OCH_3$ | $C_2H_5$ | $C_2H_5$ | $C_6H_{11}$(cyclo) | |
| 1.0306 | H | $OC_2H_5$ | $C_2H_5$ | $C_2H_5$ | $C_6H_{11}$(cyclo) | |
| 1.0307 | H | $OCH_2CH=CH_2$ | $C_2H_5$ | $C_2H_5$ | $C_6H_{11}$(cyclo) | |
| 1.0308 | H | $OCH_2CH=CHCH_3$ | $C_2H_5$ | $C_2H_5$ | $C_6H_{11}$(cyclo) | |
| 1.0309 | H | $OCH_2C(Cl)=CH_2$ | $C_2H_5$ | $C_2H_5$ | $C_6H_{11}$(cyclo) | |
| 1.0310 | H | $OCH_2CH=CHCl$ | $C_2H_5$ | $C_2H_5$ | $C_6H_{11}$(cyclo) | |
| 1.0311 | H | $OCH_2C\equiv CH$ | $C_2H_5$ | $C_2H_5$ | $C_6H_{11}$(cyclo) | |
| 1.0312 | H | $OCHF_2$ | $C_2H_5$ | $C_2H_5$ | $C_6H_{11}$(cyclo) | |
| 1.0313 | H | $OCF_3$ | $C_2H_5$ | $C_2H_5$ | $C_6H_{11}$(cyclo) | |
| 1.0314 | H | $OCF_2CHFCF_3$ | $C_2H_5$ | $C_2H_5$ | $C_6H_{11}$(cyclo) | |
| 1.0315 | H | $OC_6H_5$ | $C_2H_5$ | $C_2H_5$ | $C_6H_{11}$(cyclo) | |
| 1.0316 | H | $CF_3$ | $C_2H_5$ | $C_2H_5$ | $C_6H_{11}$(cyclo) | |
| 1.0317 | H | Br | $C_2H_5$ | $C_2H_5$ | $C_6H_{11}$(cyclo) | |
| 1.0318 | H | Cl | $C_2H_5$ | $C_2H_5$ | $C_6H_{11}$(cyclo) | |
| 1.0319 | H | F | $C_2H_5$ | $C_2H_5$ | $C_6H_{11}$(cyclo) | |
| 1.0320 | H | $SCH_3$ | $C_2H_5$ | $C_2H_5$ | $C_6H_{11}$(cyclo) | |
| 1.0321 | H | $SC_2H_5$ | $C_2H_5$ | $C_2H_5$ | $C_6H_{11}$(cyclo) | |
| 1.0322 | H | $SC_3H_7$-n | $C_2H_5$ | $C_2H_5$ | $C_6H_{11}$(cyclo) | |
| 1.0323 | H | $SO_2CH_3$ | $C_2H_5$ | $C_2H_5$ | $C_6H_{11}$(cyclo) | |
| 1.0324 | H | $SO_2C_2H_5$ | $C_2H_5$ | $C_2H_5$ | $C_6H_{11}$(cyclo) | |
| 1.0325 | H | $NO_2$ | $C_2H_5$ | $C_2H_5$ | $C_6H_{11}$(cyclo) | |
| 1.0326 | H | CN | $C_2H_5$ | $C_2H_5$ | $C_6H_{11}$(cyclo) | |
| 1.0327 | H | $CH_2OH$ | $C_2H_5$ | $C_2H_5$ | $C_6H_{11}$(cyclo) | |
| 1.0328 | H | $CH_2CH_2OH$ | $C_2H_5$ | $C_2H_5$ | $C_6H_{11}$(cyclo) | |
| 1.0329 | H | $CH_2CH_2CH_2OH$ | $C_2H_5$ | $C_2H_5$ | $C_6H_{11}$(cyclo) | |
| 1.0330 | H | $C_6H_5$ | $C_2H_5$ | $C_2H_5$ | $C_6H_{11}$(cyclo) | |
| 1.0331 | H | $CH_2Cl$ | $C_2H_5$ | $C_2H_5$ | $C_6H_{11}$(cyclo) | |
| 1.0332 | H | $CH_2CH_2Cl$ | $C_2H_5$ | $C_2H_5$ | $C_6H_{11}$(cyclo) | |
| 1.0333 | H | $CH_2CH_2CH_2Cl$ | $C_2H_5$ | $C_2H_5$ | $C_6H_{11}$(cyclo) | |

TABLE 1.04

| No. | X | Y | $R_1$ | $R_4$ | Z | phys. data |
|---|---|---|---|---|---|---|
| 1.0401 | H | H | $C_2H_5$ | $C_2H_5$ | $CH_2OCH_3$ | m.p. 52–54° C. |
| 1.0402 | H | $CH_3$ | $C_2H_5$ | $C_2H_5$ | $CH_2OCH_3$ | oil |
| 1.0403 | H | $C_2H_5$ | $C_2H_5$ | $C_2H_5$ | $CH_2OCH_3$ | oil |
| 1.0404 | H | $C_3H_7$ | $C_2H_5$ | $C_2H_5$ | $CH_2OCH_3$ | |
| 1.0405 | H | $OCH_3$ | $C_2H_5$ | $C_2H_5$ | $CH_2OCH_3$ | |
| 1.0406 | H | $OC_2H_5$ | $C_2H_5$ | $C_2H_5$ | $CH_2OCH_3$ | |
| 1.0407 | H | $OCH_2CH=CH_2$ | $C_2H_5$ | $C_2H_5$ | $CH_2OCH_3$ | |
| 1.0408 | H | $OCH_2CH=CHCH_3$ | $C_2H_5$ | $C_2H_5$ | $CH_2OCH_3$ | |
| 1.0409 | H | $OCH_2C(Cl)=CH_2$ | $C_2H_5$ | $C_2H_5$ | $CH_2OCH_3$ | |
| 1.0410 | H | $OCH_2CH=CHCl$ | $C_2H_5$ | $C_2H_5$ | $CH_2OCH_3$ | |
| 1.0411 | H | $OCH_2C\equiv CH$ | $C_2H_5$ | $C_2H_5$ | $CH_2OCH_3$ | |
| 1.0412 | H | $OCHF_2$ | $C_2H_5$ | $C_2H_5$ | $CH_2OCH_3$ | |
| 1.0413 | H | $OCF_3$ | $C_2H_5$ | $C_2H_5$ | $CH_2OCH_3$ | |
| 1.0414 | H | $OCF_2CHFCF_3$ | $C_2H_5$ | $C_2H_5$ | $CH_2OCH_3$ | |
| 1.0415 | H | $OC_6H_5$ | $C_2H_5$ | $C_2H_5$ | $CH_2OCH_3$ | |
| 1.0416 | H | $CF_3$ | $C_2H_5$ | $C_2H_5$ | $CH_2OCH_3$ | |
| 1.0417 | H | Br | $C_2H_5$ | $C_2H_5$ | $CH_2OCH_3$ | |
| 1.0418 | H | Cl | $C_2H_5$ | $C_2H_5$ | $CH_2OCH_3$ | |
| 1.0419 | H | F | $C_2H_5$ | $C_2H_5$ | $CH_2OCH_3$ | |
| 1.0420 | H | $SCH_3$ | $C_2H_5$ | $C_2H_5$ | $CH_2OCH_3$ | |
| 1.0421 | H | $SC_2H_5$ | $C_2H_5$ | $C_2H_5$ | $CH_2OCH_3$ | |
| 1.0422 | H | $SC_3H_7$-n | $C_2H_5$ | $C_2H_5$ | $CH_2OCH_3$ | |
| 1.0423 | H | $SO_2CH_3$ | $C_2H_5$ | $C_2H_5$ | $CH_2OCH_3$ | |
| 1.0424 | H | $SO_2C_2H_5$ | $C_2H_5$ | $C_2H_5$ | $CH_2OCH_3$ | |
| 1.0425 | H | $NO_2$ | $C_2H_5$ | $C_2H_5$ | $CH_2OCH_3$ | |
| 1.0426 | H | CN | $C_2H_5$ | $C_2H_5$ | $CH_2OCH_3$ | |
| 1.0427 | H | $CH_2OH$ | $C_2H_5$ | $C_2H_5$ | $CH_2OCH_3$ | |
| 1.0428 | H | $CH_2CH_2OH$ | $C_2H_5$ | $C_2H_5$ | $CH_2OCH_3$ | |
| 1.0429 | H | $CH_2CH_2CH_2OH$ | $C_2H_5$ | $C_2H_5$ | $CH_2OCH_3$ | |

TABLE 1.04-continued

| No. | X | Y | $R_1$ | $R_4$ | Z | phys. data |
|---|---|---|---|---|---|---|
| 1.0430 | H | $C_6H_5$ | $C_2H_5$ | $C_2H_5$ | $CH_2OCH_3$ | |
| 1.0431 | H | $CH_2Cl$ | $C_2H_5$ | $C_2H_5$ | $CH_2OCH_3$ | |
| 1.0432 | H | $CH_2CH_2Cl$ | $C_2H_5$ | $C_2H_5$ | $CH_2OCH_3$ | |
| 1.0433 | H | $CH_2CH_2CH_2Cl$ | $C_2H_5$ | $C_2H_5$ | $CH_2OCH_3$ | |

TABLE 1.05

| No. | X | Y | $R_1$ | $R_4$ | Z | phys. data |
|---|---|---|---|---|---|---|
| 1.0501 | H | H | $C_2H_5$ | $C_2H_5$ | $CH(CH_3)OCH_3$ | |
| 1.0502 | H | $CH_3$ | $C_2H_5$ | $C_2H_5$ | $CH(CH_3)OCH_3$ | |
| 1.0503 | H | $C_2H_5$ | $C_2H_5$ | $C_2H_5$ | $CH(CH_3)OCH_3$ | |
| 1.0504 | H | $C_3H_7$ | $C_2H_5$ | $C_2H_5$ | $CH(CH_3)OCH_3$ | |
| 1.0505 | H | $OCH_3$ | $C_2H_5$ | $C_2H_5$ | $CH(CH_3)OCH_3$ | |
| 1.0506 | H | $OC_2H_5$ | $C_2H_5$ | $C_2H_5$ | $CH(CH_3)OCH_3$ | |
| 1.0507 | H | $OCH_2CH=CH_2$ | $C_2H_5$ | $C_2H_5$ | $CH(CH_3)OCH_3$ | |
| 1.0508 | H | $OCH_2CH=CHCH_3$ | $C_2H_5$ | $C_2H_5$ | $CH(CH_3)OCH_3$ | |
| 1.0509 | H | $OCH_2C(Cl)=CH_2$ | $C_2H_5$ | $C_2H_5$ | $CH(CH_3)OCH_3$ | |
| 1.0510 | H | $OCH_2CH=CHCl$ | $C_2H_5$ | $C_2H_5$ | $CH(CH_3)OCH_3$ | |
| 1.0511 | H | $OCH_2C\equiv CH$ | $C_2H_5$ | $C_2H_5$ | $CH(CH_3)OCH_3$ | |
| 1.0512 | H | $OCHF_2$ | $C_2H_5$ | $C_2H_5$ | $CH(CH_3)OCH_3$ | |
| 1.0513 | H | $OCF_3$ | $C_2H_5$ | $C_2H_5$ | $CH(CH_3)OCH_3$ | |
| 1.0514 | H | $OCF_2CHFCF_3$ | $C_2H_5$ | $C_2H_5$ | $CH(CH_3)OCH_3$ | |
| 1.0515 | H | $OC_6H_5$ | $C_2H_5$ | $C_2H_5$ | $CH(CH_3)OCH_3$ | |
| 1.0516 | H | $CF_3$ | $C_2H_5$ | $C_2H_5$ | $CH(CH_3)OCH_3$ | |
| 1.0517 | H | Br | $C_2H_5$ | $C_2H_5$ | $CH(CH_3)OCH_3$ | |
| 1.0518 | H | Cl | $C_2H_5$ | $C_2H_5$ | $CH(CH_3)OCH_3$ | |
| 1.0519 | H | F | $C_2H_5$ | $C_2H_5$ | $CH(CH_3)OCH_3$ | |
| 1.0520 | H | $SCH_3$ | $C_2H_5$ | $C_2H_5$ | $CH(CH_3)OCH_3$ | |
| 1.0521 | H | $SC_2H_5$ | $C_2H_5$ | $C_2H_5$ | $CH(CH_3)OCH_3$ | |
| 1.0522 | H | $SC_3H_7$-n | $C_2H_5$ | $C_2H_5$ | $CH(CH_3)OCH_3$ | |
| 1.0523 | H | $SO_2CH_3$ | $C_2H_5$ | $C_2H_5$ | $CH(CH_3)OCH_3$ | |
| 1.0524 | H | $SO_2C_2H_5$ | $C_2H_5$ | $C_2H_5$ | $CH(CH_3)OCH_3$ | |
| 1.0525 | H | $NO_2$ | $C_2H_5$ | $C_2H_5$ | $CH(CH_3)OCH_3$ | |
| 1.0526 | H | CN | $C_2H_5$ | $C_2H_5$ | $CH(CH_3)OCH_3$ | |
| 1.0527 | H | $CH_2OH$ | $C_2H_5$ | $C_2H_5$ | $CH(CH_3)OCH_3$ | |
| 1.0528 | H | $CH_2CH_2OH$ | $C_2H_5$ | $C_2H_5$ | $CH(CH_3)OCH_3$ | |
| 1.0529 | H | $CH_2CH_2CH_2OH$ | $C_2H_5$ | $C_2H_5$ | $CH(CH_3)OCH_3$ | |
| 1.0530 | H | $C_6H_5$ | $C_2H_5$ | $C_2H_5$ | $CH(CH_3)OCH_3$ | |
| 1.0531 | H | $CH_2Cl$ | $C_2H_5$ | $C_2H_5$ | $CH(CH_3)OCH_3$ | |
| 1.0532 | H | $CH_2CH_2Cl$ | $C_2H_5$ | $C_2H_5$ | $CH(CH_3)OCH_3$ | |
| 1.0533 | H | $CH_2CH_2CH_2Cl$ | $C_2H_5$ | $C_2H_5$ | $CH(CH_3)OCH_3$ | |

TABLE 1.06

| No. | X | Y | $R_1$ | $R_4$ | Z | phys. data |
|---|---|---|---|---|---|---|
| 1.0601 | H | H | $C_2H_5$ | $C_2H_5$ | $CH_2OC_2H_5$ | b.p.140–145°/0.13 mbar |
| 1.0602 | H | $CH_3$ | $C_2H_5$ | $C_2H_5$ | $CH_2OC_2H_5$ | oil |
| 1.0603 | H | $C_2H_5$ | $C_2H_5$ | $C_2H_5$ | $CH_2OC_2H_5$ | oil |
| 1.0604 | H | $C_3H_7$ | $C_2H_5$ | $C_2H_5$ | $CH_2OC_2H_5$ | |
| 1.0605 | H | $OCH_3$ | $C_2H_5$ | $C_2H_5$ | $CH_2OC_2H_5$ | |
| 1.0606 | H | $OC_2H_5$ | $C_2H_5$ | $C_2H_5$ | $CH_2OC_2H_5$ | |
| 1.0607 | H | $OCH_2CH=CH_2$ | $C_2H_5$ | $C_2H_5$ | $CH_2OC_2H_5$ | |
| 1.0608 | H | $OCH_2CH=CHCH_3$ | $C_2H_5$ | $C_2H_5$ | $CH_2OC_2H_5$ | |
| 1.0609 | H | $OCH_2C(Cl)=CH_2$ | $C_2H_5$ | $C_2H_5$ | $CH_2OC_2H_5$ | |
| 1.0610 | H | $OCH_2CH=CHCl$ | $C_2H_5$ | $C_2H_5$ | $CH_2OC_2H_5$ | |
| 1.0611 | H | $OCH_2C\equiv CH$ | $C_2H_5$ | $C_2H_5$ | $CH_2OC_2H_5$ | |
| 1.0612 | H | $OCHF_2$ | $C_2H_5$ | $C_2H_5$ | $CH_2OC_2H_5$ | |
| 1.0613 | H | $OCF_3$ | $C_2H_5$ | $C_2H_5$ | $CH_2OC_2H_5$ | |
| 1.0614 | H | $OCF_2CHFCF_3$ | $C_2H_5$ | $C_2H_5$ | $CH_2OC_2H_5$ | |
| 1.0615 | H | $OC_6H_5$ | $C_2H_5$ | $C_2H_5$ | $CH_2OC_2H_5$ | |
| 1.0616 | H | $CF_3$ | $C_2H_5$ | $C_2H_5$ | $CH_2OC_2H_5$ | |
| 1.0617 | H | Br | $C_2H_5$ | $C_2H_5$ | $CH_2OC_2H_5$ | |
| 1.0618 | H | Cl | $C_2H_5$ | $C_2H_5$ | $CH_2OC_2H_5$ | |
| 1.0619 | H | F | $C_2H_5$ | $C_2H_5$ | $CH_2OC_2H_5$ | |
| 1.0620 | H | $SCH_3$ | $C_2H_5$ | $C_2H_5$ | $CH_2OC_2H_5$ | |
| 1.0621 | H | $SC_2H_5$ | $C_2H_5$ | $C_2H_5$ | $CH_2OC_2H_5$ | |
| 1.0622 | H | $SC_3H_7$-n | $C_2H_5$ | $C_2H_5$ | $CH_2OC_2H_5$ | |
| 1.0623 | H | $SO_2CH_3$ | $C_2H_5$ | $C_2H_5$ | $CH_2OC_2H_5$ | |
| 1.0624 | H | $SO_2C_2H_5$ | $C_2H_5$ | $C_2H_5$ | $CH_2OC_2H_5$ | |
| 1.0625 | H | $NO_2$ | $C_2H_5$ | $C_2H_5$ | $CH_2OC_2H_5$ | |
| 1.0626 | H | CN | $C_2H_5$ | $C_2H_5$ | $CH_2OC_2H_5$ | |
| 1.0627 | H | $CH_2OH$ | $C_2H_5$ | $C_2H_5$ | $CH_2OC_2H_5$ | |
| 1.0628 | H | $CH_2CH_2OH$ | $C_2H_5$ | $C_2H_5$ | $CH_2OC_2H_5$ | |
| 1.0629 | H | $CH_2CH_2CH_2OH$ | $C_2H_5$ | $C_2H_5$ | $CH_2OC_2H_5$ | |
| 1.0630 | H | $C_6H_5$ | $C_2H_5$ | $C_2H_5$ | $CH_2OC_2H_5$ | |
| 1.0631 | H | $CH_2Cl$ | $C_2H_5$ | $C_2H_5$ | $CH_2OC_2H_5$ | |
| 1.0632 | H | $CH_2CH_2Cl$ | $C_2H_5$ | $C_2H_5$ | $CH_2OC_2H_5$ | |

TABLE 1.06-continued

| No. | X | Y | $R_1$ | $R_4$ | Z | phys. data |
|---|---|---|---|---|---|---|
| 1.0633 | H | $CH_2CH_2CH_2Cl$ | $C_2H_5$ | $C_2H_5$ | $CH_2OC_2H_5$ | |

TABLE 1.07

| No. | X | Y | $R_1$ | $R_4$ | Z | phys. data |
|---|---|---|---|---|---|---|
| 1.0701 | H | H | $C_2H_5$ | $C_2H_5$ | $CH(CH_3)OC_2H_5$ | |
| 1.0702 | H | $CH_3$ | $C_2H_5$ | $C_2H_5$ | $CH(CH_3)OC_2H_5$ | |
| 1.0703 | H | $C_2H_5$ | $C_2H_5$ | $C_2H_5$ | $CH(CH_3)OC_2H_5$ | |
| 1.0704 | H | $C_3H_7$ | $C_2H_5$ | $C_2H_5$ | $CH(CH_3)OC_2H_5$ | |
| 1.0705 | H | $OCH_3$ | $C_2H_5$ | $C_2H_5$ | $CH(CH_3)OC_2H_5$ | |
| 1.0706 | H | $OC_2H_5$ | $C_2H_5$ | $C_2H_5$ | $CH(CH_3)OC_2H_5$ | |
| 1.0707 | H | $OCH_2CH=CH_2$ | $C_2H_5$ | $C_2H_5$ | $CH(CH_3)OC_2H_5$ | |
| 1.0708 | H | $OCH_2CH=CHCH_3$ | $C_2H_5$ | $C_2H_5$ | $CH(CH_3)OC_2H_5$ | |
| 1.0709 | H | $OCH_2C(Cl)=CH_2$ | $C_2H_5$ | $C_2H_5$ | $CH(CH_3)OC_2H_5$ | |
| 1.0710 | H | $OCH_2CH=CHCl$ | $C_2H_5$ | $C_2H_5$ | $CH(CH_3)OC_2H_5$ | |
| 1.0711 | H | $OCH_2C\equiv CH$ | $C_2H_5$ | $C_2H_5$ | $CH(CH_3)OC_2H_5$ | |
| 1.0712 | H | $OCHF_2$ | $C_2H_5$ | $C_2H_5$ | $CH(CH_3)OC_2H_5$ | |
| 1.0713 | H | $OCF_3$ | $C_2H_5$ | $C_2H_5$ | $CH(CH_3)OC_2H_5$ | |
| 1.0714 | H | $OCF_2CHFCF_3$ | $C_2H_5$ | $C_2H_5$ | $CH(CH_3)OC_2H_5$ | |
| 1.0715 | H | $OC_6H_5$ | $C_2H_5$ | $C_2H_5$ | $CH(CH_3)OC_2H_5$ | |
| 1.0716 | H | $CF_3$ | $C_2H_5$ | $C_2H_5$ | $CH(CH_3)OC_2H_5$ | |
| 1.0717 | H | Br | $C_2H_5$ | $C_2H_5$ | $CH(CH_3)OC_2H_5$ | |
| 1.0718 | H | Cl | $C_2H_5$ | $C_2H_5$ | $CH(CH_3)OC_2H_5$ | |
| 1.0719 | H | F | $C_2H_5$ | $C_2H_5$ | $CH(CH_3)OC_2H_5$ | |
| 1.0720 | H | $SCH_3$ | $C_2H_5$ | $C_2H_5$ | $CH(CH_3)OC_2H_5$ | |
| 1.0721 | H | $SC_2H_5$ | $C_2H_5$ | $C_2H_5$ | $CH(CH_3)OC_2H_5$ | |
| 1.0722 | H | $SC_3H_7$-n | $C_2H_5$ | $C_2H_5$ | $CH(CH_3)OC_2H_5$ | |
| 1.0723 | H | $SO_2CH_3$ | $C_2H_5$ | $C_2H_5$ | $CH(CH_3)OC_2H_5$ | |
| 1.0724 | H | $SO_2C_2H_5$ | $C_2H_5$ | $C_2H_5$ | $CH(CH_3)OC_2H_5$ | |
| 1.0725 | H | $NO_2$ | $C_2H_5$ | $C_2H_5$ | $CH(CH_3)OC_2H_5$ | |
| 1.0726 | H | CN | $C_2H_5$ | $C_2H_5$ | $CH(CH_3)OC_2H_5$ | |
| 1.0727 | H | $CH_2OH$ | $C_2H_5$ | $C_2H_5$ | $CH(CH_3)OC_2H_5$ | |
| 1.0728 | H | $CH_2CH_2OH$ | $C_2H_5$ | $C_2H_5$ | $CH(CH_3)OC_2H_5$ | |
| 1.0729 | H | $CH_2CH_2CH_2OH$ | $C_2H_5$ | $C_2H_5$ | $CH(CH_3)OC_2H_5$ | |
| 1.0730 | H | $C_6H_5$ | $C_2H_5$ | $C_2H_5$ | $CH(CH_3)OC_2H_5$ | |
| 1.0731 | H | $CH_2Cl$ | $C_2H_5$ | $C_2H_5$ | $CH(CH_3)OC_2H_5$ | |
| 1.0732 | H | $CH_2CH_2Cl$ | $C_2H_5$ | $C_2H_5$ | $CH(CH_3)OC_2H_5$ | |
| 1.0733 | H | $CH_2CH_2CH_2Cl$ | $C_2H_5$ | $C_2H_5$ | $CH(CH_3)OC_2H_5$ | |

TABLE 1.08

| No. | X | Y | $R_1$ | $R_4$ | Z | phys. data |
|---|---|---|---|---|---|---|
| 1.0801 | H | H | $C_2H_5$ | $C_2H_5$ | $C(CH_3)_2OCH_3$ | oil |
| 1.0802 | H | $CH_3$ | $C_2H_5$ | $C_2H_5$ | $C(CH_3)_2OCH_3$ | |
| 1.0803 | H | $C_2H_5$ | $C_2H_5$ | $C_2H_5$ | $C(CH_3)_2OCH_3$ | |
| 1.0804 | H | $C_3H_7$ | $C_2H_5$ | $C_2H_5$ | $C(CH_3)_2OCH_3$ | |
| 1.0805 | H | $OCH_3$ | $C_2H_5$ | $C_2H_5$ | $C(CH_3)_2OCH_3$ | |
| 1.0806 | H | $OC_2H_5$ | $C_2H_5$ | $C_2H_5$ | $C(CH_3)_2OCH_3$ | |
| 1.0807 | H | $OCH_2CH=CH_2$ | $C_2H_5$ | $C_2H_5$ | $C(CH_3)_2OCH_3$ | |
| 1.0808 | H | $OCH_2CH=CHCH_3$ | $C_2H_5$ | $C_2H_5$ | $C(CH_3)_2OCH_3$ | |
| 1.0809 | H | $OCH_2C(Cl)=CH_2$ | $C_2H_5$ | $C_2H_5$ | $C(CH_3)_2OCH_3$ | |
| 1.0810 | H | $OCH_2CH=CHCl$ | $C_2H_5$ | $C_2H_5$ | $C(CH_3)_2OCH_3$ | |
| 1.0811 | H | $OCH_2C\equiv CH$ | $C_2H_5$ | $C_2H_5$ | $C(CH_3)_2OCH_3$ | |
| 1.0812 | H | $OCHF_2$ | $C_2H_5$ | $C_2H_5$ | $C(CH_3)_2OCH_3$ | |
| 1.0813 | H | $OCF_3$ | $C_2H_5$ | $C_2H_5$ | $C(CH_3)_2OCH_3$ | |
| 1.0814 | H | $OCF_2CHFCF_3$ | $C_2H_5$ | $C_2H_5$ | $C(CH_3)_2OCH_3$ | |
| 1.0815 | H | $OC_6H_5$ | $C_2H_5$ | $C_2H_5$ | $C(CH_3)_2OCH_3$ | |
| 1.0816 | H | $CF_3$ | $C_2H_5$ | $C_2H_5$ | $C(CH_3)_2OCH_3$ | |
| 1.0817 | H | Br | $C_2H_5$ | $C_2H_5$ | $C(CH_3)_2OCH_3$ | |
| 1.0818 | H | Cl | $C_2H_5$ | $C_2H_5$ | $C(CH_3)_2OCH_3$ | |
| 1.0819 | H | F | $C_2H_5$ | $C_2H_5$ | $C(CH_3)_2OCH_3$ | |
| 1.0820 | H | $SCH_3$ | $C_2H_5$ | $C_2H_5$ | $C(CH_3)_2OCH_3$ | |
| 1.0821 | H | $SC_2H_5$ | $C_2H_5$ | $C_2H_5$ | $C(CH_3)_2OCH_3$ | |
| 1.0822 | H | $SC_3H_7$-n | $C_2H_5$ | $C_2H_5$ | $C(CH_3)_2OCH_3$ | |
| 1.0823 | H | $SO_2CH_3$ | $C_2H_5$ | $C_2H_5$ | $C(CH_3)_2OCH_3$ | |
| 1.0824 | H | $SO_2C_2H_5$ | $C_2H_5$ | $C_2H_5$ | $C(CH_3)_2OCH_3$ | |
| 1.0825 | H | $NO_2$ | $C_2H_5$ | $C_2H_5$ | $C(CH_3)_2OCH_3$ | |
| 1.0826 | H | CN | $C_2H_5$ | $C_2H_5$ | $C(CH_3)_2OCH_3$ | |
| 1.0827 | H | $CH_2OH$ | $C_2H_5$ | $C_2H_5$ | $C(CH_3)_2OCH_3$ | |
| 1.0828 | H | $CH_2CH_2OH$ | $C_2H_5$ | $C_2H_5$ | $C(CH_3)_2OCH_3$ | |
| 1.0829 | H | $CH_2CH_2CH_2OH$ | $C_2H_5$ | $C_2H_5$ | $C(CH_3)_2OCH_3$ | |
| 1.0830 | H | $C_6H_5$ | $C_2H_5$ | $C_2H_5$ | $C(CH_3)_2OCH_3$ | |
| 1.0831 | H | $CH_2Cl$ | $C_2H_5$ | $C_2H_5$ | $C(CH_3)_2OCH_3$ | |
| 1.0832 | H | $CH_2CH_2Cl$ | $C_2H_5$ | $C_2H_5$ | $C(CH_3)_2OCH_3$ | |
| 1.0833 | H | $CH_2CH_2CH_2Cl$ | $C_2H_5$ | $C_2H_5$ | $C(CH_3)_2OCH_3$ | |

TABLE 1.09

| No. | X | Y | $R_1$ | $R_4$ | Z | phys. data |
|---|---|---|---|---|---|---|
| 1.0901 | H | H | $C_2H_5$ | $C_2H_5$ | $CH_2OC_3H_7$ | |
| 1.0902 | H | $CH_3$ | $C_2H_5$ | $C_2H_5$ | $CH_2OC_3H_7$ | |
| 1.0903 | H | $C_2H_5$ | $C_2H_5$ | $C_2H_5$ | $CH_2OC_3H_7$ | |
| 1.0904 | H | $C_3H_7$ | $C_2H_5$ | $C_2H_5$ | $CH_2OC_3H_7$ | |
| 1.0905 | H | $OCH_3$ | $C_2H_5$ | $C_2H_5$ | $CH_2OC_3H_7$ | |
| 1.0906 | H | $OC_2H_5$ | $C_2H_5$ | $C_2H_5$ | $CH_2OC_3H_7$ | |
| 1.0907 | H | $OCH_2CH=CH_2$ | $C_2H_5$ | $C_2H_5$ | $CH_2OC_3H_7$ | |
| 1.0908 | H | $OCH_2CH=CHCH_3$ | $C_2H_5$ | $C_2H_5$ | $CH_2OC_3H_7$ | |
| 1.0909 | H | $OCH_2C(Cl)=CH_2$ | $C_2H_5$ | $C_2H_5$ | $CH_2OC_3H_7$ | |
| 1.0910 | H | $OCH_2CH=CHCl$ | $C_2H_5$ | $C_2H_5$ | $CH_2OC_3H_7$ | |
| 1.0911 | H | $OCH_2C\equiv CH$ | $C_2H_5$ | $C_2H_5$ | $CH_2OC_3H_7$ | |
| 1.0912 | H | $OCHF_2$ | $C_2H_5$ | $C_2H_5$ | $CH_2OC_3H_7$ | |
| 1.0913 | H | $OCF_3$ | $C_2H_5$ | $C_2H_5$ | $CH_2OC_3H_7$ | |
| 1.0914 | H | $OCF_2CHFCF_3$ | $C_2H_5$ | $C_2H_5$ | $CH_2OC_3H_7$ | |
| 1.0915 | H | $OC_6H_5$ | $C_2H_5$ | $C_2H_5$ | $CH_2OC_3H_7$ | |
| 1.0916 | H | $CF_3$ | $C_2H_5$ | $C_2H_5$ | $CH_2OC_3H_7$ | |
| 1.0917 | H | Br | $C_2H_5$ | $C_2H_5$ | $CH_2OC_3H_7$ | |
| 1.0918 | H | Cl | $C_2H_5$ | $C_2H_5$ | $CH_2OC_3H_7$ | |
| 1.0919 | H | F | $C_2H_5$ | $C_2H_5$ | $CH_2OC_3H_7$ | |
| 1.0920 | H | $SCH_3$ | $C_2H_5$ | $C_2H_5$ | $CH_2OC_3H_7$ | |
| 1.0921 | H | $SC_2H_5$ | $C_2H_5$ | $C_2H_5$ | $CH_2OC_3H_7$ | |
| 1.0922 | H | $SC_3H_7$-n | $C_2H_5$ | $C_2H_5$ | $CH_2OC_3H_7$ | |
| 1.0923 | H | $SO_2CH_3$ | $C_2H_5$ | $C_2H_5$ | $CH_2OC_3H_7$ | |
| 1.0924 | H | $SO_2C_2H_5$ | $C_2H_5$ | $C_2H_5$ | $CH_2OC_3H_7$ | |
| 1.0925 | H | $NO_2$ | $C_2H_5$ | $C_2H_5$ | $CH_2OC_3H_7$ | |
| 1.0926 | H | CN | $C_2H_5$ | $C_2H_5$ | $CH_2OC_3H_7$ | |
| 1.0927 | H | $CH_2OH$ | $C_2H_5$ | $C_2H_5$ | $CH_2OC_3H_7$ | |
| 1.0928 | H | $CH_2CH_2OH$ | $C_2H_5$ | $C_2H_5$ | $CH_2OC_3H_7$ | |
| 1.0929 | H | $CH_2CH_2CH_2OH$ | $C_2H_5$ | $C_2H_5$ | $CH_2OC_3H_7$ | |
| 1.0930 | H | $C_6H_5$ | $C_2H_5$ | $C_2H_5$ | $CH_2OC_3H_7$ | |
| 1.0931 | H | $CH_2Cl$ | $C_2H_5$ | $C_2H_5$ | $CH_2OC_3H_7$ | |
| 1.0932 | H | $CH_2CH_2Cl$ | $C_2H_5$ | $C_2H_5$ | $CH_2OC_3H_7$ | |
| 1.0933 | H | $CH_2CH_2CH_2Cl$ | $C_2H_5$ | $C_2H_5$ | $CH_2OC_3H_7$ | |

TABLE 1.10

| No. | X | Y | $R_1$ | $R_4$ | Z | phys. data |
|---|---|---|---|---|---|---|
| 1.1001 | H | H | $C_2H_5$ | $C_2H_5$ | $C(CH_3)C_2H_4$(cyclo) | oil |
| 1.1002 | H | $CH_3$ | $C_2H_5$ | $C_2H_5$ | $C(CH_3)C_2H_4$(cyclo) | |
| 1.1003 | H | $C_2H_5$ | $C_2H_5$ | $C_2H_5$ | $C(CH_3)C_2H_4$(cyclo) | |
| 1.1004 | H | $C_3H_7$ | $C_2H_5$ | $C_2H_5$ | $C(CH_3)C_2H_4$(cyclo) | |
| 1.1005 | H | $OCH_3$ | $C_2H_5$ | $C_2H_5$ | $C(CH_3)C_2H_4$(cyclo) | |
| 1.1006 | H | $OC_2H_5$ | $C_2H_5$ | $C_2H_5$ | $C(CH_3)C_2H_4$(cyclo) | |
| 1.1007 | H | $OCH_2CH=CH_2$ | $C_2H_5$ | $C_2H_5$ | $C(CH_3)C_2H_4$(cyclo) | |
| 1.1008 | H | $OCH_2CH=CHCH_3$ | $C_2H_5$ | $C_2H_5$ | $C(CH_3)C_2H_4$(cyclo) | |
| 1.1009 | H | $OCH_2C(Cl)=CH_2$ | $C_2H_5$ | $C_2H_5$ | $C(CH_3)C_2H_4$(cyclo) | |
| 1.1010 | H | $OCH_2CH=CHCl$ | $C_2H_5$ | $C_2H_5$ | $C(CH_3)C_2H_4$(cyclo) | |
| 1.1011 | H | $OCH_2C\equiv CH$ | $C_2H_5$ | $C_2H_5$ | $C(CH_3)C_2H_4$(cyclo) | |
| 1.1012 | H | $OCHF_2$ | $C_2H_5$ | $C_2H_5$ | $C(CH_3)C_2H_4$(cyclo) | |
| 1.1013 | H | $OCF_3$ | $C_2H_5$ | $C_2H_5$ | $C(CH_3)C_2H_4$(cyclo) | |
| 1.1014 | H | $OCF_2CHFCF_3$ | $C_2H_5$ | $C_2H_5$ | $C(CH_3)C_2H_4$(cyclo) | |
| 1.1015 | H | $OC_6H_5$ | $C_2H_5$ | $C_2H_5$ | $C(CH_3)C_2H_4$(cyclo) | |
| 1.1016 | H | $CF_3$ | $C_2H_5$ | $C_2H_5$ | $C(CH_3)C_2H_4$(cyclo) | |
| 1.1017 | H | Br | $C_2H_5$ | $C_2H_5$ | $C(CH_3)C_2H_4$(cyclo) | |
| 1.1018 | H | Cl | $C_2H_5$ | $C_2H_5$ | $C(CH_3)C_2H_4$(cyclo) | |
| 1.1019 | H | F | $C_2H_5$ | $C_2H_5$ | $C(CH_3)C_2H_4$(cyclo) | |
| 1.1020 | H | $SCH_3$ | $C_2H_5$ | $C_2H_5$ | $C(CH_3)C_2H_4$(cyclo) | |
| 1.1021 | H | $SC_2H_5$ | $C_2H_5$ | $C_2H_5$ | $C(CH_3)C_2H_4$(cyclo) | |
| 1.1022 | H | $SC_3H_7$-n | $C_2H_5$ | $C_2H_5$ | $C(CH_3)C_2H_4$(cyclo) | |
| 1.1023 | H | $SO_2CH_3$ | $C_2H_5$ | $C_2H_5$ | $C(CH_3)C_2H_4$(cyclo) | |
| 1.1024 | H | $SO_2C_2H_5$ | $C_2H_5$ | $C_2H_5$ | $C(CH_3)C_2H_4$(cyclo) | |
| 1.1025 | H | $NO_2$ | $C_2H_5$ | $C_2H_5$ | $C(CH_3)C_2H_4$(cyclo) | |
| 1.1026 | H | CN | $C_2H_5$ | $C_2H_5$ | $C(CH_3)C_2H_4$(cyclo) | |
| 1.1027 | H | $CH_2OH$ | $C_2H_5$ | $C_2H_5$ | $C(CH_3)C_2H_4$(cyclo) | |
| 1.1028 | H | $CH_2CH_2OH$ | $C_2H_5$ | $C_2H_5$ | $C(CH_3)C_2H_4$(cyclo) | |
| 1.1029 | H | $CH_2CH_2CH_2OH$ | $C_2H_5$ | $C_2H_5$ | $C(CH_3)C_2H_4$(cyclo) | |
| 1.1030 | H | $C_6H_5$ | $C_2H_5$ | $C_2H_5$ | $C(CH_3)C_2H_4$(cyclo) | |
| 1.1031 | H | $CH_2Cl$ | $C_2H_5$ | $C_2H_5$ | $C(CH_3)C_2H_4$(cyclo) | |
| 1.1032 | H | $CH_2CH_2Cl$ | $C_2H_5$ | $C_2H_5$ | $C(CH_3)C_2H_4$(cyclo) | |
| 1.1033 | H | $CH_2CH_2CH_2Cl$ | $C_2H_5$ | $C_2H_5$ | $C(CH_3)C_2H_4$(cyclo) | |

TABLE 1.11

| No. | X | Y | $R_1$ | $R_4$ | Z | phys. data |
|---|---|---|---|---|---|---|
| 1.1101 | H | H | $C_2H_5$ | $C_2H_5$ | $CH_2OC_6H_5$ | m.p. 78–79° C. |
| 1.1102 | H | $CH_3$ | $C_2H_5$ | $C_2H_5$ | $CH_2OC_6H_5$ | |
| 1.1103 | H | $C_2H_5$ | $C_2H_5$ | $C_2H_5$ | $CH_2OC_6H_5$ | |
| 1.1104 | H | $C_3H_7$ | $C_2H_5$ | $C_2H_5$ | $CH_2OC_6H_5$ | |

TABLE 1.11-continued

| No. | X | Y | R₁ | R₄ | Z | phys. data |
|---|---|---|---|---|---|---|
| 1.1105 | H | OCH₃ | C₂H₅ | C₂H₅ | CH₂OC₆H₅ | |
| 1.1106 | H | OC₂H₅ | C₂H₅ | C₂H₅ | CH₂OC₆H₅ | |
| 1.1107 | H | OCH₂CH=CH₂ | C₂H₅ | C₂H₅ | CH₂OC₆H₅ | |
| 1.1108 | H | OCH₂CH=CHCH₃ | C₂H₅ | C₂H₅ | CH₂OC₆H₅ | |
| 1.1109 | H | OCH₂C(Cl)=CH₂ | C₂H₅ | C₂H₅ | CH₂OC₆H₅ | |
| 1.1110 | H | OCH₂CH=CHCl | C₂H₅ | C₂H₅ | CH₂OC₆H₅ | |
| 1.1111 | H | OCH₂C≡CH | C₂H₅ | C₂H₅ | CH₂OC₆H₅ | |
| 1.1112 | H | OCHF₂ | C₂H₅ | C₂H₅ | CH₂OC₆H₅ | |
| 1.1113 | H | OCF₃ | C₂H₅ | C₂H₅ | CH₂OC₆H₅ | |
| 1.1114 | H | OCF₂CHFCF₃ | C₂H₅ | C₂H₅ | CH₂OC₆H₅ | |
| 1.1115 | H | OC₆H₅ | C₂H₅ | C₂H₅ | CH₂OC₆H₅ | |
| 1.1116 | H | CF₃ | C₂H₅ | C₂H₅ | CH₂OC₆H₅ | |
| 1.1117 | H | Br | C₂H₅ | C₂H₅ | CH₂OC₆H₅ | |
| 1.1118 | H | Cl | C₂H₅ | C₂H₅ | CH₂OC₆H₅ | |
| 1.1119 | H | F | C₂H₅ | C₂H₅ | CH₂OC₆H₅ | |
| 1.1120 | H | SCH₃ | C₂H₅ | C₂H₅ | CH₂OC₆H₅ | |
| 1.1121 | H | SC₂H₅ | C₂H₅ | C₂H₅ | CH₂OC₆H₅ | |
| 1.1122 | H | SC₃H₇-n | C₂H₅ | C₂H₅ | CH₂OC₆H₅ | |
| 1.1123 | H | SO₂CH₃ | C₂H₅ | C₂H₅ | CH₂OC₆H₅ | |
| 1.1124 | H | SO₂C₂H₅ | C₂H₅ | C₂H₅ | CH₂OC₆H₅ | |
| 1.1125 | H | NO₂ | C₂H₅ | C₂H₅ | CH₂OC₆H₅ | |
| 1.1126 | H | CN | C₂H₅ | C₂H₅ | CH₂OC₆H₅ | |
| 1.1127 | H | CH₂OH | C₂H₅ | C₂H₅ | CH₂OC₆H₅ | |
| 1.1128 | H | CH₂CH₂OH | C₂H₅ | C₂H₅ | CH₂OC₆H₅ | |
| 1.1129 | H | CH₂CH₂CH₂OH | C₂H₅ | C₂H₅ | CH₂OC₆H₅ | |
| 1.1130 | H | C₆H₅ | C₂H₅ | C₂H₅ | CH₂OC₆H₅ | |
| 1.1131 | H | CH₂Cl | C₂H₅ | C₂H₅ | CH₂OC₆H₅ | |
| 1.1132 | H | CH₂CH₂Cl | C₂H₅ | C₂H₅ | CH₂OC₆H₅ | |
| 1.1133 | H | CH₂CH₂CH₂Cl | C₂H₅ | C₂H₅ | CH₂OC₆H₅ | |

TABLE 1.12

| No. | X | Y | R₁ | R₄ | Z | phys. data |
|---|---|---|---|---|---|---|
| 1.1201 | H | H | C₂H₅ | C₂H₅ | furan-2-yl | oil |
| 1.1202 | H | CH₃ | C₂H₅ | C₂H₅ | furan-2-yl | |
| 1.1203 | H | C₂H₅ | C₂H₅ | C₂H₅ | furan-2-yl | |
| 1.1204 | H | C₃H₇ | C₂H₅ | C₂H₅ | furan-2-yl | |
| 1.1205 | H | OCH₃ | C₂H₅ | C₂H₅ | furan-2-yl | |
| 1.1206 | H | OC₂H₅ | C₂H₅ | C₂H₅ | furan-2-yl | |
| 1.1207 | H | OCH₂CH=CH₂ | C₂H₅ | C₂H₅ | furan-2-yl | |
| 1.1208 | H | OCH₂CH=CHCH₃ | C₂H₅ | C₂H₅ | furan-2-yl | |
| 1.1209 | H | OCH₂C(Cl)=CH₂ | C₂H₅ | C₂H₅ | furan-2-yl | |
| 1.1210 | H | OCH₂CH=CHCl | C₂H₅ | C₂H₅ | furan-2-yl | |
| 1.1211 | H | OCH₂C≡CH | C₂H₅ | C₂H₅ | furan-2-yl | |
| 1.1212 | H | OCHF₂ | C₂H₅ | C₂H₅ | furan-2-yl | |
| 1.1213 | H | OCF₃ | C₂H₅ | C₂H₅ | furan-2-yl | |
| 1.1214 | H | OCF₂CHFCF₃ | C₂H₅ | C₂H₅ | furan-2-yl | |
| 1.1215 | H | OC₆H₅ | C₂H₅ | C₂H₅ | furan-2-yl | |
| 1.1216 | H | CF₃ | C₂H₅ | C₂H₅ | furan-2-yl | |
| 1.1217 | H | Br | C₂H₅ | C₂H₅ | furan-2-yl | |
| 1.1218 | H | Cl | C₂H₅ | C₂H₅ | furan-2-yl | |
| 1.1219 | H | F | C₂H₅ | C₂H₅ | furan-2-yl | |
| 1.1220 | H | SCH₃ | C₂H₅ | C₂H₅ | furan-2-yl | |
| 1.1221 | H | SC₂H₅ | C₂H₅ | C₂H₅ | furan-2-yl | |
| 1.1222 | H | SC₃H₇-n | C₂H₅ | C₂H₅ | furan-2-yl | |
| 1.1223 | H | SO₂CH₃ | C₂H₅ | C₂H₅ | furan-2-yl | |
| 1.1224 | H | SO₂C₂H₅ | C₂H₅ | C₂H₅ | furan-2-yl | |
| 1.1225 | H | NO₂ | C₂H₅ | C₂H₅ | furan-2-yl | |
| 1.1226 | H | CN | C₂H₅ | C₂H₅ | furan-2-yl | |
| 1.1227 | H | CH₂OH | C₂H₅ | C₂H₅ | furan-2-yl | |
| 1.1228 | H | CH₂CH₂OH | C₂H₅ | C₂H₅ | furan-2-yl | |
| 1.1229 | H | CH₂CH₂CH₂OH | C₂H₅ | C₂H₅ | furan-2-yl | |
| 1.1230 | H | C₆H₅ | C₂H₅ | C₂H₅ | furan-2-yl | |
| 1.1231 | H | CH₂Cl | C₂H₅ | C₂H₅ | furan-2-yl | |
| 1.1232 | H | CH₂CH₂Cl | C₂H₅ | C₂H₅ | furan-2-yl | |
| 1.1233 | H | CH₂CH₂CH₂Cl | C₂H₅ | C₂H₅ | furan-2-yl | |

TABLE 1.13

| No. | X | Y | R₁ | R₄ | Z | phys. data |
|---|---|---|---|---|---|---|
| 1.1301 | H | H | C₂H₅ | C₂H₅ | dioxan-2-yl | oil |
| 1.1302 | H | CH₃ | C₂H₅ | C₂H₅ | dioxan-2-yl | |
| 1.1303 | H | C₂H₅ | C₂H₅ | C₂H₅ | dioxan-2-yl | |
| 1.1304 | H | C₃H₇ | C₂H₅ | C₂H₅ | dioxan-2-yl | |
| 1.1305 | H | OCH₃ | C₂H₅ | C₂H₅ | dioxan-2-yl | |
| 1.1306 | H | OC₂H₅ | C₂H₅ | C₂H₅ | dioxan-2-yl | |
| 1.1307 | H | OCH₂CH=CH₂ | C₂H₅ | C₂H₅ | dioxan-2-yl | |
| 1.1308 | H | OCH₂CH=CHCH₃ | C₂H₅ | C₂H₅ | dioxan-2-yl | |

TABLE 1.13-continued

| No. | X | Y | $R_1$ | $R_4$ | Z | phys. data |
|---|---|---|---|---|---|---|
| 1.1309 | H | $OCH_2C(Cl)=CH_2$ | $C_2H_5$ | $C_2H_5$ | dioxan-2-yl | |
| 1.1310 | H | $OCH_2CH=CHCl$ | $C_2H_5$ | $C_2H_5$ | dioxan-2-yl | |
| 1.1311 | H | $OCH_2C\equiv CH$ | $C_2H_5$ | $C_2H_5$ | dioxan-2-yl | |
| 1.1312 | H | $OCHF_2$ | $C_2H_5$ | $C_2H_5$ | dioxan-2-yl | |
| 1.1313 | H | $OCF_3$ | $C_2H_5$ | $C_2H_5$ | dioxan-2-yl | |
| 1.1314 | H | $OCF_2CHFCF_3$ | $C_2H_5$ | $C_2H_5$ | dioxan-2-yl | |
| 1.1315 | H | $OC_6H_5$ | $C_2H_5$ | $C_2H_5$ | dioxan-2-yl | |
| 1.1316 | H | $CF_3$ | $C_2H_5$ | $C_2H_5$ | dioxan-2-yl | |
| 1.1317 | H | Br | $C_2H_5$ | $C_2H_5$ | dioxan-2-yl | |
| 1.1318 | H | Cl | $C_2H_5$ | $C_2H_5$ | dioxan-2-yl | |
| 1.1319 | H | F | $C_2H_5$ | $C_2H_5$ | dioxan-2-yl | |
| 1.1320 | H | $SCH_3$ | $C_2H_5$ | $C_2H_5$ | dioxan-2-yl | |
| 1.1321 | H | $SC_2H_5$ | $C_2H_5$ | $C_2H_5$ | dioxan-2-yl | |
| 1.1322 | H | $SC_3H_7$-n | $C_2H_5$ | $C_2H_5$ | dioxan-2-yl | |
| 1.1323 | H | $SO_2CH_3$ | $C_2H_5$ | $C_2H_5$ | dioxan-2-yl | |
| 1.1324 | H | $SO_2C_2H_5$ | $C_2H_5$ | $C_2H_5$ | dioxan-2-yl | |
| 1.1325 | H | $NO_2$ | $C_2H_5$ | $C_2H_5$ | dioxan-2-yl | |
| 1.1326 | H | CN | $C_2H_5$ | $C_2H_5$ | dioxan-2-yl | |
| 1.1327 | H | $CH_2OH$ | $C_2H_5$ | $C_2H_5$ | dioxan-2-yl | |
| 1.1328 | H | $CH_2CH_2OH$ | $C_2H_5$ | $C_2H_5$ | dioxan-2-yl | |
| 1.1329 | H | $CH_2CH_2CH_2OH$ | $C_2H_5$ | $C_2H_5$ | dioxan-2-yl | |
| 1.1330 | H | $C_6H_5$ | $C_2H_5$ | $C_2H_5$ | dioxan-2-yl | |
| 1.1331 | H | $CH_2Cl$ | $C_2H_5$ | $C_2H_5$ | dioxan-2-yl | |
| 1.1332 | H | $CH_2CH_2Cl$ | $C_2H_5$ | $C_2H_5$ | dioxan-2-yl | |
| 1.1333 | H | $CH_2CH_2CH_2Cl$ | $C_2H_5$ | $C_2H_5$ | dioxan-2-yl | |

TABLE 1.14

| No. | X | Y | $R_1$ | $R_4$ | Z | phys. data |
|---|---|---|---|---|---|---|
| 1.1401 | H | H | $C_2H_5$ | $C_2H_5$ | $CH_2OC_2H_4OCH_3$ | oil |
| 1.1402 | H | $CH_3$ | $C_2H_5$ | $C_2H_5$ | $CH_2OC_2H_4OCH_3$ | |
| 1.1403 | H | $C_2H_5$ | $C_2H_5$ | $C_2H_5$ | $CH_2OC_2H_4OCH_3$ | |
| 1.1404 | H | $C_3H_7$ | $C_2H_5$ | $C_2H_5$ | $CH_2OC_2H_4OCH_3$ | |
| 1.1405 | H | $OCH_3$ | $C_2H_5$ | $C_2H_5$ | $CH_2OC_2H_4OCH_3$ | |
| 1.1406 | H | $OC_2H_5$ | $C_2H_5$ | $C_2H_5$ | $CH_2OC_2H_4OCH_3$ | |
| 1.1407 | H | $OCH_2CH=CH_2$ | $C_2H_5$ | $C_2H_5$ | $CH_2OC_2H_4OCH_3$ | |
| 1.1408 | H | $OCH_2CH=CHCH_3$ | $C_2H_5$ | $C_2H_5$ | $CH_2OC_2H_4OCH_3$ | |
| 1.1409 | H | $OCH_2C(Cl)=CH_2$ | $C_2H_5$ | $C_2H_5$ | $CH_2OC_2H_4OCH_3$ | |
| 1.1410 | H | $OCH_2CH=CHCl$ | $C_2H_5$ | $C_2H_5$ | $CH_2OC_2H_4OCH_3$ | |
| 1.1411 | H | $OCH_2C\equiv CH$ | $C_2H_5$ | $C_2H_5$ | $CH_2OC_2H_4OCH_3$ | |
| 1.1412 | H | $OCHF_2$ | $C_2H_5$ | $C_2H_5$ | $CH_2OC_2H_4OCH_3$ | |
| 1.1413 | H | $OCF_3$ | $C_2H_5$ | $C_2H_5$ | $CH_2OC_2H_4OCH_3$ | |
| 1.1414 | H | $OCF_2CHFCF_3$ | $C_2H_5$ | $C_2H_5$ | $CH_2OC_2H_4OCH_3$ | |
| 1.1415 | H | $OC_6H_5$ | $C_2H_5$ | $C_2H_5$ | $CH_2OC_2H_4OCH_3$ | |
| 1.1416 | H | $CF_3$ | $C_2H_5$ | $C_2H_5$ | $CH_2OC_2H_4OCH_3$ | |
| 1.1417 | H | Br | $C_2H_5$ | $C_2H_5$ | $CH_2OC_2H_4OCH_3$ | |
| 1.1418 | H | Cl | $C_2H_5$ | $C_2H_5$ | $CH_2OC_2H_4OCH_3$ | |
| 1.1419 | H | F | $C_2H_5$ | $C_2H_5$ | $CH_2OC_2H_4OCH_3$ | |
| 1.1420 | H | $SCH_3$ | $C_2H_5$ | $C_2H_5$ | $CH_2OC_2H_4OCH_3$ | |
| 1.1421 | H | $SC_2H_5$ | $C_2H_5$ | $C_2H_5$ | $CH_2OC_2H_4OCH_3$ | |
| 1.1422 | H | $SC_3H_7$-n | $C_2H_5$ | $C_2H_5$ | $CH_2OC_2H_4OCH_3$ | |
| 1.1423 | H | $SO_2CH_3$ | $C_2H_5$ | $C_2H_5$ | $CH_2OC_2H_4OCH_3$ | |
| 1.1424 | H | $SO_2C_2H_5$ | $C_2H_5$ | $C_2H_5$ | $CH_2OC_2H_4OCH_3$ | |
| 1.1425 | H | $NO_2$ | $C_2H_5$ | $C_2H_5$ | $CH_2OC_2H_4OCH_3$ | |
| 1.1426 | H | CN | $C_2H_5$ | $C_2H_5$ | $CH_2OC_2H_4OCH_3$ | |
| 1.1427 | H | $CH_2OH$ | $C_2H_5$ | $C_2H_5$ | $CH_2OC_2H_4OCH_3$ | |
| 1.1428 | H | $CH_2CH_2OH$ | $C_2H_5$ | $C_2H_5$ | $CH_2OC_2H_4OCH_3$ | |
| 1.1429 | H | $CH_2CH_2CH_2OH$ | $C_2H_5$ | $C_2H_5$ | $CH_2OC_2H_4OCH_3$ | |
| 1.1430 | H | $C_6H_5$ | $C_2H_5$ | $C_2H_5$ | $CH_2OC_2H_4OCH_3$ | |
| 1.1431 | H | $CH_2Cl$ | $C_2H_5$ | $C_2H_5$ | $CH_2OC_2H_4OCH_3$ | |
| 1.1432 | H | $CH_2CH_2Cl$ | $C_2H_5$ | $C_2H_5$ | $CH_2OC_2H_4OCH_3$ | |
| 1.1433 | H | $CH_2CH_2CH_2Cl$ | $C_2H_5$ | $C_2H_5$ | $CH_2OC_2H_4OCH_3$ | |

TABLE 1.15

| No. | X | Y | $R_1$ | $R_4$ | Z | phys. data |
|---|---|---|---|---|---|---|
| 1.1501 | H | H | $C_2H_5$ | $C_2H_5$ | $CH_2OC_2H_4OC_2H_4OCH_3$ | oil |
| 1.1502 | H | $CH_3$ | $C_2H_5$ | $C_2H_5$ | $CH_2OC_2H_4OC_2H_4OCH_3$ | |
| 1.1503 | H | $C_2H_5$ | $C_2H_5$ | $C_2H_5$ | $CH_2OC_2H_4OC_2H_4OCH_3$ | |
| 1.1504 | H | $C_3H_7$ | $C_2H_5$ | $C_2H_5$ | $CH_2OC_2H_4OC_2H_4OCH_3$ | |
| 1.1505 | H | $OCH_3$ | $C_2H_5$ | $C_2H_5$ | $CH_2OC_2H_4OC_2H_4OCH_3$ | |
| 1.1506 | H | $OC_2H_5$ | $C_2H_5$ | $C_2H_5$ | $CH_2OC_2H_4OC_2H_4OCH_3$ | |
| 1.1507 | H | $OCH_2CH=CH_2$ | $C_2H_5$ | $C_2H_5$ | $CH_2OC_2H_4OC_2H_4OCH_3$ | |
| 1.1508 | H | $OCH_2CH=CHCH_3$ | $C_2H_5$ | $C_2H_5$ | $CH_2OC_2H_4OC_2H_4OCH_3$ | |
| 1.1509 | H | $OCH_2C(Cl)=CH_2$ | $C_2H_5$ | $C_2H_5$ | $CH_2OC_2H_4OC_2H_4OCH_3$ | |
| 1.1510 | H | $OCH_2CH=CHCl$ | $C_2H_5$ | $C_2H_5$ | $CH_2OC_2H_4OC_2H_4OCH_3$ | |
| 1.1511 | H | $OCH_2C\equiv CH$ | $C_2H_5$ | $C_2H_5$ | $CH_2OC_2H_4OC_2H_4OCH_3$ | |
| 1.1512 | H | $OCHF_2$ | $C_2H_5$ | $C_2H_5$ | $CH_2OC_2H_4OC_2H_4OCH_3$ | |

TABLE 1.15-continued

| No. | X | Y | $R_1$ | $R_4$ | Z | phys. data |
|---|---|---|---|---|---|---|
| 1.1513 | H | $OCF_3$ | $C_2H_5$ | $C_2H_5$ | $CH_2OC_2H_4OC_2H_4OCH_3$ | |
| 1.1514 | H | $OCF_2CHFCF_3$ | $C_2H_5$ | $C_2H_5$ | $CH_2OC_2H_4OC_2H_4OCH_3$ | |
| 1.1515 | H | $OC_6H_5$ | $C_2H_5$ | $C_2H_5$ | $CH_2OC_2H_4OC_2H_4OCH_3$ | |
| 1.1516 | H | $CF_3$ | $C_2H_5$ | $C_2H_5$ | $CH_2OC_2H_4OC_2H_4OCH_3$ | |
| 1.1517 | H | Br | $C_2H_5$ | $C_2H_5$ | $CH_2OC_2H_4OC_2H_4OCH_3$ | |
| 1.1518 | H | Cl | $C_2H_5$ | $C_2H_5$ | $CH_2OC_2H_4OC_2H_4OCH_3$ | |
| 1.1519 | H | F | $C_2H_5$ | $C_2H_5$ | $CH_2OC_2H_4OC_2H_4OCH_3$ | |
| 1.1520 | H | $SCH_3$ | $C_2H_5$ | $C_2H_5$ | $CH_2OC_2H_4OC_2H_4OCH_3$ | |
| 1.1521 | H | $SC_2H_5$ | $C_2H_5$ | $C_2H_5$ | $CH_2OC_2H_4OC_2H_4OCH_3$ | |
| 1.1522 | H | $SC_3H_7$-n | $C_2H_5$ | $C_2H_5$ | $CH_2OC_2H_4OC_2H_4OCH_3$ | |
| 1.1523 | H | $SO_2CH_3$ | $C_2H_5$ | $C_2H_5$ | $CH_2OC_2H_4OC_2H_4OCH_3$ | |
| 1.1524 | H | $SO_2C_2H_5$ | $C_2H_5$ | $C_2H_5$ | $CH_2OC_2H_4OC_2H_4OCH_3$ | |
| 1.1525 | H | $NO_2$ | $C_2H_5$ | $C_2H_5$ | $CH_2OC_2H_4OC_2H_4OCH_3$ | |
| 1.1526 | H | CN | $C_2H_5$ | $C_2H_5$ | $CH_2OC_2H_4OC_2H_4OCH_3$ | |
| 1.1527 | H | $CH_2OH$ | $C_2H_5$ | $C_2H_5$ | $CH_2OC_2H_4OC_2H_4OCH_3$ | |
| 1.1528 | H | $CH_2CH_2OH$ | $C_2H_5$ | $C_2H_5$ | $CH_2OC_2H_4OC_2H_4OCH_3$ | |
| 1.1529 | H | $CH_2CH_2CH_2OH$ | $C_2H_5$ | $C_2H_5$ | $CH_2OC_2H_4OC_2H_4OCH_3$ | |
| 1.1530 | H | $C_6H_5$ | $C_2H_5$ | $C_2H_5$ | $CH_2OC_2H_4OC_2H_4OCH_3$ | |
| 1.1531 | H | $CH_2Cl$ | $C_2H_5$ | $C_2H_5$ | $CH_2OC_2H_4OC_2H_4OCH_3$ | |
| 1.1532 | H | $CH_2CH_2Cl$ | $C_2H_5$ | $C_2H_5$ | $CH_2OC_2H_4OC_2H_4OCH_3$ | |
| 1.1533 | H | $CH_2CH_2CH_2Cl$ | $C_2H_5$ | $C_2H_5$ | $CH_2OC_2H_4OC_2H_4OCH_3$ | |

TABLE 1.16

| No. | X | Y | $R_1$ | $R_4$ | Z | phys. data |
|---|---|---|---|---|---|---|
| 1.1601 | H | H | $C_2H_5$ | $C_2H_5$ | $CH_2OCH_2CONH_2$ | oil |
| 1.1602 | H | $CH_3$ | $C_2H_5$ | $C_2H_5$ | $CH_2OCH_2CONH_2$ | |
| 1.1603 | H | $C_2H_5$ | $C_2H_5$ | $C_2H_5$ | $CH_2OCH_2CONH_2$ | |
| 1.1604 | H | $C_3H_7$ | $C_2H_5$ | $C_2H_5$ | $CH_2OCH_2CONH_2$ | |
| 1.1605 | H | $OCH_3$ | $C_2H_5$ | $C_2H_5$ | $CH_2OCH_2CONH_2$ | |
| 1.1606 | H | $OC_2H_5$ | $C_2H_5$ | $C_2H_5$ | $CH_2OCH_2CONH_2$ | |
| 1.1607 | H | $OCH_2CH=CH_2$ | $C_2H_5$ | $C_2H_5$ | $CH_2OCH_2CONH_2$ | |
| 1.1608 | H | $OCH_2CH=CHCH_3$ | $C_2H_5$ | $C_2H_5$ | $CH_2OCH_2CONH_2$ | |
| 1.1609 | H | $OCH_2C(Cl)=CH_2$ | $C_2H_5$ | $C_2H_5$ | $CH_2OCH_2CONH_2$ | |
| 1.1610 | H | $OCH_2CH=CHCl$ | $C_2H_5$ | $C_2H_5$ | $CH_2OCH_2CONH_2$ | |
| 1.1611 | H | $OCH_2C\equiv CH$ | $C_2H_5$ | $C_2H_5$ | $CH_2OCH_2CONH_2$ | |
| 1.1612 | H | $OCHF_2$ | $C_2H_5$ | $C_2H_5$ | $CH_2OCH_2CONH_2$ | |
| 1.1613 | H | $OCF_3$ | $C_2H_5$ | $C_2H_5$ | $CH_2OCH_2CONH_2$ | |
| 1.1614 | H | $OCF_2CHFCF_3$ | $C_2H_5$ | $C_2H_5$ | $CH_2OCH_2CONH_2$ | |
| 1.1615 | H | $OC_6H_5$ | $C_2H_5$ | $C_2H_5$ | $CH_2OCH_2CONH_2$ | |
| 1.1616 | H | $CF_3$ | $C_2H_5$ | $C_2H_5$ | $CH_2OCH_2CONH_2$ | |
| 1.1617 | H | Br | $C_2H_5$ | $C_2H_5$ | $CH_2OCH_2CONH_2$ | |
| 1.1618 | H | Cl | $C_2H_5$ | $C_2H_5$ | $CH_2OCH_2CONH_2$ | |
| 1.1619 | H | F | $C_2H_5$ | $C_2H_5$ | $CH_2OCH_2CONH_2$ | |
| 1.1620 | H | $SCH_3$ | $C_2H_5$ | $C_2H_5$ | $CH_2OCH_2CONH_2$ | |
| 1.1621 | H | $SC_2H_5$ | $C_2H_5$ | $C_2H_5$ | $CH_2OCH_2CONH_2$ | |
| 1.1622 | H | $SC_3H_7$-n | $C_2H_5$ | $C_2H_5$ | $CH_2OCH_2CONH_2$ | |
| 1.1623 | H | $SO_2CH_3$ | $C_2H_5$ | $C_2H_5$ | $CH_2OCH_2CONH_2$ | |
| 1.1624 | H | $SO_2C_2H_5$ | $C_2H_5$ | $C_2H_5$ | $CH_2OCH_2CONH_2$ | |
| 1.1625 | H | $NO_2$ | $C_2H_5$ | $C_2H_5$ | $CH_2OCH_2CONH_2$ | |
| 1.1626 | H | CN | $C_2H_5$ | $C_2H_5$ | $CH_2OCH_2CONH_2$ | |
| 1.1627 | H | $CH_2OH$ | $C_2H_5$ | $C_2H_5$ | $CH_2OCH_2CONH_2$ | |
| 1.1628 | H | $CH_2CH_2OH$ | $C_2H_5$ | $C_2H_5$ | $CH_2OCH_2CONH_2$ | |
| 1.1629 | H | $CH_2CH_2CH_2OH$ | $C_2H_5$ | $C_2H_5$ | $CH_2OCH_2CONH_2$ | |
| 1.1630 | H | $C_6H_5$ | $C_2H_5$ | $C_2H_5$ | $CH_2OCH_2CONH_2$ | |
| 1.1631 | H | $CH_2Cl$ | $C_2H_5$ | $C_2H_5$ | $CH_2OCH_2CONH_2$ | |
| 1.1632 | H | $CH_2CH_2Cl$ | $C_2H_5$ | $C_2H_5$ | $CH_2OCH_2CONH_2$ | |
| 1.1633 | H | $CH_2CH_2CH_2Cl$ | $C_2H_5$ | $C_2H_5$ | $CH_2OCH_2CONH_2$ | |

EXAMPLE 5

Preparation of 6-cyclopropyl-2-(5-isopropyl-5-methyl-4-oxoimidazolin-2-yl)-pyridine-3-carboxylic acid

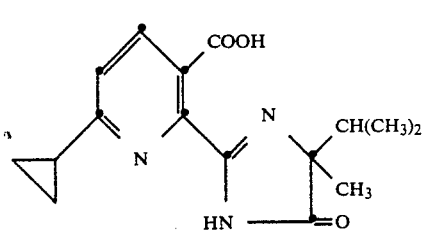

10 g of 30% sodium methoxide in methanol are added to a solution of 6 g of 6-cyclopropylpyridine-2,3-dicarboxylic acid diethyl ester and 3 g of 2-amino-2,3-dimethylbutyramide in 100 ml of ethanol and the reaction mixture is boiled under reflux for 3 hours. It is then concentrated, the residue is dissolved in a small amount of water, and the solution is saturated with sodium chloride. The pH is then adjusted to 4 with concentrated hydrochloric acid and the solution is extracted three times with 150 ml of ethyl acetate each time. The organic phase is dried over magnesium sulphate, filtered and concentrated. The residue crystallises from ether/hexane 1:2. In this manner 4 g of 6-cyclopropyl-2-(5-isopropyl-5-methyl-4-oxoimidazolin-2-yl)-pyridinecarboxylic acid having a melting point of 118°–121° are obtained.

EXAMPLE 6

Preparation of
6-methoxy-5-methyl-2-(5-isopropyl-5-methyl-4-oxoimidazolin-2-yl)-pyridine-3-carboxylic acid

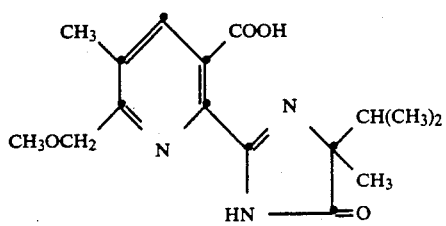

5 g of potassium tert.-butoxide are added in portions at a temperature of 80° C. to a solution of 5.7 g of 6-methoxymethyl-5-methylpyridine-2,3-dicarboxylic acid diethyl ester and 2.6 g of 2-amino-2,3-dimethylbutyramide in 200 ml of dry toluene while stirring. Once the addition of the potassium tert.-butoxide is complete, the resulting red solution is stirred for 2 hours at 80° C., the potassium salt of 2-(5-isopropyl-5-methyl-4-oxoimidazolin-2-yl)-5-ethylpyridine-3-carboxylic acid being deposited in the form of a thick crystalline slurry. The mixture is cooled to room temperature and filtered with suction, and the crystals are dried and then dissolved in 50 ml of saturated sodium chloride solution. The solution is adjusted to pH 4 with concentrated hydrochloric acid and then extracted three times with 100 ml of ethyl acetate each time. The organic phase is dried over magnesium sulphate, filtered off with suction and concentrated by evaporation. The residue crystallises from ether/hexane 1:2 yielding 2.8 g of the above acid, which has a melting point of 151°–153° C.

EXAMPLE 7

Preparation of
5-ethyl-6-methoxymethyl-2-(5-isopropyl-5-methyl-4-oxo-imidazol-2H-1-yl)-pyridine-3-carboxylic acid

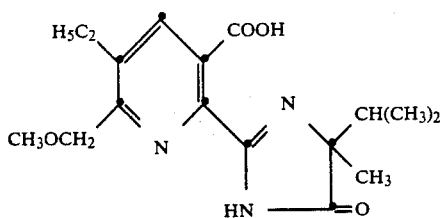

17.4 g of potassium tert.-butoxide are added to a solution of 18.3 g of 5-ethyl-6-methoxymethylpyridine-2,3-dicarboxylic acid in 300 ml of dry toluene at a temperature of 80° C. The resulting solution is then stirred for 3 hours at 80° C. and finally cooled to 15° C. The resulting crystallisate is filtered off with suction, dried and taken up in a small amount of saturated sodium chloride solution. The sodium chloride solution is adjusted to pH 4 with concentrated hydrochloric acid and then extracted three times with 150 ml of ethyl acetate each time. The organic phase is dried over magnesium sulphate, filtered off with suction and concentrated by evaporation. The residue crystallises from ether/hexane 1:2. In this manner 11.9 g of the above acid having a melting point of 134°–137° C. are obtained.

EXAMPLE 8

Preparation of
6-(thiophen-3-yl)-2-(5-isopropyl-5-methyl-4-oxo-imidazol-2-yl)-pyridine-3-carboxylic acid

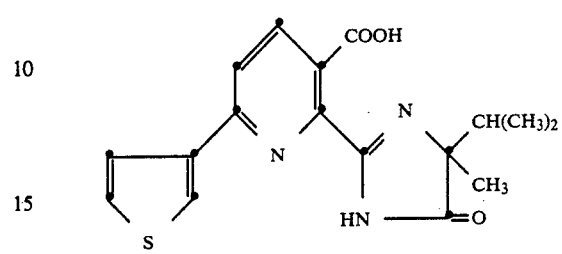

12 g of potassium tert.-butoxide are added to a solution of 14 g of 6-(thiophen-3-yl)-pyridine-2,3-dicarboxylic acid diethyl ester and 6 g of 2-amino-2,3-dimethylbutyramide in 100 ml of dry toluene while stirring and the solution is heated at 80° C. for 5 hours. The reaction solution is then poured onto ice, the phases are separated and the aqueous phase is acidified with 10 ml of glacial acetic acid. After some time the above acid crystallises out and is filtered off with suction and dried. In this manner 13.5 g of 6-(thiophen-3-yl)-2-(5-isopropyl-5-methyl-4-oxo-imidazol-2-yl)-pyridine-3-carboxylic acid having a melting point of 253°–257° C. are obtained.

The 6-(thiophen-3-yl)-pyridine-2,3-dicarboxylic acid diethyl ester required as starting material is prepared as follows:

(a) 1-morpholino-1-(thiophen-3-yl)-ethylene

A solution of 57 g of titanium tetrachloride (TiCl₄) in 100 ml of cyclohexane is added dropwise to a stirred solution of 75 g of 3-acetylthiophene and 160 g of morpholine in a liter of cyclohexane. When the addition is complete, the reaction mixture is further stirred at room temperature for 12 hours, then the precipitate is filtered off and the filtrate is concentrated by evaporation. The residue is distilled and has a boiling point of 98°/0.04 millibar. In this manner 36.5 g of 1-morpholino-1-(thiophen-3-yl)-ethylene are obtained in the form of a colourless oil.

(b) A solution of 25 g of this ethylene in 50 ml of ethanol is stirred with 31 g of ethoxymethyleneoxalacetic acid ester ($C_2H_5OCH=C(COOC_2H_5)COCOOC_2H_5$).

After 2 hours 27.5 g of a 9.3% solution of ammonia in absolute alcohol are added thereto and the reaction mixture is stirred for a further hour at room temperature. Crystals separate out from the solution on standing overnight. They are filtered off and recrystallised from toluene/hexane. In this manner 22.5 g of 6-(thiophen-3-yl)-pyridine-2,3dicarboxylic acid diethyl ester having a melting point of 100°–101.5° C. are obtained.

The 2-(5-isopropyl-5-methyl-4-oxo-imidazol-2-yl)-pyridine-3-carboxylic acids (nicotinic acids) of formula III listed in Tables 2.00 to 2.26 are prepared analogously to Examples 5 to 8.

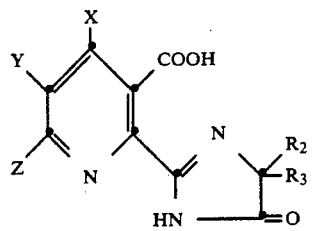

(III)

TABLE 2.00

| No. | X | Y | Z | phys. data |
|---|---|---|---|---|
| 2.0001 | H | H | $C_3H_5$(cyclo) | m.p. 118–121° C. |
| 2.0002 | H | $CH_3$ | $C_3H_5$(cyclo) | m.p. 206–208° C. |
| 2.0003 | H | $C_2H_5$ | $C_3H_5$(cyclo) | m.p. 169–172° C. |
| 2.0004 | H | $C_3H_7$ | $C_3H_5$(cyclo) | |
| 2.0005 | H | $OCH_3$ | $C_3H_5$(cyclo) | |
| 2.0006 | H | $OC_2H_5$ | $C_3H_5$(cyclo) | |
| 2.0007 | H | $OCH_2CH=CH_2$ | $C_3H_5$(cyclo) | |
| 2.0008 | H | $OCH_2CH=CHCH_3$ | $C_3H_5$(cyclo) | |
| 2.0009 | H | $OCH_2C(Cl)=CH_2$ | $C_3H_5$(cyclo) | |
| 2.0010 | H | $OCH_2CH=CHCl$ | $C_3H_5$(cyclo) | |
| 2.0011 | H | $OCH_2C\equiv CH$ | $C_3H_5$(cyclo) | |
| 2.0012 | H | $OCHF_2$ | $C_3H_5$(cyclo) | |
| 2.0013 | H | $OCF_3$ | $C_3H_5$(cyclo) | |
| 2.0014 | H | $OCF_2CHFCF_3$ | $C_3H_5$(cyclo) | |
| 2.0015 | H | $OC_6H_5$ | $C_3H_5$(cyclo) | |
| 2.0016 | H | $CF_3$ | $C_3H_5$(cyclo) | |
| 2.0017 | H | Br | $C_3H_5$(cyclo) | foam |
| 2.0018 | H | Cl | $C_3H_5$(cyclo) | |
| 2.0019 | H | F | $C_3H_5$(cyclo) | |
| 2.0020 | H | $SCH_3$ | $C_3H_5$(cyclo) | |
| 2.0021 | H | $SC_2H_5$ | $C_3H_5$(cyclo) | |
| 2.0022 | H | $SC_3H_7$-n | $C_3H_5$(cyclo) | |
| 2.0023 | H | $SO_2CH_3$ | $C_3H_5$(cyclo) | |
| 2.0024 | H | $SO_2C_2H_5$ | $C_3H_5$(cyclo) | |
| 2.0025 | H | $NO_2$ | $C_3H_5$(cyclo) | |
| 2.0026 | H | CN | $C_3H_5$(cyclo) | |
| 2.0027 | H | $CH_2OH$ | $C_3H_5$(cyclo) | |
| 2.0028 | H | $CH_2CH_2OH$ | $C_3H_5$(cyclo) | |
| 2.0029 | H | $CH_2CH_2CH_2OH$ | $C_3H_5$(cyclo) | |
| 2.0030 | H | $C_6H_5$ | $C_3H_5$(cyclo) | |
| 2.0031 | H | $CH_2Cl$ | $C_3H_5$(cyclo) | |
| 2.0032 | H | $CH_2CH_2Cl$ | $C_3H_5$(cyclo) | |
| 2.0033 | H | $CH_2CH_2CH_2Cl$ | $C_3H_5$(cyclo) | |

TABLE 2.01

| No. | X | Y | Z | phys. data |
|---|---|---|---|---|
| 2.0101 | H | H | $C_4H_7$(cyclo) | |
| 2.0102 | H | $CH_3$ | $C_4H_7$(cyclo) | |
| 2.0103 | H | $C_2H_5$ | $C_4H_7$(cyclo) | |
| 2.0104 | H | $C_3H_7$ | $C_4H_7$(cyclo) | |
| 2.0105 | H | $OCH_3$ | $C_4H_7$(cyclo) | |
| 2.0106 | H | $OC_2H_5$ | $C_4H_7$(cyclo) | |
| 2.0107 | H | $OCH_2CH=CH_2$ | $C_4H_7$(cyclo) | |
| 2.0108 | H | $OCH_2CH=CHCH_3$ | $C_4H_7$(cyclo) | |
| 2.0109 | H | $OCH_2C(Cl)=CH_2$ | $C_4H_7$(cyclo) | |
| 2.0110 | H | $OCH_2CH=CHCl$ | $C_4H_7$(cyclo) | |
| 2.0111 | H | $OCH_2C\equiv CH$ | $C_4H_7$(cyclo) | |
| 2.0112 | H | $OCHF_2$ | $C_4H_7$(cyclo) | |
| 2.0113 | H | $OCF_3$ | $C_4H_7$(cyclo) | |
| 2.0114 | H | $OCF_2CHFCF_3$ | $C_4H_7$(cyclo) | |
| 2.0115 | H | $OC_6H_5$ | $C_4H_7$(cyclo) | |
| 2.0116 | H | $CF_3$ | $C_4H_7$(cyclo) | |
| 2.0117 | H | Br | $C_4H_7$(cyclo) | |
| 2.0118 | H | Cl | $C_4H_7$(cyclo) | |
| 2.0119 | H | F | $C_4H_7$(cyclo) | |
| 2.0120 | H | $SCH_3$ | $C_4H_7$(cyclo) | |
| 2.0121 | H | $SC_2H_5$ | $C_4H_7$(cyclo) | |
| 2.0122 | H | $SC_3H_7$-n | $C_4H_7$(cyclo) | |
| 2.0123 | H | $SO_2CH_3$ | $C_4H_7$(cyclo) | |
| 2.0124 | H | $SO_2C_2H_5$ | $C_4H_7$(cyclo) | |
| 2.0125 | H | $NO_2$ | $C_4H_7$(cyclo) | |
| 2.0126 | H | CN | $C_4H_7$(cyclo) | |

TABLE 2.01-continued

| No. | X | Y | Z | phys. data |
|---|---|---|---|---|
| 2.0127 | H | $CH_2OH$ | $C_4H_7$(cyclo) | |
| 2.0128 | H | $CH_2CH_2OH$ | $C_4H_7$(cyclo) | |
| 2.0129 | H | $CH_2CH_2CH_2OH$ | $C_4H_7$(cyclo) | |
| 2.0130 | H | $C_6H_5$ | $C_4H_7$(cyclo) | |
| 2.0131 | H | $CH_2Cl$ | $C_4H_7$(cyclo) | |
| 2.0132 | H | $CH_2CH_2Cl$ | $C_4H_7$(cyclo) | |
| 2.0133 | H | $CH_2CH_2CH_2Cl$ | $C_4H_7$(cyclo) | |

TABLE 2.02

| No. | X | Y | Z | phys. data |
|---|---|---|---|---|
| 2.0201 | H | H | $C_5H_9$(cyclo) | |
| 2.0202 | H | $CH_3$ | $C_5H_9$(cyclo) | |
| 2.0203 | H | $C_2H_5$ | $C_5H_9$(cyclo) | |
| 2.0204 | H | $C_3H_7$ | $C_5H_9$(cyclo) | |
| 2.0205 | H | $OCH_3$ | $C_5H_9$(cyclo) | |
| 2.0206 | H | $OC_2H_5$ | $C_5H_9$(cyclo) | |
| 2.0207 | H | $OCH_2CH=CH_2$ | $C_5H_9$(cyclo) | |
| 2.0208 | H | $OCH_2CH=CHCH_3$ | $C_5H_9$(cyclo) | |
| 2.0209 | H | $OCH_2C(Cl)=CH_2$ | $C_5H_9$(cyclo) | |
| 2.0210 | H | $OCH_2CH=CHCl$ | $C_5H_9$(cyclo) | |
| 2.0211 | H | $OCH_2C\equiv CH$ | $C_5H_9$(cyclo) | |
| 2.0212 | H | $OCHF_2$ | $C_5H_9$(cyclo) | |
| 2.0213 | H | $OCF_3$ | $C_5H_9$(cyclo) | |
| 2.0214 | H | $OCF_2CHFCF_3$ | $C_5H_9$(cyclo) | |
| 2.0215 | H | $OC_6H_5$ | $C_5H_9$(cyclo) | |
| 2.0216 | H | $CF_3$ | $C_5H_9$(cyclo) | |
| 2.0217 | H | Br | $C_5H_9$(cyclo) | |
| 2.0218 | H | Cl | $C_5H_9$(cyclo) | |
| 2.0219 | H | F | $C_5H_9$(cyclo) | |
| 2.0220 | H | $SCH_3$ | $C_5H_9$(cyclo) | |
| 2.0221 | H | $SC_2H_5$ | $C_5H_9$(cyclo) | |
| 2.0222 | H | $SC_3H_7$-n | $C_5H_9$(cyclo) | |
| 2.0223 | H | $SO_2CH_3$ | $C_5H_9$(cyclo) | |
| 2.0224 | H | $SO_2C_2H_5$ | $C_5H_9$(cyclo) | |
| 2.0225 | H | $NO_2$ | $C_5H_9$(cyclo) | |
| 2.0226 | H | CN | $C_5H_9$(cyclo) | |
| 2.0227 | H | $CH_2OH$ | $C_5H_9$(cyclo) | |
| 2.0228 | H | $CH_2CH_2OH$ | $C_5H_9$(cyclo) | |
| 2.0229 | H | $CH_2CH_2CH_2OH$ | $C_5H_9$(cyclo) | |
| 2.0230 | H | $C_6H_5$ | $C_5H_9$(cyclo) | |
| 2.0231 | H | $CH_2Cl$ | $C_5H_9$(cyclo) | |
| 2.0232 | H | $CH_2CH_2Cl$ | $C_5H_9$(cyclo) | |
| 2.0233 | H | $CH_2CH_2CH_2Cl$ | $C_5H_9$(cyclo) | |

TABLE 2.03

| No. | X | Y | Z | phys. data |
|---|---|---|---|---|
| 2.0301 | H | H | $C_6H_{11}$(cyclo) | m.p. 188–190° C. |
| 2.0302 | H | $CH_3$ | $C_6H_{11}$(cyclo) | |
| 2.0303 | H | $C_2H_5$ | $C_6H_{11}$(cyclo) | |
| 2.0304 | H | $C_3H_7$ | $C_6H_{11}$(cyclo) | |
| 2.0305 | H | $OCH_3$ | $C_6H_{11}$(cyclo) | |
| 2.0306 | H | $OC_2H_5$ | $C_6H_{11}$(cyclo) | |
| 2.0307 | H | $OCH_2CH=CH_2$ | $C_6H_{11}$(cyclo) | |
| 2.0308 | H | $OCH_2CH=CHCH_3$ | $C_6H_{11}$(cyclo) | |
| 2.0309 | H | $OCH_2C(Cl)=CH_2$ | $C_6H_{11}$(cyclo) | |
| 2.0310 | H | $OCH_2CH=CHCl$ | $C_6H_{11}$(cyclo) | |
| 2.0311 | H | $OCH_2C\equiv CH$ | $C_6H_{11}$(cyclo) | |
| 2.0312 | H | $OCHF_2$ | $C_6H_{11}$(cyclo) | |
| 2.0313 | H | $OCF_3$ | $C_6H_{11}$(cyclo) | |
| 2.0314 | H | $OCF_2CHFCF_3$ | $C_6H_{11}$(cyclo) | |
| 2.0315 | H | $OC_6H_5$ | $C_6H_{11}$(cyclo) | |
| 2.0316 | H | $CF_3$ | $C_6H_{11}$(cyclo) | |
| 2.0317 | H | Br | $C_6H_{11}$(cyclo) | |
| 2.0318 | H | Cl | $C_6H_{11}$(cyclo) | |
| 2.0319 | H | F | $C_6H_{11}$(cyclo) | |
| 2.0320 | H | $SCH_3$ | $C_6H_{11}$(cyclo) | |
| 2.0321 | H | $SC_2H_5$ | $C_6H_{11}$(cyclo) | |
| 2.0322 | H | $SC_3H_7$-n | $C_6H_{11}$(cyclo) | |
| 2.0323 | H | $SO_2CH_3$ | $C_6H_{11}$(cyclo) | |
| 2.0324 | H | $SO_2C_2H_5$ | $C_6H_{11}$(cyclo) | |
| 2.0325 | H | $NO_2$ | $C_6H_{11}$(cyclo) | |
| 2.0326 | H | CN | $C_6H_{11}$(cyclo) | |
| 2.0327 | H | $CH_2OH$ | $C_6H_{11}$(cyclo) | |
| 2.0328 | H | $CH_2CH_2OH$ | $C_6H_{11}$(cyclo) | |
| 2.0329 | H | $CH_2CH_2CH_2OH$ | $C_6H_{11}$(cyclo) | |

TABLE 2.03-continued

| No. | X | Y | Z | phys. data |
|---|---|---|---|---|
| 2.0330 | H | $C_6H_5$ | $C_6H_{11}$(cyclo) | |
| 2.0331 | H | $CH_2Cl$ | $C_6H_{11}$(cyclo) | |
| 2.0332 | H | $CH_2CH_2Cl$ | $C_6H_{11}$(cyclo) | |
| 2.0333 | H | $CH_2CH_2CH_2Cl$ | $C_6H_{11}$(cyclo) | |

TABLE 2.04

| No. | X | Y | Z | phys. data |
|---|---|---|---|---|
| 2.0401 | H | H | $CH_2OCH_3$ | m.p. 168–169° C. |
| 2.0402 | H | $CH_3$ | $CH_2OCH_3$ | m.p. 151–153° C. |
| 2.0403 | H | $C_2H_5$ | $CH_2OCH_3$ | m.p. 134–137° C. |
| 2.0404 | H | $C_3H_7$ | $CH_2OCH_3$ | |
| 2.0405 | H | $OCH_3$ | $CH_2OCH_3$ | |
| 2.0406 | H | $OC_2H_5$ | $CH_2OCH_3$ | |
| 2.0407 | H | $OCH_2CH=CH_2$ | $CH_2OCH_3$ | |
| 2.0408 | H | $OCH_2CH=CHCH_3$ | $CH_2OCH_3$ | |
| 2.0409 | H | $OCH_2C(Cl)=CH_2$ | $CH_2OCH_3$ | |
| 2.0410 | H | $OCH_2CH=CHCl$ | $CH_2OCH_3$ | |
| 2.0411 | H | $OCH_2C\equiv CH$ | $CH_2OCH_3$ | |
| 2.0412 | H | $OCHF_2$ | $CH_2OCH_3$ | |
| 2.0413 | H | $OCF_3$ | $CH_2OCH_3$ | |
| 2.0414 | H | $OCF_2CHFCF_3$ | $CH_2OCH_3$ | |
| 2.0415 | H | $OC_6H_5$ | $CH_2OCH_3$ | |
| 2.0416 | H | $CF_3$ | $CH_2OCH_3$ | |
| 2.0417 | H | Br | $CH_2OCH_3$ | |
| 2.0418 | H | Cl | $CH_2OCH_3$ | |
| 2.0419 | H | F | $CH_2OCH_3$ | |
| 2.0420 | H | $SCH_3$ | $CH_2OCH_3$ | |
| 2.0421 | H | $SC_2H_5$ | $CH_2OCH_3$ | |
| 2.0422 | H | $SC_3H_7$-n | $CH_2OCH_3$ | |
| 2.0423 | H | $SO_2CH_3$ | $CH_2OCH_3$ | |
| 2.0424 | H | $SO_2C_2H_5$ | $CH_2OCH_3$ | |
| 2.0425 | H | $NO_2$ | $CH_2OCH_3$ | |
| 2.0426 | H | CN | $CH_2OCH_3$ | |
| 2.0427 | H | $CH_2OH$ | $CH_2OCH_3$ | |
| 2.0428 | H | $CH_2CH_2OH$ | $CH_2OCH_3$ | |
| 2.0429 | H | $CH_2CH_2CH_2OH$ | $CH_2OCH_3$ | |
| 2.0430 | H | $C_6H_5$ | $CH_2OCH_3$ | |
| 2.0431 | H | $CH_2Cl$ | $CH_2OCH_3$ | |
| 2.0432 | H | $CH_2CH_2Cl$ | $CH_2OCH_3$ | |
| 2.0433 | H | $CH_2CH_2CH_2Cl$ | $CH_2OCH_3$ | |
| 2.0434 | $CH_3$ | $CH_3$ | $CH_2OCH_3$ | oil |

TABLE 2.05

| No. | X | Y | Z | phys. data |
|---|---|---|---|---|
| 2.0501 | H | H | $CH(CH_3)OCH_3$ | |
| 2.0502 | H | $CH_3$ | $CH(CH_3)OCH_3$ | |
| 2.0503 | H | $C_2H_5$ | $CH(CH_3)OCH_3$ | |
| 2.0504 | H | $C_3H_7$ | $CH(CH_3)OCH_3$ | |
| 2.0505 | H | $OCH_3$ | $CH(CH_3)OCH_3$ | |
| 2.0506 | H | $OC_2H_5$ | $CH(CH_3)OCH_3$ | |
| 2.0507 | H | $OCH_2CH=CH_2$ | $CH(CH_3)OCH_3$ | |
| 2.0508 | H | $OCH_2CH=CHCH_3$ | $CH(CH_3)OCH_3$ | |
| 2.0509 | H | $OCH_2C(Cl)=CH_2$ | $CH(CH_3)OCH_3$ | |
| 2.0510 | H | $OCH_2CH=CHCl$ | $CH(CH_3)OCH_3$ | |
| 2.0511 | H | $OCH_2C\equiv CH$ | $CH(CH_3)OCH_3$ | |
| 2.0512 | H | $OCHF_2$ | $CH(CH_3)OCH_3$ | |
| 2.0513 | H | $OCF_3$ | $CH(CH_3)OCH_3$ | |
| 2.0514 | H | $OCF_2CHFCF_3$ | $CH(CH_3)OCH_3$ | |
| 2.0515 | H | $OC_6H_5$ | $CH(CH_3)OCH_3$ | |
| 2.0516 | H | $CF_3$ | $CH(CH_3)OCH_3$ | |
| 2.0517 | H | Br | $CH(CH_3)OCH_3$ | |
| 2.0518 | H | Cl | $CH(CH_3)OCH_3$ | |
| 2.0519 | H | F | $CH(CH_3)OCH_3$ | |
| 2.0520 | H | $SCH_3$ | $CH(CH_3)OCH_3$ | |
| 2.0521 | H | $SC_2H_5$ | $CH(CH_3)OCH_3$ | |
| 2.0522 | H | $SC_3H_7$-n | $CH(CH_3)OCH_3$ | |
| 2.0523 | H | $SO_2CH_3$ | $CH(CH_3)OCH_3$ | |
| 2.0524 | H | $SO_2C_2H_5$ | $CH(CH_3)OCH_3$ | |
| 2.0525 | H | $NO_2$ | $CH(CH_3)OCH_3$ | |
| 2.0526 | H | CN | $CH(CH_3)OCH_3$ | |
| 2.0527 | H | $CH_2OH$ | $CH(CH_3)OCH_3$ | |
| 2.0528 | H | $CH_2CH_2OH$ | $CH(CH_3)OCH_3$ | |
| 2.0529 | H | $CH_2CH_2CH_2OH$ | $CH(CH_3)OCH_3$ | |
| 2.0530 | H | $C_6H_5$ | $CH(CH_3)OCH_3$ | |
| 2.0531 | H | $CH_2Cl$ | $CH(CH_3)OCH_3$ | |
| 2.0532 | H | $CH_2CH_2Cl$ | $CH(CH_3)OCH_3$ | |
| 2.0533 | H | $CH_2CH_2CH_2Cl$ | $CH(CH_3)OCH_3$ | |

TABLE 2.06

| No. | X | Y | Z | phys. data |
|---|---|---|---|---|
| 2.0601 | H | H | $CH_2OC_2H_5$ | m.p. 144–151° C. |
| 2.0602 | H | $CH_3$ | $CH_2OC_2H_5$ | m.p. 159–162° C. |
| 2.0603 | H | $C_2H_5$ | $CH_2OC_2H_5$ | m.p. 143–145° C. |
| 2.0604 | H | $C_3H_7$ | $CH_2OC_2H_5$ | |
| 2.0605 | H | $OCH_3$ | $CH_2OC_2H_5$ | |
| 2.0606 | H | $OC_2H_5$ | $CH_2OC_2H_5$ | |
| 2.0607 | H | $OCH_2CH=CH_2$ | $CH_2OC_2H_5$ | |
| 2.0608 | H | $OCH_2CH=CHCH_3$ | $CH_2OC_2H_5$ | |
| 2.0609 | H | $OCH_2C(Cl)=CH_2$ | $CH_2OC_2H_5$ | |
| 2.0610 | H | $OCH_2CH=CHCl$ | $CH_2OC_2H_5$ | |
| 2.0611 | H | $OCH_2C\equiv CH$ | $CH_2OC_2H_5$ | |
| 2.0612 | H | $OCHF_2$ | $CH_2OC_2H_5$ | |
| 2.0613 | H | $OCF_3$ | $CH_2OC_2H_5$ | |
| 2.0614 | H | $OCF_2CHFCF_3$ | $CH_2OC_2H_5$ | |
| 2.0615 | H | $OC_6H_5$ | $CH_2OC_2H_5$ | |
| 2.0616 | H | $CF_3$ | $CH_2OC_2H_5$ | |
| 2.0617 | H | Br | $CH_2OC_2H_5$ | |
| 2.0618 | H | Cl | $CH_2OC_2H_5$ | |
| 2.0619 | H | F | $CH_2OC_2H_5$ | |
| 2.0620 | H | $SCH_3$ | $CH_2OC_2H_5$ | |
| 2.0621 | H | $SC_2H_5$ | $CH_2OC_2H_5$ | |
| 2.0622 | H | $SC_3H_7$-n | $CH_2OC_2H_5$ | |
| 2.0623 | H | $SO_2CH_3$ | $CH_2OC_2H_5$ | |
| 2.0624 | H | $SO_2C_2H_5$ | $CH_2OC_2H_5$ | |
| 2.0625 | H | $NO_2$ | $CH_2OC_2H_5$ | |
| 2.0626 | H | CN | $CH_2OC_2H_5$ | |
| 2.0627 | H | $CH_2OH$ | $CH_2OC_2H_5$ | |
| 2.0628 | H | $CH_2CH_2OH$ | $CH_2OC_2H_5$ | |
| 2.0629 | H | $CH_2CH_2CH_2OH$ | $CH_2OC_2H_5$ | |
| 2.0630 | H | $C_6H_5$ | $CH_2OC_2H_5$ | |
| 2.0631 | H | $CH_2Cl$ | $CH_2OC_2H_5$ | |
| 2.0632 | H | $CH_2CH_2Cl$ | $CH_2OC_2H_5$ | |
| 2.0633 | H | $CH_2CH_2CH_2Cl$ | $CH_2OC_2H_5$ | |

TABLE 2.07

| No. | X | Y | Z | phys. data |
|---|---|---|---|---|
| 2.0701 | H | H | $CH(CH_3)OC_2H_5$ | |
| 2.0702 | H | $CH_3$ | $CH(CH_3)OC_2H_5$ | |
| 2.0703 | H | $C_2H_5$ | $CH(CH_3)OC_2H_5$ | |
| 2.0704 | H | $C_3H_7$ | $CH(CH_3)OC_2H_5$ | |
| 2.0705 | H | $OCH_3$ | $CH(CH_3)OC_2H_5$ | |
| 2.0706 | H | $OC_2H_5$ | $CH(CH_3)OC_2H_5$ | |
| 2.0707 | H | $OCH_2CH=CH_2$ | $CH(CH_3)OC_2H_5$ | |
| 2.0708 | H | $OCH_2CH=CHCH_3$ | $CH(CH_3)OC_2H_5$ | |
| 2.0709 | H | $OCH_2C(Cl)=CH_2$ | $CH(CH_3)OC_2H_5$ | |
| 2.0710 | H | $OCH_2CH=CHCl$ | $CH(CH_3)OC_2H_5$ | |
| 2.0711 | H | $OCH_2C\equiv CH$ | $CH(CH_3)OC_2H_5$ | |
| 2.0712 | H | $OCHF_2$ | $CH(CH_3)OC_2H_5$ | |
| 2.0713 | H | $OCF_3$ | $CH(CH_3)OC_2H_5$ | |
| 2.0714 | H | $OCF_2CHFCF_3$ | $CH(CH_3)OC_2H_5$ | |
| 2.0715 | H | $OC_6H_5$ | $CH(CH_3)OC_2H_5$ | |
| 2.0716 | H | $CF_3$ | $CH(CH_3)OC_2H_5$ | |
| 2.0717 | H | Br | $CH(CH_3)OC_2H_5$ | |
| 2.0718 | H | Cl | $CH(CH_3)OC_2H_5$ | |
| 2.0719 | H | F | $CH(CH_3)OC_2H_5$ | |
| 2.0720 | H | $SCH_3$ | $CH(CH_3)OC_2H_5$ | |
| 2.0721 | H | $SC_2H_5$ | $CH(CH_3)OC_2H_5$ | |
| 2.0722 | H | $SC_3H_7$-n | $CH(CH_3)OC_2H_5$ | |
| 2.0723 | H | $SO_2CH_3$ | $CH(CH_3)OC_2H_5$ | |
| 2.0724 | H | $SO_2C_2H_5$ | $CH(CH_3)OC_2H_5$ | |
| 2.0725 | H | $NO_2$ | $CH(CH_3)OC_2H_5$ | |
| 2.0726 | H | CN | $CH(CH_3)OC_2H_5$ | |
| 2.0727 | H | $CH_2OH$ | $CH(CH_3)OC_2H_5$ | |
| 2.0728 | H | $CH_2CH_2OH$ | $CH(CH_3)OC_2H_5$ | |
| 2.0729 | H | $CH_2CH_2CH_2OH$ | $CH(CH_3)OC_2H_5$ | |
| 2.0730 | H | $C_6H_5$ | $CH(CH_3)OC_2H_5$ | |
| 2.0731 | H | $CH_2Cl$ | $CH(CH_3)OC_2H_5$ | |
| 2.0732 | H | $CH_2CH_2Cl$ | $CH(CH_3)OC_2H_5$ | |

TABLE 2.07-continued

| No. | X | Y | Z | phys. data |
|---|---|---|---|---|
| 2.0733 | H | $CH_2CH_2CH_2Cl$ | $CH(CH_3)OC_2H_5$ | |

TABLE 2.08

| No. | X | Y | Z | phys. data |
|---|---|---|---|---|
| 2.0801 | H | H | $C(CH_3)_2OCH_3$ | |
| 2.0802 | H | $CH_3$ | $C(CH_3)_2OCH_3$ | |
| 2.0803 | H | $C_2H_5$ | $C(CH_3)_2OCH_3$ | |
| 2.0804 | H | $C_3H_7$ | $C(CH_3)_2OCH_3$ | |
| 2.0805 | H | $OCH_3$ | $C(CH_3)_2OCH_3$ | |
| 2.0806 | H | $OC_2H_5$ | $C(CH_3)_2OCH_3$ | |
| 2.0807 | H | $OCH_2CH=CH_2$ | $C(CH_3)_2OCH_3$ | |
| 2.0808 | H | $OCH_2CH=CHCH_3$ | $C(CH_3)_2OCH_3$ | |
| 2.0809 | H | $OCH_2C(Cl)=CH_2$ | $C(CH_3)_2OCH_3$ | |
| 2.0810 | H | $OCH_2CH=CHCl$ | $C(CH_3)_2OCH_3$ | |
| 2.0811 | H | $OCH_2C\equiv CH$ | $C(CH_3)_2OCH_3$ | |
| 2.0812 | H | $OCHF_2$ | $C(CH_3)_2OCH_3$ | |
| 2.0813 | H | $OCF_3$ | $C(CH_3)_2OCH_3$ | |
| 2.0814 | H | $OCF_2CHFCF_3$ | $C(CH_3)_2OCH_3$ | |
| 2.0815 | H | $OC_6H_5$ | $C(CH_3)_2OCH_3$ | |
| 2.0816 | H | $CF_3$ | $C(CH_3)_2OCH_3$ | |
| 2.0817 | H | Br | $C(CH_3)_2OCH_3$ | |
| 2.0818 | H | Cl | $C(CH_3)_2OCH_3$ | |
| 2.0819 | H | F | $C(CH_3)_2OCH_3$ | |
| 2.0820 | H | $SCH_3$ | $C(CH_3)_2OCH_3$ | |
| 2.0821 | H | $SC_2H_5$ | $C(CH_3)_2OCH_3$ | |
| 2.0822 | H | $SC_3H_7$-n | $C(CH_3)_2OCH_3$ | |
| 2.0823 | H | $SO_2CH_3$ | $C(CH_3)_2OCH_3$ | |
| 2.0824 | H | $SO_2C_2H_5$ | $C(CH_3)_2OCH_3$ | |
| 2.0825 | H | $NO_2$ | $C(CH_3)_2OCH_3$ | |
| 2.0826 | H | CN | $C(CH_3)_2OCH_3$ | |
| 2.0827 | H | $CH_2OH$ | $C(CH_3)_2OCH_3$ | |
| 2.0828 | H | $CH_2CH_2OH$ | $C(CH_3)_2OCH_3$ | |
| 2.0829 | H | $CH_2CH_2CH_2OH$ | $C(CH_3)_2OCH_3$ | |
| 2.0830 | H | $C_6H_5$ | $C(CH_3)_2OCH_3$ | |
| 2.0831 | H | $CH_2Cl$ | $C(CH_3)_2OCH_3$ | |
| 2.0832 | H | $CH_2CH_2Cl$ | $C(CH_3)_2OCH_3$ | |
| 2.0833 | H | $CH_2CH_2CH_2Cl$ | $C(CH_3)_2OCH_3$ | |

TABLE 2.09

| No. | X | Y | Z | phys. data |
|---|---|---|---|---|
| 2.0901 | H | H | $CH_2OC_3H_7$ | |
| 2.0902 | H | $CH_3$ | $CH_2OC_3H_7$ | |
| 2.0903 | H | $C_2H_5$ | $CH_2OC_3H_7$ | |
| 2.0904 | H | $C_3H_7$ | $CH_2OC_3H_7$ | |
| 2.0905 | H | $OCH_3$ | $CH_2OC_3H_7$ | |
| 2.0906 | H | $OC_2H_5$ | $CH_2OC_3H_7$ | |
| 2.0907 | H | $OCH_2CH=CH_2$ | $CH_2OC_3H_7$ | |
| 2.0908 | H | $OCH_2CH=CHCH_3$ | $CH_2OC_3H_7$ | |
| 2.0909 | H | $OCH_2C(Cl)=CH_2$ | $CH_2OC_3H_7$ | |
| 2.0910 | H | $OCH_2CH=CHCl$ | $CH_2OC_3H_7$ | |
| 2.0911 | H | $OCH_2C\equiv CH$ | $CH_2OC_3H_7$ | |
| 2.0912 | H | $OCHF_2$ | $CH_2OC_3H_7$ | |
| 2.0913 | H | $OCF_3$ | $CH_2OC_3H_7$ | |
| 2.0914 | H | $OCF_2CHFCF_3$ | $CH_2OC_3H_7$ | |
| 2.0915 | H | $OC_6H_5$ | $CH_2OC_3H_7$ | |
| 2.0916 | H | $CF_3$ | $CH_2OC_3H_7$ | |
| 2.0917 | H | Br | $CH_2OC_3H_7$ | |
| 2.0918 | H | Cl | $CH_2OC_3H_7$ | |
| 2.0919 | H | F | $CH_2OC_3H_7$ | |
| 2.0920 | H | $SCH_3$ | $CH_2OC_3H_7$ | |
| 2.0921 | H | $SC_2H_5$ | $CH_2OC_3H_7$ | |
| 2.0922 | H | $SC_3H_7$-n | $CH_2OC_3H_7$ | |
| 2.0923 | H | $SO_2CH_3$ | $CH_2OC_3H_7$ | |
| 2.0924 | H | $SO_2C_2H_5$ | $CH_2OC_3H_7$ | |
| 2.0925 | H | $NO_2$ | $CH_2OC_3H_7$ | |
| 2.0926 | H | CN | $CH_2OC_3H_7$ | |
| 2.0927 | H | $CH_2OH$ | $CH_2OC_3H_7$ | |
| 2.0928 | H | $CH_2CH_2OH$ | $CH_2OC_3H_7$ | |
| 2.0929 | H | $CH_2CH_2CH_2OH$ | $CH_2OC_3H_7$ | |
| 2.0930 | H | $C_6H_5$ | $CH_2OC_3H_7$ | |
| 2.0931 | H | $CH_2Cl$ | $CH_2OC_3H_7$ | |
| 2.0932 | H | $CH_2CH_2Cl$ | $CH_2OC_3H_7$ | |
| 2.0933 | H | $CH_2CH_2CH_2Cl$ | $CH_2OC_3H_7$ | |

TABLE 2.10

| No. | X | Y | Z | phys. data |
|---|---|---|---|---|
| 2.1001 | H | H | $C(CH_3)C_2H_4$(cyclo) | m.p. 149–154° C. |
| 2.1002 | H | $CH_3$ | $C(CH_3)C_2H_4$(cyclo) | |
| 2.1003 | H | $C_2H_5$ | $C(CH_3)C_2H_4$(cyclo) | |
| 2.1004 | H | $C_3H_7$ | $C(CH_3)C_2H_4$(cyclo) | |
| 2.1005 | H | $OCH_3$ | $C(CH_3)C_2H_4$(cyclo) | |
| 2.1006 | H | $OC_2H_5$ | $C(CH_3)C_2H_4$(cyclo) | |
| 2.1007 | H | $OCH_2CH=CH_2$ | $C(CH_3)C_2H_4$(cyclo) | |
| 2.1008 | H | $OCH_2CH=CHCH_3$ | $C(CH_3)C_2H_4$(cyclo) | |
| 2.1009 | H | $OCH_2C(Cl)=CH_2$ | $C(CH_3)C_2H_4$(cyclo) | |
| 2.1010 | H | $OCH_2CH=CHCl$ | $C(CH_3)C_2H_4$(cyclo) | |
| 2.1011 | H | $OCH_2C\equiv CH$ | $C(CH_3)C_2H_4$(cyclo) | |
| 2.1012 | H | $OCHF_2$ | $C(CH_3)C_2H_4$(cyclo) | |
| 2.1013 | H | $OCF_3$ | $C(CH_3)C_2H_4$(cyclo) | |
| 2.1014 | H | $OCF_2CHFCF_3$ | $C(CH_3)C_2H_4$(cyclo) | |
| 2.1015 | H | $OC_6H_5$ | $C(CH_3)C_2H_4$(cyclo) | |
| 2.1016 | H | $CF_3$ | $C(CH_3)C_2H_4$(cyclo) | |
| 2.1017 | H | Br | $C(CH_3)C_2H_4$(cyclo) | |
| 2.1018 | H | Cl | $C(CH_3)C_2H_4$(cyclo) | |
| 2.1019 | H | F | $C(CH_3)C_2H_4$(cyclo) | |
| 2.1020 | H | $SCH_3$ | $C(CH_3)C_2H_4$(cyclo) | |
| 2.1021 | H | $SC_2H_5$ | $C(CH_3)C_2H_4$(cyclo) | |
| 2.1022 | H | $SC_3H_7$-n | $C(CH_3)C_2H_4$(cyclo) | |
| 2.1023 | H | $SO_2CH_3$ | $C(CH_3)C_2H_4$(cyclo) | |
| 2.1024 | H | $SO_2C_2H_5$ | $C(CH_3)C_2H_4$(cyclo) | |
| 2.1025 | H | $NO_2$ | $C(CH_3)C_2H_4$(cyclo) | |
| 2.1026 | H | CN | $C(CH_3)C_2H_4$(cyclo) | |
| 2.1027 | H | $CH_2OH$ | $C(CH_3)C_2H_4$(cyclo) | |
| 2.1028 | H | $CH_2CH_2OH$ | $C(CH_3)C_2H_4$(cyclo) | |
| 2.1029 | H | $CH_2CH_2CH_2OH$ | $C(CH_3)C_2H_4$(cyclo) | |
| 2.1030 | H | $C_6H_5$ | $C(CH_3)C_2H_4$(cyclo) | |
| 2.1031 | H | $CH_2Cl$ | $C(CH_3)C_2H_4$(cyclo) | |
| 2.1032 | H | $CH_2CH_2Cl$ | $C(CH_3)C_2H_4$(cyclo) | |
| 2.1033 | H | $CH_2CH_2CH_2Cl$ | $C(CH_3)C_2H_4$(cyclo) | |

TABLE 2.11

| No. | X | Y | Z | phys. data |
|---|---|---|---|---|
| 2.1101 | H | H | $CH_2OC_6H_5$ | m.p. 157–162° C. |
| 2.1102 | H | $CH_3$ | $CH_2OC_6H_5$ | |
| 2.1103 | H | $C_2H_5$ | $CH_2OC_6H_5$ | |
| 2.1104 | H | $C_3H_7$ | $CH_2OC_6H_5$ | |
| 2.1105 | H | $OCH_3$ | $CH_2OC_6H_5$ | |
| 2.1106 | H | $OC_2H_5$ | $CH_2OC_6H_5$ | |
| 2.1107 | H | $OCH_2CH=CH_2$ | $CH_2OC_6H_5$ | |
| 2.1108 | H | $OCH_2CH=CHCH_3$ | $CH_2OC_6H_5$ | |
| 2.1109 | H | $OCH_2C(Cl)=CH_2$ | $CH_2OC_6H_5$ | |
| 2.1110 | H | $OCH_2CH=CHCl$ | $CH_2OC_6H_5$ | |
| 2.1111 | H | $OCH_2C\equiv CH$ | $CH_2OC_6H_5$ | |
| 2.1112 | H | $OCHF_2$ | $CH_2OC_6H_5$ | |
| 2.1113 | H | $OCF_3$ | $CH_2OC_6H_5$ | |
| 2.1114 | H | $OCF_2CHFCF_3$ | $CH_2OC_6H_5$ | |
| 2.1115 | H | $OC_6H_5$ | $CH_2OC_6H_5$ | |
| 2.1116 | H | $CF_3$ | $CH_2OC_6H_5$ | |
| 2.1117 | H | Br | $CH_2OC_6H_5$ | |
| 2.1118 | H | Cl | $CH_2OC_6H_5$ | |
| 2.1119 | H | F | $CH_2OC_6H_5$ | |
| 2.1120 | H | $SCH_3$ | $CH_2OC_6H_5$ | |
| 2.1121 | H | $SC_2H_5$ | $CH_2OC_6H_5$ | |
| 2.1122 | H | $SC_3H_7$-n | $CH_2OC_6H_5$ | |
| 2.1123 | H | $SO_2CH_3$ | $CH_2OC_6H_5$ | |
| 2.1124 | H | $SO_2C_2H_5$ | $CH_2OC_6H_5$ | |
| 2.1125 | H | $NO_2$ | $CH_2OC_6H_5$ | |
| 2.1126 | H | CN | $CH_2OC_6H_5$ | |
| 2.1127 | H | $CH_2OH$ | $CH_2OC_6H_5$ | |
| 2.1128 | H | $CH_2CH_2OH$ | $CH_2OC_6H_5$ | |
| 2.1129 | H | $CH_2CH_2CH_2OH$ | $CH_2OC_6H_5$ | |
| 2.1130 | H | $C_6H_5$ | $CH_2OC_6H_5$ | |
| 2.1131 | H | $CH_2Cl$ | $CH_2OC_6H_5$ | |
| 2.1132 | H | $CH_2CH_2Cl$ | $CH_2OC_6H_5$ | |
| 2.1133 | H | $CH_2CH_2CH_2Cl$ | $CH_2OC_6H_5$ | |

TABLE 2.12

| No. | X | Y | Z | phys. data |
|---|---|---|---|---|
| 2.1201 | H | H | furan-2-yl | m.p. 197–199° C. |

TABLE 2.12-continued

| No. | X | Y | Z | phys. data |
|---|---|---|---|---|
| 2.1202 | H | CH$_3$ | furan-2-yl | |
| 2.1203 | H | C$_2$H$_5$ | furan-2-yl | |
| 2.1204 | H | C$_3$H$_7$ | furan-2-yl | |
| 2.1205 | H | OCH$_3$ | furan-2-yl | |
| 2.1206 | H | OC$_2$H$_5$ | furan-2-yl | |
| 2.1207 | H | OCH$_2$CH=CH$_2$ | furan-2-yl | |
| 2.1208 | H | OCH$_2$CH=CHCH$_3$ | furan-2-yl | |
| 2.1209 | H | OCH$_2$C(Cl)=CH$_2$ | furan-2-yl | |
| 2.1210 | H | OCH$_2$CH=CHCl | furan-2-yl | |
| 2.1211 | H | OCH$_2$C≡CH | furan-2-yl | |
| 2.1212 | H | OCHF$_2$ | furan-2-yl | |
| 2.1213 | H | OCF$_3$ | furan-2-yl | |
| 2.1214 | H | OCF$_2$CHFCF$_3$ | furan-2-yl | |
| 2.1215 | H | OC$_6$H$_5$ | furan-2-yl | |
| 2.1216 | H | CF$_3$ | furan-2-yl | |
| 2.1217 | H | Br | furan-2-yl | |
| 2.1218 | H | Cl | furan-2-yl | |
| 2.1219 | H | F | furan-2-yl | |
| 2.1220 | H | SCH$_3$ | furan-2-yl | |
| 2.1221 | H | SC$_2$H$_5$ | furan-2-yl | |
| 2.1222 | H | SC$_3$H$_7$-n | furan-2-yl | |
| 2.1223 | H | SO$_2$CH$_3$ | furan-2-yl | |
| 2.1224 | H | SO$_2$C$_2$H$_5$ | furan-2-yl | |
| 2.1225 | H | NO$_2$ | furan-2-yl | |
| 2.1226 | H | CN | furan-2-yl | |
| 2.1227 | H | CH$_2$OH | furan-2-yl | |
| 2.1228 | H | CH$_2$CH$_2$OH | furan-2-yl | |
| 2.1229 | H | CH$_2$CH$_2$CH$_2$OH | furan-2-yl | |
| 2.1230 | H | C$_6$H$_5$ | furan-2-yl | |
| 2.1231 | H | CH$_2$Cl | furan-2-yl | |
| 2.1232 | H | CH$_2$CH$_2$Cl | furan-2-yl | |
| 2.1233 | H | CH$_2$CH$_2$CH$_2$Cl | furan-2-yl | |

TABLE 2.13

| No. | X | Y | Z | phys. data |
|---|---|---|---|---|
| 2.1301 | H | H | dioxan-2-yl | m.p. 203–206° C. |
| 2.1302 | H | CH$_3$ | dioxan-2-yl | |
| 2.1303 | H | C$_2$H$_5$ | dioxan-2-yl | |
| 2.1304 | H | C$_3$H$_7$ | dioxan-2-yl | |
| 2.1305 | H | OCH$_3$ | dioxan-2-yl | |
| 2.1306 | H | OC$_2$H$_5$ | dioxan-2-yl | |
| 2.1307 | H | OCH$_2$CH=CH$_2$ | dioxan-2-yl | |
| 2.1308 | H | OCH$_2$CH=CHCH$_3$ | dioxan-2-yl | |
| 2.1309 | H | OCH$_2$C(Cl)=CH$_2$ | dioxan-2-yl | |
| 2.1310 | H | OCH$_2$CH=CHCl | dioxan-2-yl | |
| 2.1311 | H | OCH$_2$C≡CH | dioxan-2-yl | |
| 2.1312 | H | OCHF$_2$ | dioxan-2-yl | |
| 2.1313 | H | OCF$_3$ | dioxan-2-yl | |
| 2.1314 | H | OCF$_2$CHFCF$_3$ | dioxan-2-yl | |
| 2.1315 | H | OC$_6$H$_5$ | dioxan-2-yl | |
| 2.1316 | H | CF$_3$ | dioxan-2-yl | |
| 2.1317 | H | Br | dioxan-2-yl | |
| 2.1318 | H | Cl | dioxan-2-yl | |
| 2.1319 | H | F | dioxan-2-yl | |
| 2.1320 | H | SCH$_3$ | dioxan-2-yl | |
| 2.1321 | H | SC$_2$H$_5$ | dioxan-2-yl | |
| 2.1322 | H | SC$_3$H$_7$-n | dioxan-2-yl | |
| 2.1323 | H | SO$_2$CH$_3$ | dioxan-2-yl | |
| 2.1324 | H | SO$_2$C$_2$H$_5$ | dioxan-2-yl | |
| 2.1325 | H | NO$_2$ | dioxan-2-yl | |
| 2.1326 | H | CN | dioxan-2-yl | |
| 2.1327 | H | CH$_2$OH | dioxan-2-yl | |
| 2.1328 | H | CH$_2$CH$_2$OH | dioxan-2-yl | |
| 2.1329 | H | CH$_2$CH$_2$CH$_2$OH | dioxan-2-yl | |
| 2.1330 | H | C$_6$H$_5$ | dioxan-2-yl | |
| 2.1331 | H | CH$_2$Cl | dioxan-2-yl | |
| 2.1332 | H | CH$_2$CH$_2$Cl | dioxan-2-yl | |
| 2.1333 | H | CH$_2$CH$_2$CH$_2$Cl | dioxan-2-yl | |

TABLE 2.14

| No. | X | Y | Z | phys. data |
|---|---|---|---|---|
| 2.1401 | H | H | CH$_2$OC$_2$H$_4$OCH$_3$ | resin |
| 2.1402 | H | CH$_3$ | CH$_2$OC$_2$H$_4$OCH$_3$ | |
| 2.1403 | H | C$_2$H$_5$ | CH$_2$OC$_2$H$_4$OCH$_3$ | |
| 2.1404 | H | C$_3$H$_7$ | CH$_2$OC$_2$H$_4$OCH$_3$ | |
| 2.1405 | H | OCH$_3$ | CH$_2$OC$_2$H$_4$OCH$_3$ | |
| 2.1406 | H | OC$_2$H$_5$ | CH$_2$OC$_2$H$_4$OCH$_3$ | |
| 2.1407 | H | OCH$_2$CH=CH$_2$ | CH$_2$OC$_2$H$_4$OCH$_3$ | |
| 2.1408 | H | OCH$_2$CH=CHCH$_3$ | CH$_2$OC$_2$H$_4$OCH$_3$ | |
| 2.1409 | H | OCH$_2$C(Cl)=CH$_2$ | CH$_2$OC$_2$H$_4$OCH$_3$ | |
| 2.1410 | H | OCH$_2$CH=CHCl | CH$_2$OC$_2$H$_4$OCH$_3$ | |
| 2.1411 | H | OCH$_2$C≡CH | CH$_2$OC$_2$H$_4$OCH$_3$ | |
| 2.1412 | H | OCHF$_2$ | CH$_2$OC$_2$H$_4$OCH$_3$ | |
| 2.1413 | H | OCF$_{3x}$ | CH$_2$OC$_2$H$_4$OCH$_3$ | |
| 2.1414 | H | OCF$_2$CHFCF$_3$ | CH$_2$OC$_2$H$_4$OCH$_3$ | |
| 2.1415 | H | OC$_6$H$_5$ | CH$_2$OC$_2$H$_4$OCH$_3$ | |
| 2.1416 | H | CF$_3$ | CH$_2$OC$_2$H$_4$OCH$_3$ | |
| 2.1417 | H | Br | CH$_2$OC$_2$H$_4$OCH$_3$ | |
| 2.1418 | H | Cl | CH$_2$OC$_2$H$_4$OCH$_3$ | |
| 2.1419 | H | F | CH$_2$OC$_2$H$_4$OCH$_3$ | |
| 2.1420 | H | SCH$_3$ | CH$_2$OC$_2$H$_4$OCH$_3$ | |
| 2.1421 | H | SC$_2$H$_5$ | CH$_2$OC$_2$H$_4$OCH$_3$ | |
| 2.1422 | H | SC$_3$H$_7$-n | CH$_2$OC$_2$H$_4$OCH$_3$ | |
| 2.1423 | H | SO$_2$CH$_3$ | CH$_2$OC$_2$H$_4$OCH$_3$ | |
| 2.1424 | H | SO$_2$C$_2$H$_5$ | CH$_2$OC$_2$H$_4$OCH$_3$ | |
| 2.1425 | H | NO$_2$ | CH$_2$OC$_2$H$_4$OCH$_3$ | |
| 2.1426 | H | CN | CH$_2$OC$_2$H$_4$OCH$_3$ | |
| 2.1427 | H | CH$_2$OH | CH$_2$OC$_2$H$_4$OCH$_3$ | |
| 2.1428 | H | CH$_2$CH$_2$OH | CH$_2$OC$_2$H$_4$OCH$_3$ | |
| 2.1429 | H | CH$_2$CH$_2$CH$_2$OH | CH$_2$OC$_2$H$_4$OCH$_3$ | |
| 2.1430 | H | C$_6$H$_5$ | CH$_2$OC$_2$H$_4$OCH$_3$ | |
| 2.1431 | H | CH$_2$Cl | CH$_2$OC$_2$H$_4$OCH$_3$ | |
| 2.1432 | H | CH$_2$CH$_2$Cl | CH$_2$OC$_2$H$_4$OCH$_3$ | |
| 2.1433 | H | CH$_2$CH$_2$CH$_2$Cl | CH$_2$OC$_2$H$_4$OCH$_3$ | |

TABLE 2.15

| No. | X | Y | Z | phys. data |
|---|---|---|---|---|
| 2.1501 | H | H | CH$_2$OC$_2$H$_4$OC$_2$H$_4$OCH$_3$ | |
| 2.1502 | H | CH$_3$ | CH$_2$OC$_2$H$_4$OC$_2$H$_4$OCH$_3$ | |
| 2.1503 | H | C$_2$H$_5$ | CH$_2$OC$_2$H$_4$OC$_2$H$_4$OCH$_3$ | |
| 2.1504 | H | C$_3$H$_7$ | CH$_2$OC$_2$H$_4$OC$_2$H$_4$OCH$_3$ | |
| 2.1505 | H | OCH$_3$ | CH$_2$OC$_2$H$_4$OC$_2$H$_4$OCH$_3$ | |
| 2.1506 | H | OC$_2$H$_5$ | CH$_2$OC$_2$H$_4$OC$_2$H$_4$OCH$_3$ | |
| 2.1507 | H | OCH$_2$CH=CH$_2$ | CH$_2$OC$_2$H$_4$OC$_2$H$_4$OCH$_3$ | |
| 2.1508 | H | OCH$_2$CH=CHCH$_3$ | CH$_2$OC$_2$H$_4$OC$_2$H$_4$OCH$_3$ | |
| 2.1509 | H | OCH$_2$C(Cl)=CH$_2$ | CH$_2$OC$_2$H$_4$OC$_2$H$_4$OCH$_3$ | |
| 2.1510 | H | OCH$_2$CH=CHCl | CH$_2$OC$_2$H$_4$OC$_2$H$_4$OCH$_3$ | |
| 2.1511 | H | OCH$_2$C≡CH | CH$_2$OC$_2$H$_4$OC$_2$H$_4$OCH$_3$ | |
| 2.1512 | H | OCHF$_2$ | CH$_2$OC$_2$H$_4$OC$_2$H$_4$OCH$_3$ | |
| 2.1513 | H | OCF$_3$ | CH$_2$OC$_2$H$_4$OC$_2$H$_4$OCH$_3$ | |
| 2.1514 | H | OCF$_2$CHFCF$_3$ | CH$_2$OC$_2$H$_4$OC$_2$H$_4$OCH$_3$ | |
| 2.1515 | H | OC$_6$H$_5$ | CH$_2$OC$_2$H$_4$OC$_2$H$_4$OCH$_3$ | |
| 2.1516 | H | CF$_3$ | CH$_2$OC$_2$H$_4$OC$_2$H$_4$OCH$_3$ | |
| 2.1517 | H | Br | CH$_2$OC$_2$H$_4$OC$_2$H$_4$OCH$_3$ | |
| 2.1518 | H | Cl | CH$_2$OC$_2$H$_4$OC$_2$H$_4$OCH$_3$ | |
| 2.1519 | H | F | CH$_2$OC$_2$H$_4$OC$_2$H$_4$OCH$_3$ | |
| 2.1520 | H | SCH$_3$ | CH$_2$OC$_2$H$_4$OC$_2$H$_4$OCH$_3$ | |
| 2.1521 | H | SC$_2$H$_5$ | CH$_2$OC$_2$H$_4$OC$_2$H$_4$OCH$_3$ | |
| 2.1522 | H | SC$_3$H$_7$-n | CH$_2$OC$_2$H$_4$OC$_2$H$_4$OCH$_3$ | |
| 2.1523 | H | SO$_2$CH$_3$ | CH$_2$OC$_2$H$_4$OC$_2$H$_4$OCH$_3$ | |
| 2.1524 | H | SO$_2$C$_2$H$_5$ | CH$_2$OC$_2$H$_4$OC$_2$H$_4$OCH$_3$ | |
| 2.1525 | H | NO$_2$ | CH$_2$OC$_2$H$_4$OC$_2$H$_4$OCH$_3$ | |
| 2.1526 | H | CN | CH$_2$OC$_2$H$_4$OC$_2$H$_4$OCH$_3$ | |
| 2.1527 | H | CH$_2$OH | CH$_2$OC$_2$H$_4$OC$_2$H$_4$OCH$_3$ | |
| 2.1528 | H | CH$_2$CH$_2$OH | CH$_2$OC$_2$H$_4$OC$_2$H$_4$OCH$_3$ | |
| 2.1529 | H | CH$_2$CH$_2$CH$_2$OH | CH$_2$OC$_2$H$_4$OC$_2$H$_4$OCH$_3$ | |
| 2.1530 | H | C$_6$H$_5$ | CH$_2$OC$_2$H$_4$OC$_2$H$_4$OCH$_3$ | |
| 2.1531 | H | CH$_2$Cl | CH$_2$OC$_2$H$_4$OC$_2$H$_4$OCH$_3$ | |
| 2.1532 | H | CH$_2$CH$_2$Cl | CH$_2$OC$_2$H$_4$OC$_2$H$_4$OCH$_3$ | |
| 2.11533 | H | CH$_2$CH$_2$CH$_2$Cl | CH$_2$OC$_2$H$_4$OC$_2$H$_4$OCH$_3$ | |

TABLE 2.16

| No. | X | Y | Z | phys. data |
|---|---|---|---|---|
| 2.1601 | H | H | CH$_2$OCH$_2$CONH$_2$ | wax |
| 2.1602 | H | CH$_3$ | CH$_2$OCH$_2$CONH$_2$ | |
| 2.1603 | H | C$_2$H$_5$ | CH$_2$OCH$_2$CONH$_2$ | |
| 2.1604 | H | C$_3$H$_7$ | CH$_2$OCH$_2$CONH$_2$ | |
| 2.1605 | H | OCH$_3$ | CH$_2$OCH$_2$CONH$_2$ | |
| 2.1606 | H | OC$_2$H$_5$ | CH$_2$OCH$_2$CONH$_2$ | |
| 2.1607 | H | OCH$_2$CH=CH$_2$ | CH$_2$OCH$_2$CONH$_2$ | |

TABLE 2.16-continued

| No. | X | Y | Z | phys. data |
|---|---|---|---|---|
| 2.1608 | H | OCH$_2$CH=CHCH$_3$ | CH$_2$OCH$_2$CONH$_2$ | |
| 2.1609 | H | OCH$_2$C(Cl)=CH$_2$ | CH$_2$OCH$_2$CONH$_2$ | |
| 2.1610 | H | OCH$_2$CH=CHCl | CH$_2$OCH$_2$CONH$_2$ | |
| 2.1611 | H | OCH$_2$C≡CH | CH$_2$OCH$_2$CONH$_2$ | |
| 2.1612 | H | OCHF$_2$ | CH$_2$OCH$_2$CONH$_2$ | |
| 2.1613 | H | OCF$_3$ | CH$_2$OCH$_2$CONH$_2$ | |
| 2.1614 | H | OCF$_2$CHFCF$_3$ | CH$_2$OCH$_2$CONH$_2$ | |
| 2.1615 | H | OC$_6$H$_5$ | CH$_2$OCH$_2$CONH$_2$ | |
| 2.1616 | H | CF$_3$ | CH$_2$OCH$_2$CONH$_2$ | |
| 2.1617 | H | Br | CH$_2$OCH$_2$CONH$_2$ | |
| 2.1618 | H | Cl | CH$_2$OCH$_2$CONH$_2$ | |
| 2.1619 | H | F | CH$_2$OCH$_2$CONH$_2$ | |
| 2.1620 | H | SCH$_3$ | CH$_2$OCH$_2$CONH$_2$ | |
| 2.1621 | H | SC$_2$H$_5$ | CH$_2$OCH$_2$CONH$_2$ | |
| 2.1622 | H | SC$_3$H$_7$-n | CH$_2$OCH$_2$CONH$_2$ | |
| 2.1623 | H | SO$_2$CH$_3$ | CH$_2$OCH$_2$CONH$_2$ | |
| 2.1624 | H | SO$_2$C$_2$H$_5$ | CH$_2$OCH$_2$CONH$_2$ | |
| 2.1625 | H | NO$_2$ | CH$_2$OCH$_2$CONH$_2$ | |
| 2.1626 | H | CN | CH$_2$OCH$_2$CONH$_2$ | |
| 2.1627 | H | CH$_2$OH | CH$_2$OCH$_2$CONH$_2$ | |
| 2.1628 | H | CH$_2$CH$_2$OH | CH$_2$OCH$_2$CONH$_2$ | |
| 2.1629 | H | CH$_2$CH$_2$CH$_2$OH | CH$_2$OCH$_2$CONH$_2$ | |
| 2.1630 | H | C$_6$H$_5$ | CH$_2$OCH$_2$CONH$_2$ | |
| 2.1631 | H | CH$_2$Cl | CH$_2$OCH$_2$CONH$_2$ | |
| 2.1632 | H | CH$_2$CH$_2$Cl | CH$_2$OCH$_2$CONH$_2$ | |
| 2.1633 | H | CH$_2$CH$_2$CH$_2$Cl | CH$_2$OCH$_2$CONH$_2$ | |

TABLE 2.17

| No. | X | Y | Z | phys. data |
|---|---|---|---|---|
| 2.1701 | H | H | thiophen-2-yl | m.p. 247–248° C. |
| 2.1702 | H | CH$_3$ | thiophen-2-yl | |
| 2.1703 | H | C$_2$H$_5$ | thiophen-2-yl | |
| 2.1704 | H | C$_3$H$_7$ | thiophen-2-yl | |
| 2.1705 | H | OCH$_3$ | thiophen-2-yl | |
| 2.1706 | H | OC$_2$H$_5$ | thiophen-2-yl | |
| 2.1707 | H | OCH$_2$CH=CH$_2$ | thiophen-2-yl | |
| 2.1708 | H | OCH$_2$CH=CHCH$_3$ | thiophen-2-yl | |
| 2.1700 | H | OCH$_2$C(Cl)=CH$_2$ | thiophen-2-yl | |
| 2.1710 | H | OCH$_2$CH=CHCl | thiophen-2-yl | |
| 2.1711 | H | OCH$_2$C≡CH | thiophen-2-yl | |
| 2.1712 | H | OCHF$_2$ | thiophen-2-yl | |
| 2.1713 | H | OCF$_3$ | thiophen-2-yl | |
| 2.1714 | H | OCF$_2$CHFCF$_3$ | thiophen-2-yl | |
| 2.1715 | H | OC$_6$H$_5$ | thiophen-2-yl | |
| 2.1716 | H | CF$_3$ | thiophen-2-yl | |
| 2.1717 | H | Br | thiophen-2-yl | |
| 2.1718 | H | Cl | thiophen-2-yl | |
| 2.1719 | H | F | thiophen-2-yl | |
| 2.1720 | H | SCH$_3$ | thiophen-2-yl | |
| 2.1721 | H | SC$_2$H$_5$ | thiophen-2-yl | |
| 2.1722 | H | SC$_3$H$_7$-n | thiophen-2-yl | |
| 2.1723 | H | SO$_2$CH$_3$ | thiophen-2-yl | |
| 2.1724 | H | SO$_2$C$_2$H$_5$ | thiophen-2-yl | |
| 2.1725 | H | NO$_2$ | thiophen-2-yl | |
| 2.1726 | H | CN | thiophen-2-yl | |
| 2.1727 | H | CH$_2$OH | thiophen-2-yl | |
| 2.1728 | H | CH$_2$CH$_2$OH | thiophen-2-yl | |
| 2.1729 | H | CH$_2$CH$_2$CH$_2$OH | thiophen-2-yl | |
| 2.1730 | H | C$_6$H$_5$ | thiophen-2-yl | |
| 2.1731 | H | CH$_2$Cl | thiophen-2-yl | |
| 2.1732 | H | CH$_2$CH$_2$Cl | thiophen-2-yl | |
| 2.1733 | H | CH$_2$CH$_2$CH$_2$Cl | thiophen-2-yl | |

TABLE 2.18

| No. | X | Y | Z | phys. data |
|---|---|---|---|---|
| 2.1801 | H | H | thiophen-3-yl | m.p. 247–248° C. |
| 2.1802 | H | CH$_3$ | thiophen-3-yl | |
| 2.1803 | H | C$_2$H$_5$ | thiophen-3-yl | |
| 2.1804 | H | C$_3$H$_7$ | thiophen-3-yl | |
| 2.1805 | H | OCH$_3$ | thiophen-3-yl | |
| 2.1806 | H | OC$_2$H$_5$ | thiophen-3-yl | |
| 2.1807 | H | OCH$_2$CH=CH$_2$ | thiophen-3-yl | |
| 2.1808 | H | OCH$_2$CH=CHCH$_3$ | thiophen-3-yl | |
| 2.1809 | H | OCH$_2$C(Cl)=CH$_2$ | thiophen-3-yl | |
| 2.1810 | H | OCH$_2$CH=CHCl | thiophen-3-yl | |
| 2.1811 | H | OCH$_2$C≡CH | thiophen-3-yl | |
| 2.1812 | H | OCHF$_2$ | thiophen-3-yl | |
| 2.1813 | H | OCF$_3$ | thiophen-3-yl | |
| 2.1814 | H | OCF$_2$CHFCF$_3$ | thiophen-3-yl | |
| 2.1815 | H | OC$_6$H$_5$ | thiophen-3-yl | |
| 2.1816 | H | CF$_3$ | thiophen-3-yl | |
| 2.1817 | H | Br | thiophen-3-yl | |
| 2.1818 | H | Cl | thiophen-3-yl | |
| 2.1819 | H | F | thiophen-3-yl | |
| 2.1820 | H | SCH$_3$ | thiophen-3-yl | |
| 2.1821 | H | SC$_2$H$_5$ | thiophen-3-yl | |
| 2.1822 | H | SC$_3$H$_7$-n | thiophen-3-yl | |
| 2.1823 | H | SO$_2$CH$_3$ | thiophen-3-yl | |
| 2.1824 | H | SO$_2$C$_2$H$_5$ | thiophen-3-yl | |
| 2.1825 | H | NO$_2$ | thiophen-3-yl | |
| 2.1826 | H | CN | thiophen-3-yl | |
| 2.1827 | H | CH$_2$OH | thiophen-3-yl | |
| 2.1828 | H | CH$_2$CH$_2$OH | thiophen-3-yl | |
| 2.1829 | H | CH$_2$CH$_2$CH$_2$OH | thiophen-3-yl | |
| 2.1830 | H | C$_6$H$_5$ | thiophen-3-yl | |
| 2.1831 | H | CH$_2$Cl | thiophen-3-yl | |
| 2.1832 | H | CH$_2$CH$_2$Cl | thiophen-3-yl | |
| 2.1833 | H | CH$_2$CH$_2$CH$_2$Cl | thiophen-3-yl | |

TABLE 2.19

| No. | X | Y | Z | phys. data |
|---|---|---|---|---|
| 2.1901 | H | H | pyridin-3-yl | m.p. 240–242° C. |
| 2.1902 | H | CH$_3$ | pyridin-3-yl | |
| 2.1903 | H | C$_2$H$_5$ | pyridin-3-yl | |
| 2.1904 | H | C$_3$H$_7$ | pyridin-3-yl | |
| 2.1905 | H | OCH$_3$ | pyridin-3-yl | |
| 2.1906 | H | OC$_2$H$_5$ | pyridin-3-yl | |
| 2.1907 | H | OCH$_2$CH=CH$_2$ | pyridin-3-yl | |
| 2.1908 | H | OCH$_2$CH=CHCH$_3$ | pyridin-3-yl | |
| 2.1909 | H | OCH$_2$C(Cl)=CH$_2$ | pyridin-3-yl | |
| 2.1910 | H | OCH$_2$CH=CHCl | pyridin-3-yl | |
| 2.1911 | H | OCH$_2$C≡CH | pyridin-3-yl | |
| 2.1912 | H | OCHF$_2$ | pyridin-3-yl | |
| 2.1913 | H | OCF$_3$ | pyridin-3-yl | |
| 2.1914 | H | OCF$_2$CHFCF$_3$ | pyridin-3-yl | |
| 2.1915 | H | OC$_6$H$_5$ | pyridin-3-yl | |
| 2.1916 | H | CF$_3$ | pyridin-3-yl | |
| 2.1917 | H | Br | pyridin-3-yl | |
| 2.1918 | H | Cl | pyridin-3-yl | |
| 2.1919 | H | F | pyridin-3-yl | |
| 2.1920 | H | SCH$_3$ | pyridin-3-yl | |
| 2.1921 | H | SC$_2$H$_5$ | pyridin-3-yl | |
| 2.1922 | H | SC$_3$H$_7$-n | pyridin-3-yl | |
| 2.1923 | H | SO$_2$CH$_3$ | pyridin-3-yl | |
| 2.1924 | H | SO$_2$C$_2$H$_5$ | pyridin-3-yl | |
| 2.1925 | H | NO$_2$ | pyridin-3-yl | |
| 2.1926 | H | CN | pyridin-3-yl | |
| 2.1927 | H | CH$_2$OH | pyridin-3-yl | |
| 2.1928 | H | CH$_2$CH$_2$OH | pyridin-3-yl | |
| 2.1929 | H | CH$_2$CH$_2$CH$_2$OH | pyridin-3-yl | |
| 2.1930 | H | C$_6$H$_5$ | pyridin-3-yl | |
| 2.1931 | H | CH$_2$Cl | pyridin-3-yl | |
| 2.1932 | H | CH$_2$CH$_2$Cl | pyridin-3-yl | |
| 2.1933 | H | CH$_2$CH$_2$CH$_2$Cl | pyridin-3-yl | |

TABLE 2.20

| No. | X | Y | Z | phys. data |
|---|---|---|---|---|
| 2.2001 | H | H | pyridin-4-yl | |
| 2.2002 | H | CH$_3$ | pyridin-4-yl | |
| 2.2003 | H | C$_2$H$_5$ | pyridin-4-yl | |
| 2.2004 | H | C$_3$H$_7$ | pyridin-4-yl | |
| 2.2005 | H | OCH$_3$ | pyridin-4-yl | |
| 2.2006 | H | OC$_2$H$_5$ | pyridin-4-yl | |
| 2.2007 | H | OCH$_2$CH=CH$_2$ | pyridin-4-yl | |
| 2.2008 | H | OCH$_2$CH=CHCH$_3$ | pyridin-4-yl | |
| 2.2009 | H | OCH$_2$C(Cl)=CH$_2$ | pyridin-4-yl | |
| 2.2010 | H | OCH$_2$CH=CHCl | pyridin-4-yl | |
| 2.2011 | H | OCH$_2$C≡CH | pyridin-4-yl | |
| 2.2012 | H | OCHF$_2$ | pyridin-4-yl | |

TABLE 2.20-continued

| No. | X | Y | Z | phys. data |
|---|---|---|---|---|
| 2.2013 | H | OCF$_3$ | pyridin-4-yl | |
| 2.2014 | H | OCF$_2$CHFCF$_3$ | pyridin-4-yl | |
| 2.2015 | H | OC$_6$H$_5$ | pyridin-4-yl | |
| 2.2016 | H | CF$_3$ | pyridin-4-yl | |
| 2.2017 | H | Br | pyridin-4-yl | |
| 2.2018 | H | Cl | pyridin-4-yl | |
| 2.2019 | H | F | pyridin-4-yl | |
| 2.2020 | H | SCH$_3$ | pyridin-4-yl | |
| 2.2021 | H | SC$_2$H$_5$ | pyridin-4-yl | |
| 2.2022 | H | SC$_3$H$_7$-n | pyridin-4-yl | |
| 2.2023 | H | SO$_2$CH$_3$ | pyridin-4-yl | |
| 2.2024 | H | SO$_2$C$_2$H$_5$ | pyridin-4-yl | |
| 2.2025 | H | NO$_2$ | pyridin-4-yl | |
| 2.2026 | H | CN | pyridin-4-yl | |
| 2.2027 | H | CH$_2$OH | pyridin-4-yl | |
| 2.2028 | H | CH$_2$CH$_2$OH | pyridin-4-yl | |
| 2.2029 | H | CH$_2$CH$_2$CH$_2$OH | pyridin-4-yl | |
| 2.2030 | H | C$_6$H$_5$ | pyridin-4-yl | |
| 2.2031 | H | CH$_2$Cl | pyridin-4-yl | |
| 2.2032 | H | CH$_2$CH$_2$Cl | pyridin-4-yl | |
| 2.2033 | H | CH$_2$CH$_2$CH$_2$Cl | pyridin-4-yl | |

TABLE 2.21

| No. | X | Y | Z | phys. data |
|---|---|---|---|---|
| 2.2101 | H | H | pyridin-2-yl | |
| 2.2102 | H | CH$_3$ | pyridin-2-yl | |
| 2.2103 | H | C$_2$H$_5$ | pyridin-2-yl | |
| 2.2104 | H | C$_3$H$_7$ | pyridin-2-yl | |
| 2.2105 | H | OCH$_3$ | pyridin-2-yl | |
| 2.2106 | H | OC$_2$H$_5$ | pyridin-2-yl | |
| 2.2107 | H | OCH$_2$CH=CH$_2$ | pyridin-2-yl | |
| 2.2108 | H | OCH$_2$CH=CHCH$_3$ | pyridin-2-yl | |
| 2.2109 | H | OCH$_2$C(Cl)=CH$_2$ | pyridin-2-yl | |
| 2.2110 | H | OCH$_2$CH=CHCl | pyridin-2-yl | |
| 2.2111 | H | OCH$_2$C≡CH | pyridin-2-yl | |
| 2.2112 | H | OCHF$_2$ | pyridin-2-yl | |
| 2.2113 | H | OCF$_3$ | pyridin-2-yl | |
| 2.2114 | H | OCF$_2$CHFCF$_3$ | pyridin-2-yl | |
| 2.2115 | H | OC$_6$H$_5$ | pyridin-2-yl | |
| 2.2116 | H | CF$_3$ | pyridin-2-yl | |
| 2.2117 | H | Br | pyridin-2-yl | |
| 2.2118 | H | Cl | pyridin-2-yl | |
| 2.2119 | H | F | pyridin-2-yl | |
| 2.2120 | H | SCH$_3$ | pyridin-2-yl | |
| 2.2121 | H | SC$_2$H$_5$ | pyridin-2-yl | |
| 2.2122 | H | SC$_3$H$_7$-n | pyridin-2-yl | |
| 2.2123 | H | SO$_2$CH$_3$ | pyridin-2-yl | |
| 2.2124 | H | SO$_2$C$_2$H$_5$ | pyridin-2-yl | |
| 2.2125 | H | NO$_2$ | pyridin-2-yl | |
| 2.2126 | H | CN | pyridin-2-yl | |
| 2.2127 | H | CH$_2$OH | pyridin-2-yl | |
| 2.2128 | H | CH$_2$CH$_2$OH | pyridin-2-yl | |
| 2.2129 | H | CH$_2$CH$_2$CH$_2$OH | pyridin-2-yl | |
| 2.2130 | H | C$_6$H$_5$ | pyridin-2-yl | |
| 2.2131 | H | CH$_2$Cl | pyridin-2-yl | |
| 2.2132 | H | CH$_2$CH$_2$Cl | pyridin-2-yl | |
| 2.2133 | H | CH$_2$CH$_2$CH$_2$Cl | pyridin-2-yl | |

TABLE 2.22

| No. | X | Y | Z | phys. data |
|---|---|---|---|---|
| 2.2201 | H | H | furan-3-yl | |
| 2.2202 | H | CH$_3$ | furan-3-yl | |
| 2.2203 | H | C$_2$H$_5$ | furan-3-yl | |
| 2.2204 | H | C$_3$H$_7$ | furan-3-yl | |
| 2.2205 | H | OCH$_3$ | furan-3-yl | |
| 2.2206 | H | OC$_2$H$_5$ | furan-3-yl | |
| 2.2207 | H | OCH$_2$CH=CH$_2$ | furan-3-yl | |
| 2.2208 | H | OCH$_2$CH=CHCH$_3$ | furan-3-yl | |
| 2.2209 | H | OCH$_2$C(Cl)=CH$_2$ | furan-3-yl | |
| 2.2210 | H | OCH$_2$CH=CHCl | furan-3-yl | |
| 2.2211 | H | OCH$_2$C≡CH | furan-3-yl | |
| 2.2212 | H | OCHF$_2$ | furan-3-yl | |
| 2.2213 | H | OCF$_3$ | furan-3-yl | |
| 2.2214 | H | OCF$_2$CHFCF$_3$ | furan-3-yl | |
| 2.2215 | H | OC$_6$H$_5$ | furan-3-yl | |
| 2.2216 | H | CF$_3$ | furan-3-yl | |
| 2.2217 | H | Br | furan-3-yl | |
| 2.2218 | H | Cl | furan-3-yl | |
| 2.2219 | H | F | furan-3-yl | |
| 2.2220 | H | SCH$_3$ | furan-3-yl | |
| 2.2221 | H | SC$_2$H$_5$ | furan-3-yl | |
| 2.2222 | H | SC$_3$H$_7$-n | furan-3-yl | |
| 2.2223 | H | SO$_2$CH$_3$ | furan-3-yl | |
| 2.2224 | H | SO$_2$C$_2$H$_5$ | furan-3-yl | |
| 2.2225 | H | NO$_2$ | furan-3-yl | |
| 2.2226 | H | CN | furan-3-yl | |
| 2.2227 | H | CH$_2$OH | furan-3-yl | |
| 2.2228 | H | CH$_2$CH$_2$OH | furan-3-yl | |
| 2.2229 | H | CH$_2$CH$_2$CH$_2$OH | furan-3-yl | |
| 2.2230 | H | C$_6$H$_5$ | furan-3-yl | |
| 2.2231 | H | CH$_2$Cl | furan-3-yl | |
| 2.2232 | H | CH$_2$CH$_2$Cl | furan-3-yl | |
| 2.2233 | H | CH$_2$CH$_2$CH$_2$Cl | furan-3-yl | |

TABLE 2.23

| No. | X | Y | Z | phys. data |
|---|---|---|---|---|
| 2.2301 | H | H | 4-methylpyrimidin-6-yl | |
| 2.2302 | H | CH$_3$ | 4-methylpyrimidin-6-yl | |
| 2.2303 | H | C$_2$H$_5$ | 4-methylpyrimidin-6-yl | |
| 2.2304 | H | C$_3$H$_7$ | 4-methylpyrimidin-6-yl | |
| 2.2305 | H | OCH$_3$ | 4-methylpyrimidin-6-yl | |
| 2.2306 | H | OC$_2$H$_5$ | 4-methylpyrimidin-6-yl | |
| 2.2307 | H | OCH$_2$CH=CH$_2$ | 4-methylpyrimidin-6-yl | |
| 2.2308 | H | OCH$_2$CH=CHCH$_3$ | 4-methylpyrimidin-6-yl | |
| 2.2309 | H | OCH$_2$C(Cl)=CH$_2$ | 4-methylpyrimidin-6-yl | |
| 2.2310 | H | OCH$_2$CH=CHCl | 4-methylpyrimidin-6-yl | |
| 2.2311 | H | OCH$_2$C≡CH | 4-methylpyrimidin-6-yl | |
| 2.2312 | H | OCHF$_2$ | 4-methylpyrimidin-6-yl | |
| 2.2313 | H | OCF$_3$ | 4-methylpyrimidin-6-yl | |
| 2.2314 | H | OCF$_2$CHFCF$_3$ | 4-methylpyrimidin-6-yl | |
| 2.2315 | H | OC$_6$H$_5$ | 4-methylpyrimidin-6-yl | |
| 2.2316 | H | CF$_3$ | 4-methylpyrimidin-6-yl | |
| 2.2317 | H | Br | 4-methylpyrimidin-6-yl | |
| 2.2318 | H | Cl | 4-methylpyrimidin-6-yl | |
| 2.2319 | H | F | 4-methylpyrimidin-6-yl | |
| 2.2320 | H | SCH$_3$ | 4-methylpyrimidin-6-yl | |
| 2.2321 | H | SC$_2$H$_5$ | 4-methylpyrimidin-6-yl | |
| 2.2322 | H | SC$_3$H$_7$-n | 4-methylpyrimidin-6-yl | |
| 2.2323 | H | SO$_2$CH$_3$ | 4-methylpyrimidin-6-yl | |
| 2.2324 | H | SO$_2$C$_2$H$_5$ | 4-methylpyrimidin-6-yl | |
| 2.2325 | H | NO$_2$ | 4-methylpyrimidin-6-yl | |
| 2.2326 | H | CN | 4-methylpyrimidin-6-yl | |
| 2.2327 | H | CH$_2$OH | 4-methylpyrimidin-6-yl | |
| 2.2328 | H | CH$_2$CH$_2$OH | 4-methylpyrimidin-6-yl | |
| 2.2329 | H | CH$_2$CH$_2$CH$_2$OH | 4-methylpyrimidin-6-yl | |
| 2.2330 | H | C$_6$H$_5$ | 4-methylpyrimidin-6-yl | |
| 2.2331 | H | CH$_2$Cl | 4-methylpyrimidin-6-yl | |
| 2.2332 | H | CH$_2$CH$_2$Cl | 4-methylpyrimidin-6-yl | |
| 2.2333 | H | CH$_2$CH$_2$CH$_2$Cl | 4-methylpyrimidin-6-yl | |

TABLE 2.24

| No. | X | Y | Z | phys. data |
|---|---|---|---|---|
| 2.2401 | H | H | 1,3,5-triazin-2-yl | |
| 2.2402 | H | CH$_3$ | 1,3,5-triazin-2-yl | |
| 2.2403 | H | C$_2$H$_5$ | 1,3,5-triazin-2-yl | |
| 2.2404 | H | C$_3$H$_7$ | 1,3,5-triazin-2-yl | |
| 2.2405 | H | OCH$_3$ | 1,3,5-triazin-2-yl | |
| 2.2406 | H | OC$_2$H$_5$ | 1,3,5-triazin-2-yl | |
| 2.2407 | H | OCH$_2$CH=CH$_2$ | 1,3,5-triazin-2-yl | |
| 2.2408 | H | OCH$_2$CH=CHCH$_3$ | 1,3,5-triazin-2-yl | |
| 2.2409 | H | OCH$_2$C(Cl)=CH$_2$ | 1,3,5-triazin-2-yl | |
| 2.2410 | H | OCH$_2$CH=CHCl | 1,3,5-triazin-2-yl | |
| 2.2411 | H | OCH$_2$C≡CH | 1,3,5-triazin-2-yl | |
| 2.2412 | H | OCHF$_2$ | 1,3,5-triazin-2-yl | |
| 2.2413 | H | OCF$_3$ | 1,3,5-triazin-2-yl | |
| 2.2414 | H | OCF$_2$CHFCF$_3$ | 1,3,5-triazin-2-yl | |
| 2.2415 | H | OC$_6$H$_5$ | 1,3,5-triazin-2-yl | |
| 2.2416 | H | CF$_3$ | 1,3,5-triazin-2-yl | |
| 2.2417 | H | Br | 1,3,5-triazin-2-yl | |
| 2.2418 | H | Cl | 1,3,5-triazin-2-yl | |
| 2.2419 | H | F | 1,3,5-triazin-2-yl | |

TABLE 2.24-continued

| No. | X | Y | Z | phys. data |
|---|---|---|---|---|
| 2.2420 | H | SCH3 | 1,3,5-triazin-2-yl | |
| 2.2421 | H | SC2H5 | 1,3,5-triazin-2-yl | |
| 2.2422 | H | SC3H7-n | 1,3,5-triazin-2-yl | |
| 2.2423 | H | SO2CH3 | 1,3,5-triazin-2-yl | |
| 2.2424 | H | SO2C2H5 | 1,3,5-triazin-2-yl | |
| 2.2426 | H | NO2 | 1,3,5-triazin-2-yl | |
| 2.2426 | H | CN | 1,3,5-triazin-2-yl | |
| 2.2427 | H | CH2OH | 1,3,5-triazin-2-yl | |
| 2.2428 | H | CH2CH2OH | 1,3,5-triazin-2-yl | |
| 2.2429 | H | CH2CH2CH2OH | 1,3,5-triazin-2-yl | |
| 2.2430 | H | C6H5 | 1,3,5-triazin-2-yl | |
| 2.2431 | H | CH2Cl | 1,3,5-triazin-2-yl | |
| 2.2432 | H | CH2CH2Cl | 1,3,5-triazin-2-yl | |
| 2.2433 | H | CH2CH2CH2Cl | 1,3,5-triazin-2-yl | |

TABLE 2.25

| No. | X | Y | Z | phys. data |
|---|---|---|---|---|
| 2.2501 | H | H | oxazol-2-yl | |
| 2.2502 | H | CH3 | oxazol-2-yl | |
| 2.2503 | H | C2H5 | oxazol-2-yl | |
| 2.2504 | H | C3H7 | oxazol-2-yl | |
| 2.2505 | H | OCH3 | oxazol-2-yl | |
| 2.2506 | H | OC2H5 | oxazol-2-yl | |
| 2.2507 | H | OCH2CH=CH2 | oxazol-2-yl | |
| 2.2508 | H | OCH2CH=CHCH3 | oxazol-2-yl | |
| 2.2509 | H | OCH2C(Cl)=CH2 | oxazol-2-yl | |
| 2.2510 | H | OCH2CH=CHCl | oxazol-2-yl | |
| 2.2511 | H | OCH2C≡CH | oxazol-2-yl | |
| 2.2512 | H | OCHF2 | oxazol-2-yl | |
| 2.2513 | H | OCF3 | oxazol-2-yl | |
| 2.2514 | H | OCF2CHFCF3 | oxazol-2-yl | |
| 2.2515 | H | OC6H5 | oxazol-2-yl | |
| 2.2516 | H | CF3 | oxazol-2-yl | |
| 2.2517 | H | Br | oxazol-2-yl | |
| 2.2518 | H | Cl | oxazol-2-yl | |
| 2.2519 | H | F | oxazol-2-yl | |
| 2.2520 | H | SCH3 | oxazol-2-yl | |
| 2.2521 | H | SC2H5 | oxazol-2-yl | |
| 2.2522 | H | SC3H7-n | oxazol-2-yl | |
| 2.2523 | H | SO2CH3 | oxazol-2-yl | |
| 2.2524 | H | SO2C2H5 | oxazol-2-yl | |
| 2.2525 | H | NO2 | oxazol-2-yl | |
| 2.2526 | H | CN | oxazol-2-yl | |
| 2.2527 | H | CH2OH | oxazol-2-yl | |
| 2.2528 | H | CH2CH2OH | oxazol-2-yl | |
| 2.2529 | H | CH2CH2CH2OH | oxazol-2-yl | |
| 2.2530 | H | C6H5 | oxazol-2-yl | |
| 2.2531 | H | CH2Cl | oxazol-2-yl | |
| 2.2532 | H | CH2CH2Cl | oxazol-2-yl | |
| 2.2533 | H | CH2CH2CH2Cl | oxazol-2-yl | |

TABLE 2.26

| No. | X | Y | Z | phys. data |
|---|---|---|---|---|
| 2.2601 | H | H | triazol-2-yl | |
| 2.2602 | H | CH3 | triazol-2-yl | |
| 2.2603 | H | C2H5 | triazol-2-yl | |
| 2.2604 | H | C3H7 | triazol-2-yl | |
| 2.2605 | H | OCH3 | triazol-2-yl | |
| 2.2606 | H | OC2H5 | triazol-2-yl | |
| 2.2607 | H | OCH2CH=CH2 | triazol-2-yl | |
| 2.2608 | H | OCH2CH=CHCH3 | triazol-2-yl | |
| 2.2609 | H | OCH2C(Cl)=CH2 | triazol-2-yl | |
| 2.2610 | H | OCH2CH=CHCl | triazol-2-yl | |
| 2.2611 | H | OCH2C≡CH | triazol-2-yl | |
| 2.2612 | H | OCHF2 | triazol-2-yl | |
| 2.2613 | H | OCF3 | triazol-2-yl | |
| 2.2614 | H | OCF2CHFCF3 | triazol-2-yl | |
| 2.2615 | H | OC6H5 | triazol-2-yl | |
| 2.2616 | H | CF3 | triazol-2-yl | |
| 2.2617 | H | Br | triazol-2-yl | |
| 2.2618 | H | Cl | triazol-2-yl | |
| 2.2619 | H | F | triazol-2-yl | |
| 2.2620 | H | SCH3 | triazol-2-yl | |
| 2.2621 | H | SC2H5 | triazol-2-yl | |
| 2.2622 | H | SC3H7-n | triazol-2-yl | |
| 2.2623 | H | SO2CH3 | triazol-2-yl | |

TABLE 2.26-continued

| No. | X | Y | Z | phys. data |
|---|---|---|---|---|
| 2.2624 | H | SO2C2H5 | triazol-2-yl | |
| 2.2625 | H | NO2 | triazol-2-yl | |
| 2.2626 | H | CN | triazol-2-yl | |
| 2.2627 | H | CH2OH | triazol-2-yl | |
| 2.2628 | H | CH2CH2OH | triazol-2-yl | |
| 2.2629 | H | CH2CH2CH2OH | triazol-2-yl | |
| 2.2630 | H | C6H5 | triazol-2-yl | |
| 2.2631 | H | CH2Cl | triazol-2-yl | |
| 2.2632 | H | CH2CH2Cl | triazol-2-yl | |
| 2.2633 | H | CH2CH2CH2Cl | triazol-2-yl | |

EXAMPLE 9

Preparation of
8-cyclopropyl-2,7-dimethyl-3,5-dioxo-2-isopropyl-imidazo[2',1':1,2]5H-pyrrolo[3,4-6]pyridine

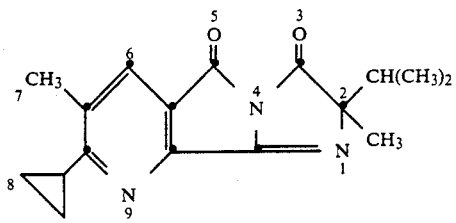

A solution of 13 g of 6-cyclopropyl-5-methyl-2-(5-isopropyl-5-methyl-4-oxo-imidazolin-2-yl)-pyridine-3-carboxylic acid and 9.3 g of dicyclohexylcarbodiimide in 200 ml of methylene chloride is stirred for one hour at room temperature. The reaction mixture is then filtered and the filtrate is concentrated. The residue is stirred with ether and crystallises. In this manner 7.2 g of the title compound having a melting point of 184°-187° C. are obtained.

EXAMPLE 10

Preparation of
7-ethyl-3,5-dioxo-2-isopropyl-8-methoxymethyl-2-methyl-imidazo[2,1:5,1]5H-pyrrolo[3,4-e]pyridine

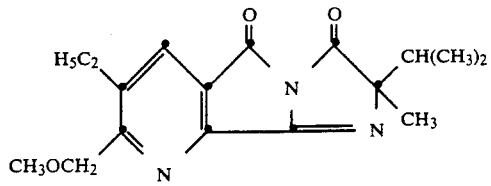

4.9 g of dicyclohexylcarbodiimide are added to a solution of 7.9 g of 5-ethyl-6-methoxymethyl-2-(5-isopropyl-5-methyl-4-oxo-imidazolin-2-yl)-pyridine-3-carboxylic acid in 150 ml of methylene chloride and the reaction mixture is stirred for one hour at room temperature. It is then filtered, the filtrate is concentrated and the residue is stirred with ether. In this manner 3.4 g of crystalline title product having a melting point of 121°-123° C. are obtained.

The tricyclic compounds of Tables 3.01 to 3.16 are prepared in a manner analogous to that described in Examples 9 and 10.

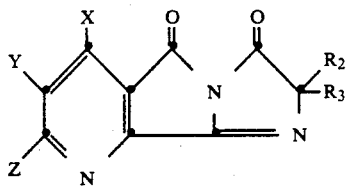

(II)

TABLE 3.00

| No. | X | Y | Z | phys. data |
|---|---|---|---|---|
| 3.0001 | H | H | C₃H₅(cyclo) | |
| 3.0002 | H | CH₃ | C₃H₅(cyclo) | m.p. 187–192° C. |
| 3.0003 | H | C₂H₅ | C₃H₅(cyclo) | m.p. 170–180° C. |
| 3.0004 | H | C₃H₇ | C₃H₅(cyclo) | |
| 3.0005 | H | OCH₃ | C₃H₅(cyclo) | |
| 3.0006 | H | OC₂H₅ | C₃H₅(cyclo) | |
| 3.0007 | H | OCH₂CH=CH₂ | C₃H₅(cyclo) | |
| 3.0008 | H | OCH₂CH=CHCH₃ | C₃H₅(cyclo) | |
| 3.0009 | H | OCH₂C(Cl)=CH₂ | C₃H₅(cyclo) | |
| 3.0010 | H | OCH₂CH=CHCl | C₃H₅(cyclo) | |
| 3.0011 | H | OCH₂C≡CH | C₃H₅(cyclo) | |
| 3.0012 | H | OCHF₂ | C₃H₅(cyclo) | |
| 3.0013 | H | OCF₃ | C₃H₅(cyclo) | |
| 3.0014 | H | OCF₂CHFCF₃ | C₃H₅(cyclo) | |
| 3.0015 | H | OC₆H₅ | C₃H₅(cyclo) | |
| 3.0016 | H | CF₃ | C₃H₅(cyclo) | |
| 3.0017 | H | Br | C₃H₅(cyclo) | |
| 3.0018 | H | Cl | C₃H₅(cyclo) | |
| 3.0019 | H | F | C₃H₅(cyclo) | |
| 3.0020 | H | SCH₃ | C₃H₅(cyclo) | |
| 3.0021 | H | SC₂H₅ | C₃H₅(cyclo) | |
| 3.0022 | H | SC₃H₇-n | C₃H₅(cyclo) | |
| 3.0023 | H | SO₂CH₃ | C₃H₅(cyclo) | |
| 3.0024 | H | SO₂C₂H₅ | C₃H₅(cyclo) | |
| 3.0025 | H | NO₂ | C₃H₅(cyclo) | |
| 3.0026 | H | CN | C₃H₅(cyclo) | |
| 3.0027 | H | CH₂OH | C₃H₅(cyclo) | |
| 3.0028 | H | CH₂CH₂OH | C₃H₅(cyclo) | |
| 3.0029 | H | CH₂CH₂CH₂OH | C₃H₅(cyclo) | |
| 3.0030 | H | C₆H₅ | C₃H₅(cyclo) | |
| 3.0031 | H | CH₂Cl | C₃H₅(cyclo) | |
| 3.0032 | H | CH₂CH₂Cl | C₃H₅(cyclo) | |
| 3.0033 | H | CH₂CH₂CH₂Cl | C₃H₅(cyclo) | |

TABLE 3.01

| No. | X | Y | Z | phys. data |
|---|---|---|---|---|
| 3.0101 | H | H | C₄H₇(cyclo) | |
| 3.0102 | H | CH₃ | C₄H₇(cyclo) | |
| 3.0103 | H | C₂H₅ | C₄H₇(cyclo) | |
| 3.0104 | H | C₃H₇ | C₄H₇(cyclo) | |
| 3.0105 | H | OCH₃ | C₄H₇(cyclo) | |
| 3.0106 | H | OC₂H₅ | C₄H₇(cyclo) | |
| 3.0107 | H | OCH₂CH=CH₂ | C₄H₇(cyclo) | |
| 3.0108 | H | OCH₂CH=CHCH₃ | C₄H₇(cyclo) | |
| 3.0109 | H | OCH₂C(Cl)=CH₂ | C₄H₇(cyclo) | |
| 3.0110 | H | OCH₂CH=CHCl | C₄H₇(cyclo) | |
| 3.0111 | H | OCH₂C≡CH | C₄H₇(cyclo) | |
| 3.0112 | H | OCHF₂ | C₄H₇(cyclo) | |
| 3.0113 | H | OCF₃ | C₄H₇(cyclo) | |
| 3.0114 | H | OCF₂CHFCF₃ | C₄H₇(cyclo) | |
| 3.0115 | H | OC₆H₅ | C₄H₇(cyclo) | |
| 3.0116 | H | CF₃ | C₄H₇(cyclo) | |
| 3.0117 | H | Br | C₄H₇(cyclo) | |
| 3.0118 | H | Cl | C₄H₇(cyclo) | |
| 3.0119 | H | F | C₄H₇(cyclo) | |
| 3.0120 | H | SCH₃ | C₄H₇(cyclo) | |
| 3.0121 | H | SC₂H₅ | C₄H₇(cyclo) | |
| 3.0122 | H | SC₃H₇-n | C₄H₇(cyclo) | |
| 3.0123 | H | SO₂CH₃ | C₄H₇(cyclo) | |
| 3.0124 | H | SO₂C₂H₅ | C₄H₇(cyclo) | |
| 3.0125 | H | NO₂ | C₄H₇(cyclo) | |
| 3.0126 | H | CN | C₄H₇(cyclo) | |
| 3.0127 | H | CH₂OH | C₄H₇(cyclo) | |
| 3.0128 | H | CH₂CH₂OH | C₄H₇(cyclo) | |
| 3.0129 | H | CH₂CH₂CH₂OH | C₄H₇(cyclo) | |

TABLE 3.01-continued

| No. | X | Y | Z | phys. data |
|---|---|---|---|---|
| 3.0130 | H | C₆H₅ | C₄H₇(cyclo) | |
| 3.0131 | H | CH₂Cl | C₄H₇(cyclo) | |
| 3.0132 | H | CH₂CH₂Cl | C₄H₇(cyclo) | |
| 3.0133 | H | CH₂CH₂CH₂Cl | C₄H₇(cyclo) | |

TABLE 3.02

| No. | X | Y | Z | phys. data |
|---|---|---|---|---|
| 3.0201 | H | H | C₅H₉(cyclo) | |
| 3.0202 | H | CH₃ | C₅H₉(cyclo) | |
| 3.0203 | H | C₂H₅ | C₅H₉(cyclo) | |
| 3.0204 | H | C₃H₇ | C₅H₉(cyclo) | |
| 3.0205 | H | OCH₃ | C₅H₉(cyclo) | |
| 3.0206 | H | OC₂H₅ | C₅H₉(cyclo) | |
| 3.0207 | H | OCH₂CH=CH₂ | C₅H₉(cyclo) | |
| 3.0208 | H | OCH₂CH=CHCH₃ | C₅H₉(cyclo) | |
| 3.0209 | H | OCH₂C(Cl)=CH₂ | C₅H₉(cyclo) | |
| 3.0210 | H | OCH₂CH=CHCl | C₅H₉(cyclo) | |
| 3.0211 | H | OCH₂C≡CH | C₅H₉(cyclo) | |
| 3.0212 | H | OCHF₂ | C₅H₉(cyclo) | |
| 3.0213 | H | OCF₃ | C₅H₉(cyclo) | |
| 3.0214 | H | OCF₂CHFCF₃ | C₅H₉(cyclo) | |
| 3.0215 | H | OC₆H₅ | C₅H₉(cyclo) | |
| 3.0216 | H | CF₃ | C₅H₉(cyclo) | |
| 3.0217 | H | Br | C₅H₉(cyclo) | |
| 3.0218 | H | Cl | C₅H₉(cyclo) | |
| 3.0219 | H | F | C₅H₉(cyclo) | |
| 3.0220 | H | SCH₃ | C₅H₉(cyclo) | |
| 3.0221 | H | SC₂H₅ | C₅H₉(cyclo) | |
| 3.0222 | H | SC₃H₇-n | C₅H₉(cyclo) | |
| 3.0223 | H | SO₂CH₃ | C₅H₉(cyclo) | |
| 3.0224 | H | SO₂C₂H₅ | C₅H₉(cyclo) | |
| 3.0225 | H | NO₂ | C₅H₉(cyclo) | |
| 3.0226 | H | CN | C₅H₉(cyclo) | |
| 3.0227 | H | CH₂OH | C₅H₉(cyclo) | |
| 3.0228 | H | CH₂CH₂OH | C₅H₉(cyclo) | |
| 3.0229 | H | CH₂CH₂CH₂OH | C₅H₉(cyclo) | |
| 3.0230 | H | C₆H₅ | C₅H₉(cyclo) | |
| 3.0231 | H | CH₂Cl | C₅H₉(cyclo) | |
| 3.0232 | H | CH₂CH₂Cl | C₅H₉(cyclo) | |
| 3.0233 | H | CH₂CH₂CH₂Cl | C₅H₉(cyclo) | |

TABLE 3.03

| No. | X | Y | Z | phys. data |
|---|---|---|---|---|
| 3.0301 | H | H | C₆H₁₁(cyclo) | |
| 3.0302 | H | CH₃ | C₆H₁₁(cyclo) | |
| 3.0303 | H | C₂H₅ | C₆H₁₁(cyclo) | |
| 3.0304 | H | C₃H₇ | C₆H₁₁(cyclo) | |
| 3.0305 | H | OCH₃ | C₆H₁₁(cyclo) | |
| 3.0306 | H | OC₂H₅ | C₆H₁₁(cyclo) | |
| 3.0307 | H | OCH₂CH=CH₂ | C₆H₁₁(cyclo) | |
| 3.0308 | H | OCH₂CH=CHCH₃ | C₆H₁₁(cyclo) | |
| 3.0309 | H | OCH₂C(Cl)=CH₂ | C₆H₁₁(cyclo) | |
| 3.0310 | H | OCH₂CH=CHCl | C₆H₁₁(cyclo) | |
| 3.0311 | H | OCH₂C≡CH | C₆H₁₁(cyclo) | |
| 3.0312 | H | OCHF₂ | C₆H₁₁(cyclo) | |
| 3.0313 | H | OCF₃ | C₆H₁₁(cyclo) | |
| 3.0314 | H | OCF₂CHFCF₃ | C₆H₁₁(cyclo) | |
| 3.0315 | H | OC₆H₅ | C₆H₁₁(cyclo) | |
| 3.0316 | H | CF₃ | C₆H₁₁(cyclo) | |
| 3.0317 | H | Br | C₆H₁₁(cyclo) | |
| 3.0318 | H | Cl | C₆H₁₁(cyclo) | |
| 3.0319 | H | F | C₆H₁₁(cyclo) | |
| 3.0320 | H | SCH₃ | C₆H₁₁(cyclo) | |
| 3.0321 | H | SC₂H₅ | C₆H₁₁(cyclo) | |
| 3.0322 | H | SC₃H₇-n | C₆H₁₁(cyclo) | |
| 3.0323 | H | SO₂CH₃ | C₆H₁₁(cyclo) | |
| 3.0324 | H | SO₂C₂H₅ | C₆H₁₁(cyclo) | |
| 3.0325 | H | NO₂ | C₆H₁₁(cyclo) | |
| 3.0326 | H | CN | C₆H₁₁(cyclo) | |
| 3.0327 | H | CH₂OH | C₆H₁₁(cyclo) | |
| 3.0328 | H | CH₂CH₂OH | C₆H₁₁(cyclo) | |
| 3.0329 | H | CH₂CH₂CH₂OH | C₆H₁₁(cyclo) | |
| 3.0330 | H | C₆H₅ | C₆H₁₁(cyclo) | |
| 3.0331 | H | CH₂Cl | C₆H₁₁(cyclo) | |
| 3.0332 | H | CH₂CH₂Cl | C₆H₁₁(cyclo) | |

TABLE 3.03-continued

| No. | X | Y | Z | phys. data |
|---|---|---|---|---|
| 3.0333 | H | $CH_2CH_2CH_2Cl$ | $C_6H_{11}(cyclo)$ | |

TABLE 3.04

| No. | X | Y | Z | phys. data |
|---|---|---|---|---|
| 3.0401 | H | H | $CH_2OCH_3$ | |
| 3.0402 | H | $CH_3$ | $CH_2OCH_3$ | |
| 3.0403 | H | $C_2H_5$ | $CH_2OCH_3$ | 121–123° C. |
| 3.0404 | H | $C_3H_7$ | $CH_2OCH_3$ | |
| 3.0405 | H | $OCH_3$ | $CH_2OCH_3$ | |
| 3.0406 | H | $OC_2H_5$ | $CH_2OCH_3$ | |
| 3.0407 | H | $OCH_2CH=CH_2$ | $CH_2OCH_3$ | |
| 3.0408 | H | $OCH_2CH=CHCH_3$ | $CH_2OCH_3$ | |
| 3.0409 | H | $OCH_2C(Cl)=CH_2$ | $CH_2OCH_3$ | |
| 3.0410 | H | $OCH_2CH=CHCl$ | $CH_2OCH_3$ | |
| 3.0411 | H | $OCH_2C\equiv CH$ | $CH_2OCH_3$ | |
| 3.0412 | H | $OCHF_2$ | $CH_2OCH_3$ | |
| 3.0413 | H | $OCF_3$ | $CH_2OCH_3$ | |
| 3.0414 | H | $OCF_2CHFCF_3$ | $CH_2OCH_3$ | |
| 3.0415 | H | $OC_6H_5$ | $CH_2OCH_3$ | |
| 3.0416 | H | $CF_3$ | $CH_2OCH_3$ | |
| 3.0417 | H | Br | $CH_2OCH_3$ | |
| 3.0418 | H | Cl | $CH_2OCH_3$ | |
| 3.0419 | H | F | $CH_2OCH_3$ | |
| 3.0420 | H | $SCH_3$ | $CH_2OCH_3$ | |
| 3.0421 | H | $SC_2H_5$ | $CH_2OCH_3$ | |
| 3.0422 | H | $SC_3H_7$-n | $CH_2OCH_3$ | |
| 3.0423 | H | $SO_2CH_3$ | $CH_2OCH_3$ | |
| 3.0424 | H | $SO_2C_2H_5$ | $CH_2OCH_3$ | |
| 3.0425 | H | $NO_2$ | $CH_2OCH_3$ | |
| 3.0426 | H | CN | $CH_2OCH_3$ | |
| 3.0427 | H | $CH_2OH$ | $CH_2OCH_3$ | |
| 3.0428 | H | $CH_2CH_2OH$ | $CH_2OCH_3$ | |
| 3.0429 | H | $CH_2CH_2CH_2OH$ | $CH_2OCH_3$ | |
| 3.0430 | H | $C_6H_5$ | $CH_2OCH_3$ | |
| 3.0431 | H | $CH_2Cl$ | $CH_2OCH_3$ | |
| 3.0432 | H | $CH_2CH_2Cl$ | $CH_2OCH_3$ | |
| 3.0433 | H | $CH_2CH_2CH_2Cl$ | $CH_2OCH_3$ | |

TABLE 3.05

| No. | X | Y | Z | phys. data |
|---|---|---|---|---|
| 3.0501 | H | H | $CH(CH_3)OCH_3$ | |
| 3.0502 | H | $CH_3$ | $CH(CH_3)OCH_3$ | |
| 3.0503 | H | $C_2H_5$ | $CH(CH_3)OCH_3$ | |
| 3.0504 | H | $C_3H_7$ | $CH(CH_3)OCH_3$ | |
| 3.0505 | H | $OCH_3$ | $CH(CH_3)OCH_3$ | |
| 3.0506 | H | $OC_2H_5$ | $CH(CH_3)OCH_3$ | |
| 3.0507 | H | $OCH_2CH=CH_2$ | $CH(CH_3)OCH_3$ | |
| 3.0508 | H | $OCH_2CH=CHCH_3$ | $CH(CH_3)OCH_3$ | |
| 3.0509 | H | $OCH_2C(Cl)=CH_2$ | $CH(CH_3)OCH_3$ | |
| 3.0510 | H | $OCH_2CH=CHCl$ | $CH(CH_3)OCH_3$ | |
| 3.0511 | H | $OCH_2C\equiv CH$ | $CH(CH_3)OCH_3$ | |
| 3.0512 | H | $OCHF_2$ | $CH(CH_3)OCH_3$ | |
| 3.0513 | H | $OCF_3$ | $CH(CH_3)OCH_3$ | |
| 3.0514 | H | $OCF_2CHFCF_3$ | $CH(CH_3)OCH_3$ | |
| 3.0515 | H | $OC_6H_5$ | $CH(CH_3)OCH_3$ | |
| 3.0516 | H | $CF_3$ | $CH(CH_3)OCH_3$ | |
| 3.0517 | H | Br | $CH(CH_3)OCH_3$ | |
| 3.0518 | H | Cl | $CH(CH_3)OCH_3$ | |
| 3.0519 | H | F | $CH(CH_3)OCH_3$ | |
| 3.0520 | H | $SCH_3$ | $CH(CH_3)OCH_3$ | |
| 3.0521 | H | $SC_2H_5$ | $CH(CH_3)OCH_3$ | |
| 3.0522 | H | $SC_3H_7$-n | $CH(CH_3)OCH_3$ | |
| 3.0523 | H | $SO_2CH_3$ | $CH(CH_3)OCH_3$ | |
| 3.0524 | H | $SO_2C_2H_5$ | $CH(CH_3)OCH_3$ | |
| 3.0525 | H | $NO_2$ | $CH(CH_3)OCH_3$ | |
| 3.0526 | H | CN | $CH(CH_3)OCH_3$ | |
| 3.0527 | H | $CH_2OH$ | $CH(CH_3)OCH_3$ | |
| 3.0528 | H | $CH_2CH_2OH$ | $CH(CH_3)OCH_3$ | |
| 3.0529 | H | $CH_2CH_2CH_2OH$ | $CH(CH_3)OCH_3$ | |
| 3.0530 | H | $C_6H_5$ | $CH(CH_3)OCH_3$ | |
| 3.0531 | H | $CH_2Cl$ | $CH(CH_3)OCH_3$ | |
| 3.0532 | H | $CH_2CH_2Cl$ | $CH(CH_3)OCH_3$ | |
| 3.0533 | H | $CH_2CH_2CH_2Cl$ | $CH(CH_3)OCH_3$ | |

TABLE 3.06

| No. | X | Y | Z | phys. data |
|---|---|---|---|---|
| 3.0601 | H | H | $CH_2OC_2H_5$ | resin |
| 3.0602 | H | $CH_3$ | $CH_2OC_2H_5$ | |
| 3.0603 | H | $C_2H_5$ | $CH_2OC_2H_5$ | |
| 3.0604 | H | $C_3H_7$ | $CH_2OC_2H_5$ | |
| 3.0605 | H | $OCH_3$ | $CH_2OC_2H_5$ | |
| 3.0606 | H | $OC_2H_5$ | $CH_2OC_2H_5$ | |
| 3.0607 | H | $OCH_2CH=CH_2$ | $CH_2OC_2H_5$ | |
| 3.0608 | H | $OCH_2CH=CHCH_3$ | $CH_2OC_2H_5$ | |
| 3.0609 | H | $OCH_2C(Cl)=CH_2$ | $CH_2OC_2H_5$ | |
| 3.0610 | H | $OCH_2CH=CHCl$ | $CH_2OC_2H_5$ | |
| 3.0611 | H | $OCH_2C\equiv CH$ | $CH_2OC_2H_5$ | |
| 3.0612 | H | $OCHF_2$ | $CH_2OC_2H_5$ | |
| 3.0613 | H | $OCF_3$ | $CH_2OC_2H_5$ | |
| 3.0614 | H | $OCF_2CHFCF_3$ | $CH_2OC_2H_5$ | |
| 3.0615 | H | $OC_6H_5$ | $CH_2OC_2H_5$ | |
| 3.0616 | H | $CF_3$ | $CH_2OC_2H_5$ | |
| 3.0617 | H | Br | $CH_2OC_2H_5$ | |
| 3.0618 | H | Cl | $CH_2OC_2H_5$ | |
| 3.0619 | H | F | $CH_2OC_2H_5$ | |
| 3.0620 | H | $SCH_3$ | $CH_2OC_2H_5$ | |
| 3.0621 | H | $SC_2H_5$ | $CH_2OC_2H_5$ | |
| 3.0622 | H | $SC_3H_7$-n | $CH_2OC_2H_5$ | |
| 3.0623 | H | $SO_2CH_3$ | $CH_2OC_2H_5$ | |
| 3.0624 | H | $SO_2C_2H_5$ | $CH_2OC_2H_5$ | |
| 3.0625 | H | $NO_2$ | $CH_2OC_2H_5$ | |
| 3.0626 | H | CN | $CH_2OC_2H_5$ | |
| 3.0627 | H | $CH_2OH$ | $CH_2OC_2H_5$ | |
| 3.0628 | H | $CH_2CH_2OH$ | $CH_2OC_2H_5$ | |
| 3.0629 | H | $CH_2CH_2CH_2OH$ | $CH_2OC_2H_5$ | |
| 3.0630 | H | $C_6H_5$ | $CH_2OC_2H_5$ | |
| 3.0631 | H | $CH_2Cl$ | $CH_2OC_2H_5$ | |
| 3.0632 | H | $CH_2CH_2Cl$ | $CH_2OC_2H_5$ | |
| 3.0633 | H | $CH_2CH_2CH_2Cl$ | $CH_2OC_2H_5$ | |

TABLE 3.07

| No. | X | Y | Z | phys. data |
|---|---|---|---|---|
| 3.0701 | H | H | $CH(CH_3)OC_2H_5$ | |
| 3.0702 | H | $CH_3$ | $CH(CH_3)OC_2H_5$ | |
| 3.0703 | H | $C_2H_5$ | $CH(CH_3)OC_2H_5$ | |
| 3.0704 | H | $C_3H_7$ | $CH(CH_3)OC_2H_5$ | |
| 3.0705 | H | $OCH_3$ | $CH(CH_3)OC_2H_5$ | |
| 3.0706 | H | $OC_2H_5$ | $CH(CH_3)OC_2H_5$ | |
| 3.0707 | H | $OCH_2CH=CH_2$ | $CH(CH_3)OC_2H_5$ | |
| 3.0708 | H | $OCH_2CH=CHCH_3$ | $CH(CH_3)OC_2H_5$ | |
| 3.0709 | H | $OCH_2C(Cl)=CH_2$ | $CH(CH_3)OC_2H_5$ | |
| 3.0710 | H | $OCH_2CH=CHCl$ | $CH(CH_3)OC_2H_5$ | |
| 3.0711 | H | $OCH_2C\equiv CH$ | $CH(CH_3)OC_2H_5$ | |
| 3.0712 | H | $OCHF_2$ | $CH(CH_3)OC_2H_5$ | |
| 3.0713 | H | $OCF_3$ | $CH(CH_3)OC_2H_5$ | |
| 3.0714 | H | $OCF_2CHFCF_3$ | $CH(CH_3)OC_2H_5$ | |
| 3.0715 | H | $OC_6H_5$ | $CH(CH_3)OC_2H_5$ | |
| 3.0716 | H | $CF_3$ | $CH(CH_3)OC_2H_5$ | |
| 3.0717 | H | Br | $CH(CH_3)OC_2H_5$ | |
| 3.0718 | H | Cl | $CH(CH_3)OC_2H_5$ | |
| 3.0719 | H | F | $CH(CH_3)OC_2H_5$ | |
| 3.0720 | H | $SCH_3$ | $CH(CH_3)OC_2H_5$ | |
| 3.0721 | H | $SC_2H_5$ | $CH(CH_3)OC_2H_5$ | |
| 3.0722 | H | $SC_3H_7$-n | $CH(CH_3)OC_2H_5$ | |
| 3.0723 | H | $SO_2CH_3$ | $CH(CH_3)OC_2H_5$ | |
| 3.0724 | H | $SO_2C_2H_5$ | $CH(CH_3)OC_2H_5$ | |
| 3.0725 | H | $NO_2$ | $CH(CH_3)OC_2H_5$ | |
| 3.0726 | H | CN | $CH(CH_3)OC_2H_5$ | |
| 3.0727 | H | $CH_2OH$ | $CH(CH_3)OC_2H_5$ | |
| 3.0728 | H | $CH_2CH_2OH$ | $CH(CH_3)OC_2H_5$ | |
| 3.0729 | H | $CH_2CH_2CH_2OH$ | $CH(CH_3)OC_2H_5$ | |
| 3.0730 | H | $C_6H_5$ | $CH(CH_3)OC_2H_5$ | |
| 3.0731 | H | $CH_2Cl$ | $CH(CH_3)OC_2H_5$ | |
| 3.0732 | H | $CH_2CH_2Cl$ | $CH(CH_3)OC_2H_5$ | |
| 3.0733 | H | $CH_2CH_2CH_2Cl$ | $CH(CH_3)OC_2H_5$ | |

TABLE 3.08

| No. | X | Y | Z | phys. data |
|---|---|---|---|---|
| 3.0801 | H | H | $C(CH_3)_2OCH_3$ | |
| 3.0802 | H | $CH_3$ | $C(CH_3)_2OCH_3$ | |
| 3.0803 | H | $C_2H_5$ | $C(CH_3)_2OCH_3$ | |

TABLE 3.08-continued

| No. | X | Y | Z | phys. data |
|---|---|---|---|---|
| 3.0804 | H | C3H7 | C(CH3)2OCH3 | |
| 3.0805 | H | OCH3 | C(CH3)2OCH3 | |
| 3.0806 | H | OC2H5 | C(CH3)2OCH3 | |
| 3.0807 | H | OCH2CH=CH2 | C(CH3)2OCH3 | |
| 3.0808 | H | OCH2CH=CHCH3 | C(CH3)2OCH3 | |
| 3.0809 | H | OCH2C(Cl)=CH2 | C(CH3)2OCH3 | |
| 3.0810 | H | OCH2CH=CHCl | C(CH3)2OCH3 | |
| 3.0811 | H | OCH2C≡CH | C(CH3)2OCH3 | |
| 3.0812 | H | OCHF2 | C(CH3)2OCH3 | |
| 3.0813 | H | OCF3 | C(CH3)2OCH3 | |
| 3.0814 | H | OCF2CHFCF3 | C(CH3)2OCH3 | |
| 3.0815 | H | OC6H5 | C(CH3)2OCH3 | |
| 3.0816 | H | CF3 | C(CH3)2OCH3 | |
| 3.0817 | H | Br | C(CH3)2OCH3 | |
| 3.0818 | H | Cl | C(CH3)2OCH3 | |
| 3.0819 | H | F | C(CH3)2OCH3 | |
| 3.0820 | H | SCH3 | C(CH3)2OCH3 | |
| 3.0821 | H | SC2H5 | C(CH3)2OCH3 | |
| 3.0822 | H | SC3H7-n | C(CH3)2OCH3 | |
| 3.0823 | H | SO2CH3 | C(CH3)2OCH3 | |
| 3.0824 | H | SO2C2H5 | C(CH3)2OCH3 | |
| 3.0825 | H | NO2 | C(CH3)2OCH3 | |
| 3.0826 | H | CN | C(CH3)2OCH3 | |
| 3.0827 | H | CH2OH | C(CH3)2OCH3 | |
| 3.0828 | H | CH2CH2OH | C(CH3)2OCH3 | |
| 3.0829 | H | CH2CH2CH2OH | C(CH3)2OCH3 | |
| 3.0830 | H | C6H5 | C(CH3)2OCH3 | |
| 3.0831 | H | CH2Cl | C(CH3)2OCH3 | |
| 3.0832 | H | CH2CH2Cl | C(CH3)2OCH3 | |
| 3.0833 | H | CH2CH2CH2Cl | C(CH3)2OCH3 | |

TABLE 3.09

| No. | X | Y | Z | phys. data |
|---|---|---|---|---|
| 3.0901 | H | H | CH2OC3H7 | |
| 3.0902 | H | CH3 | CH2OC3H7 | |
| 3.0903 | H | C2H5 | CH2OC3H7 | |
| 3.0904 | H | C3H7 | CH2OC3H7 | |
| 3.0905 | H | OCH3 | CH2OC3H7 | |
| 3.0906 | H | OC2H5 | CH2OC3H7 | |
| 3.0907 | H | OCH2CH=CH2 | CH2OC3H7 | |
| 3.0908 | H | OCH2CH=CHCH3 | CH2OC3H7 | |
| 3.0909 | H | OCH2C(Cl)=CH2 | CH2OC3H7 | |
| 3.0910 | H | OCH2CH=CHCl | CH2OC3H7 | |
| 3.0911 | H | OCH2C≡CH | CH2OC3H7 | |
| 3.0912 | H | OCHF2 | CH2OC3H7 | |
| 3.0913 | H | OCF3 | CH2OC3H7 | |
| 3.0914 | H | OCF2CHFCF3 | CH2OC3H7 | |
| 3.0915 | H | OC6H5 | CH2OC3H7 | |
| 3.0916 | H | CF3 | CH2OC3H7 | |
| 3.0917 | H | Br | CH2OC3H7 | |
| 3.0918 | H | Cl | CH2OC3H7 | |
| 3.0919 | H | F | CH2OC3H7 | |
| 3.0920 | H | SCH3 | CH2OC3H7 | |
| 3.0921 | H | SC2H5 | CH2OC3H7 | |
| 3.0922 | H | SC3H7-n | CH2OC3H7 | |
| 3.0923 | H | SO2CH3 | CH2OC3H7 | |
| 3.0924 | H | SO2C2H5 | CH2OC3H7 | |
| 3.0925 | H | NO2 | CH2OC3H7 | |
| 3.0926 | H | CN | CH2OC3H7 | |
| 3.0927 | H | CH2OH | CH2OC3H7 | |
| 3.0928 | H | CH2CH2OH | CH2OC3H7 | |
| 3.0929 | H | CH2CH2CH2OH | CH2OC3H7 | |
| 3.0930 | H | C6H5 | CH2OC3H7 | |
| 3.0931 | H | CH2Cl | CH2OC3H7 | |
| 3.0932 | H | CH2CH2Cl | CH2OC3H7 | |
| 3.0933 | H | CH2CH2CH2Cl | CH2OC3H7 | |

TABLE 3.10

| No. | X | Y | Z | phys. data |
|---|---|---|---|---|
| 3.1001 | H | H | C(CH3)C2H4(cyclo) | |
| 3.1002 | H | CH3 | C(CH3)C2H4(cyclo) | |
| 3.1003 | H | C2H5 | C(CH3)C2H4(cyclo) | |
| 3.1004 | H | C3H7 | C(CH3)C2H4(cyclo) | |
| 3.1005 | H | OCH3 | C(CH3)C2H4(cyclo) | |
| 3.1006 | H | OC2H5 | C(CH3)C2H4(cyclo) | |

TABLE 3.10-continued

| No. | X | Y | Z | phys. data |
|---|---|---|---|---|
| 3.1007 | H | OCH2CH=CH2 | C(CH3)C2H4(cyclo) | |
| 3.1008 | H | OCH2CH=CHCH3 | C(CH3)C2H4(cyclo) | |
| 3.1009 | H | OCH2C(Cl)=CH2 | C(CH3)C2H4(cyclo) | |
| 3.1010 | H | OCH2CH=CHCl | C(CH3)C2H4(cyclo) | |
| 3.1011 | H | OCH2C≡CH | C(CH3)C2H4(cyclo) | |
| 3.1012 | H | OCHF2 | C(CH3)C2H4(cyclo) | |
| 3.1013 | H | OCF3 | C(CH3)C2H4(cyclo) | |
| 3.1014 | H | OCF2CHFCF3 | C(CH3)C2H4(cyclo) | |
| 3.1015 | H | OC6H5 | C(CH3)C2H4(cyclo) | |
| 3.1016 | H | CF3 | C(CH3)C2H4(cyclo) | |
| 3.1017 | H | Br | C(CH3)C2H4(cyclo) | |
| 3.1018 | H | Cl | C(CH3)C2H4(cyclo) | |
| 3.1019 | H | F | C(CH3)C2H4(cyclo) | |
| 3.1020 | H | SCH3 | C(CH3)C2H4(cyclo) | |
| 3.1021 | H | SC2H5 | C(CH3)C2H4(cyclo) | |
| 3.1022 | H | SC3H7-n | C(CH3)C2H4(cyclo) | |
| 3.1023 | H | SO2CH3 | C(CH3)C2H4(cyclo) | |
| 3.1024 | H | SO2C2H5 | C(CH3)C2H4(cyclo) | |
| 3.1025 | H | NO2 | C(CH3)C2H4(cyclo) | |
| 3.1026 | H | CN | C(CH3)C2H4(cyclo) | |
| 3.1027 | H | CH2OH | C(CH3)C2H4(cyclo) | |
| 3.1028 | H | CH2CH2OH | C(CH3)C2H4(cyclo) | |
| 3.1029 | H | CH2CH2CH2OH | C(CH3)C2H4(cyclo) | |
| 3.1030 | H | C6H5 | C(CH3)C2H4(cyclo) | |
| 3.1031 | H | CH2Cl | C(CH3)C2H4(cyclo) | |
| 3.1032 | H | CH2CH2Cl | C(CH3)C2H4(cyclo) | |
| 3.1033 | H | CH2CH2CH2Cl | C(CH3)C2H4(cyclo) | |

TABLE 3.11

| No. | X | Y | Z | phys. data |
|---|---|---|---|---|
| 3.1101 | H | H | CH2OC6H5 | |
| 3.1102 | H | CH3 | CH2OC6H5 | |
| 3.1103 | H | C2H5 | CH2OC6H5 | |
| 3.1104 | H | C3H7 | CH2OC6H5 | |
| 3.1105 | H | OCH3 | CH2OC6H5 | |
| 3.1106 | H | OC2H5 | CH2OC6H5 | |
| 3.1107 | H | OCH2CH=CH2 | CH2OC6H5 | |
| 3.1108 | H | OCH2CH=CHCH3 | CH2OC6H5 | |
| 3.1109 | H | OCH2C(Cl)=CH2 | CH2OC6H5 | |
| 3.1110 | H | OCH2CH=CHCl | CH2OC6H5 | |
| 3.1111 | H | OCH2C≡CH | CH2OC6H5 | |
| 3.1112 | H | OCHF2 | CH2OC6H5 | |
| 3.1113 | H | OCF3 | CH2OC6H5 | |
| 3.1114 | H | OCF2CHFCF3 | CH2OC6H5 | |
| 3.1115 | H | OC6H5 | CH2OC6H5 | |
| 3.1116 | H | CF3 | CH2OC6H5 | |
| 3.1117 | H | Br | CH2OC6H5 | |
| 3.1118 | H | Cl | CH2OC6H5 | |
| 3.1119 | H | F | CH2OC6H5 | |
| 3.1120 | H | SCH3 | CH2OC6H5 | |
| 3.1121 | H | SC2H5 | CH2OC6H5 | |
| 3.1122 | H | SC3H7-n | CH2OC6H5 | |
| 3.1123 | H | SO2CH3 | CH2OC6H5 | |
| 3.1124 | H | SO2C2H5 | CH2OC6H5 | |
| 3.1125 | H | NO2 | CH2OC6H5 | |
| 3.1126 | H | CN | CH2OC6H5 | |
| 3.1127 | H | CH2OH | CH2OC6H5 | |
| 3.1128 | H | CH2CH2OH | CH2OC6H5 | |
| 3.1129 | H | CH2CH2CH2OH | CH2OC6H5 | |
| 3.1130 | H | C6H5 | CH2OC6H5 | |
| 3.1131 | H | CH2Cl | CH2OC6H5 | |
| 3.1132 | H | CH2CH2Cl | CH2OC6H5 | |
| 3.1133 | H | CH2CH2CH2Cl | CH2OC6H5 | |

TABLE 3.12

| No. | X | Y | Z | phys. data |
|---|---|---|---|---|
| 3.1201 | H | H | furan-2-yl | |
| 3.1202 | H | CH3 | furan-2-yl | |
| 3.1203 | H | C2H5 | furan-2-yl | |
| 3.1204 | H | C3H7 | furan-2-yl | |
| 3.1205 | H | OCH3 | furan-2-yl | |
| 3.1206 | H | OC2H5 | furan-2-yl | |
| 3.1207 | H | OCH2CH=CH2 | furan-2-yl | |
| 3.1208 | H | OCH2CH=CHCH3 | furan-2-yl | |
| 3.1209 | H | OCH2C(Cl)=CH2 | furan-2-yl | |

TABLE 3.12-continued

| No. | X | Y | Z | phys. data |
|---|---|---|---|---|
| 3.1210 | H | OCH$_2$CH=CHCl | furan-2-yl | |
| 3.1211 | H | OCH$_2$C≡CH | furan-2-yl | |
| 3.1212 | H | OCHF$_2$ | furan-2-yl | |
| 3.1213 | H | OCF$_3$ | furan-2-yl | |
| 3.1214 | H | OCF$_2$CHFCF$_3$ | furan-2-yl | |
| 3.1215 | H | OC$_6$H$_5$ | furan-2-yl | |
| 3.1216 | H | CF$_3$ | furan-2-yl | |
| 3.1217 | H | Br | furan-2-yl | |
| 3.1218 | H | Cl | furan-2-yl | |
| 3.1219 | H | F | furan-2-yl | |
| 3.1220 | H | SCH$_3$ | furan-2-yl | |
| 3.1221 | H | SC$_2$H$_5$ | furan-2-yl | |
| 3.1222 | H | SC$_3$H$_7$-n | furan-2-yl | |
| 3.1223 | H | SO$_2$CH$_3$ | furan-2-yl | |
| 3.1224 | H | SO$_2$C$_2$H$_5$ | furan-2-yl | |
| 3.1225 | H | NO$_2$ | furan-2-yl | |
| 3.1226 | H | CN | furan-2-yl | |
| 3.1227 | H | CH$_2$OH | furan-2-yl | |
| 3.1228 | H | CH$_2$CH$_2$OH | furan-2-yl | |
| 3.1229 | H | CH$_2$CH$_2$CH$_2$OH | furan-2-yl | |
| 3.1230 | H | C$_6$H$_5$ | furan-2-yl | |
| 3.1231 | H | CH$_2$Cl | furan-2-yl | |
| 3.1232 | H | CH$_2$CH$_2$Cl | furan-2-yl | |
| 3.1233 | H | CH$_2$CH$_2$CH$_2$Cl | furan-2-yl | |

TABLE 3.13

| No. | X | Y | Z | phys. data |
|---|---|---|---|---|
| 3.1301 | H | H | dioxan-2-yl | |
| 3.1302 | H | CH$_3$ | dioxan-2-yl | |
| 3.1303 | H | C$_2$H$_5$ | dioxan-2-yl | |
| 3.1304 | H | C$_3$H$_7$ | dioxan-2-yl | |
| 3.1305 | H | OCH$_3$ | dioxan-2-yl | |
| 3.1306 | H | OC$_2$H$_5$ | dioxan-2-yl | |
| 3.1307 | H | OCH$_2$CH=CH$_2$ | dioxan-2-yl | |
| 3.1308 | H | OCH$_2$CH=CHCH$_3$ | dioxan-2-yl | |
| 3.1309 | H | OCH$_2$C(Cl)=CH$_2$ | dioxan-2-yl | |
| 3.1310 | H | OCH$_2$CH=CHCl | dioxan-2-yl | |
| 3.1311 | H | OCH$_2$C≡CH | dioxan-2-yl | |
| 3.1312 | H | OCHF$_2$ | dioxan-2-yl | |
| 3.1313 | H | OCF$_3$ | dioxan-2-yl | |
| 3.1314 | H | OCF$_2$CHFCF$_3$ | dioxan-2-yl | |
| 3.1315 | H | OC$_6$H$_5$ | dioxan-2-yl | |
| 3.1316 | H | CF$_3$ | dioxan-2-yl | |
| 3.1317 | H | Br | dioxan-2-yl | |
| 3.1318 | H | Cl | dioxan-2-yl | |
| 3.1319 | H | F | dioxan-2-yl | |
| 3.1320 | H | SCH$_3$ | dioxan-2-yl | |
| 3.1321 | H | SC$_2$H$_5$ | dioxan-2-yl | |
| 3.1322 | H | SC$_3$H$_7$-n | dioxan-2-yl | |
| 3.1323 | H | SO$_2$CH$_3$ | dioxan-2-yl | |
| 3.1324 | H | SO$_2$C$_2$H$_5$ | dioxan-2-yl | |
| 3.1325 | H | NO$_2$ | dioxan-2-yl | |
| 3.1326 | H | CN | dioxan-2-yl | |
| 3.1327 | H | CH$_2$OH | dioxan-2-yl | |
| 3.1328 | H | CH$_2$CH$_2$OH | dioxan-2-yl | |
| 3.1329 | H | CH$_2$CH$_2$CH$_2$OH | dioxan-2-yl | |
| 3.1330 | H | C$_6$H$_5$ | dioxan-2-yl | |
| 3.1331 | H | CH$_2$Cl | dioxan-2-yl | |
| 3.1332 | H | CH$_2$CH$_2$Cl | dioxan-2-yl | |
| 3.1333 | H | CH$_2$CH$_2$CH$_2$Cl | dioxan-2-yl | |

TABLE 3.14

| No. | X | Y | Z | phys. data |
|---|---|---|---|---|
| 3.1401 | H | H | CH$_2$OC$_2$H$_4$OCH$_3$ | |
| 3.1402 | H | CH$_3$ | CH$_2$OC$_2$H$_4$OCH$_3$ | |
| 3.1403 | H | C$_2$H$_5$ | CH$_2$OC$_2$H$_4$OCH$_3$ | |
| 3.1404 | H | C$_3$H$_7$ | CH$_2$OC$_2$H$_4$OCH$_3$ | |
| 3.1405 | H | OCH$_3$ | CH$_2$OC$_2$H$_4$OCH$_3$ | |
| 3.1406 | H | OC$_2$H$_5$ | CH$_2$OC$_2$H$_4$OCH$_3$ | |
| 3.1407 | H | OCH$_2$CH=CH$_2$ | CH$_2$OC$_2$H$_4$OCH$_3$ | |
| 3.1408 | H | OCH$_2$CH=CHCH$_3$ | CH$_2$OC$_2$H$_4$OCH$_3$ | |
| 3.1409 | H | OCH$_2$C(Cl)=CH$_2$ | CH$_2$OC$_2$H$_4$OCH$_3$ | |
| 3.1410 | H | OCH$_2$CH=CHCl | CH$_2$OC$_2$H$_4$OCH$_3$ | |
| 3.1411 | H | OCH$_2$C≡CH | CH$_2$OC$_2$H$_4$OCH$_3$ | |
| 3.1412 | H | OCHF$_2$ | CH$_2$OC$_2$H$_4$OCH$_3$ | |
| 3.1413 | H | OCF$_3$ | CH$_2$OC$_2$H$_4$OCH$_3$ | |
| 3.1414 | H | OCF$_2$CHFCF$_3$ | CH$_2$OC$_2$H$_4$OCH$_3$ | |
| 3.1415 | H | OC$_6$H$_5$ | CH$_2$OC$_2$H$_4$OCH$_3$ | |
| 3.1416 | H | CF$_3$ | CH$_2$OC$_2$H$_4$OCH$_3$ | |
| 3.1417 | H | Br | CH$_2$OC$_2$H$_4$OCH$_3$ | |
| 3.1418 | H | Cl | CH$_2$OC$_2$H$_4$OCH$_3$ | |
| 3.1419 | H | F | CH$_2$OC$_2$H$_4$OCH$_3$ | |
| 3.1420 | H | SCH$_3$ | CH$_2$OC$_2$H$_4$OCH$_3$ | |
| 3.1421 | H | SC$_2$H$_5$ | CH$_2$OC$_2$H$_4$OCH$_3$ | |
| 3.1422 | H | SC$_3$H$_7$-n | CH$_2$OC$_2$H$_4$OCH$_3$ | |
| 3.1423 | H | SO$_2$CH$_3$ | CH$_2$OC$_2$H$_4$OCH$_3$ | |
| 3.1424 | H | SO$_2$C$_2$H$_5$ | CH$_2$OC$_2$H$_4$OCH$_3$ | |
| 3.1425 | H | NO$_2$ | CH$_2$OC$_2$H$_4$OCH$_3$ | |
| 3.1426 | H | CN | CH$_2$OC$_2$H$_4$OCH$_3$ | |
| 3.1427 | H | CH$_2$OH | CH$_2$OC$_2$H$_4$OCH$_3$ | |
| 3.1428 | H | CH$_2$CH$_2$OH | CH$_2$OC$_2$H$_4$OCH$_3$ | |
| 3.1429 | H | CH$_2$CH$_2$CH$_2$OH | CH$_2$OC$_2$H$_4$OCH$_3$ | |
| 3.1430 | H | C$_6$H$_5$ | CH$_2$OC$_2$H$_4$OCH$_3$ | |
| 3.1431 | H | CH$_2$Cl | CH$_2$OC$_2$H$_4$OCH$_3$ | |
| 3.1432 | H | CH$_2$CH$_2$Cl | CH$_2$OC$_2$H$_4$OCH$_3$ | |
| 3.1433 | H | CH$_2$CH$_2$CH$_2$Cl | CH$_2$OC$_2$H$_4$OCH$_3$ | |

TABLE 3.15

| No. | X | Y | Z | phys. data |
|---|---|---|---|---|
| 3.1501 | H | H | CH$_2$OC$_2$H$_4$OC$_2$H$_4$OCH$_3$ | |
| 3.1502 | H | CH$_3$ | CH$_2$OC$_2$H$_4$OC$_2$H$_4$OCH$_3$ | |
| 3.1503 | H | C$_2$H$_5$ | CH$_2$OC$_2$H$_4$OC$_2$H$_4$OCH$_3$ | |
| 3.1504 | H | C$_3$H$_7$ | CH$_2$OC$_2$H$_4$OC$_2$H$_4$OCH$_3$ | |
| 3.1505 | H | OCH$_3$ | CH$_2$OC$_2$H$_4$OC$_2$H$_4$OCH$_3$ | |
| 3.1506 | H | OC$_2$H$_5$ | CH$_2$OC$_2$H$_4$OC$_2$H$_4$OCH$_3$ | |
| 3.1507 | H | OCH$_2$CH=CH$_2$ | CH$_2$OC$_2$H$_4$OC$_2$H$_4$OCH$_3$ | |
| 3.1508 | H | OCH$_2$CH=CHCH$_3$ | CH$_2$OC$_2$H$_4$OC$_2$H$_4$OCH$_3$ | |
| 3.1509 | H | OCH$_2$C(Cl)=CH$_2$ | CH$_2$OC$_2$H$_4$OC$_2$H$_4$OCH$_3$ | |
| 3.1510 | H | OCH$_2$CH=CHCl | CH$_2$OC$_2$H$_4$OC$_2$H$_4$OCH$_3$ | |
| 3.1511 | H | OCH$_2$C≡CH | CH$_2$OC$_2$H$_4$OC$_2$H$_4$OCH$_3$ | |
| 3.1512 | H | OCHF$_2$ | CH$_2$OC$_2$H$_4$OC$_2$H$_4$OCH$_3$ | |
| 3.1513 | H | OCF$_3$ | CH$_2$OC$_2$H$_4$OC$_2$H$_4$OCH$_3$ | |
| 3.1514 | H | OCF$_2$CHFCF$_3$ | CH$_2$OC$_2$H$_4$OC$_2$H$_4$OCH$_3$ | |
| 3.1515 | H | OC$_6$H$_5$ | CH$_2$OC$_2$H$_4$OC$_2$H$_4$OCH$_3$ | |
| 3.1516 | H | CF$_3$ | CH$_2$OC$_2$H$_4$OC$_2$H$_4$OCH$_3$ | |
| 3.1517 | H | Br | CH$_2$OC$_2$H$_4$OC$_2$H$_4$OCH$_3$ | |
| 3.1518 | H | Cl | CH$_2$OC$_2$H$_4$OC$_2$H$_4$OCH$_3$ | |
| 3.1519 | H | F | CH$_2$OC$_2$H$_4$OC$_2$H$_4$OCH$_3$ | |
| 3.1520 | H | SCH$_3$ | CH$_2$OC$_2$H$_4$OC$_2$H$_4$OCH$_3$ | |
| 3.1521 | H | SC$_2$H$_5$ | CH$_2$OC$_2$H$_4$OC$_2$H$_4$OCH$_3$ | |
| 3.1522 | H | SC$_3$H$_7$-n | CH$_2$OC$_2$H$_4$OC$_2$H$_4$OCH$_3$ | |
| 3.1523 | H | SO$_2$CH$_3$ | CH$_2$OC$_2$H$_4$OC$_2$H$_4$OCH$_3$ | |
| 3.1524 | H | SO$_2$C$_2$H$_5$ | CH$_2$OC$_2$H$_4$OC$_2$H$_4$OCH$_3$ | |
| 3.1525 | H | NO$_2$ | CH$_2$OC$_2$H$_4$OC$_2$H$_4$OCH$_3$ | |
| 3.1526 | H | CN | CH$_2$OC$_2$H$_4$OC$_2$H$_4$OCH$_3$ | |
| 3.1527 | H | CH$_2$OH | CH$_2$OC$_2$H$_4$OC$_2$H$_4$OCH$_3$ | |
| 3.1528 | H | CH$_2$CH$_2$OH | CH$_2$OC$_2$H$_4$OC$_2$H$_4$OCH$_3$ | |
| 3.1529 | H | CH$_2$CH$_2$CH$_2$OH | CH$_2$OC$_2$H$_4$OC$_2$H$_4$OCH$_3$ | |
| 3.1530 | H | C$_6$H$_5$ | CH$_2$OC$_2$H$_4$OC$_2$H$_4$OCH$_3$ | |
| 3.1531 | H | CH$_2$Cl | CH$_2$OC$_2$H$_4$OC$_2$H$_4$OCH$_3$ | |
| 3.1532 | H | CH$_2$CH$_2$Cl | CH$_2$OC$_2$H$_4$OC$_2$H$_4$OCH$_3$ | |
| 3.1533 | H | CH$_2$CH$_2$CH$_2$Cl | CH$_2$OC$_2$H$_4$OC$_2$H$_4$OCH$_3$ | |

TABLE 3.16

| No. | X | Y | Z | phys. data |
|---|---|---|---|---|
| 3.1601 | H | H | CH$_2$OCH$_2$CONH$_2$ | |
| 3.1602 | H | CH$_3$ | CH$_2$OCH$_2$CONH$_2$ | |
| 3.1603 | H | C$_2$H$_5$ | CH$_2$OCH$_2$CONH$_2$ | |
| 3.1604 | H | C$_3$H$_7$ | CH$_2$OCH$_2$CONH$_2$ | |
| 3.1605 | H | OCH$_3$ | CH$_2$OCH$_2$CONH$_2$ | |
| 3.1606 | H | OC$_2$H$_5$ | CH$_2$OCH$_2$CONH$_2$ | |
| 3.1607 | H | OCH$_2$CH=CH$_2$ | CH$_2$OCH$_2$CONH$_2$ | |
| 3.1608 | H | OCH$_2$CH=CHCH$_3$ | CH$_2$OCH$_2$CONH$_2$ | |
| 3.1609 | H | OCH$_2$C(Cl)=CH$_2$ | CH$_2$OCH$_2$CONH$_2$ | |
| 3.1610 | H | OCH$_2$CH=CHCl | CH$_2$OCH$_2$CONH$_2$ | |
| 3.1611 | H | OCH$_2$C≡CH | CH$_2$OCH$_2$CONH$_2$ | |
| 3.1612 | H | OCHF$_2$ | CH$_2$OCH$_2$CONH$_2$ | |
| 3.1613 | H | OCF$_3$ | CH$_2$OCH$_2$CONH$_2$ | |

TABLE 3.16-continued

| No. | X | Y | Z |
|---|---|---|---|
| 3.1614 | H | OCF₂CHFCF₃ | CH₂OCH₂CONH₂ |
| 3.1615 | H | OC₆H₅ | CH₂OCH₂CONH₂ |
| 3.1616 | H | CF₃ | CH₂OCH₂CONH₂ |
| 3.1617 | H | Br | CH₂OCH₂CONH₂ |
| 3.1618 | H | Cl | CH₂OCH₂CONH₂ |
| 3.1619 | H | F | CH₂OCH₂CONH₂ |
| 3.1620 | H | SCH₃ | CH₂OCH₂CONH₂ |
| 3.1621 | H | SC₂H₅ | CH₂OCH₂CONH₂ |
| 3.1622 | H | SC₃H₇-n | CH₂OCH₂CONH₂ |
| 3.1623 | H | SO₂CH₃ | CH₂OCH₂CONH₂ |
| 3.1624 | H | SO₂C₂H₅ | CH₂OCH₂CONH₂ |
| 3.1625 | H | NO₂ | CH₂OCH₂CONH₂ |
| 3.1626 | H | CN | CH₂OCH₂CONH₂ |
| 3.1627 | H | CH₂OH | CH₂OCH₂CONH₂ |
| 3.1628 | H | CH₂CH₂OH | CH₂OCH₂CONH₂ |
| 3.1629 | H | CH₂CH₂CH₂OH | CH₂OCH₂CONH₂ |
| 3.1630 | H | C₆H₅ | CH₂OCH₂CONH₂ |
| 3.1631 | H | CH₂Cl | CH₂OCH₂CONH₂ |
| 3.1632 | H | CH₂CH₂Cl | CH₂OCH₂CONH₂ |
| 3.1633 | H | CH₂CH₂CH₂Cl | CH₂OCH₂CONH₂ |

EXAMPLE 11

Preparation of
5-ethyl-2-(5-isopropyl-5-methyl-4-oxo-imidazolin-2-yl)-6-methoxymethylpyridine-3-carboxylic acid methyl ester

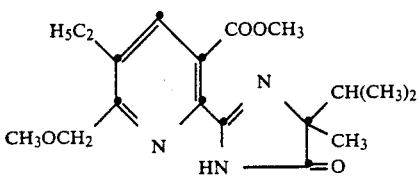

3.4 g of 7-ethyl-8-methoxymethyl-2-isopropyl-2-methyl-2H-imidazo[1,2:1′,2′]pyrrolo[3,4-b]pyridine-3,5-dione are added at room temperature to a mixture of 0.37 g of methanol and 60 g of triethylamine in 30 ml of methylene chloride while stirring. When a homogeneous solution has been obtained this solution is left to stand for 2 days at room temperature. It is then concentrated by evaporation and the residue is chromatographed over a column of silica gel using ether. After evaporation of the ether 2.8 g of crystalline title substance having a melting point of 87°-90° C. remain.

The esters of Tables 4.00 to 4.016 of formula I are prepared analogously to Example 11

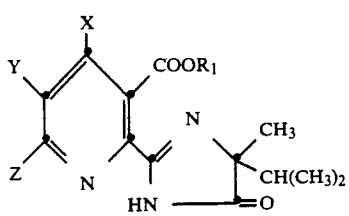

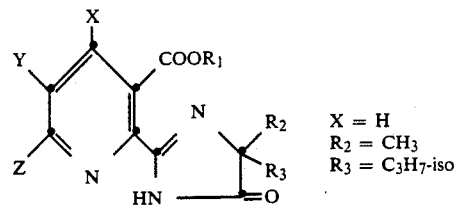

$X = H$
$R_2 = CH_3$
$R_3 = C_3H_7$-iso

TABLE 4.00

| No. | X | Y | R₁ | Z | phys. data |
|---|---|---|---|---|---|
| 4.0001 | H | H | CH₃ | C₃H₅(cyclo) | |
| 4.0002 | H | CH₃ | CH₃ | C₃H₅(cyclo) | m.p. 184–187° C. |
| 4.0003 | H | C₂H₅ | CH₃ | C₃H₅(cyclo) | m.p. 167–168° C. |
| 4.0004 | H | C₃H₇ | CH₃ | C₃H₅(cyclo) | |
| 4.0005 | H | OCH₃ | CH₃ | C₃H₅(cyclo) | |
| 4.0006 | H | OC₂H₅ | CH₃ | C₃H₅(cyclo) | |
| 4.0007 | H | OCH₂CH=CH₂ | CH₃ | C₃H₅(cyclo) | |
| 4.0008 | H | OCH₂CH=CHCH₃ | CH₃ | C₃H₅(cyclo) | |
| 4.0009 | H | OCH₂C(Cl)=CH₂ | CH₃ | C₃H₅(cyclo) | |
| 4.0010 | H | OCH₂CH=CHCl | CH₃ | C₃H₅(cyclo) | |
| 4.0011 | H | OCH₂C≡CH | CH₃ | C₃H₅(cyclo) | |
| 4.0012 | H | OCHF₂ | CH₃ | C₃H₅(cyclo) | |
| 4.0013 | H | OCF₃ | CH₃ | C₃H₅(cyclo) | |
| 4.0014 | H | OCF₂CHFCF₃ | CH₃ | C₃H₅(cyclo) | |
| 4.0015 | H | OC₆H₅ | CH₃ | C₃H₅(cyclo) | |
| 4.0016 | H | CF₃ | CH₃ | C₃H₅(cyclo) | |
| 4.0017 | H | Br | CH₃ | C₃H₅(cyclo) | |
| 4.0018 | H | Cl | CH₃ | C₃H₅(cyclo) | |
| 4.0019 | H | F | CH₃ | C₃H₅(cyclo) | |
| 4.0020 | H | SCH₃ | CH₃ | C₃H₅(cyclo) | |
| 4.0021 | H | SC₂H₅ | CH₃ | C₃H₅(cyclo) | |
| 4.0022 | H | SC₃H₇-n | CH₃ | C₃H₅(cyclo) | |
| 4.0023 | H | SO₂CH₃ | CH₃ | C₃H₅(cyclo) | |
| 4.0024 | H | SO₂C₂H₅ | CH₃ | C₃H₅(cyclo) | |
| 4.0025 | H | NO₂ | CH₃ | C₃H₅(cyclo) | |
| 4.0026 | H | CN | CH₃ | C₃H₅(cyclo) | |
| 4.0027 | H | CH₂OH | CH₃ | C₃H₅(cyclo) | |
| 4.0028 | H | CH₂CH₂OH | CH₃ | C₃H₅(cyclo) | |
| 4.0029 | H | CH₂CH₂CH₂OH | CH₃ | C₃H₅(cyclo) | |
| 4.0030 | H | C₆H₅ | CH₃ | C₃H₅(cyclo) | |
| 4.0031 | H | CH₂Cl | CH₃ | C₃H₅(cyclo) | |
| 4.0032 | H | CH₂CH₂Cl | CH₃ | C₃H₅(cyclo) | |
| 4.0033 | H | CH₂CH₂CH₂Cl | CH₃ | C₃H₅(cyclo) | |

TABLE 4.01

| No. | X | Y | R₁ | Z | phys. data |
|---|---|---|---|---|---|
| 4.0101 | H | H | C₂H₅ | C₄H₇(cyclo) | |
| 4.0102 | H | CH₃ | C₂H₅ | C₄H₇(cyclo) | |
| 4.0103 | H | C₂H₅ | C₂H₅ | C₄H₇(cyclo) | |
| 4.0140 | H | C₃H₇ | C₂H₅ | C₄H₇(cyclo) | |
| 4.0105 | H | OCH₃ | C₂H₅ | C₄H₇(cyclo) | |
| 4.0106 | H | OC₂H₅ | C₂H₅ | C₄H₇(cyclo) | |
| 4.0107 | H | OCH₂CH=CH₂ | C₂H₅ | C₄H₇(cyclo) | |
| 4.0108 | H | OCH₂CH=CHCH₃ | C₂H₅ | C₄H₇(cyclo) | |
| 4.0109 | H | OCH₂C(Cl)=CH₂ | C₂H₅ | C₄H₇(cyclo) | |
| 4.0110 | H | OCH₂CH=CHCl | C₂H₅ | C₄H₇(cyclo) | |
| 4.0111 | H | OCH₂C≡CH | C₂H₅ | C₄H₇(cyclo) | |
| 4.0112 | H | OCHF₂ | C₂H₅ | C₄H₇(cyclo) | |
| 4.0113 | H | OCF₃ | C₂H₅ | C₄H₇(cyclo) | |
| 4.0114 | H | OCF₂CHFCF₃ | C₂H₅ | C₄H₇(cyclo) | |
| 4.0115 | H | OC₆H₅ | C₂H₅ | C₄H₇(cyclo) | |
| 4.0116 | H | CF₃ | C₂H₅ | C₄H₇(cyclo) | |
| 4.0117 | H | Br | C₂H₅ | C₄H₇(cyclo) | |
| 4.0118 | H | Cl | C₂H₅ | C₄H₇(cyclo) | |
| 4.0119 | H | F | C₂H₅ | C₄H₇(cyclo) | |
| 4.0120 | H | SCH₃ | C₂H₅ | C₄H₇(cyclo) | |
| 4.0121 | H | SC₂H₅ | C₂H₅ | C₄H₇(cyclo) | |
| 4.0122 | H | SC₃H₇-n | C₂H₅ | C₄H₇(cyclo) | |
| 4.0123 | H | SO₂CH₃ | C₂H₅ | C₄H₇(cyclo) | |
| 4.0124 | H | SO₂C₂H₅ | C₂H₅ | C₄H₇(cyclo) | |
| 4.0125 | H | NO₂ | C₂H₅ | C₄H₇(cyclo) | |
| 4.0126 | H | CN | C₂H₅ | C₄H₇(cyclo) | |

TABLE 4.01-continued

| No. | X | Y | $R_1$ | Z | phys. data |
|---|---|---|---|---|---|
| 4.0127 | H | $CH_2OH$ | $C_2H_5$ | $C_4H_7$(cyclo) | |
| 4.0128 | H | $CH_2CH_2OH$ | $C_2H_5$ | $C_4H_7$(cyclo) | |
| 4.0129 | H | $CH_2CH_2CH_2OH$ | $C_2H_5$ | $C_4H_7$(cyclo) | |
| 4.0130 | H | $C_6H_5$ | $C_2H_5$ | $C_4H_7$(cyclo) | |
| 4.0131 | H | $CH_2Cl$ | $C_2H_5$ | $C_4H_7$(cyclo) | |
| 4.0132 | H | $CH_2CH_2Cl$ | $C_2H_5$ | $C_4H_7$(cyclo) | |
| 4.0133 | H | $CH_2CH_2CH_2Cl$ | $C_2H_5$ | $C_4H_7$(cyclo) | |

TABLE 4.02

| No. | X | Y | $R_1$ | Z | phys. data |
|---|---|---|---|---|---|
| 4.0201 | H | H | $CH_3$ | $C_5H_9$(cyclo) | |
| 4.0202 | H | $CH_3$ | $CH_3$ | $C_5H_9$(cyclo) | |
| 4.0203 | H | $C_2H_5$ | $CH_3$ | $C_5H_9$(cyclo) | |
| 4.0204 | H | $C_3H_7$ | $CH_3$ | $C_5H_9$(cyclo) | |
| 4.0205 | H | $OCH_3$ | $CH_3$ | $C_5H_9$(cyclo) | |
| 4.0206 | H | $OC_2H_5$ | $CH_3$ | $C_5H_9$(cyclo) | |
| 4.0207 | H | $OCH_2CH=CH_2$ | $CH_3$ | $C_5H_9$(cyclo) | |
| 4.0208 | H | $OCH_2CH=CHCH_3$ | $CH_3$ | $C_5H_9$(cyclo) | |
| 4.0209 | H | $OCH_2C(Cl)=CH_2$ | $CH_3$ | $C_5H_9$(cyclo) | |
| 4.0210 | H | $OCH_2CH=CHCl$ | $CH_3$ | $C_5H_9$(cyclo) | |
| 4.0211 | H | $OCH_2C\equiv CH$ | $CH_3$ | $C_5H_9$(cyclo) | |
| 4.0212 | H | $OCHF_2$ | $CH_3$ | $C_5H_9$(cyclo) | |
| 4.0213 | H | $OCF_3$ | $CH_3$ | $C_5H_9$(cyclo) | |
| 4.0214 | H | $OCF_2CHFCF_3$ | $CH_3$ | $C_5H_9$(cyclo) | |
| 4.0215 | H | $OC_6H_5$ | $CH_3$ | $C_5H_9$(cyclo) | |
| 4.0216 | H | $CF_3$ | $CH_3$ | $C_5H_9$(cyclo) | |
| 4.0217 | H | Br | $CH_3$ | $C_5H_9$(cyclo) | |
| 4.0218 | H | Cl | $CH_3$ | $C_5H_9$(cyclo) | |
| 4.0219 | H | F | $CH_3$ | $C_5H_9$(cyclo) | |
| 4.0220 | H | $SCH_3$ | $CH_3$ | $C_5H_9$(cyclo) | |
| 4.0221 | H | $SC_2H_5$ | $CH_3$ | $C_5H_9$(cyclo) | |
| 4.0222 | H | $SC_3H_7$-n | $CH_3$ | $C_5H_9$(cyclo) | |
| 4.0223 | H | $SO_2CH_3$ | $CH_3$ | $C_5H_9$(cyclo) | |
| 4.0224 | H | $SO_2C_2H_5$ | $CH_3$ | $C_5H_9$(cyclo) | |
| 4.0225 | H | $NO_2$ | $CH_3$ | $C_5H_9$(cyclo) | |
| 4.0226 | H | CN | $CH_3$ | $C_5H_9$(cyclo) | |
| 4.0227 | H | $CH_2OH$ | $CH_3$ | $C_5H_9$(cyclo) | |
| 4.0228 | H | $CH_2CH_2OH$ | $CH_3$ | $C_5H_9$(cyclo) | |
| 4.0229 | H | $CH_2CH_2CH_2OH$ | $CH_3$ | $C_5H_9$(cyclo) | |
| 4.0230 | H | $C_6H_5$ | $CH_3$ | $C_5H_9$(cyclo) | |
| 4.0231 | H | $CH_2Cl$ | $CH_3$ | $C_5H_9$(cyclo) | |
| 4.0232 | H | $CH_2CH_2Cl$ | $CH_3$ | $C_5H_9$(cyclo) | |
| 4.0233 | H | $CH_2CH_2CH_2Cl$ | $CH_3$ | $C_5H_9$(cyclo) | |

TABLE 4.03

| No. | X | Y | $R_1$ | Z | phys. data |
|---|---|---|---|---|---|
| 4.0301 | H | H | $CH_3$ | $C_6H_{11}$(cyclo) | |
| 4.0302 | H | $CH_3$ | $CH_3$ | $C_6H_{11}$(cyclo) | |
| 4.0303 | H | $C_2H_5$ | $CH_3$ | $C_6H_{11}$(cyclo) | |
| 4.0304 | H | $C_3H_7$ | $CH_3$ | $C_6H_{11}$(cyclo) | |
| 4.0305 | H | $OCH_3$ | $CH_3$ | $C_6H_{11}$(cyclo) | |
| 4.0306 | H | $OC_2H_5$ | $CH_3$ | $C_6H_{11}$(cyclo) | |
| 4.0307 | H | $OCH_2CH=CH_2$ | $CH_3$ | $C_6H_{11}$(cyclo) | |
| 4.0308 | H | $OCH_2CH=CHCH_3$ | $CH_3$ | $C_6H_{11}$(cyclo) | |
| 4.0309 | H | $OCH_2C(Cl)=CH_2$ | $CH_3$ | $C_6H_{11}$(cyclo) | |
| 4.0310 | H | $OCH_2CH=CHCl$ | $CH_3$ | $C_6H_{11}$(cyclo) | |
| 4.0311 | H | $OCH_2C\equiv CH$ | $CH_3$ | $C_6H_{11}$(cyclo) | |
| 4.0312 | H | $OCHF_2$ | $CH_3$ | $C_6H_{11}$(cyclo) | |
| 4.0313 | H | $OCF_3$ | $CH_3$ | $C_6H_{11}$(cyclo) | |
| 4.0314 | H | $OCF_2CHFCF_3$ | $CH_3$ | $C_6H_{11}$(cyclo) | |
| 4.0315 | H | $OC_6H_5$ | $CH_3$ | $C_6H_{11}$(cyclo) | |
| 4.0316 | H | $CF_3$ | $CH_3$ | $C_6H_{11}$(cyclo) | |
| 4.0317 | H | Br | $CH_3$ | $C_6H_{11}$(cyclo) | |
| 4.0318 | H | Cl | $CH_3$ | $C_6H_{11}$(cyclo) | |
| 4.0319 | H | F | $CH_3$ | $C_6H_{11}$(cyclo) | |
| 4.0320 | H | $SCH_3$ | $CH_3$ | $C_6H_{11}$(cyclo) | |
| 4.0321 | H | $SC_2H_5$ | $CH_3$ | $C_6H_{11}$(cyclo) | |
| 4.0322 | H | $SC_3H_7$-n | $CH_3$ | $C_6H_{11}$(cyclo) | |
| 4.0323 | H | $SO_2CH_3$ | $CH_3$ | $C_6H_{11}$(cyclo) | |
| 4.0324 | H | $SO_2C_2H_5$ | $CH_3$ | $C_6H_{11}$(cyclo) | |
| 4.0325 | H | $NO_2$ | $CH_3$ | $C_6H_{11}$(cyclo) | |
| 4.0326 | H | CN | $CH_3$ | $C_6H_{11}$(cyclo) | |
| 4.0327 | H | $CH_2OH$ | $CH_3$ | $C_6H_{11}$(cyclo) | |

TABLE 4.03-continued

| No. | X | Y | $R_1$ | Z | phys. data |
|---|---|---|---|---|---|
| 4.0328 | H | $CH_2CH_2OH$ | $CH_3$ | $C_6H_{11}$(cyclo) | |
| 4.0329 | H | $CH_2CH_2CH_2OH$ | $CH_3$ | $C_6H_{11}$(cyclo) | |
| 4.0330 | H | $C_6H_5$ | $CH_3$ | $C_6H_{11}$(cyclo) | |
| 4.0331 | H | $CH_2Cl$ | $CH_3$ | $C_6H_{11}$(cyclo) | |
| 4.0332 | H | $CH_2CH_2Cl$ | $CH_3$ | $C_6H_{11}$(cyclo) | |
| 4.0333 | H | $CH_2CH_2CH_2Cl$ | $CH_3$ | $C_6H_{11}$(cyclo) | |

TABLE 4.04

| No. | X | Y | $R_1$ | Z | phys. data |
|---|---|---|---|---|---|
| 4.0401 | H | H | $CH_3$ | $CH_2OCH_3$ | |
| 4.0402 | H | $CH_3$ | $CH_3$ | $CH_2OCH_3$ | |
| 4.0403 | H | $C_2H_5$ | $CH_3$ | $CH_2OCH_3$ | m.p. 87–90° C. |
| 4.0404 | H | $C_3H_7$ | $CH_3$ | $CH_2OCH_3$ | |
| 4.0405 | H | $OCH_3$ | $CH_3$ | $CH_2OCH_3$ | |
| 4.0406 | H | $OC_2H_5$ | $CH_3$ | $CH_2OCH_3$ | |
| 4.0407 | H | $OCH_2CH=CH_2$ | $CH_3$ | $CH_2OCH_3$ | |
| 4.0408 | H | $OCH_2CH=CHCH_3$ | $CH_3$ | $CH_2OCH_3$ | |
| 4.0409 | H | $OCH_2C(Cl)=CH_2$ | $CH_3$ | $CH_2OCH_3$ | |
| 4.0410 | H | $OCH_2CH=CHCl$ | $CH_3$ | $CH_2OCH_3$ | |
| 4.0411 | H | $OCH_2C\equiv CH$ | $CH_3$ | $CH_2OCH_3$ | |
| 4.0412 | H | $OCHF_2$ | $CH_3$ | $CH_2OCH_3$ | |
| 4.0413 | H | $OCF_3$ | $CH_3$ | $CH_2OCH_3$ | |
| 4.0414 | H | $OCF_2CHFCF_3$ | $CH_3$ | $CH_2OCH_3$ | |
| 4.0415 | H | $OC_6H_5$ | $CH_3$ | $CH_2OCH_3$ | |
| 4.0416 | H | $CF_3$ | $CH_3$ | $CH_2OCH_3$ | |
| 4.0417 | H | Br | $CH_3$ | $CH_2OCH_3$ | |
| 4.0418 | H | Cl | $CH_3$ | $CH_2OCH_3$ | |
| 4.0419 | H | F | $CH_3$ | $CH_2OCH_3$ | |
| 4.0420 | H | $SCH_3$ | $CH_3$ | $CH_2OCH_3$ | |
| 4.0421 | H | $SC_2H_5$ | $CH_3$ | $CH_2OCH_3$ | |
| 4.0422 | H | $SC_3H_7$-n | $CH_3$ | $CH_2OCH_3$ | |
| 4.0423 | H | $SO_2CH_3$ | $CH_3$ | $CH_2OCH_3$ | |
| 4.0424 | H | $SO_2C_2H_5$ | $CH_3$ | $CH_2OCH_3$ | |
| 4.0425 | H | $NO_2$ | $CH_3$ | $CH_2OCH_3$ | |
| 4.0426 | H | CN | $CH_3$ | $CH_2OCH_3$ | |
| 4.0427 | H | $CH_2OH$ | $CH_3$ | $CH_2OCH_3$ | |
| 4.0428 | H | $CH_2CH_2OH$ | $CH_3$ | $CH_2OCH_3$ | |
| 4.0429 | H | $CH_2CH_2CH_2OH$ | $CH_3$ | $CH_2OCH_3$ | |
| 4.0430 | H | $C_6H_5$ | $CH_3$ | $CH_2OCH_3$ | |
| 4.0431 | H | $CH_2Cl$ | $CH_3$ | $CH_2OCH_3$ | |
| 4.0432 | H | $CH_2CH_2Cl$ | $CH_3$ | $CH_2OCH_3$ | |
| 4.0433 | H | $CH_2CH_2CH_2Cl$ | $CH_3$ | $CH_2OCH_3$ | |

TABLE 4.05

| No. | X | Y | $R_1$ | Z | phys. data |
|---|---|---|---|---|---|
| 4.0501 | H | H | $CH_3$ | $CH(CH_3)OCH_3$ | |
| 4.0502 | H | $CH_3$ | $CH_3$ | $CH(CH_3)OCH_3$ | |
| 4.0503 | H | $C_2H_5$ | $CH_3$ | $CH(CH_3)OCH_3$ | |
| 4.0504 | H | $C_3H_7$ | $CH_3$ | $CH(CH_3)OCH_3$ | |
| 4.0505 | H | $OCH_3$ | $CH_3$ | $CH(CH_3)OCH_3$ | |
| 4.0506 | H | $OC_2H_5$ | $CH_3$ | $CH(CH_3)OCH_3$ | |
| 4.0507 | H | $OCH_2CH=CH_2$ | $CH_3$ | $CH(CH_3)OCH_3$ | |
| 4.0508 | H | $OCH_2CH=CHCH_3$ | $CH_3$ | $CH(CH_3)OCH_3$ | |
| 4.0509 | H | $OCH_2C(Cl)=CH_2$ | $CH_3$ | $CH(CH_3)OCH_3$ | |
| 4.0510 | H | $OCH_2CH=CHCl$ | $CH_3$ | $CH(CH_3)OCH_3$ | |
| 4.0511 | H | $OCH_2C\equiv CH$ | $CH_3$ | $CH(CH_3)OCH_3$ | |
| 4.0512 | H | $OCHF_2$ | $CH_3$ | $CH(CH_3)OCH_3$ | |
| 4.0513 | H | $OCF_3$ | $CH_3$ | $CH(CH_3)OCH_3$ | |
| 4.0514 | H | $OCF_2CHFCF_3$ | $CH_3$ | $CH(CH_3)OCH_3$ | |
| 4.0515 | H | $OC_6H_5$ | $CH_3$ | $CH(CH_3)OCH_3$ | |
| 4.0516 | H | $CF_3$ | $CH_3$ | $CH(CH_3)OCH_3$ | |
| 4.0517 | H | Br | $CH_3$ | $CH(CH_3)OCH_3$ | |
| 4.0518 | H | Cl | $CH_3$ | $CH(CH_3)OCH_3$ | |
| 4.0519 | H | F | $CH_3$ | $CH(CH_3)OCH_3$ | |
| 4.0520 | H | $SCH_3$ | $CH_3$ | $CH(CH_3)OCH_3$ | |
| 4.0521 | H | $SC_2H_5$ | $CH_3$ | $CH(CH_3)OCH_3$ | |
| 4.0522 | H | $SC_3H_7$-n | $CH_3$ | $CH(CH_3)OCH_3$ | |
| 4.0523 | H | $SO_2CH_3$ | $CH_3$ | $CH(CH_3)OCH_3$ | |
| 4.0524 | H | $SO_2C_2H_5$ | $CH_3$ | $CH(CH_3)OCH_3$ | |
| 4.0525 | H | $NO_2$ | $CH_3$ | $CH(CH_3)OCH_3$ | |
| 4.0526 | H | CN | $CH_3$ | $CH(CH_3)OCH_3$ | |
| 4.0527 | H | $CH_2OH$ | $CH_3$ | $CH(CH_3)OCH_3$ | |
| 4.0528 | H | $CH_2CH_2OH$ | $CH_3$ | $CH(CH_3)OCH_3$ | |

TABLE 4.05-continued

| No. | X | Y | R$_1$ | Z | phys. data |
|---|---|---|---|---|---|
| 4.0529 | H | CH$_2$CH$_2$CH$_2$OH | CH$_3$ | CH(CH$_3$)OCH$_3$ | |
| 4.0530 | H | C$_6$H$_5$ | CH$_3$ | CH(CH$_3$)OCH$_3$ | |
| 4.0531 | H | CH$_2$Cl | CH$_3$ | CH(CH$_3$)OCH$_3$ | |
| 4.0532 | H | CH$_2$CH$_2$Cl | CH$_3$ | CH(CH$_3$)OCH$_3$ | |
| 4.0533 | H | CH$_2$CH$_2$CH$_2$Cl | CH$_3$ | CH(CH$_3$)OCH$_3$ | |

TABLE 4.06

| No. | X | Y | R$_1$ | Z | phys. data |
|---|---|---|---|---|---|
| 4.0601 | H | H | CH$_3$ | CH$_2$OC$_2$H$_5$ | |
| 4.0602 | H | CH$_3$ | CH$_3$ | CH$_2$OC$_2$H$_5$ | |
| 4.0603 | H | C$_2$H$_5$ | CH$_3$ | CH$_2$OC$_2$H$_5$ | |
| 4.0604 | H | C$_3$H$_7$ | CH$_3$ | CH$_2$OC$_2$H$_5$ | |
| 4.0605 | H | OCH$_3$ | CH$_3$ | CH$_2$OC$_2$H$_5$ | |
| 4.0606 | H | OC$_2$H$_5$ | CH$_3$ | CH$_2$OC$_2$H$_5$ | |
| 4.0607 | H | OCH$_2$CH=CH$_2$ | CH$_3$ | CH$_2$OC$_2$H$_5$ | |
| 4.0608 | H | OCH$_2$CH=CHCH$_3$ | CH$_3$ | CH$_2$OC$_2$H$_5$ | |
| 4.0609 | H | OCH$_2$C(Cl)=CH$_2$ | CH$_3$ | CH$_2$OC$_2$H$_5$ | |
| 4.0610 | H | OCH$_2$CH=CHCl | CH$_3$ | CH$_2$OC$_2$H$_5$ | |
| 4.0611 | H | OCH$_2$C≡CH | CH$_3$ | CH$_2$OC$_2$H$_5$ | |
| 4.0612 | H | OCHF$_2$ | CH$_3$ | CH$_2$OC$_2$H$_5$ | |
| 4.0613 | H | OCF$_3$ | CH$_3$ | CH$_2$OC$_2$H$_5$ | |
| 4.0614 | H | OCF$_2$CHFCF$_3$ | CH$_3$ | CH$_2$OC$_2$H$_5$ | |
| 4.0615 | H | OC$_6$H$_5$ | CH$_3$ | CH$_2$OC$_2$H$_5$ | |
| 4.0616 | H | CF$_3$ | CH$_3$ | CH$_2$OC$_2$H$_5$ | |
| 4.0617 | H | Br | CH$_3$ | CH$_2$OC$_2$H$_5$ | |
| 4.0618 | H | Cl | CH$_3$ | CH$_2$OC$_2$H$_5$ | |
| 4.0619 | H | F | CH$_3$ | CH$_2$OC$_2$H$_5$ | |
| 4.0620 | H | SCH$_3$ | CH$_3$ | CH$_2$OC$_2$H$_5$ | |
| 4.0621 | H | SC$_2$H$_5$ | CH$_3$ | CH$_2$OC$_2$H$_5$ | |
| 4.0622 | H | SC$_3$H$_7$-n | CH$_3$ | CH$_2$OC$_2$H$_5$ | |
| 4.0623 | H | SO$_2$CH$_3$ | CH$_3$ | CH$_2$OC$_2$H$_5$ | |
| 4.0624 | H | SO$_2$C$_2$H$_5$ | CH$_3$ | CH$_2$OC$_2$H$_5$ | |
| 4.0625 | H | NO$_2$ | CH$_3$ | CH$_2$OC$_2$H$_5$ | |
| 4.0626 | H | CN | CH$_3$ | CH$_2$OC$_2$H$_5$ | |
| 4.0627 | H | CH$_2$OH | CH$_3$ | CH$_2$OC$_2$H$_5$ | |
| 4.0628 | H | CH$_2$CH$_2$OH | CH$_3$ | CH$_2$OC$_2$H$_5$ | |
| 4.0629 | H | CH$_2$CH$_2$CH$_2$OH | CH$_3$ | CH$_2$OC$_2$H$_5$ | |
| 4.0630 | H | C$_6$H$_5$ | CH$_3$ | CH$_2$OC$_2$H$_5$ | |
| 4.0631 | H | CH$_2$Cl | CH$_3$ | CH$_2$OC$_2$H$_5$ | |
| 4.0632 | H | CH$_2$CH$_2$Cl | CH$_3$ | CH$_2$OC$_2$H$_5$ | |
| 4.0633 | H | CH$_2$CH$_2$CH$_2$Cl | CH$_3$ | CH$_2$OC$_2$H$_5$ | |

TABLE 4.07

| No. | X | Y | R$_1$ | Z | phys. data |
|---|---|---|---|---|---|
| 4.0701 | H | H | CH$_3$ | CH(CH$_3$)OC$_2$H$_5$ | |
| 4.0702 | H | CH$_3$ | CH$_3$ | CH(CH$_3$)OC$_2$H$_5$ | |
| 4.0703 | H | C$_2$H$_5$ | CH$_3$ | CH(CH$_3$)OC$_2$H$_5$ | |
| 4.0704 | H | C$_3$H$_7$ | CH$_3$ | CH(CH$_3$)OC$_2$H$_5$ | |
| 4.0705 | H | OCH$_3$ | CH$_3$ | CH(CH$_3$)OC$_2$H$_5$ | |
| 4.0706 | H | OC$_2$H$_5$ | CH$_3$ | CH(CH$_3$)OC$_2$H$_5$ | |
| 4.0707 | H | OCH$_2$CH=CH$_2$ | CH$_3$ | CH(CH$_3$)OC$_2$H$_5$ | |
| 4.0708 | H | OCH$_2$CH=CHCH$_3$ | CH$_3$ | CH(CH$_3$)OC$_2$H$_5$ | |
| 4.0709 | H | OCH$_2$C(Cl)=CH$_2$ | CH$_3$ | CH(CH$_3$)OC$_2$H$_5$ | |
| 4.0710 | H | OCH$_2$CH=CHCl | CH$_3$ | CH(CH$_3$)OC$_2$H$_5$ | |
| 4.0711 | H | OCH$_2$C≡CH | CH$_3$ | CH(CH$_3$)OC$_2$H$_5$ | |
| 4.0712 | H | OCHF$_2$ | CH$_3$ | CH(CH$_3$)OC$_2$H$_5$ | |
| 4.0713 | H | OCF$_3$ | CH$_3$ | CH(CH$_3$)OC$_2$H$_5$ | |
| 4.0714 | H | OCF$_2$CHFCF$_3$ | CH$_3$ | CH(CH$_3$)OC$_2$H$_5$ | |
| 4.0715 | H | OC$_6$H$_5$ | CH$_3$ | CH(CH$_3$)OC$_2$H$_5$ | |
| 4.0716 | H | CF$_3$ | CH$_3$ | CH(CH$_3$)OC$_2$H$_5$ | |
| 4.0717 | H | Br | CH$_3$ | CH(CH$_3$)OC$_2$H$_5$ | |
| 4.0718 | H | Cl | CH$_3$ | CH(CH$_3$)OC$_2$H$_5$ | |
| 4.0719 | H | F | CH$_3$ | CH(CH$_3$)OC$_2$H$_5$ | |
| 4.0720 | H | SCH$_3$ | CH$_3$ | CH(CH$_3$)OC$_2$H$_5$ | |
| 4.0721 | H | SC$_2$H$_5$ | CH$_3$ | CH(CH$_3$)OC$_2$H$_5$ | |
| 4.0722 | H | SC$_3$H$_7$-n | CH$_3$ | CH(CH$_3$)OC$_2$H$_5$ | |
| 4.0723 | H | SO$_2$CH$_3$ | CH$_3$ | CH(CH$_3$)OC$_2$H$_5$ | |
| 4.0724 | H | SO$_2$C$_2$H$_5$ | CH$_3$ | CH(CH$_3$)OC$_2$H$_5$ | |
| 4.0725 | H | NO$_2$ | CH$_3$ | CH(CH$_3$)OC$_2$H$_5$ | |
| 4.0726 | H | CN | CH$_3$ | CH(CH$_3$)OC$_2$H$_5$ | |
| 4.0727 | H | CH$_2$OH | CH$_3$ | CH(CH$_3$)OC$_2$H$_5$ | |
| 4.0728 | H | CH$_2$CH$_2$OH | CH$_3$ | CH(CH$_3$)OC$_2$H$_5$ | |
| 4.0729 | H | CH$_2$CH$_2$CH$_2$OH | CH$_3$ | CH(CH$_3$)OC$_2$H$_5$ | |

TABLE 4.07-continued

| No. | X | Y | R$_1$ | Z | phys. data |
|---|---|---|---|---|---|
| 4.0730 | H | C$_6$H$_5$ | CH$_3$ | CH(CH$_3$)OC$_2$H$_5$ | |
| 4.0731 | H | CH$_2$Cl | CH$_3$ | CH(CH$_3$)OC$_2$H$_5$ | |
| 4.0732 | H | CH$_2$CH$_2$Cl | CH$_3$ | CH(CH$_3$)OC$_2$H$_5$ | |
| 4.0733 | H | CH$_2$CH$_2$CH$_2$Cl | CH$_3$ | CH(CH$_3$)OC$_2$H$_5$ | |

TABLE 4.08

| No. | X | Y | R$_1$ | Z | phys. data |
|---|---|---|---|---|---|
| 4.0801 | H | H | CH$_3$ | C(CH$_3$)$_2$OCH$_3$ | |
| 4.0802 | H | CH$_3$ | CH$_3$ | C(CH$_3$)$_2$OCH$_3$ | |
| 4.0803 | H | C$_2$H$_5$ | CH$_3$ | C(CH$_3$)$_2$OCH$_3$ | |
| 4.0804 | H | C$_3$H$_7$ | CH$_3$ | C(CH$_3$)$_2$OCH$_3$ | |
| 4.0805 | H | OCH$_3$ | CH$_3$ | C(CH$_3$)$_2$OCH$_3$ | |
| 4.0806 | H | OC$_2$H$_5$ | CH$_3$ | C(CH$_3$)$_2$OCH$_3$ | |
| 4.0807 | H | OCH$_2$CH=CH$_2$ | CH$_3$ | C(CH$_3$)$_2$OCH$_3$ | |
| 4.0808 | H | OCH$_2$CH=CHCH$_3$ | CH$_3$ | C(CH$_3$)$_2$OCH$_3$ | |
| 4.0809 | H | OCH$_2$C(Cl)=CH$_2$ | CH$_3$ | C(CH$_3$)$_2$OCH$_3$ | |
| 4.0810 | H | OCH$_2$CH=CHCl | CH$_3$ | C(CH$_3$)$_2$OCH$_3$ | |
| 4.0811 | H | OCH$_2$C≡CH | CH$_3$ | C(CH$_3$)$_2$OCH$_3$ | |
| 4.0812 | H | OCHF$_2$ | CH$_3$ | C(CH$_3$)$_2$OCH$_3$ | |
| 4.0813 | H | OCF$_3$ | CH$_3$ | C(CH$_3$)$_2$OCH$_3$ | |
| 4.0814 | H | OCF$_2$CHFCF$_3$ | CH$_3$ | C(CH$_3$)$_2$OCH$_3$ | |
| 4.0815 | H | OC$_6$H$_5$ | CH$_3$ | C(CH$_3$)$_2$OCH$_3$ | |
| 4.0816 | H | CF$_3$ | CH$_3$ | C(CH$_3$)$_2$OCH$_3$ | |
| 4.0817 | H | Br | CH$_3$ | C(CH$_3$)$_2$OCH$_3$ | |
| 4.0818 | H | Cl | CH$_3$ | C(CH$_3$)$_2$OCH$_3$ | |
| 4.0819 | H | F | CH$_3$ | C(CH$_3$)$_2$OCH$_3$ | |
| 4.0820 | H | SCH$_3$ | CH$_3$ | C(CH$_3$)$_2$OCH$_3$ | |
| 4.0821 | H | SC$_2$H$_5$ | CH$_3$ | C(CH$_3$)$_2$OCH$_3$ | |
| 4.0822 | H | SC$_3$H$_7$-n | CH$_3$ | C(CH$_3$)$_2$OCH$_3$ | |
| 4.0823 | H | SO$_2$CH$_3$ | CH$_3$ | C(CH$_3$)$_2$OCH$_3$ | |
| 4.0824 | H | SO$_2$C$_2$H$_5$ | CH$_3$ | C(CH$_3$)$_2$OCH$_3$ | |
| 4.0825 | H | NO$_2$ | CH$_3$ | C(CH$_3$)$_2$OCH$_3$ | |
| 4.0826 | H | CN | CH$_3$ | C(CH$_3$)$_2$OCH$_3$ | |
| 4.0827 | H | CH$_2$OH | CH$_3$ | C(CH$_3$)$_2$OCH$_3$ | |
| 4.0828 | H | CH$_2$CH$_2$OH | CH$_3$ | C(CH$_3$)$_2$OCH$_3$ | |
| 4.0829 | H | CH$_2$CH$_2$CH$_2$OH | CH$_3$ | C(CH$_3$)$_2$OCH$_3$ | |
| 4.0830 | H | C$_6$H$_5$ | CH$_3$ | C(CH$_3$)$_2$OCH$_3$ | |
| 4.0831 | H | CH$_2$Cl | CH$_3$ | C(CH$_3$)$_2$OCH$_3$ | |
| 4.0832 | H | CH$_2$CH$_2$Cl | CH$_3$ | C(CH$_3$)$_2$OCH$_3$ | |
| 4.0833 | H | CH$_2$CH$_2$CH$_2$Cl | CH$_3$ | C(CH$_3$)$_2$OCH$_3$ | |

TABLE 4.09

| No. | X | Y | R$_1$ | Z | phys. data |
|---|---|---|---|---|---|
| 4.0901 | H | H | CH$_3$ | CH$_2$OC$_3$H$_7$ | |
| 4.0902 | H | CH$_3$ | CH$_3$ | CH$_2$OC$_3$H$_7$ | |
| 4.0903 | H | C$_2$H$_5$ | CH$_3$ | CH$_2$OC$_3$H$_7$ | |
| 4.0904 | H | C$_3$H$_7$ | CH$_3$ | CH$_2$OC$_3$H$_7$ | |
| 4.0905 | H | OCH$_3$ | CH$_3$ | CH$_2$OC$_3$H$_7$ | |
| 4.0906 | H | OC$_2$H$_5$ | CH$_3$ | CH$_2$OC$_3$H$_7$ | |
| 4.0907 | H | OCH$_2$CH=CH$_2$ | CH$_3$ | CH$_2$OC$_3$H$_7$ | |
| 4.0908 | H | OCH$_2$CH=CHCH$_3$ | CH$_3$ | CH$_2$OC$_3$H$_7$ | |
| 4.0909 | H | OCH$_2$C(Cl)=CH$_2$ | CH$_3$ | CH$_2$OC$_3$H$_7$ | |
| 4.0910 | H | OCH$_2$CH=CHCl | CH$_3$ | CH$_2$OC$_3$H$_7$ | |
| 4.0911 | H | OCH$_2$C≡CH | CH$_3$ | CH$_2$OC$_3$H$_7$ | |
| 4.0912 | H | OCHF$_2$ | CH$_3$ | CH$_2$OC$_3$H$_7$ | |
| 4.0913 | H | OCF$_3$ | CH$_3$ | CH$_2$OC$_3$H$_7$ | |
| 4.0914 | H | OCF$_2$CHFCF$_3$ | CH$_3$ | CH$_2$OC$_3$H$_7$ | |
| 4.0915 | H | OC$_6$H$_5$ | CH$_3$ | CH$_2$OC$_3$H$_7$ | |
| 4.0916 | H | CF$_3$ | CH$_3$ | CH$_2$OC$_3$H$_7$ | |
| 4.0917 | H | Br | CH$_3$ | CH$_2$OC$_3$H$_7$ | |
| 4.0918 | H | Cl | CH$_3$ | CH$_2$OC$_3$H$_7$ | |
| 4.0919 | H | F | CH$_3$ | CH$_2$OC$_3$H$_7$ | |
| 4.0920 | H | SCH$_3$ | CH$_3$ | CH$_2$OC$_3$H$_7$ | |
| 4.0921 | H | SC$_2$H$_5$ | CH$_3$ | CH$_2$OC$_3$H$_7$ | |
| 4.0922 | H | SC$_3$H$_7$-n | CH$_3$ | CH$_2$OC$_3$H$_7$ | |
| 4.0923 | H | SO$_2$CH$_3$ | CH$_3$ | CH$_2$OC$_3$H$_7$ | |
| 4.0924 | H | SO$_2$C$_2$H$_5$ | CH$_3$ | CH$_2$OC$_3$H$_7$ | |
| 4.0925 | H | NO$_2$ | CH$_3$ | CH$_2$OC$_3$H$_7$ | |
| 4.0926 | H | CN | CH$_3$ | CH$_2$OC$_3$H$_7$ | |
| 4.0927 | H | CH$_2$OH | CH$_3$ | CH$_2$OC$_3$H$_7$ | |
| 4.0928 | H | CH$_2$CH$_2$OH | CH$_3$ | CH$_2$OC$_3$H$_7$ | |
| 4.0929 | H | CH$_2$CH$_2$CH$_2$OH | CH$_3$ | CH$_2$OC$_3$H$_7$ | |
| 4.0930 | H | C$_6$H$_5$ | CH$_3$ | CH$_2$OC$_3$H$_7$ | |

TABLE 4.09-continued

| No. | X | Y | $R_1$ | Z | phys. data |
|---|---|---|---|---|---|
| 4.0931 | H | $CH_2Cl$ | $CH_3$ | $CH_2OC_3H_7$ | |
| 4.0932 | H | $CH_2CH_2Cl$ | $CH_3$ | $CH_2OC_3H_7$ | |
| 4.0933 | H | $CH_2CH_2CH_2Cl$ | $CH_3$ | $CH_2OC_3H_7$ | |

TABLE 4.10

| No. | X | Y | $R_1$ | Z | phys. data |
|---|---|---|---|---|---|
| 4.1001 | H | H | $CH_3$ | $C(CH_3)C_2H_4(cyclo)$ | m.p. 160–161° C. |
| 4.1002 | H | $CH_3$ | $CH_3$ | $C(CH_3)C_2H_4(cyclo)$ | |
| 4.1003 | H | $C_2H_5$ | $CH_3$ | $C(CH_3)C_2H_4(cyclo)$ | |
| 4.1004 | H | $C_3H_7$ | $CH_3$ | $C(CH_3)C_2H_4(cyclo)$ | |
| 4.1005 | H | $OCH_3$ | $CH_3$ | $C(CH_3)C_2H_4(cyclo)$ | |
| 4.1006 | H | $OC_2H_5$ | $CH_3$ | $C(CH_3)C_2H_4(cyclo)$ | |
| 4.1007 | H | $OCH_2CH=CH_2$ | $CH_3$ | $C(CH_3)C_2H_4(cyclo)$ | |
| 4.1008 | H | $OCH_2CH=CHCH_3$ | $CH_3$ | $C(CH_3)C_2H_4(cyclo)$ | |
| 4.1009 | H | $OCH_2C(Cl)=CH_2$ | $CH_3$ | $C(CH_3)C_2H_4(cyclo)$ | |
| 4.1010 | H | $OCH_2CH=CHCl$ | $CH_3$ | $C(CH_3)C_2H_4(cyclo)$ | |
| 4.1011 | H | $OCH_2C\equiv CH$ | $CH_3$ | $C(CH_3)C_2H_4(cyclo)$ | |
| 4.1012 | H | $OCHF_2$ | $CH_3$ | $C(CH_3)C_2H_4(cyclo)$ | |
| 4.1013 | H | $OCF_3$ | $CH_3$ | $C(CH_3)C_2H_4(cyclo)$ | |
| 4.1014 | H | $OCF_2CHFCF_3$ | $CH_3$ | $C(CH_3)C_2H_4(cyclo)$ | |
| 4.1015 | H | $OC_6H_5$ | $CH_3$ | $C(CH_3)C_2H_4(cyclo)$ | |
| 4.1016 | H | $CF_3$ | $CH_3$ | $C(CH_3)C_2H_4(cyclo)$ | |
| 4.1017 | H | Br | $CH_3$ | $C(CH_3)C_2H_4(cyclo)$ | |
| 4.1018 | H | Cl | $CH_3$ | $C(CH_3)C_2H_4(cyclo)$ | |
| 4.1019 | H | F | $CH_3$ | $C(CH_3)C_2H_4(cyclo)$ | |
| 4.1020 | H | $SCH_3$ | $CH_3$ | $C(CH_3)C_2H_4(cyclo)$ | |
| 4.1021 | H | $SC_2H_5$ | $CH_3$ | $C(CH_3)C_2H_4(cyclo)$ | |
| 4.1022 | H | $SC_3H_7$-n | $CH_3$ | $C(CH_3)C_2H_4(cyclo)$ | |
| 4.1023 | H | $SO_2CH_3$ | $CH_3$ | $C(CH_3)C_2H_4(cyclo)$ | |
| 4.1024 | H | $SO_2C_2H_5$ | $CH_3$ | $C(CH_3)C_2H_4(cyclo)$ | |
| 4.1025 | H | $NO_2$ | $CH_3$ | $C(CH_3)C_2H_4(cyclo)$ | |
| 4.1026 | H | CN | $CH_3$ | $C(CH_3)C_2H_4(cyclo)$ | |
| 4.1027 | H | $CH_2OH$ | $CH_3$ | $C(CH_3)C_2H_4(cyclo)$ | |
| 4.1028 | H | $CH_2CH_2OH$ | $CH_3$ | $C(CH_3)C_2H_4(cyclo)$ | |
| 4.1029 | H | $CH_2CH_2CH_2OH$ | $CH_3$ | $C(CH_3)C_2H_4(cyclo)$ | |
| 4.1030 | H | $C_6H_5$ | $CH_3$ | $C(CH_3)C_2H_4(cyclo)$ | |
| 4.1031 | H | $CH_2Cl$ | $CH_3$ | $C(CH_3)C_2H_4(cyclo)$ | |
| 4.1032 | H | $CH_2CH_2Cl$ | $CH_3$ | $C(CH_3)C_2H_4(cyclo)$ | |
| 4.1033 | H | $CH_2CH_2CH_2Cl$ | $CH_3$ | $C(CH_3)C_2H_4(cyclo)$ | |

TABLE 4.11

| No. | X | Y | $R_1$ | Z | phys. data |
|---|---|---|---|---|---|
| 4.1101 | H | H | $CH_3$ | $CH_2OC_6H_5$ | |
| 4.1102 | H | $CH_3$ | $CH_3$ | $CH_2OC_6H_5$ | |
| 4.1103 | H | $C_2H_5$ | $CH_3$ | $CH_2OC_6H_5$ | |
| 4.1104 | H | $C_3H_7$ | $CH_3$ | $CH_2OC_6H_5$ | |
| 4.1105 | H | $OCH_3$ | $CH_3$ | $CH_2OC_6H_5$ | |
| 4.1106 | H | $OC_2H_5$ | $CH_3$ | $CH_2OC_6H_5$ | |
| 4.1107 | H | $OCH_2CH=CH_2$ | $CH_3$ | $CH_2OC_6H_5$ | |
| 4.1108 | H | $OCH_2CH=CHCH_3$ | $CH_3$ | $CH_2OC_6H_5$ | |
| 4.1109 | H | $OCH_2C(Cl)=CH_2$ | $CH_3$ | $CH_2OC_6H_5$ | |
| 4.1110 | H | $OCH_2CH=CHCl$ | $CH_3$ | $CH_2OC_6H_5$ | |
| 4.1111 | H | $OCH_2C\equiv CH$ | $CH_3$ | $CH_2OC_6H_5$ | |
| 4.1112 | H | $OCHF_2$ | $CH_3$ | $CH_2OC_6H_5$ | |
| 4.1113 | H | $OCF_3$ | $CH_3$ | $CH_2OC_6H_5$ | |
| 4.1114 | H | $OCF_2CHFCF_3$ | $CH_3$ | $CH_2OC_6H_5$ | |
| 4.1115 | H | $OC_6H_5$ | $CH_3$ | $CH_2OC_6H_5$ | |
| 4.1116 | H | $CF_3$ | $CH_3$ | $CH_2OC_6H_5$ | |
| 4.1117 | H | Br | $CH_3$ | $CH_2OC_6H_5$ | |
| 4.1118 | H | Cl | $CH_3$ | $CH_2OC_6H_5$ | |
| 4.1119 | H | F | $CH_3$ | $CH_2OC_6H_5$ | |
| 4.1120 | H | $SCH_3$ | $CH_3$ | $CH_2OC_6H_5$ | |
| 4.1121 | H | $SC_2H_5$ | $CH_3$ | $CH_2OC_6H_5$ | |
| 4.1122 | H | $SC_3H_7$-n | $CH_3$ | $CH_2OC_6H_5$ | |
| 4.1123 | H | $SO_2CH_3$ | $CH_3$ | $CH_2OC_6H_5$ | |
| 4.1124 | H | $SO_2C_2H_5$ | $CH_3$ | $CH_2OC_6H_5$ | |
| 4.1125 | H | $NO_2$ | $CH_3$ | $CH_2OC_6H_5$ | |
| 4.1126 | H | CN | $CH_3$ | $CH_2OC_6H_5$ | |
| 4.1127 | H | $CH_2OH$ | $CH_3$ | $CH_2OC_6H_5$ | |
| 4.1128 | H | $CH_2CH_2OH$ | $CH_3$ | $CH_2OC_6H_5$ | |
| 4.1129 | H | $CH_2CH_2CH_2OH$ | $CH_3$ | $CH_2OC_6H_5$ | |
| 4.1130 | H | $C_6H_5$ | $CH_3$ | $CH_2OC_6H_5$ | |
| 4.1131 | H | $CH_2Cl$ | $CH_3$ | $CH_2OC_6H_5$ | |
| 4.1132 | H | $CH_2CH_2Cl$ | $CH_3$ | $CH_2OC_6H_5$ | |

TABLE 4.11-continued

| No. | X | Y | $R_1$ | Z | phys. data |
|---|---|---|---|---|---|
| 4.1133 | H | $CH_2CH_2CH_2Cl$ | $CH_3$ | $CH_2OC_6H_5$ | |

TABLE 4.12

| No. | X | Y | $R_1$ | Z | phys. data |
|---|---|---|---|---|---|
| 4.1201 | H | H | $CH_3$ | furan-2-yl | |
| 4.1202 | H | $CH_3$ | $CH_3$ | furan-2-yl | |
| 4.1203 | H | $C_2H_5$ | $CH_3$ | furan-2-yl | |
| 4.1204 | H | $C_3H_7$ | $CH_3$ | furan-2-yl | |
| 4.1205 | H | $OCH_3$ | $CH_3$ | furan-2-yl | |
| 4.1206 | H | $OC_2H_5$ | $CH_3$ | furan-2-yl | |
| 4.1207 | H | $OCH_2CH=CH_2$ | $CH_3$ | furan-2-yl | |
| 4.1208 | H | $OCH_2CH=CHCH_3$ | $CH_3$ | furan-2-yl | |
| 4.1209 | H | $OCH_2C(Cl)=CH_2$ | $CH_3$ | furan-2-yl | |
| 4.1210 | H | $OCH_2CH=CHCl$ | $CH_3$ | furan-2-yl | |
| 4.1211 | H | $OCH_2C\equiv CH$ | $CH_3$ | furan-2-yl | |
| 4.1212 | H | $OCHF_2$ | $CH_3$ | furan-2-yl | |
| 4.1213 | H | $OCF_3$ | $CH_3$ | furan-2-yl | |
| 4.1214 | H | $OCF_2CHFCF_3$ | $CH_3$ | furan-2-yl | |
| 4.1215 | H | $OC_6H_5$ | $CH_3$ | furan-2-yl | |
| 4.1216 | H | $CF_3$ | $CH_3$ | furan-2-yl | |
| 4.1217 | H | Br | $CH_3$ | furan-2-yl | |
| 4.1218 | H | Cl | $CH_3$ | furan-2-yl | |
| 4.1219 | H | F | $CH_3$ | furan-2-yl | |
| 4.1220 | H | $SCH_3$ | $CH_3$ | furan-2-yl | |
| 4.1221 | H | $SC_2H_5$ | $CH_3$ | furan-2-yl | |
| 4.1222 | H | $SC_3H_7$-n | $CH_3$ | furan-2-yl | |
| 4.1223 | H | $SO_2CH_3$ | $CH_3$ | furan-2-yl | |
| 4.1224 | H | $SO_2C_2H_5$ | $CH_3$ | furan-2-yl | |
| 4.1225 | H | $NO_2$ | $CH_3$ | furan-2-yl | |
| 4.1226 | H | CN | $CH_3$ | furan-2-yl | |
| 4.1227 | H | $CH_2OH$ | $CH_3$ | furan-2-yl | |
| 4.1228 | H | $CH_2CH_2OH$ | $CH_3$ | furan-2-yl | |
| 4.1229 | H | $CH_2CH_2CH_2OH$ | $CH_3$ | furan-2-yl | |
| 4.1230 | H | $C_6H_5$ | $CH_3$ | furan-2-yl | |
| 4.1231 | H | $CH_2Cl$ | $CH_3$ | furan-2-yl | |
| 4.1232 | H | $CH_2CH_2Cl$ | $CH_3$ | furan-2-yl | |

TABLE 4.12-continued

| No. | X | Y | R$_1$ | Z | phys. data |
|---|---|---|---|---|---|
| 4.1233 | H | CH$_2$CH$_2$CH$_2$Cl | CH$_3$ | furan-2-yl | |

TABLE 4.13

| No. | X | Y | R$_1$ | Z | phys. data |
|---|---|---|---|---|---|
| 4.1301 | H | H | CH$_3$ | dioxan-2-yl | |
| 4.1302 | H | CH$_3$ | CH$_3$ | dioxan-2-yl | |
| 4.1303 | H | C$_2$H$_5$ | CH$_3$ | dioxan-2-yl | |
| 4.1304 | H | C$_3$H$_7$ | CH$_3$ | dioxan-2-yl | |
| 4.1305 | H | OCH$_3$ | CH$_3$ | dioxan-2-yl | |
| 4.1306 | H | OC$_2$H$_5$ | CH$_3$ | dioxan-2-yl | |
| 4.1307 | H | OCH$_2$CH=CH$_2$ | CH$_3$ | dioxan-2-yl | |
| 4.1308 | H | OCH$_2$CH=CHCH$_3$ | CH$_3$ | dioxan-2-yl | |
| 4.1309 | H | OCH$_2$C(Cl)=CH$_2$ | CH$_3$ | dioxan-2-yl | |
| 4.1310 | H | OCH$_2$CH=CHCl | CH$_3$ | dioxan-2-yl | |
| 4.1311 | H | OCH$_2$C≡CH | CH$_3$ | dioxan-2-yl | |
| 4.1312 | H | OCHF$_2$ | CH$_3$ | dioxan-2-yl | |
| 4.1313 | H | OCF$_3$ | CH$_3$ | dioxan-2-yl | |
| 4.1314 | H | OCF$_2$CHFCF$_3$ | CH$_3$ | dioxan-2-yl | |
| 4.1315 | H | OC$_6$H$_5$ | CH$_3$ | dioxan-2-yl | |
| 4.1316 | H | CF$_3$ | CH$_3$ | dioxan-2-yl | |
| 4.1317 | H | Br | CH$_3$ | dioxan-2-yl | |
| 4.1318 | H | Cl | CH$_3$ | dioxan-2-yl | |
| 4.1319 | H | F | CH$_3$ | dioxan-2-yl | |
| 4.1320 | H | SCH$_3$ | CH$_3$ | dioxan-2-yl | |
| 4.1321 | H | SC$_2$H$_5$ | CH$_3$ | dioxan-2-yl | |
| 4.1322 | H | SC$_3$H$_7$-n | CH$_3$ | dioxan-2-yl | |
| 4.1323 | H | SO$_2$CH$_3$ | CH$_3$ | dioxan-2-yl | |
| 4.1324 | H | SO$_2$C$_2$H$_5$ | CH$_3$ | dioxan-2-yl | |
| 4.1325 | H | NO$_2$ | CH$_3$ | dioxan-2-yl | |
| 4.1326 | H | CN | CH$_3$ | dioxan-2-yl | |
| 4.1327 | H | CH$_2$OH | CH$_3$ | dioxan-2-yl | |
| 4.1328 | H | CH$_2$CH$_2$OH | CH$_3$ | dioxan-2-yl | |
| 4.1329 | H | CH$_2$CH$_2$CH$_2$OH | CH$_3$ | dioxan-2-yl | |
| 4.1330 | H | C$_6$H$_5$ | CH$_3$ | dioxan-2-yl | |
| 4.1331 | H | CH$_2$Cl | CH$_3$ | dioxan-2-yl | |
| 4.1332 | H | CH$_2$CH$_2$Cl | CH$_3$ | dioxan-2-yl | |

TABLE 4.13-continued

| No. | X | Y | R$_1$ | Z | phys. data |
|---|---|---|---|---|---|
| 4.1333 | H | CH$_2$CH$_2$CH$_2$Cl | CH$_3$ | dioxan-2-yl | |

TABLE 4.14

| No. | X | Y | R$_1$ | Z | phys. data |
|---|---|---|---|---|---|
| 4.1401 | H | H | CH$_3$ | CH$_2$OC$_2$H$_4$OCH$_3$ | |
| 4.1402 | H | CH$_3$ | CH$_3$ | CH$_2$OC$_2$H$_4$OCH$_3$ | |
| 4.1403 | H | C$_2$H$_5$ | CH$_3$ | CH$_2$OC$_2$H$_4$OCH$_3$ | |
| 4.1404 | H | C$_3$H$_7$ | CH$_3$ | CH$_2$OC$_2$H$_4$OCH$_3$ | |
| 4.1405 | H | OCH$_3$ | CH$_3$ | CH$_2$OC$_2$H$_4$OCH$_3$ | |
| 4.1406 | H | OC$_2$H$_5$ | CH$_3$ | CH$_2$OC$_2$H$_4$OCH$_3$ | |
| 4.1407 | H | OCH$_2$CH=CH$_2$ | CH$_3$ | CH$_2$OC$_2$H$_4$OCH$_3$ | |
| 4.1408 | H | OCH$_2$CH=CHCH$_3$ | CH$_3$ | CH$_2$OC$_2$H$_4$OCH$_3$ | |
| 4.1409 | H | OCH$_2$C(Cl)=CH$_2$ | CH$_3$ | CH$_2$OC$_2$H$_4$OCH$_3$ | |
| 4.1410 | H | OCH$_2$CH=CHCl | CH$_3$ | CH$_2$OC$_2$H$_4$OCH$_3$ | |
| 4.1411 | H | OCH$_2$C≡CH | CH$_3$ | CH$_2$OC$_2$H$_4$OCH$_3$ | |
| 4.1412 | H | OCHF$_2$ | CH$_3$ | CH$_2$OC$_2$H$_4$OCH$_3$ | |
| 4.1413 | H | OCF$_3$ | CH$_3$ | CH$_2$OC$_2$H$_4$OCH$_3$ | |
| 4.1414 | H | OCF$_2$CHFCF$_3$ | CH$_3$ | CH$_2$OC$_2$H$_4$OCH$_3$ | |
| 4.1415 | H | OC$_6$H$_5$ | CH$_3$ | CH$_2$OC$_2$H$_4$OCH$_3$ | |
| 4.1416 | H | CF$_3$ | CH$_3$ | CH$_2$OC$_2$H$_4$OCH$_3$ | |
| 4.1417 | H | Br | CH$_3$ | CH$_2$OC$_2$H$_4$OCH$_3$ | |
| 4.1418 | H | Cl | CH$_3$ | CH$_2$OC$_2$H$_4$OCH$_3$ | |
| 4.1419 | H | F | CH$_3$ | CH$_2$OC$_2$H$_4$OCH$_3$ | |
| 4.1420 | H | SCH$_3$ | CH$_3$ | CH$_2$OC$_2$H$_4$OCH$_3$ | |
| 4.1421 | H | SC$_2$H$_5$ | CH$_3$ | CH$_2$OC$_2$H$_4$OCH$_3$ | |
| 4.1422 | H | SC$_3$H$_7$-n | CH$_3$ | CH$_2$OC$_2$H$_4$OCH$_3$ | |
| 4.1423 | H | SO$_2$CH$_3$ | CH$_3$ | CH$_2$OC$_2$H$_4$OCH$_3$ | |
| 4.1424 | H | SO$_2$C$_2$H$_5$ | CH$_3$ | CH$_2$OC$_2$H$_4$OCH$_3$ | |
| 4.1425 | H | NO$_2$ | CH$_3$ | CH$_2$OC$_2$H$_4$OCH$_3$ | |
| 4.1426 | H | CN | CH$_3$ | CH$_2$OC$_2$H$_4$OCH$_3$ | |
| 4.1427 | H | CH$_2$OH | CH$_3$ | CH$_2$OC$_2$H$_4$OCH$_3$ | |
| 4.1428 | H | CH$_2$CH$_2$OH | CH$_3$ | CH$_2$OC$_2$H$_4$OCH$_3$ | |
| 4.1429 | H | CH$_2$CH$_2$CH$_2$OH | CH$_3$ | CH$_2$OC$_2$H$_4$OCH$_3$ | |
| 4.1430 | H | C$_6$H$_5$ | CH$_3$ | CH$_2$OC$_2$H$_4$OCH$_3$ | |
| 4.1431 | H | CH$_2$Cl | CH$_3$ | CH$_2$OC$_2$H$_4$OCH$_3$ | |
| 4.1432 | H | CH$_2$CH$_2$Cl | CH$_3$ | CH$_2$OC$_2$H$_4$OCH$_3$ | |
| 4.1433 | H | CH$_2$CH$_2$CH$_2$Cl | CH$_3$ | CH$_2$OC$_2$H$_4$OCH$_3$ | |

TABLE 4.15

| No. | X | Y | R$_1$ | Z | phys. data |
|---|---|---|---|---|---|
| 4.1501 | H | H | CH$_3$ | CH$_2$OC$_2$H$_4$OC$_2$H$_4$OCH$_3$ | |
| 4.1502 | H | CH$_3$ | CH$_3$ | CH$_2$OC$_2$H$_4$OC$_2$H$_4$OCH$_3$ | |
| 4.1503 | H | C$_2$H$_5$ | CH$_3$ | CH$_2$OC$_2$H$_4$OC$_2$H$_4$OCH$_3$ | |
| 4.1504 | H | C$_3$H$_7$ | CH$_3$ | CH$_2$OC$_2$H$_4$OC$_2$H$_4$OCH$_3$ | |
| 4.1505 | H | OCH$_3$ | CH$_3$ | CH$_2$OC$_2$H$_4$OC$_2$H$_4$OCH$_3$ | |
| 4.1506 | H | OC$_2$H$_5$ | CH$_3$ | CH$_2$OC$_2$H$_4$OC$_2$H$_4$OCH$_3$ | |
| 4.1507 | H | OCH$_2$CH=CH$_2$ | CH$_3$ | CH$_2$OC$_2$H$_4$OC$_2$H$_4$OCH$_3$ | |
| 4.1508 | H | OCH$_2$CH=CHCH$_3$ | CH$_3$ | CH$_2$OC$_2$H$_4$OC$_2$H$_4$OCH$_3$ | |
| 4.1509 | H | OCH$_2$C(Cl)=CH$_2$ | CH$_3$ | CH$_2$OC$_2$H$_4$OC$_2$H$_4$OCH$_3$ | |
| 4.1510 | H | OCH$_2$CH=CHCl | CH$_3$ | CH$_2$OC$_2$H$_4$OC$_2$H$_4$OCH$_3$ | |
| 4.1511 | H | OCH$_2$C≡CH | CH$_3$ | CH$_2$OC$_2$H$_4$OC$_2$H$_4$OCH$_3$ | |
| 4.1512 | H | OCHF$_2$ | CH$_3$ | CH$_2$OC$_2$H$_4$OC$_2$H$_4$OCH$_3$ | |
| 4.1513 | H | OCF$_3$ | CH$_3$ | CH$_2$OC$_2$H$_4$OC$_2$H$_4$OCH$_3$ | |
| 4.1514 | H | OCF$_2$CHFCF$_3$ | CH$_3$ | CH$_2$OC$_2$H$_4$OC$_2$H$_4$OCH$_3$ | |
| 4.1515 | H | OC$_6$H$_5$ | CH$_3$ | CH$_2$OC$_2$H$_4$OC$_2$H$_4$OCH$_3$ | |
| 4.1516 | H | CF$_3$ | CH$_3$ | CH$_2$OC$_2$H$_4$OC$_2$H$_4$OCH$_3$ | |
| 4.1517 | H | Br | CH$_3$ | CH$_2$OC$_2$H$_4$OC$_2$H$_4$OCH$_3$ | |
| 4.1518 | H | Cl | CH$_3$ | CH$_2$OC$_2$H$_4$OC$_2$H$_4$OCH$_3$ | |
| 4.1519 | H | F | CH$_3$ | CH$_2$OC$_2$H$_4$OC$_2$H$_4$OCH$_3$ | |
| 4.1520 | H | SCH$_3$ | CH$_3$ | CH$_2$OC$_2$H$_4$OC$_2$H$_4$OCH$_3$ | |
| 4.1521 | H | SC$_2$H$_5$ | CH$_3$ | CH$_2$OC$_2$H$_4$OC$_2$H$_4$OCH$_3$ | |
| 4.1522 | H | SC$_3$H$_7$-n | CH$_3$ | CH$_2$OC$_2$H$_4$OC$_2$H$_4$OCH$_3$ | |
| 4.1523 | H | SO$_2$CH$_3$ | CH$_3$ | CH$_2$OC$_2$H$_4$OC$_2$H$_4$OCH$_3$ | |
| 4.1524 | H | SO$_2$C$_2$H$_5$ | CH$_3$ | CH$_2$OC$_2$H$_4$OC$_2$H$_4$OCH$_3$ | |
| 4.1525 | H | NO$_2$ | CH$_3$ | CH$_2$OC$_2$H$_4$OC$_2$H$_4$OCH$_3$ | |
| 4.1526 | H | CN | CH$_3$ | CH$_2$OC$_2$H$_4$OC$_2$H$_4$OCH$_3$ | |
| 4.1527 | H | CH$_2$OH | CH$_3$ | CH$_2$OC$_2$H$_4$OC$_2$H$_4$OCH$_3$ | |
| 4.1528 | H | CH$_2$CH$_2$OH | CH$_3$ | CH$_2$OC$_2$H$_4$OC$_2$H$_4$OCH$_3$ | |
| 4.1529 | H | CH$_2$CH$_2$CH$_2$OH | CH$_3$ | CH$_2$OC$_2$H$_4$OC$_2$H$_4$OCH$_3$ | |
| 4.1530 | H | C$_6$H$_5$ | CH$_3$ | CH$_2$OC$_2$H$_4$OC$_2$H$_4$OCH$_3$ | |
| 4.1531 | H | CH$_2$Cl | CH$_3$ | CH$_2$OC$_2$H$_4$OC$_2$H$_4$OCH$_3$ | |
| 4.1532 | H | CH$_2$CH$_2$Cl | CH$_3$ | CH$_2$OC$_2$H$_4$OC$_2$H$_4$OCH$_3$ | |
| 4.1533 | H | CH$_2$CH$_2$CH$_2$Cl | CH$_3$ | CH$_2$OC$_2$H$_4$OC$_2$H$_4$OCH$_3$ | |

TABLE 4.16

| No. | X | Y | $R_1$ | Z | phys. data |
|---|---|---|---|---|---|
| 4.1601 | H | H | $CH_3$ | $CH_2OCH_2CONH_2$ | |
| 4.1602 | H | $CH_3$ | $CH_3$ | $CH_2OCH_2CONH_2$ | |
| 4.1603 | H | $C_2H_5$ | $CH_3$ | $CH_2OCH_2CONH_2$ | |
| 4.1604 | H | $C_3H_7$ | $CH_3$ | $CH_2OCH_2CONH_2$ | |
| 4.1605 | H | $OCH_3$ | $CH_3$ | $CH_2OCH_2CONH_2$ | |
| 4.1606 | H | $OC_2H_5$ | $CH_3$ | $CH_2OCH_2CONH_2$ | |
| 4.1607 | H | $OCH_2CH=CH_2$ | $CH_3$ | $CH_2OCH_2CONH_2$ | |
| 4.1608 | H | $OCH_2CH=CHCH_3$ | $CH_3$ | $CH_2OCH_2CONH_2$ | |
| 4.1609 | H | $OCH_2C(Cl)=CH_2$ | $CH_3$ | $CH_2OCH_2CONH_2$ | |
| 4.1610 | H | $OCH_2CH=CHCl$ | $CH_3$ | $CH_2OCH_2CONH_2$ | |
| 4.1611 | H | $OCH_2C\equiv CH$ | $CH_3$ | $CH_2OCH_2CONH_2$ | |
| 4.1612 | H | $OCHF_2$ | $CH_3$ | $CH_2OCH_2CONH_2$ | |
| 4.1613 | H | $OCF_3$ | $CH_3$ | $CH_2OCH_2CONH_2$ | |
| 4.1614 | H | $OCF_2CHFCF_3$ | $CH_3$ | $CH_2OCH_2CONH_2$ | |
| 4.1615 | H | $OC_6H_5$ | $CH_3$ | $CH_2OCH_2CONH_2$ | |
| 4.1616 | H | $CF_3$ | $CH_3$ | $CH_2OCH_2CONH_2$ | |
| 4.1617 | H | Br | $CH_3$ | $CH_2OCH_2CONH_2$ | |
| 4.1618 | H | Cl | $CH_3$ | $CH_2OCH_2CONH_2$ | |
| 4.1619 | H | F | $CH_3$ | $CH_2OCH_2CONH_2$ | |
| 4.1620 | H | $SCH_3$ | $CH_3$ | $CH_2OCH_2CONH_2$ | |
| 4.1621 | H | $SC_2H_5$ | $CH_3$ | $CH_2OCH_2CONH_2$ | |
| 4.1622 | H | $SC_3H_7$-n | $CH_3$ | $CH_2OCH_2CONH_2$ | |
| 4.1623 | H | $SO_2CH_3$ | $CH_3$ | $CH_2OCH_2CONH_2$ | |
| 4.1624 | H | $SO_2C_2H_5$ | $CH_3$ | $CH_2OCH_2CONH_2$ | |
| 4.1625 | H | $NO_2$ | $CH_3$ | $CH_2OCH_2CONH_2$ | |
| 4.1626 | H | CN | $CH_3$ | $CH_2OCH_2CONH_2$ | |
| 4.1627 | H | $CH_2OH$ | $CH_3$ | $CH_2OCH_2CONH_2$ | |
| 4.1628 | H | $CH_2CH_2OH$ | $CH_3$ | $CH_2OCH_2CONH_2$ | |
| 4.1629 | H | $CH_2CH_2CH_2OH$ | $CH_3$ | $CH_2OCH_2CONH_2$ | |
| 4.1630 | H | $C_6H_5$ | $CH_3$ | $CH_2OCH_2CONH_2$ | |
| 4.1631 | H | $CH_2Cl$ | $CH_3$ | $CH_2OCH_2CONH_2$ | |
| 4.1632 | H | $CH_2CH_2Cl$ | $CH_3$ | $CH_2OCH_2CONH_2$ | |
| 4.1633 | H | $CH_2CH_2CH_2Cl$ | $CH_3$ | $CH_2OCH_2CONH_2$ | |

EXAMPLE 12

Preparation of 6-ethoxymethylpyridine-2,3-dicarboxylic acid

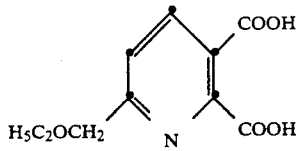

37.4 g of 6-ethoxymethylpyridine-2,3-carboxylic acid diethyl ester are added to a solution of 0.5 g of tetrabutylammonium bromide in 140 ml of aqueous 15% sodium hydroxide solution while stirring. A slightly exothermic reaction is observed. The reaction mixture is then stirred for 3 hours at room temperature and subsequently extensively concentrated by evaporation, the disodium salt of 6-ethoxymethylpyridine-2,3-dicarboxylic acid being precipitated. 50 ml of water are added to the residue which is extracted with ether. 0.5 g of educt remain in the ether extract. The aqueous phase is acidified to pH 2 with concentrated hydrochloric acid and then extracted 5 times with 100 ml of ethyl acetate each time. The organic phases are collected, dried over magnesium sulphate and concentrated by evaporation. 26 g of the above acid are obtained in the form of a honey-yellow resinous substance.

EXAMPLE 13

Preparation of 6-phenoxymethylpyridine-2,3-dicarboxylic acid

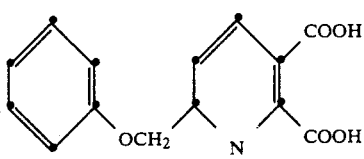

42 g of 6-phenoxymethylpyridine-2,3-dicarboxylic acid diethyl ester are added to a solution of 0.5 g of tetrabutylammonium bromide in 140 ml of 15% aqueous sodium hydroxide solution while stirring. The resulting suspension is heated to 80° and stirred for one hour. The reaction mixture is then diluted with 300 ml of water and the solution is acidified to pH 2 using concentrated hydrochloric acid, during the course of which a precipitate forms which is filtered off with suction. The filtration residue is stirred with methylene chloride/tetrahydrofuran and filtered. The filtrate is dried over magnesium sulphate, concentrated and combined with the contents of the suction filter. After the whole has been dried again over phosphorus pentoxide, 34 g of the above acid, having a melting point of 270° with decomposition, are obtained.

The pyridine-2,3-dicarboxylic acids of formula VI listed in Tables 6.00 and 6.01 are prepared in a manner analogous to that described in Examples 12 and 13.

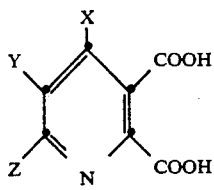

(VI)

TABLE 6.00

| No. | X | Y | Z | phys. data |
|---|---|---|---|---|
| 6.0001 | H | H | $C_3H_5$(cyclo) | |
| 6.0002 | H | $CH_3$ | $C_3H_5$(cyclo) | |
| 6.0003 | H | $C_2H_5$ | $C_3H_5$(cyclo) | |
| 6.0004 | H | $C_3H_7$ | $C_3H_5$(cyclo) | |
| 6.0005 | H | $OCH_3$ | $C_3H_5$(cyclo) | |
| 6.0006 | H | $OC_2H_5$ | $C_3H_5$(cyclo) | |
| 6.0007 | H | $OCH_2CH=CH_2$ | $C_3H_5$(cyclo) | |
| 6.0008 | H | $OCH_2CH=CHCH_3$ | $C_3H_5$(cyclo) | |
| 6.0009 | H | $OCH_2C(Cl)=CH_2$ | $C_3H_5$(cyclo) | |
| 6.0010 | H | $OCH_2CH=CHCl$ | $C_3H_5$(cyclo) | |
| 6.0011 | H | $OCH_2C\equiv CH$ | $C_3H_5$(cyclo) | |
| 6.0012 | H | $OCHF_2$ | $C_3H_5$(cyclo) | |
| 6.0013 | H | $OCF_3$ | $C_3H_5$(cyclo) | |
| 6.0014 | H | $OCF_2CHFCF_3$ | $C_3H_5$(cyclo) | |
| 6.0015 | H | $OC_6H_5$ | $C_3H_5$(cyclo) | |
| 6.0016 | H | $CF_3$ | $C_3H_5$(cyclo) | |
| 6.0017 | H | Br | $C_3H_5$(cyclo) | |
| 6.0018 | H | Cl | $C_3H_5$(cyclo) | |
| 6.0019 | H | F | $C_3H_5$(cyclo) | |
| 6.0020 | H | $SCH_3$ | $C_3H_5$(cyclo) | |
| 6.0021 | H | $SC_2H_5$ | $C_3H_5$(cyclo) | |
| 6.0022 | H | $SC_3H_7$-n | $C_3H_5$(cyclo) | |
| 6.0023 | H | $SO_2CH_3$ | $C_3H_5$(cyclo) | |
| 6.0024 | H | $SO_2C_2H_5$ | $C_3H_5$(cyclo) | |
| 6.0025 | H | $NO_2$ | $C_3H_5$(cyclo) | |
| 6.0026 | H | CN | $C_3H_5$(cyclo) | |
| 6.0027 | H | $CH_2OH$ | $C_3H_5$(cyclo) | |
| 6.0028 | H | $CH_2CH_2OH$ | $C_3H_5$(cyclo) | |
| 6.0029 | H | $CH_2CH_2CH_2OH$ | $C_3H_5$(cyclo) | |
| 6.0030 | H | $C_6H_5$ | $C_3H_5$(cyclo) | |
| 6.0031 | H | $CH_2Cl$ | $C_3H_5$(cyclo) | |
| 6.0032 | H | $CH_2CH_2Cl$ | $C_3H_5$(cyclo) | |
| 6.0033 | H | $CH_2CH_2CH_2Cl$ | $C_3H_5$(cyclo) | |

TABLE 6.01

| No. | X | Y | Z | phys. data |
|---|---|---|---|---|
| 6.0101 | H | H | $CH_2OC_2H_5$ | |
| 6.0102 | H | $CH_3$ | $CH_2OC_2H_5$ | |
| 6.0103 | H | $C_2H_5$ | $CH_2OC_2H_5$ | |
| 6.0104 | H | $C_3H_7$ | $CH_2OC_2H_5$ | |
| 6.0105 | H | $OCH_3$ | $CH_2OC_2H_5$ | |
| 6.0213 | H | $OCF_3$ | $CH_2OC_2H_5$ | |
| 6.0214 | H | $OCF_2CHFCF_3$ | $CH_2OC_2H_5$ | |
| 6.0215 | H | $OC_6H_5$ | $CH_2OC_2H_5$ | |
| 6.0216 | H | $CF_3$ | $CH_2OC_2H_5$ | |
| 6.0217 | H | Br | $CH_2OC_2H_5$ | |
| 6.0218 | H | Cl | $CH_2OC_2H_5$ | |
| 6.0219 | H | F | $CH_2OC_2H_5$ | |
| 6.0220 | H | $SCH_3$ | $CH_2OC_2H_5$ | |
| 6.0221 | H | $SC_2H_5$ | $CH_2OC_2H_5$ | |
| 6.0222 | H | $SC_3H_7$-n | $CH_2OC_2H_5$ | |
| 6.0223 | H | $SO_2CH_3$ | $CH_2OC_2H_5$ | |
| 6.0224 | H | $SO_2C_2H_5$ | $CH_2OC_2H_5$ | |
| 6.0225 | H | $NO_2$ | $CH_2OC_2H_5$ | |
| 6.0226 | H | CN | $CH_2OC_2H_5$ | |
| 6.0227 | H | $CH_2OH$ | $CH_2OC_2H_5$ | |
| 6.0228 | H | $CH_2CH_2OH$ | $CH_2OC_2H_5$ | |
| 6.0229 | H | $CH_2CH_2CH_2OH$ | $CH_2OC_2H_5$ | |
| 6.0230 | H | $C_6H_5$ | $CH_2OC_2H_5$ | |
| 6.0231 | H | $CH_2Cl$ | $CH_2OC_2H_5$ | |
| 6.0232 | H | $CH_2CH_2Cl$ | $CH_2OC_2H_5$ | |
| 6.0233 | H | $CH_2CH_2CH_2Cl$ | $CH_2OC_2H_5$ | |

EXAMPLE 14

Preparation of 6-ethoxymethylpyridine-2,3-dicarboxylic acid anhydride

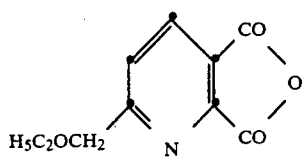

21 g of 6-ethoxymethylpyridine-2,3-dicarboxylic acid are added to a mixture of 100 ml of dimethoxyethane, 28 ml of acetic anhydride and 15 ml of pyridine while stirring and the whole is further stirred for 6 hours at room temperature before being concentrated by evaporation under a high vacuum. 20 g of anhydride remain in the form of an oily liquid with a refractive index $n_D^{22}$ of 1.5480.

EXAMPLE 15

Preparation of 6-phenoxymethylpyridine-2,3-dicarboxylic acid anhydride

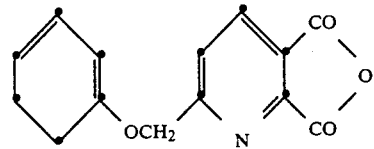

30 g of 6-phenoxymethylpyridine-2,3-dicarboxylic acid are added to a mixture of 100 ml of dimethoxyethane, 28 ml of acetic anhydride and 15 ml of pyridine while stirring and the reaction mixture is further stirred for one hour at room temperature. The whole is then concentrated by evaporation under a high vacuum. The above anhydride remains in the form of a light-coloured oil.

The pyridine-2,3-dicarboxylic acid anhydrides of formula VII listed in Tables 7.00 to 7.02 are prepared in a manner analogous to that described in Example 14 and 15.

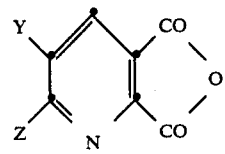

(VII)

TABLE 7.00

| No. | X | Y | Z | phys. data |
|---|---|---|---|---|
| 7.0001 | H | H | $C_3H_5$(cyclo) | |
| 7.0002 | H | $CH_3$ | $C_3H_5$(cyclo) | |
| 7.0003 | H | $C_2H_5$ | $C_3H_5$(cyclo) | |
| 7.0004 | H | $C_3H_7$ | $C_3H_5$(cyclo) | |
| 7.0005 | H | $OCH_3$ | $C_3H_5$(cyclo) | |
| 7.0006 | H | $OC_2H_5$ | $C_3H_5$(cyclo) | |
| 7.0007 | H | $OCH_2CH=CH_2$ | $C_3H_5$(cyclo) | |
| 7.0008 | H | $OCH_2CH=CHCH_3$ | $C_3H_5$(cyclo) | |
| 7.0009 | H | $OCH_2C(Cl)=CH_2$ | $C_3H_5$(cyclo) | |
| 7.0010 | H | $OCH_2CH=CHCl$ | $C_3H_5$(cyclo) | |
| 7.0011 | H | $OCH_2C\equiv CH$ | $C_3H_5$(cyclo) | |
| 7.0012 | H | $OCHF_2$ | $C_3H_5$(cyclo) | |
| 7.0013 | H | $OCF_3$ | $C_3H_5$(cyclo) | |

TABLE 7.00-continued

| No. | X | Y | Z | phys. data |
|---|---|---|---|---|
| 7.0014 | H | OCF$_2$CHFCF$_3$ | C$_3$H$_5$(cyclo) | |
| 7.0015 | H | OC$_6$H$_5$ | C$_3$H$_5$(cyclo) | |
| 7.0016 | H | CF$_3$ | C$_3$H$_5$(cyclo) | |
| 7.0017 | H | Br | C$_3$H$_5$(cyclo) | |
| 7.0018 | H | Cl | C$_3$H$_5$(cyclo) | |
| 7.0019 | H | F | C$_3$H$_5$(cyclo) | |
| 7.0020 | H | SCH$_3$ | C$_3$H$_5$(cyclo) | |
| 7.0021 | H | SC$_2$H$_5$ | C$_3$H$_5$(cyclo) | |
| 7.0022 | H | SC$_3$H$_7$-n | C$_3$H$_5$(cyclo) | |
| 7.0023 | H | SO$_2$CH$_3$ | C$_3$H$_5$(cyclo) | |
| 7.0024 | H | SO$_2$C$_2$H$_5$ | C$_3$H$_5$(cyclo) | |
| 7.0025 | H | NO$_2$ | C$_3$H$_5$(cyclo) | |
| 7.0026 | H | CN | C$_3$H$_5$(cyclo) | |
| 7.0027 | H | CH$_2$OH | C$_3$H$_5$(cyclo) | |
| 7.0028 | H | CH$_2$CH$_2$OH | C$_3$H$_5$(cyclo) | |
| 7.0029 | H | CH$_2$CH$_2$CH$_2$OH | C$_3$H$_5$(cyclo) | |
| 7.0030 | H | C$_6$H$_5$ | C$_3$H$_5$(cyclo) | |
| 7.0031 | H | CH$_2$Cl | C$_3$H$_5$(cyclo) | |
| 7.0032 | H | CH$_2$CH$_2$Cl | C$_3$H$_5$(cyclo) | |
| 7.0033 | H | CH$_2$CH$_2$CH$_2$Cl | C$_3$H$_5$(cyclo) | |

TABLE 7.01

| No. | X | Y | Z | phys. data |
|---|---|---|---|---|
| 7.0101 | H | H | CH$_2$OC$_2$H$_5$ | |
| 7.0102 | H | CH$_3$ | CH$_2$OC$_2$H$_5$ | |
| 7.0103 | H | C$_2$H$_5$ | CH$_2$OC$_2$H$_5$ | |
| 7.0104 | H | C$_3$H$_7$ | CH$_2$OC$_2$H$_5$ | |
| 7.0105 | H | OCH$_3$ | CH$_2$OC$_2$H$_5$ | |
| 7.0106 | H | OC$_2$H$_5$ | CH$_2$OC$_2$H$_5$ | |
| 7.0107 | H | OCH$_2$CH=CH$_2$ | CH$_2$OC$_2$H$_5$ | |
| 7.0108 | H | OCH$_2$CH=CHCH$_3$ | CH$_2$OC$_2$H$_5$ | |
| 7.0109 | H | OCH$_2$C(Cl)=CH$_2$ | CH$_2$OC$_2$H$_5$ | |
| 7.0110 | H | OCH$_2$CH=CHCl | CH$_2$OC$_2$H$_5$ | |
| 7.0111 | H | OCH$_2$C≡CH | CH$_2$OC$_2$H$_5$ | |
| 7.0112 | H | OCHF$_2$ | CH$_2$OC$_2$H$_5$ | |
| 7.0113 | H | OCF$_3$ | CH$_2$OC$_2$H$_5$ | |
| 7.0114 | H | OCF$_2$CHFCF$_3$ | CH$_2$OC$_2$H$_5$ | |
| 7.0115 | H | OC$_6$H$_5$ | CH$_2$OC$_2$H$_5$ | |
| 7.0116 | H | CF$_3$ | CH$_2$OC$_2$H$_5$ | |
| 7.0117 | H | Br | CH$_2$OC$_2$H$_5$ | |
| 7.0118 | H | Cl | CH$_2$OC$_2$H$_5$ | |
| 7.0119 | H | F | CH$_2$OC$_2$H$_5$ | |
| 7.0120 | H | SCH$_3$ | CH$_2$OC$_2$H$_5$ | |
| 7.0121 | H | SC$_2$H$_5$ | CH$_2$OC$_2$H$_5$ | |
| 7.0122 | H | SC$_3$H$_7$-n | CH$_2$OC$_2$H$_5$ | |
| 7.0123 | H | SO$_2$CH$_3$ | CH$_2$OC$_2$H$_5$ | |
| 7.0124 | H | SO$_2$C$_2$H$_5$ | CH$_2$OC$_2$H$_5$ | |
| 7.0125 | H | NO$_2$ | CH$_2$OC$_2$H$_5$ | |
| 7.0126 | H | CN | CH$_2$OC$_2$H$_5$ | |
| 7.0127 | H | CH$_2$OH | CH$_2$OC$_2$H$_5$ | |
| 7.0128 | H | CH$_2$CH$_2$OH | CH$_2$OC$_2$H$_5$ | |
| 7.0129 | H | CH$_2$CH$_2$CH$_2$OH | CH$_2$OC$_2$H$_5$ | |
| 7.0130 | H | C$_6$H$_5$ | CH$_2$OC$_2$H$_5$ | |
| 7.0131 | H | CH$_2$Cl | CH$_2$OC$_2$H$_5$ | |
| 7.0132 | H | CH$_2$CH$_2$Cl | CH$_2$OC$_2$H$_5$ | |
| 7.0133 | H | CH$_2$CH$_2$CH$_2$Cl | CH$_2$OC$_2$H$_5$ | |

TABLE 7.02

| No. | X | Y | Z | phys. data |
|---|---|---|---|---|
| 7.0201 | H | H | CH$_2$OC$_6$H$_5$ | |
| 7.0202 | H | CH$_3$ | CH$_2$OC$_6$H$_5$ | |
| 7.0203 | H | C$_2$H$_5$ | CH$_2$OC$_6$H$_5$ | |
| 7.0204 | H | C$_3$H$_7$ | CH$_2$OC$_6$H$_5$ | |
| 7.0205 | H | OCH$_3$ | CH$_2$OC$_6$H$_5$ | |
| 7.0206 | H | OC$_2$H$_5$ | CH$_2$OC$_6$H$_5$ | |
| 7.0207 | H | OCH$_2$CH=CH$_2$ | CH$_2$OC$_6$H$_5$ | |

TABLE 7.02-continued

| No. | X | Y | Z | phys. data |
|---|---|---|---|---|
| 7.0208 | H | OCH$_2$CH=CHCH$_3$ | CH$_2$OC$_6$H$_5$ | |
| 7.0209 | H | OCH$_2$C(Cl)=CH$_2$ | CH$_2$OC$_6$H$_5$ | |
| 7.0210 | H | OCH$_2$CH=CHCl | CH$_2$OC$_6$H$_5$ | |
| 7.0211 | H | OCH$_2$C≡CH | CH$_2$OC$_6$H$_5$ | |
| 7.0212 | H | OCHF$_2$ | CH$_2$OC$_6$H$_5$ | |
| 7.0213 | H | OCF$_3$ | CH$_2$OC$_6$H$_5$ | |
| 7.0214 | H | OCF$_2$CHFCF$_3$ | CH$_2$OC$_6$H$_5$ | |
| 7.0215 | H | OC$_6$H$_5$ | CH$_2$OC$_6$H$_5$ | |
| 7.0216 | H | CF$_3$ | CH$_2$OC$_6$H$_5$ | |
| 7.0217 | H | Br | CH$_2$OC$_6$H$_5$ | |
| 7.0218 | H | Cl | CH$_2$OC$_6$H$_5$ | |
| 7.0219 | H | F | CH$_2$OC$_6$H$_5$ | |
| 7.0220 | H | SCH$_3$ | CH$_2$OC$_6$H$_5$ | |
| 7.0221 | H | SC$_2$H$_5$ | CH$_2$OC$_6$H$_5$ | |
| 7.0222 | H | SC$_3$H$_7$-n | CH$_2$OC$_6$H$_5$ | |
| 7.0223 | H | SO$_2$CH$_3$ | CH$_2$OC$_6$H$_5$ | |
| 7.0224 | H | SO$_2$C$_2$H$_5$ | CH$_2$OC$_6$H$_5$ | |
| 7.0225 | H | NO$_2$ | CH$_2$OC$_6$H$_5$ | |
| 7.0226 | H | CN | CH$_2$OC$_6$H$_5$ | |
| 7.0227 | H | CH$_2$OH | CH$_2$OC$_6$H$_5$ | |
| 7.0228 | H | CH$_2$CH$_2$OH | CH$_2$OC$_6$H$_5$ | |
| 7.0229 | H | CH$_2$CH$_2$CH$_2$OH | CH$_2$OC$_6$H$_5$ | |
| 7.0230 | H | C$_6$H$_5$ | CH$_2$OC$_6$H$_5$ | |
| 7.0231 | H | CH$_2$Cl | CH$_2$OC$_6$H$_5$ | |
| 7.0232 | H | CH$_2$CH$_2$Cl | CH$_2$OC$_6$H$_5$ | |
| 7.0233 | H | CH$_2$CH$_2$CH$_2$Cl | CH$_2$OC$_6$H$_5$ | |

EXAMPLE 16

Preparation of 2-(N-2-methyl-valylamide)-carbamoyl-6-phenoxymethyl-nicotinic acid

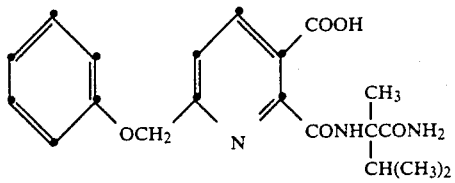

13 g of 2-methyl-valinamide are added to a solution of 2.55 g of 6-phenoxymethylpyridine-2,3-dicarboxylic acid in 30 ml of tetrahydrofuran while stirring and the reaction mixture is further stirred for 14 hours at room temperature before being concentrated by evaporation. An oily residue remains, which is purified by crystallisation from ether/petroleum ether. 3.4 g of white crystals having a melting point of 108°–110° are obtained.

The 2-carbamoyl-nicotinic acid derivatives of formula VIII listed in Tables 8.00 to 8.02 are prepared in a manner analogous to that described in Example 16.

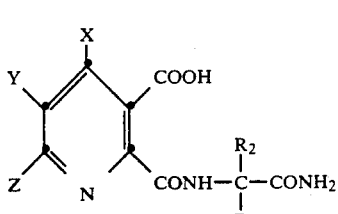

(VII)

TABLE 8.00

| No. | X | Y | R$_2$ | R$_3$ | Z | phys. data |
|---|---|---|---|---|---|---|
| 8.0001 | H | H | CH$_3$ | C$_3$H$_7$(iso) | C$_3$H$_5$(cyclo) | |
| 8.0002 | H | CH$_3$ | CH$_3$ | C$_3$H$_7$(iso) | C$_3$H$_5$(cyclo) | |
| 8.0003 | H | C$_2$H$_5$ | CH$_3$ | C$_3$H$_7$(iso) | C$_3$H$_5$(cyclo) | |
| 8.0004 | H | C$_3$H$_7$ | CH$_3$ | C$_3$H$_7$(iso) | C$_3$H$_5$(cyclo) | |
| 8.0005 | H | OCH$_3$ | CH$_3$ | C$_3$H$_7$(iso) | C$_3$H$_5$(cyclo) | |

TABLE 8.00-continued

| No. | X | Y | R₂ | R₃ | Z | phys. data |
|---|---|---|---|---|---|---|
| 8.0006 | H | OC₂H₅ | CH₃ | C₃H₇(iso) | C₃H₅(cyclo) | |
| 8.0007 | H | OCH₂CH=CH₂ | CH₃ | C₃H₇(iso) | C₃H₅(cyclo) | |
| 8.0008 | H | OCH₂CH=CHCH₃ | CH₃ | C₃H₇(iso) | C₃H₅(cyclo) | |
| 8.0009 | H | OCH₂C(Cl)=CH₂ | CH₃ | C₃H₇(iso) | C₃H₅(cyclo) | |
| 8.0010 | H | OCH₂CH=CHCl | CH₃ | C₃H₇(iso) | C₃H₅(cyclo) | |
| 8.0011 | H | OCH₂C≡CH | CH₃ | C₃H₇(iso) | C₃H₅(cyclo) | |
| 8.0012 | H | OCHF₂ | CH₃ | C₃H₇(iso) | C₃H₅(cyclo) | |
| 8.0013 | H | OCF₃ | CH₃ | C₃H₇(iso) | C₃H₅(cyclo) | |
| 8.0014 | H | OCF₂CHFCF₃ | CH₃ | C₃H₇(iso) | C₃H₅(cyclo) | |
| 8.0015 | H | OC₆H₅ | CH₃ | C₃H₇(iso) | C₃H₅(cyclo) | |
| 8.0016 | H | CF₃ | CH₃ | C₃H₇(iso) | C₃H₅(cyclo) | |
| 8.0017 | H | Br | CH₃ | C₃H₇(iso) | C₃H₅(cyclo) | |
| 8.0018 | H | Cl | CH₃ | C₃H₇(iso) | C₃H₅(cyclo) | |
| 8.0019 | H | F | CH₃ | C₃H₇(iso) | C₃H₅(cyclo) | |
| 8.0020 | H | SCH₃ | CH₃ | C₃H₇(iso) | C₃H₅(cyclo) | |
| 8.0021 | H | SCH₃ | CH₃ | C₃H₇(iso) | C₃H₅(cyclo) | |
| 8.0022 | H | SC₃H₇-n | CH₃ | C₃H₇(iso) | C₃H₅(cyclo) | |
| 8.0023 | H | SO₂CH₃ | CH₃ | C₃H₇(iso) | C₃H₅(cyclo) | |
| 8.0024 | H | SO₂CH₃ | CH₃ | C₃H₇(iso) | C₃H₅(cyclo) | |
| 8.0025 | H | NO₂ | CH₃ | C₃H₇(iso) | C₃H₅(cyclo) | |
| 8.0026 | H | CN | CH₃ | C₃H₇(iso) | C₃H₅(cyclo) | |
| 8.0027 | H | CH₂OH | CH₃ | C₃H₇(iso) | C₃H₅(cyclo) | |
| 8.0028 | H | CH₂CH₂OH | CH₃ | C₃H₇(iso) | C₃H₅(cyclo) | |
| 8.0029 | H | CH₂CH₂CH₂OH | CH₃ | C₃H₇(iso) | C₃H₅(cyclo) | |
| 8.0030 | H | C₆H₅ | CH₃ | C₃H₇(iso) | C₃H₅(cyclo) | |
| 8.0031 | H | CH₂Cl | CH₃ | C₃H₇(iso) | C₃H₅(cyclo) | |
| 8.0032 | H | CH₂CH₂Cl | CH₃ | C₃H₇(iso) | C₃H₅(cyclo) | |
| 8.0033 | H | CH₂CH₂CH₂Cl | CH₃ | C₃H₇(iso) | C₃H₅(cyclo) | |

TABLE 8.01

| No. | X | Y | R₂ | R₃ | Z | phys. data |
|---|---|---|---|---|---|---|
| 8.0101 | H | H | CH₃ | C₃H₇(iso) | CH₂OC₂H₅ | |
| 8.0102 | H | CH₃ | CH₃ | C₃H₇(iso) | CH₂OC₂H₅ | |
| 8.0103 | H | C₂H₅ | CH₃ | C₃H₇(iso) | CH₂OC₂H₅ | |
| 8.0104 | H | C₃H₇ | CH₃ | C₃H₇(iso) | CH₂OC₂H₅ | |
| 8.0105 | H | OCH₃ | CH₃ | C₃H₇(iso) | CH₂OC₂H₅ | |
| 8.0106 | H | OC₂H₅ | CH₃ | C₃H₇(iso) | CH₂OC₂H₅ | |
| 8.0107 | H | OCH₂CH=CH₂ | CH₃ | C₃H₇(iso) | CH₂OC₂H₅ | |
| 8.0108 | H | OCH₂CH=CHCH₃ | CH₃ | C₃H₇(iso) | CH₂OC₂H₅ | |
| 8.0109 | H | OCH₂C(Cl)=CH₂ | CH₃ | C₃H₇(iso) | CH₂OC₂H₅ | |
| 8.0110 | H | OCH₂CH=CHCl | CH₃ | C₃H₇(iso) | CH₂OC₂H₅ | |
| 8.0111 | H | OCH₂C≡CH | CH₃ | C₃H₇(iso) | CH₂OC₂H₅ | |
| 8.0112 | H | OCHF₂ | CH₃ | C₃H₇(iso) | CH₂OC₂H₅ | |
| 8.0113 | H | OCF₃ | CH₃ | C₃H₇(iso) | CH₂OC₂H₅ | |
| 8.0114 | H | OCF₂CHFCF₃ | CH₃ | C₃H₇(iso) | CH₂OC₂H₅ | |
| 8.0115 | H | OC₆H₅ | CH₃ | C₃H₇(iso) | CH₂OC₂H₅ | |
| 8.0116 | H | CF₃ | CH₃ | C₃H₇(iso) | CH₂OC₂H₅ | |
| 8.0117 | H | Br | CH₃ | C₃H₇(iso) | CH₂OC₂H₅ | |
| 8.0118 | H | Cl | CH₃ | C₃H₇(iso) | CH₂OC₂H₅ | |
| 8.0119 | H | F | CH₃ | C₃H₇(iso) | CH₂OC₂H₅ | |
| 8.0120 | H | SCH₃ | CH₃ | C₃H₇(iso) | CH₂OC₂H₅ | |
| 8.0121 | H | SCH₃ | CH₃ | C₃H₇(iso) | CH₂OC₂H₅ | |
| 8.0122 | H | SC₃H₇-n | CH₃ | C₃H₇(iso) | CH₂OC₂H₅ | |
| 8.0123 | H | SO₂CH₃ | CH₃ | C₃H₇(iso) | CH₂OC₂H₅ | |
| 8.0124 | H | SO₂CH₃ | CH₃ | C₃H₇(iso) | CH₂OC₂H₅ | |
| 8.0125 | H | NO₂ | CH₃ | C₃H₇(iso) | CH₂OC₂H₅ | |
| 8.0126 | H | CN | CH₃ | C₃H₇(iso) | CH₂OC₂H₅ | |
| 8.0127 | H | CH₂OH | CH₃ | C₃H₇(iso) | CH₂OC₂H₅ | |
| 8.0128 | H | CH₂CH₂OH | CH₃ | C₃H₇(iso) | CH₂OC₂H₅ | |
| 8.0129 | H | CH₂CH₂CH₂OH | CH₃ | C₃H₇(iso) | CH₂OC₂H₅ | |
| 8.0130 | H | C₆H₅ | CH₃ | C₃H₇(iso) | CH₂OC₂H₅ | |
| 8.0131 | H | CH₂Cl | CH₃ | C₃H₇(iso) | CH₂OC₂H₅ | |
| 8.0132 | H | CH₂CH₂Cl | CH₃ | C₃H₇(iso) | CH₂OC₂H₅ | |
| 8.0133 | H | CH₂CH₂CH₂Cl | CH₃ | C₃H₇(iso) | CH₂OC₂H₅ | |

TABLE 8.02

| No. | X | Y | R₂ | R₃ | Z | phys. data |
|---|---|---|---|---|---|---|
| 8.0101 | H | H | CH₃ | C₃H₇(iso) | CH₂OC₆H₅ | |
| 8.0202 | H | CH₃ | CH₃ | C₃H₇(iso) | CH₂OC₆H₅ | |
| 8.0203 | H | C₂H₅ | CH₃ | C₃H₇(iso) | CH₂OC₆H₅ | |
| 8.0204 | H | C₃H₇ | CH₃ | C₃H₇(iso) | CH₂OC₆H₅ | |
| 8.0205 | H | OCH₃ | CH₃ | C₃H₇(iso) | CH₂OC₆H₅ | |
| 8.0206 | H | OC₂H₅ | CH₃ | C₃H₇(iso) | CH₂OC₆H₅ | |
| 8.0207 | H | OCH₂CH=CH₂ | CH₃ | C₃H₇(iso) | CH₂OC₆H₅ | |
| 8.0208 | H | OCH₂CH=CHCH₃ | CH₃ | C₃H₇(iso) | CH₂OC₆H₅ | |
| 8.0209 | H | OCH₂C(Cl)=CH₂ | CH₃ | C₃H₇(iso) | CH₂OC₆H₅ | |

TABLE 8.02-continued

| No. | X | Y | R$_2$ | R$_3$ | Z | phys. data |
|---|---|---|---|---|---|---|
| 8.0210 | H | OCH$_2$CH=CHCl | CH$_3$ | C$_3$H$_7$(iso) | CH$_2$OC$_6$H$_5$ | |
| 8.0211 | H | OCH$_2$C≡CH | CH$_3$ | C$_3$H$_7$(iso) | CH$_2$OC$_6$H$_5$ | |
| 8.0212 | H | OCHF$_2$ | CH$_3$ | C$_3$H$_7$(iso) | CH$_2$OC$_6$H$_5$ | |
| 8.0213 | H | OCF$_3$ | CH$_3$ | C$_3$H$_7$(iso) | CH$_2$OC$_6$H$_5$ | |
| 8.0214 | H | OCF$_2$CHFCF$_3$ | CH$_3$ | C$_3$H$_7$(iso) | CH$_2$OC$_6$H$_5$ | |
| 8.0215 | H | OC$_6$H$_5$ | CH$_3$ | C$_3$H$_7$(iso) | CH$_2$OC$_6$H$_5$ | |
| 8.0216 | H | CF$_3$ | CH$_3$ | C$_3$H$_7$(iso) | CH$_2$OC$_6$H$_5$ | |
| 8.0217 | H | Br | CH$_3$ | C$_3$H$_7$(iso) | CH$_2$OC$_6$H$_5$ | |
| 8.0218 | H | Cl | CH$_3$ | C$_3$H$_7$(iso) | CH$_2$OC$_6$H$_5$ | |
| 8.0219 | H | F | CH$_3$ | C$_3$H$_7$(iso) | CH$_2$OC$_6$H$_5$ | |
| 8.0220 | H | SCH$_3$ | CH$_3$ | C$_3$H$_7$(iso) | CH$_2$OC$_6$H$_5$ | |
| 8.0221 | H | SCH$_3$ | CH$_3$ | C$_3$H$_7$(iso) | CH$_2$OC$_6$H$_5$ | |
| 8.0222 | H | SC$_3$H$_7$-n | CH$_3$ | C$_3$H$_7$(iso) | CH$_2$OC$_6$H$_5$ | |
| 8.0223 | H | SO$_2$CH$_3$ | CH$_3$ | C$_3$H$_7$(iso) | CH$_2$OC$_6$H$_5$ | |
| 8.0224 | H | SO$_2$CH$_3$ | CH$_3$ | C$_3$H$_7$(iso) | CH$_2$OC$_6$H$_5$ | |
| 8.0225 | H | NO$_2$ | CH$_3$ | C$_3$H$_7$(iso) | CH$_2$OC$_6$H$_5$ | |
| 8.0226 | H | CN | CH$_3$ | C$_3$H$_7$(iso) | CH$_2$OC$_6$H$_5$ | |
| 8.0227 | H | CH$_2$OH | CH$_3$ | C$_3$H$_7$(iso) | CH$_2$OC$_6$H$_5$ | |
| 8.0228 | H | CH$_2$CH$_2$OH | CH$_3$ | C$_3$H$_7$(iso) | CH$_2$OC$_6$H$_5$ | |
| 8.0229 | H | CH$_2$CH$_2$CH$_2$OH | CH$_3$ | C$_3$H$_7$(iso) | CH$_2$OC$_6$H$_5$ | |
| 8.0230 | H | C$_6$H$_5$ | CH$_3$ | C$_3$H$_7$(iso) | CH$_2$OC$_6$H$_5$ | |
| 8.0231 | H | CH$_2$Cl | CH$_3$ | C$_3$H$_7$(iso) | CH$_2$OC$_6$H$_5$ | |
| 8.0232 | H | CH$_2$CH$_2$Cl | CH$_3$ | C$_3$H$_7$(iso) | CH$_2$OC$_6$H$_5$ | |
| 8.0233 | H | CH$_2$CH$_2$CH$_2$Cl | CH$_3$ | C$_3$H$_7$(iso) | CH$_2$OC$_6$H$_5$ | |

EXAMPLE 17

Preparation of 2-(N-valylnitrile)carbamoyl-6-phenoxymethyl-nicotinic acid

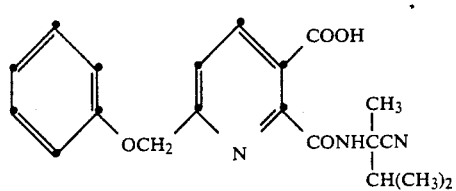

1.2 g of 2-methylvalylnitrile (2-amino-2-isopropyl-2-methyl-acetonitrile) are added to a solution of 2.55 g of 6-phenoxymethylpyridine-2,3-dicarboxylic acid anhydride in 3.0 ml of tetrahydrofuran while stirring and the reaction mixture is further stirred for one hour at room temperature before being concentrated by evaporation in vacuo. The residue is triturated in a small amount of ether and crystallises. In this manner 3.2 g of the above nicotinic acid with a melting point of 82°–87° are obtained.

The nicotinic acid derivatives of formula IX listed in Tables 9.00 to 9.02 are prepared analogously to Example 18.

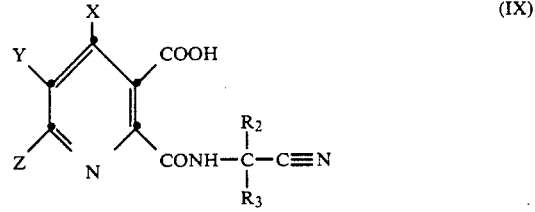
(IX)

TABLE 9.00

| No. | X | Y | R$_2$ | R$_3$ | Z | phys. data |
|---|---|---|---|---|---|---|
| 9.0001 | H | H | CH$_3$ | C$_3$H$_7$(iso) | C$_3$H$_5$(cyclo) | |
| 9.0002 | H | CH$_3$ | CH$_3$ | C$_3$H$_7$(iso) | C$_3$H$_5$(cyclo) | |
| 9.0003 | H | C$_2$H$_5$ | CH$_3$ | C$_3$H$_7$(iso) | C$_3$H$_5$(cyclo) | |
| 9.0004 | H | C$_3$H$_7$ | CH$_3$ | C$_3$H$_7$(iso) | C$_3$H$_5$(cyclo) | |
| 9.0005 | H | OCH$_3$ | CH$_3$ | C$_3$H$_7$(iso) | C$_3$H$_5$(cyclo) | |
| 9.0006 | H | OC$_2$H$_5$ | CH$_3$ | C$_3$H$_7$(iso) | C$_3$H$_5$(cyclo) | |
| 9.0007 | H | OCH$_2$CH=CH$_2$ | CH$_3$ | C$_3$H$_7$(iso) | C$_3$H$_5$(cyclo) | |
| 9.0008 | H | OCH$_2$CH=CHCH$_3$ | CH$_3$ | C$_3$H$_7$(iso) | C$_3$H$_5$(cyclo) | |
| 9.0009 | H | OCH$_2$C(Cl)=CH$_2$ | CH$_3$ | C$_3$H$_7$(iso) | C$_3$H$_5$(cyclo) | |
| 9.0010 | H | OCH$_2$CH=CHCl | CH$_3$ | C$_3$H$_7$(iso) | C$_3$H$_5$(cyclo) | |
| 9.0011 | H | OCH$_2$C≡CH | CH$_3$ | C$_3$H$_7$(iso) | C$_3$H$_5$(cyclo) | |
| 9.0012 | H | OCHF$_2$ | CH$_3$ | C$_3$H$_7$(iso) | C$_3$H$_5$(cyclo) | |
| 9.0013 | H | OCF$_3$ | CH$_3$ | C$_3$H$_7$(iso) | C$_3$H$_5$(cyclo) | |
| 9.0014 | H | OCF$_2$CHFCF$_3$ | CH$_3$ | C$_3$H$_7$(iso) | C$_3$H$_5$(cyclo) | |
| 9.0015 | H | OC$_6$H$_5$ | CH$_3$ | C$_3$H$_7$(iso) | C$_3$H$_5$(cyclo) | |
| 9.0016 | H | CF$_3$ | CH$_3$ | C$_3$H$_7$(iso) | C$_3$H$_5$(cyclo) | |
| 9.0017 | H | Br | CH$_3$ | C$_3$H$_7$(iso) | C$_3$H$_5$(cyclo) | |
| 9.0018 | H | Cl | CH$_3$ | C$_3$H$_7$(iso) | C$_3$H$_5$(cyclo) | |
| 9.0019 | H | F | CH$_3$ | C$_3$H$_7$(iso) | C$_3$H$_5$(cyclo) | |
| 9.0020 | H | SCH$_3$ | CH$_3$ | C$_3$H$_7$(iso) | C$_3$H$_5$(cyclo) | |
| 9.0021 | H | SCH$_3$ | CH$_3$ | C$_3$H$_7$(iso) | C$_3$H$_5$(cyclo) | |
| 9.0022 | H | SC$_3$H$_7$-n | CH$_3$ | C$_3$H$_7$(iso) | C$_3$H$_5$(cyclo) | |
| 9.0023 | H | SO$_2$CH$_3$ | CH$_3$ | C$_3$H$_7$(iso) | C$_3$H$_5$(cyclo) | |
| 9.0024 | H | SO$_2$CH$_3$ | CH$_3$ | C$_3$H$_7$(iso) | C$_3$H$_5$(cyclo) | |
| 9.0025 | H | NO$_2$ | CH$_3$ | C$_3$H$_7$(iso) | C$_3$H$_5$(cyclo) | |
| 9.0026 | H | CN | CH$_3$ | C$_3$H$_7$(iso) | C$_3$H$_5$(cyclo) | |
| 9.0027 | H | CH$_2$OH | CH$_3$ | C$_3$H$_7$(iso) | C$_3$H$_5$(cyclo) | |
| 9.0028 | H | CH$_2$CH$_2$OH | CH$_3$ | C$_3$H$_7$(iso) | C$_3$H$_5$(cyclo) | |

TABLE 9.00-continued

| No. | X | Y | R₂ | R₃ | Z | phys. data |
|---|---|---|---|---|---|---|
| 9.0029 | H | CH₂CH₂CH₂OH | CH₃ | C₃H₇(iso) | C₃H₅(cyclo) | |
| 9.0030 | H | C₆H₅ | CH₃ | C₃H₇(iso) | C₃H₅(cyclo) | |
| 9.0031 | H | CH₂Cl | CH₃ | C₃H₇(iso) | C₃H₅(cyclo) | |
| 9.0032 | H | CH₂CH₂Cl | CH₃ | C₃H₇(iso) | C₃H₅(cyclo) | |
| 9.0033 | H | CH₂CH₂CH₂Cl | CH₃ | C₃H₇(iso) | C₃H₅(cyclo) | |

TABLE 9.01

| No. | X | Y | R₂ | R₃ | Z | phys. data |
|---|---|---|---|---|---|---|
| 9.0101 | H | H | CH₃ | C₃H₇(iso) | CH₂OC₂H₅ | |
| 9.0102 | H | CH₃ | CH₃ | C₃H₇(iso) | CH₂OC₂H₅ | |
| 9.0103 | H | C₂H₅ | CH₃ | C₃H₇(iso) | CH₂OC₂H₅ | |
| 9.0104 | H | C₃H₇ | CH₃ | C₃H₇(iso) | CH₂OC₂H₅ | |
| 9.0105 | H | OCH₃ | CH₃ | C₃H₇(iso) | CH₂OC₂H₅ | |
| 9.0106 | H | OC₂H₅ | CH₃ | C₃H₇(iso) | CH₂OC₂H₅ | |
| 9.0107 | H | OCH₂CH=CH₂ | CH₃ | C₃H₇(iso) | CH₂OC₂H₅ | |
| 9.0108 | H | OCH₂CH=CHCH₃ | CH₃ | C₃H₇(iso) | CH₂OC₂H₅ | |
| 9.0109 | H | OCH₂C(Cl)=CH₂ | CH₃ | C₃H₇(iso) | CH₂OC₂H₅ | |
| 9.0110 | H | OCH₂CH=CHCl | CH₃ | C₃H₇(iso) | CH₂OC₂H₅ | |
| 9.0111 | H | OCH₂C≡CH | CH₃ | C₃H₇(iso) | CH₂OC₂H₅ | |
| 9.0112 | H | OCHF₂ | CH₃ | C₃H₇(iso) | CH₂OC₂H₅ | |
| 9.0113 | H | OCF₃ | CH₃ | C₃H₇(iso) | CH₂OC₂H₅ | |
| 9.0114 | H | OCF₂CHFCF₃ | CH₃ | C₃H₇(iso) | CH₂OC₂H₅ | |
| 9.0115 | H | OC₆H₅ | CH₃ | C₃H₇(iso) | CH₂OC₂H₅ | |
| 9.0116 | H | CF₃ | CH₃ | C₃H₇(iso) | CH₂OC₂H₅ | |
| 9.0117 | H | Br | CH₃ | C₃H₇(iso) | CH₂OC₂H₅ | |
| 9.0118 | H | Cl | CH₃ | C₃H₇(iso) | CH₂OC₂H₅ | |
| 9.0119 | H | F | CH₃ | C₃H₇(iso) | CH₂OC₂H₅ | |
| 9.0120 | H | SCH₃ | CH₃ | C₃H₇(iso) | CH₂OC₂H₅ | |
| 9.0121 | H | SCH₃ | CH₃ | C₃H₇(iso) | CH₂OC₂H₅ | |
| 9.0122 | H | SC₃H₇-n | CH₃ | C₃H₇(iso) | CH₂OC₂H₅ | |
| 9.0123 | H | SO₂CH₃ | CH₃ | C₃H₇(iso) | CH₂OC₂H₅ | |
| 9.0124 | H | SO₂CH₃ | CH₃ | C₃H₇(iso) | CH₂OC₂H₅ | |
| 9.0125 | H | NO₂ | CH₃ | C₃H₇(iso) | CH₂OC₂H₅ | |
| 9.0126 | H | CN | CH₃ | C₃H₇(iso) | CH₂OC₂H₅ | |
| 9.0127 | H | CH₂OH | CH₃ | C₃H₇(iso) | CH₂OC₂H₅ | |
| 9.0128 | H | CH₂CH₂OH | CH₃ | C₃H₇(iso) | CH₂OC₂H₅ | |
| 9.0129 | H | CH₂CH₂CH₂OH | CH₃ | C₃H₇(iso) | CH₂OC₂H₅ | |
| 9.0130 | H | C₆H₅ | CH₃ | C₃H₇(iso) | CH₂OC₂H₅ | |
| 9.0131 | H | CH₂Cl | CH₃ | C₃H₇(iso) | CH₂OC₂H₅ | |
| 9.0132 | H | CH₂CH₂Cl | CH₃ | C₃H₇(iso) | CH₂OC₂H₅ | |
| 9.0133 | H | CH₂CH₂CH₂Cl | CH₃ | C₃H₇(iso) | CH₂OC₂H₅ | |

TABLE 9.02

| No. | X | Y | R₂ | R₃ | Z | phys. data |
|---|---|---|---|---|---|---|
| 9.0201 | H | H | CH₃ | C₃H₇(iso) | CH₂OC₆H₅ | m.p. 82-87° |
| 9.0202 | H | CH₃ | CH₃ | C₃H₇(iso) | CH₂OC₆H₅ | |
| 9.0203 | H | C₂H₅ | CH₃ | C₃H₇(iso) | CH₂OC₆H₅ | |
| 9.0204 | H | C₃H₇ | CH₃ | C₃H₇(iso) | CH₂OC₆H₅ | |
| 9.0205 | H | OCH₃ | CH₃ | C₃H₇(iso) | CH₂OC₆H₅ | |
| 9.0206 | H | OC₂H₅ | CH₃ | C₃H₇(iso) | CH₂OC₆H₅ | |
| 9.0207 | H | OCH₂CH=CH₂ | CH₃ | C₃H₇(iso) | CH₂OC₆H₅ | |
| 9.0208 | H | OCH₂CH=CHCH₃ | CH₃ | C₃H₇(iso) | CH₂OC₆H₅ | |
| 9.0209 | H | OCH₂C(Cl)=CH₂ | CH₃ | C₃H₇(iso) | CH₂OC₆H₅ | |
| 9.0210 | H | OCH₂CH=CHCl | CH₃ | C₃H₇(iso) | CH₂OC₆H₅ | |
| 9.0211 | H | OCH₂C≡CH | CH₃ | C₃H₇(iso) | CH₂OC₆H₅ | |
| 9.0212 | H | OCHF₂ | CH₃ | C₃H₇(iso) | CH₂OC₆H₅ | |
| 9.0213 | H | OCF₃ | CH₃ | C₃H₇(iso) | CH₂OC₆H₅ | |
| 9.0214 | H | OCF₂CHFCF₃ | CH₃ | C₃H₇(iso) | CH₂OC₆H₅ | |
| 9.0215 | H | OC₆H₅ | CH₃ | C₃H₇(iso) | CH₂OC₆H₅ | |
| 9.0216 | H | CF₃ | CH₃ | C₃H₇(iso) | CH₂OC₆H₅ | |
| 9.0217 | H | Br | CH₃ | C₃H₇(iso) | CH₂OC₆H₅ | |
| 9.0218 | H | Cl | CH₃ | C₃H₇(iso) | CH₂OC₆H₅ | |
| 9.0219 | H | F | CH₃ | C₃H₇(iso) | CH₂OC₆H₅ | |
| 9.0220 | H | SCH₃ | CH₃ | C₃H₇(iso) | CH₂OC₆H₅ | |
| 9.0221 | H | SCH₃ | CH₃ | C₃H₇(iso) | CH₂OC₆H₅ | |
| 9.0222 | H | SC₃H₇-n | CH₃ | C₃H₇(iso) | CH₂OC₆H₅ | |
| 9.0223 | H | SO₂CH₃ | CH₃ | C₃H₇(iso) | CH₂OC₆H₅ | |
| 9.0224 | H | SO₂CH₃ | CH₃ | C₃H₇(iso) | CH₂OC₆H₅ | |
| 9.0225 | H | NO₂ | CH₃ | C₃H₇(iso) | CH₂OC₆H₅ | |
| 9.0226 | H | CN | CH₃ | C₃H₇(iso) | CH₂OC₆H₅ | |
| 9.0227 | H | CH₂OH | CH₃ | C₃H₇(iso) | CH₂OC₆H₅ | |
| 9.0228 | H | CH₂CH₂OH | CH₃ | C₃H₇(iso) | CH₂OC₆H₅ | |
| 9.0229 | H | CH₂CH₂CH₂OH | CH₃ | C₃H₇(iso) | CH₂OC₆H₅ | |
| 9.0230 | H | C₆H₅ | CH₃ | C₃H₇(iso) | CH₂OC₆H₅ | |
| 9.0231 | H | CH₂Cl | CH₃ | C₃H₇(iso) | CH₂OC₆H₅ | |
| 9.0232 | H | CH₂CH₂Cl | CH₃ | C₃H₇(iso) | CH₂OC₆H₅ | |

TABLE 9.02-continued

| No. | X | Y | R₂ | R₃ | Z | phys. data |
|---|---|---|---|---|---|---|
| 9.0233 | H | CH₂CH₂CH₂Cl | CH₃ | C₃H₇(iso) | CH₂OC₆H₅ | |

EXAMPLE 18

Preparation of N-(2-isopropyl-2-methyl-glycylnitrile)-6-phenoxymethylpyridine-2,3-dicarboxylic acid imide

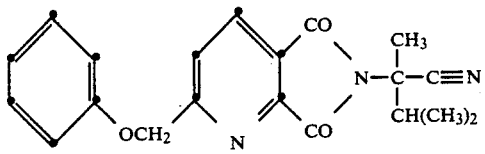

0.02 parts of sodium acetate is added to a solution of one part of 2-(N-valylnitrile)carbamoyl-6-phenoxymethylnicotinic acid (Example 17) in 4 parts of acetic anhydride and the mixture is stirred under reflux for 6 hours at 110°. It is then concentrated by evaporation and the residue is taken up in some toluene and again concentrated by evaporation.

The residue is triturated in ether/hexane, and the resulting crystalline mass is filtered off with suction, then dissolved in methylene chloride and filtered on silica gel. After evaporation of the methylene chloride 0.85 parts of the above imide remain.

The pyridine-2,3-dicarboxylic acid imides of formula X listed in Tables 10.00 to 10.02 are prepared in a manner analogous to that described in Example 18.

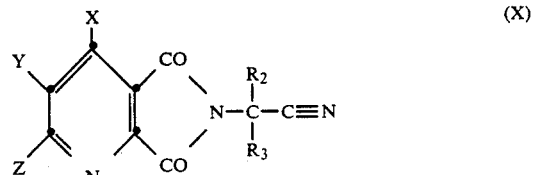 (X)

TABLE 10.00

| No. | X | Y | R₂ | R₃ | Z | phys. data |
|---|---|---|---|---|---|---|
| 10.0001 | H | H | CH₃ | C₃H₇(iso) | C₃H₅(cyclo) | |
| 10.0002 | H | CH₃ | CH₃ | C₃H₇(iso) | C₃H₅(cyclo) | |
| 10.0003 | H | C₂H₅ | CH₃ | C₃H₇(iso) | C₃H₅(cyclo) | |
| 10.0004 | H | C₃H₇ | CH₃ | C₃H₇(iso) | C₃H₅(cyclo) | |
| 10.0005 | H | OCH₃ | CH₃ | C₃H₇(iso) | C₃H₅(cyclo) | |
| 10.0006 | H | OC₂H₅ | CH₃ | C₃H₇(iso) | C₃H₅(cyclo) | |
| 10.0007 | H | OCH₂CH=CH₂ | CH₃ | C₃H₇(iso) | C₃H₅(cyclo) | |
| 10.0008 | H | OCH₂CH=CHCH₃ | CH₃ | C₃H₇(iso) | C₃H₅(cyclo) | |
| 10.0009 | H | OCH₂C(Cl)=CH₂ | CH₃ | C₃H₇(iso) | C₃H₅(cyclo) | |
| 10.0010 | H | OCH₂CH=CHCl | CH₃ | C₃H₇(iso) | C₃H₅(cyclo) | |
| 10.0011 | H | OCH₂C≡CH | CH₃ | C₃H₇(iso) | C₃H₅(cyclo) | |
| 10.0012 | H | OCHF₂ | CH₃ | C₃H₇(iso) | C₃H₅(cyclo) | |
| 10.0013 | H | OCF₃ | CH₃ | C₃H₇(iso) | C₃H₅(cyclo) | |
| 10.0014 | H | OCF₂CHFCF₃ | CH₃ | C₃H₇(iso) | C₃H₅(cyclo) | |
| 10.0015 | H | OC₆H₅ | CH₃ | C₃H₇(iso) | C₃H₅(cyclo) | |
| 10.0016 | H | CF₃ | CH₃ | C₃H₇(iso) | C₃H₅(cyclo) | |
| 10.0017 | H | Br | CH₃ | C₃H₇(iso) | C₃H₅(cyclo) | |
| 10.0018 | H | Cl | CH₃ | C₃H₇(iso) | C₃H₅(cyclo) | |
| 10.0019 | H | F | CH₃ | C₃H₇(iso) | C₃H₅(cyclo) | |
| 10.0020 | H | SCH₃ | CH₃ | C₃H₇(iso) | C₃H₅(cyclo) | |
| 10.0021 | H | SCH₃ | CH₃ | C₃H₇(iso) | C₃H₅(cyclo) | |
| 10.0022 | H | SC₃H₇-n | CH₃ | C₃H₇(iso) | C₃H₅(cyclo) | |
| 10.0023 | H | SO₂CH₃ | CH₃ | C₃H₇(iso) | C₃H₅(cyclo) | |
| 10.0024 | H | SO₂CH₃ | CH₃ | C₃H₇(iso) | C₃H₅(cyclo) | |
| 10.0025 | H | NO₂ | CH₃ | C₃H₇(iso) | C₃H₅(cyclo) | |
| 10.0026 | H | CN | CH₃ | C₃H₇(iso) | C₃H₅(cyclo) | |
| 10.0027 | H | CH₂OH | CH₃ | C₃H₇(iso) | C₃H₅(cyclo) | |
| 10.0028 | H | CH₂CH₂OH | CH₃ | C₃H₇(iso) | C₃H₅(cyclo) | |
| 10.0029 | H | CH₂CH₂CH₂OH | CH₃ | C₃H₇(iso) | C₃H₅(cyclo) | |
| 10.0030 | H | C₆H₅ | CH₃ | C₃H₇(iso) | C₃H₅(cyclo) | |
| 10.0031 | H | CH₂Cl | CH₃ | C₃H₇(iso) | C₃H₅(cyclo) | |
| 10.0032 | H | CH₂CH₂Cl | CH₃ | C₃H₇(iso) | C₃H₅(cyclo) | |
| 10.0033 | H | CH₂CH₂CH₂Cl | CH₃ | C₃H₇(iso) | C₃H₅(cyclo) | |

TABLE 10.01

| No. | X | Y | R₂ | R₃ | Z | phys. data |
|---|---|---|---|---|---|---|
| 10.0101 | H | H | CH₃ | C₃H₇(iso) | CH₂OC₂H₅ | |
| 10.0102 | H | CH₃ | CH₃ | C₃H₇(iso) | CH₂OC₂H₅ | |
| 10.0103 | H | C₂H₅ | CH₃ | C₃H₇(iso) | CH₂OC₂H₅ | |
| 10.0104 | H | C₃H₇ | CH₃ | C₃H₇(iso) | CH₂OC₂H₅ | |
| 10.0105 | H | OCH₃ | CH₃ | C₃H₇(iso) | CH₂OC₂H₅ | |
| 10.0106 | H | OC₂H₅ | CH₃ | C₃H₇(iso) | CH₂OC₂H₅ | |
| 10.0107 | H | OCH₂CH=CH₂ | CH₃ | C₃H₇(iso) | CH₂OC₂H₅ | |
| 10.0108 | H | OCH₂CH=CHCH₃ | CH₃ | C₃H₇(iso) | CH₂OC₂H₅ | |
| 10.0109 | H | OCH₂C(Cl)=CH₂ | CH₃ | C₃H₇(iso) | CH₂OC₂H₅ | |
| 10.0110 | H | OCH₂CH=CHCl | CH₃ | C₃H₇(iso) | CH₂OC₂H₅ | |
| 10.0111 | H | OCH₂C≡CH | CH₃ | C₃H₇(iso) | CH₂OC₂H₅ | |
| 10.0112 | H | OCHF₂ | CH₃ | C₃H₇(iso) | CH₂OC₂H₅ | |

TABLE 10.01-continued

| No. | X | Y | $R_2$ | $R_3$ | Z | phys. data |
|---|---|---|---|---|---|---|
| 10.0113 | H | $OCF_3$ | $CH_3$ | $C_3H_7(iso)$ | $CH_2OC_2H_5$ | |
| 10.0114 | H | $OCF_2CHFCF_3$ | $CH_3$ | $C_3H_7(iso)$ | $CH_2OC_2H_5$ | |
| 10.0115 | H | $OC_6H_5$ | $CH_3$ | $C_3H_7(iso)$ | $CH_2OC_2H_5$ | |
| 10.0116 | H | $CF_3$ | $CH_3$ | $C_3H_7(iso)$ | $CH_2OC_2H_5$ | |
| 10.0117 | H | Br | $CH_3$ | $C_3H_7(iso)$ | $CH_2OC_2H_5$ | |
| 10.0118 | H | Cl | $CH_3$ | $C_3H_7(iso)$ | $CH_2OC_2H_5$ | |
| 10.0119 | H | F | $CH_3$ | $C_3H_7(iso)$ | $CH_2OC_2H_5$ | |
| 10.0120 | H | $SCH_3$ | $CH_3$ | $C_3H_7(iso)$ | $CH_2OC_2H_5$ | |
| 10.0121 | H | $SCH_3$ | $CH_3$ | $C_3H_7(iso)$ | $CH_2OC_2H_5$ | |
| 10.0122 | H | $SC_3H_7\text{-}n$ | $CH_3$ | $C_3H_7(iso)$ | $CH_2OC_2H_5$ | |
| 10.0123 | H | $SO_2CH_3$ | $CH_3$ | $C_3H_7(iso)$ | $CH_2OC_2H_5$ | |
| 10.0124 | H | $SO_2CH_3$ | $CH_3$ | $C_3H_7(iso)$ | $CH_2OC_2H_5$ | |
| 10.0125 | H | $NO_2$ | $CH_3$ | $C_3H_7(iso)$ | $CH_2OC_2H_5$ | |
| 10.0126 | H | CN | $CH_3$ | $C_3H_7(iso)$ | $CH_2OC_2H_5$ | |
| 10.0127 | H | $CH_2OH$ | $CH_3$ | $C_3H_7(iso)$ | $CH_2OC_2H_5$ | |
| 10.0128 | H | $CH_2CH_2OH$ | $CH_3$ | $C_3H_7(iso)$ | $CH_2OC_2H_5$ | |
| 10.0129 | H | $CH_2CH_2CH_2OH$ | $CH_3$ | $C_3H_7(iso)$ | $CH_2OC_2H_5$ | |
| 10.0130 | H | $C_6H_5$ | $CH_3$ | $C_3H_7(iso)$ | $CH_2OC_2H_5$ | |
| 10.0131 | H | $CH_2Cl$ | $CH_3$ | $C_3H_7(iso)$ | $CH_2OC_2H_5$ | |
| 10.0132 | H | $CH_2CH_2Cl$ | $CH_3$ | $C_3H_7(iso)$ | $CH_2OC_2H_5$ | |
| 10.0133 | H | $CH_2CH_2CH_2Cl$ | $CH_3$ | $C_3H_7(iso)$ | $CH_2OC_2H_5$ | |

TABLE 10.02

| No. | X | Y | $R_2$ | $R_3$ | Z | phys. data |
|---|---|---|---|---|---|---|
| 10.0201 | H | H | $CH_3$ | $C_3H_7(iso)$ | $CH_2OC_6H_5$ | |
| 10.0202 | H | $CH_3$ | $CH_3$ | $C_3H_7(iso)$ | $CH_2OC_6H_5$ | |
| 10.0203 | H | $C_2H_5$ | $CH_3$ | $C_3H_7(iso)$ | $CH_2OC_6H_5$ | |
| 10.0204 | H | $C_3H_7$ | $CH_3$ | $C_3H_7(iso)$ | $CH_2OC_6H_5$ | |
| 10.0205 | H | $OCH_3$ | $CH_3$ | $C_3H_7(iso)$ | $CH_2OC_6H_5$ | |
| 10.0206 | H | $OC_2H_5$ | $CH_3$ | $C_3H_7(iso)$ | $CH_2OC_6H_5$ | |
| 10.0207 | H | $OCH_2CH=CH_2$ | $CH_3$ | $C_3H_7(iso)$ | $CH_2OC_6H_5$ | |
| 10.0208 | H | $OCH_2CH=CHCH_3$ | $CH_3$ | $C_3H_7(iso)$ | $CH_2OC_6H_5$ | |
| 10.0209 | H | $OCH_2C(Cl)=CH_2$ | $CH_3$ | $C_3H_7(iso)$ | $CH_2OC_6H_5$ | |
| 10.0210 | H | $OCH_2CH=CHCl$ | $CH_3$ | $C_3H_7(iso)$ | $CH_2OC_6H_5$ | |
| 10.0211 | H | $OCH_2C\equiv CH$ | $CH_3$ | $C_3H_7(iso)$ | $CH_2OC_6H_5$ | |
| 10.0212 | H | $OCHF_2$ | $CH_3$ | $C_3H_7(iso)$ | $CH_2OC_6H_5$ | |
| 10.0213 | H | $OCF_3$ | $CH_3$ | $C_3H_7(iso)$ | $CH_2OC_6H_5$ | |
| 10.0214 | H | $OCF_2CHFCF_3$ | $CH_3$ | $C_3H_7(iso)$ | $CH_2OC_6H_5$ | |
| 10.0215 | H | $OC_6H_5$ | $CH_3$ | $C_3H_7(iso)$ | $CH_2OC_6H_5$ | |
| 10.0216 | H | $CF_3$ | $CH_3$ | $C_3H_7(iso)$ | $CH_2OC_6H_5$ | |
| 10.0217 | H | Br | $CH_3$ | $C_3H_7(iso)$ | $CH_2OC_6H_5$ | |
| 10.0218 | H | Cl | $CH_3$ | $C_3H_7(iso)$ | $CH_2OC_6H_5$ | |
| 10.0219 | H | F | $CH_3$ | $C_3H_7(iso)$ | $CH_2OC_6H_5$ | |
| 10.0220 | H | $SCH_3$ | $CH_3$ | $C_3H_7(iso)$ | $CH_2OC_6H_5$ | |
| 10.0221 | H | $SCH_3$ | $CH_3$ | $C_3H_7(iso)$ | $CH_2OC_6H_5$ | |
| 10.0222 | H | $SC_3H_7\text{-}n$ | $CH_3$ | $C_3H_7(iso)$ | $CH_2OC_6H_5$ | |
| 10.0223 | H | $SO_2CH_3$ | $CH_3$ | $C_3H_7(iso)$ | $CH_2OC_6H_5$ | |
| 10.0224 | H | $SO_2CH_3$ | $CH_3$ | $C_3H_7(iso)$ | $CH_2OC_6H_5$ | |
| 10.0225 | H | $NO_2$ | $CH_3$ | $C_3H_7(iso)$ | $CH_2OC_6H_5$ | |
| 10.0226 | H | CN | $CH_3$ | $C_3H_7(iso)$ | $CH_2OC_6H_5$ | |
| 10.0227 | H | $CH_2OH$ | $CH_3$ | $C_3H_7(iso)$ | $CH_2OC_6H_5$ | |
| 10.0228 | H | $CH_2CH_2OH$ | $CH_3$ | $C_3H_7(iso)$ | $CH_2OC_6H_5$ | |
| 10.0229 | H | $CH_2CH_2CH_2OH$ | $CH_3$ | $C_3H_7(iso)$ | $CH_2OC_6H_5$ | |
| 10.0230 | H | $C_6H_5$ | $CH_3$ | $C_3H_7(iso)$ | $CH_2OC_6H_5$ | |
| 10.0231 | H | $CH_2Cl$ | $CH_3$ | $C_3H_7(iso)$ | $CH_2OC_6H_5$ | |
| 10.0232 | H | $CH_2CH_2Cl$ | $CH_3$ | $C_3H_7(iso)$ | $CH_2OC_6H_5$ | |
| 10.0233 | H | $CH_2CH_2CH_2Cl$ | $CH_3$ | $C_3H_7(iso)$ | $CH_2OC_6H_5$ | |

EXAMPLE 19

Preparation of
N-(2-methylvalylamide)-6-phenoxymethylpyridine-2,3-carboxylic acid imide

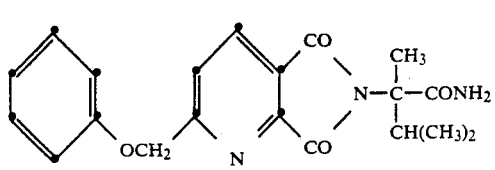

While stirring, and maintaining the reaction temperature below 70° by cooling, one part of 2-phenoxymethyl-5,7-dihydro-α-isopropyl-α-methyl-5,7-dioxo-OH-pyrrolo[3,4-6]pyridine-6-acetonitrile [N-(2-isopropyl-2-methylglycylnitrile)-6-phenoxymethylpyridine-2,3-dicarboxylic acid imide of Example 18] is added to one part of concentrated sulphuric acid. When the addition is complete, the reaction mixture is further stirred for one hour at 65°, then cooled, and poured onto 12 parts of ice. 1.5 parts of sodium acetate are added to the resulting mixture while stirring and, after 2 hours, the mixture is filtered with suction. The filtration residue is washed with sodium acetate solution and water and dried over phosphorus pentoxide. In this manner 0.82 parts of the above imide are obtained.

The pyridine-2,3-dicarboxylic acid imides of formula XI listed in Tables 11.00 to 11.02 are prepared in a manner analogous to that described in Example 19.

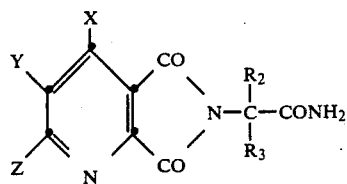

(XI)

TABLE 11.00

| No. | X | Y | R₂ | R₃ | Z | phys. data |
|---|---|---|---|---|---|---|
| 11.0001 | H | H | CH₃ | C₃H₇(iso) | C₃H₅(cyclo) | |
| 11.0002 | H | CH₃ | CH₃ | C₃H₇(iso) | C₃H₅(cyclo) | |
| 11.0003 | H | C₂H₅ | CH₃ | C₃H₇(iso) | C₃H₅(cyclo) | |
| 11.0004 | H | C₃H₇ | CH₃ | C₃H₇(iso) | C₃H₅(cyclo) | |
| 11.0005 | H | OCH₃ | CH₃ | C₃H₇(iso) | C₃H₅(cyclo) | |
| 11.0006 | H | OC₂H₅ | CH₃ | C₃H₇(iso) | C₃H₅(cyclo) | |
| 11.0007 | H | OCH₂CH=CH₂ | CH₃ | C₃H₇(iso) | C₃H₅(cyclo) | |
| 11.0008 | H | OCH₂CH=CHCH₃ | CH₃ | C₃H₇(iso) | C₃H₅(cyclo) | |
| 11.0009 | H | OCH₂C(Cl)=CH₂ | CH₃ | C₃H₇(iso) | C₃H₅(cyclo) | |
| 11.0010 | H | OCH₂CH=CHCl | CH₃ | C₃H₇(iso) | C₃H₅(cyclo) | |
| 11.0011 | H | OCH₂C≡CH | CH₃ | C₃H₇(iso) | C₃H₅(cyclo) | |
| 11.0012 | H | OCHF₂ | CH₃ | C₃H₇(iso) | C₃H₅(cyclo) | |
| 11.0013 | H | OCF₃ | CH₃ | C₃H₇(iso) | C₃H₅(cyclo) | |
| 11.0014 | H | OCF₂CHFCF₃ | CH₃ | C₃H₇(iso) | C₃H₅(cyclo) | |
| 11.0015 | H | OC₆H₅ | CH₃ | C₃H₇(iso) | C₃H₅(cyclo) | |
| 11.0016 | H | CF₃ | CH₃ | C₃H₇(iso) | C₃H₅(cyclo) | |
| 11.0017 | H | Br | CH₃ | C₃H₇(iso) | C₃H₅(cyclo) | |
| 11.0018 | H | Cl | CH₃ | C₃H₇(iso) | C₃H₅(cyclo) | |
| 11.0019 | H | F | CH₃ | C₃H₇(iso) | C₃H₅(cyclo) | |
| 11.0020 | H | SCH₃ | CH₃ | C₃H₇(iso) | C₃H₅(cyclo) | |
| 11.0021 | H | SCH₃ | CH₃ | C₃H₇(iso) | C₃H₅(cyclo) | |
| 11.0022 | H | SC₃H₇-n | CH₃ | C₃H₇(iso) | C₃H₅(cyclo) | |
| 11.0023 | H | SO₂CH₃ | CH₃ | C₃H₇(iso) | C₃H₅(cyclo) | |
| 11.0024 | H | SO₂CH₃ | CH₃ | C₃H₇(iso) | C₃H₅(cyclo) | |
| 11.0025 | H | NO₂ | CH₃ | C₃H₇(iso) | C₃H₅(cyclo) | |
| 11.0026 | H | CN | CH₃ | C₃H₇(iso) | C₃H₅(cyclo) | |
| 11.0027 | H | CH₂OH | CH₃ | C₃H₇(iso) | C₃H₅(cyclo) | |
| 11.0028 | H | CH₂CH₂OH | CH₃ | C₃H₇(iso) | C₃H₅(cyclo) | |
| 11.0029 | H | CH₂CH₂CH₂OH | CH₃ | C₃H₇(iso) | C₃H₅(cyclo) | |
| 11.0030 | H | C₆H₅ | CH₃ | C₃H₇(iso) | C₃H₅(cyclo) | |
| 11.0031 | H | CH₂Cl | CH₃ | C₃H₇(iso) | C₃H₅(cyclo) | |
| 11.0032 | H | CH₂CH₂Cl | CH₃ | C₃H₇(iso) | C₃H₅(cyclo) | |
| 11.0033 | H | CH₂CH₂CH₂Cl | CH₃ | C₃H₇(iso) | C₃H₅(cyclo) | |

TABLE 11.01

| No. | X | Y | R₂ | R₃ | Z | phys. data |
|---|---|---|---|---|---|---|
| 11.0101 | H | H | CH₃ | C₃H₇(iso) | CH₂OC₂H₅ | |
| 11.0102 | H | CH₃ | CH₃ | C₃H₇(iso) | CH₂OC₂H₅ | |
| 11.0103 | H | C₂H₅ | CH₃ | C₃H₇(iso) | CH₂OC₂H₅ | |
| 11.0104 | H | C₃H₇ | CH₃ | C₃H₇(iso) | CH₂OC₂H₅ | |
| 11.0105 | H | OCH₃ | CH₃ | C₃H₇(iso) | CH₂OC₂H₅ | |
| 11.0106 | H | OC₂H₅ | CH₃ | C₃H₇(iso) | CH₂OC₂H₅ | |
| 11.0107 | H | OCH₂CH=CH₂ | CH₃ | C₃H₇(iso) | CH₂OC₂H₅ | |
| 11.0108 | H | OCH₂CH=CHCH₃ | CH₃ | C₃H₇(iso) | CH₂OC₂H₅ | |
| 11.0109 | H | OCH₂C(Cl)=CH₂ | CH₃ | C₃H₇(iso) | CH₂OC₂H₅ | |
| 11.0110 | H | OCH₂CH=CHCl | CH₃ | C₃H₇(iso) | CH₂OC₂H₅ | |
| 11.0111 | H | OCH₂C≡CH | CH₃ | C₃H₇(iso) | CH₂OC₂H₅ | |
| 11.0112 | H | OCHF₂ | CH₃ | C₃H₇(iso) | CH₂OC₂H₅ | |
| 11.0113 | H | OCF₃ | CH₃ | C₃H₇(iso) | CH₂OC₂H₅ | |
| 11.0114 | H | OCF₂CHFCF₃ | CH₃ | C₃H₇(iso) | CH₂OC₂H₅ | |
| 11.0115 | H | OC₆H₅ | CH₃ | C₃H₇(iso) | CH₂OC₂H₅ | |
| 11.0116 | H | CF₃ | CH₃ | C₃H₇(iso) | CH₂OC₂H₅ | |
| 11.0117 | H | Br | CH₃ | C₃H₇(iso) | CH₂OC₂H₅ | |
| 11.0118 | H | Cl | CH₃ | C₃H₇(iso) | CH₂OC₂H₅ | |
| 11.0119 | H | F | CH₃ | C₃H₇(iso) | CH₂OC₂H₅ | |
| 11.0120 | H | SCH₃ | CH₃ | C₃H₇(iso) | CH₂OC₂H₅ | |
| 11.0121 | H | SCH₃ | CH₃ | C₃H₇(iso) | CH₂OC₂H₅ | |
| 11.0122 | H | SC₃H₇-n | CH₃ | C₃H₇(iso) | CH₂OC₂H₅ | |
| 11.0123 | H | SO₂CH₃ | CH₃ | C₃H₇(iso) | CH₂OC₂H₅ | |
| 11.0124 | H | SO₂CH₃ | CH₃ | C₃H₇(iso) | CH₂OC₂H₅ | |
| 11.0125 | H | NO₂ | CH₃ | C₃H₇(iso) | CH₂OC₂H₅ | |
| 11.0126 | H | CN | CH₃ | C₃H₇(iso) | CH₂OC₂H₅ | |
| 11.0127 | H | CH₂OH | CH₃ | C₃H₇(iso) | CH₂OC₂H₅ | |
| 11.0128 | H | CH₂CH₂OH | CH₃ | C₃H₇(iso) | CH₂OC₂H₅ | |
| 11.0129 | H | CH₂CH₂CH₂OH | CH₃ | C₃H₇(iso) | CH₂OC₂H₅ | |
| 11.0130 | H | C₆H₅ | CH₃ | C₃H₇(iso) | CH₂OC₂H₅ | |
| 11.0131 | H | CH₂Cl | CH₃ | C₃H₇(iso) | CH₂OC₂H₅ | |

TABLE 11.01-continued

| No. | X | Y | $R_2$ | $R_3$ | Z | phys. data |
|---|---|---|---|---|---|---|
| 11.0132 | H | $CH_2CH_2Cl$ | $CH_3$ | $C_3H_7$(iso) | $CH_2OC_2H_5$ | |
| 11.0133 | H | $CH_2CH_2CH_2Cl$ | $CH_3$ | $C_3H_7$(iso) | $CH_2OC_2H_5$ | |

TABLE 11.02

| No. | X | Y | $R_2$ | $R_3$ | Z | phys. data |
|---|---|---|---|---|---|---|
| 11.0201 | H | H | $CH_3$ | $C_3H_7$(iso) | $CH_2OC_6H_5$ | |
| 11.0202 | H | $CH_3$ | $CH_3$ | $C_3H_7$(iso) | $CH_2OC_6H_5$ | |
| 11.0203 | H | $C_2H_5$ | $CH_3$ | $C_3H_7$(iso) | $CH_2OC_6H_5$ | |
| 11.0204 | H | $C_3H_7$ | $CH_3$ | $C_3H_7$(iso) | $CH_2OC_6H_5$ | |
| 11.0205 | H | $OCH_3$ | $CH_3$ | $C_3H_7$(iso) | $CH_2OC_6H_5$ | |
| 11.0206 | H | $OC_2H_5$ | $CH_3$ | $C_3H_7$(iso) | $CH_2OC_6H_5$ | |
| 11.0207 | H | $OCH_2CH=CH_2$ | $CH_3$ | $C_3H_7$(iso) | $CH_2OC_6H_5$ | |
| 11.0208 | H | $OCH_2CH=CHCH_3$ | $CH_3$ | $C_3H_7$(iso) | $CH_2OC_6H_5$ | |
| 11.0209 | H | $OCH_2C(Cl)=CH_2$ | $CH_3$ | $C_3H_7$(iso) | $CH_2OC_6H_5$ | |
| 11.0210 | H | $OCH_2CH=CHCl$ | $CH_3$ | $C_3H_7$(iso) | $CH_2OC_6H_5$ | |
| 11.0211 | H | $OCH_2C\equiv CH$ | $CH_3$ | $C_3H_7$(iso) | $CH_2OC_6H_5$ | |
| 11.0212 | H | $OCHF_2$ | $CH_3$ | $C_3H_7$(iso) | $CH_2OC_6H_5$ | |
| 11.0213 | H | $OCF_3$ | $CH_3$ | $C_3H_7$(iso) | $CH_2OC_6H_5$ | |
| 11.0214 | H | $OCF_2CHFCF_3$ | $CH_3$ | $C_3H_7$(iso) | $CH_2OC_6H_5$ | |
| 11.0215 | H | $OC_6H_5$ | $CH_3$ | $C_3H_7$(iso) | $CH_2OC_6H_5$ | |
| 11.0216 | H | $CF_3$ | $CH_3$ | $C_3H_7$(iso) | $CH_2OC_6H_5$ | |
| 11.0217 | H | Br | $CH_3$ | $C_3H_7$(iso) | $CH_2OC_6H_5$ | |
| 11.0218 | H | Cl | $CH_3$ | $C_3H_7$(iso) | $CH_2OC_6H_5$ | |
| 11.0219 | H | F | $CH_3$ | $C_3H_7$(iso) | $CH_2OC_6H_5$ | |
| 11.0220 | H | $SCH_3$ | $CH_3$ | $C_3H_7$(iso) | $CH_2OC_6H_5$ | |
| 11.0221 | H | $SCH_3$ | $CH_3$ | $C_3H_7$(iso) | $CH_2OC_6H_5$ | |
| 11.0222 | H | $SC_3H_7$-n | $CH_3$ | $C_3H_7$(iso) | $CH_2OC_6H_5$ | |
| 11.0223 | H | $SO_2CH_3$ | $CH_3$ | $C_3H_7$(iso) | $CH_2OC_6H_5$ | |
| 11.0224 | H | $SO_2CH_3$ | $CH_3$ | $C_3H_7$(iso) | $CH_2OC_6H_5$ | |
| 11.0225 | H | $NO_2$ | $CH_3$ | $C_3H_7$(iso) | $CH_2OC_6H_5$ | |
| 11.0226 | H | CN | $CH_3$ | $C_3H_7$(iso) | $CH_2OC_6H_5$ | |
| 11.0227 | H | $CH_2OH$ | $CH_3$ | $C_3H_7$(iso) | $CH_2OC_6H_5$ | |
| 11.0228 | H | $CH_2CH_2OH$ | $CH_3$ | $C_3H_7$(iso) | $CH_2OC_6H_5$ | |
| 11.0229 | H | $CH_2CH_2CH_2OH$ | $CH_3$ | $C_3H_7$(iso) | $CH_2OC_6H_5$ | |
| 11.0230 | H | $C_6H_5$ | $CH_3$ | $C_3H_7$(iso) | $CH_2OC_6H_5$ | |
| 11.0231 | H | $CH_2Cl$ | $CH_3$ | $C_3H_7$(iso) | $CH_2OC_6H_5$ | |
| 11.0232 | H | $CH_2CH_2Cl$ | $CH_3$ | $C_3H_7$(iso) | $CH_2OC_6H_5$ | |
| 11.0233 | H | $CH_2CH_2CH_2Cl$ | $CH_3$ | $C_3H_7$(iso) | $CH_2OC_6H_5$ | |

EXAMPLE 20

Preparation of 3-isopropyl-3-methyl-8-phenoxymethyl-1H-imidazo[1',2':1,2]pyrrolo[3,4-6]pyridine-2,5(3H,96H)-dione.

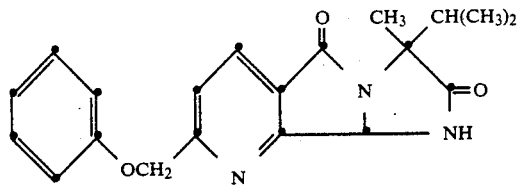

1 part of N-(2-methylvalylamide)-6-phenoxymethyl-pyridine-2,3-dicarboxylic acid imide (Example 19) are dissolved in 9 parts of toluene and the solution is boiled on a water separator for 15 hours. It is then cooled and 0.2 parts of a 50% sodium hydride mineral oil suspension are added to the dry toluene solution. The suspension is boiled at reflux for 24 hours and filtered while still hot. The solution is then concentrated by evaporation and the crystalline precipitate is freed of mineral oil using hexane and then dried in vacuo. In this manner 0.78 parts of the above tricyclic compound are obtained.

The tricyclic compounds of formula XII listed in Tables 12.00 to 12.02 are prepared in a manner analogous to that described in Example 20.

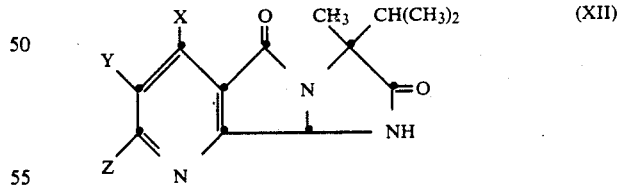

(XII)

TABLE 12.00

| No. | X | Y | $R_2$ | $R_3$ | Z | phys. data |
|---|---|---|---|---|---|---|
| 12.0001 | H | H | $CH_3$ | $C_3H_7$(iso) | $C_3H_5$(cyclo) | |
| 12.0002 | H | $CH_3$ | $CH_3$ | $C_3H_7$(iso) | $C_3H_5$(cyclo) | |
| 12.0003 | H | $C_2H_5$ | $CH_3$ | $C_3H_7$(iso) | $C_3H_5$(cyclo) | |
| 12.0004 | H | $C_3H_7$ | $CH_3$ | $C_3H_7$(iso) | $C_3H_5$(cyclo) | |
| 12.0005 | H | $OCH_3$ | $CH_3$ | $C_3H_7$(iso) | $C_3H_5$(cyclo) | |
| 12.0006 | H | $OC_2H_5$ | $CH_3$ | $C_3H_7$(iso) | $C_3H_5$(cyclo) | |
| 12.0007 | H | $OCH_2CH=CH_2$ | $CH_3$ | $C_3H_7$(iso) | $C_3H_5$(cyclo) | |
| 12.0008 | H | $OCH_2CH=CHCH_3$ | $CH_3$ | $C_3H_7$(iso) | $C_3H_5$(cyclo) | |
| 12.0009 | H | $OCH_2C(Cl)=CH_2$ | $CH_3$ | $C_3H_7$(iso) | $C_3H_5$(cyclo) | |
| 12.0010 | H | $OCH_2CH=CHCl$ | $CH_3$ | $C_3H_7$(iso) | $C_3H_5$(cyclo) | |

TABLE 12.00-continued

| No. | X | Y | R₂ | R₃ | Z | phys. data |
|---|---|---|---|---|---|---|
| 12.0011 | H | OCH₂C≡CH | CH₃ | C₃H₇(iso) | C₃H₅(cyclo) | |
| 12.0012 | H | OCHF₂ | CH₃ | C₃H₇(iso) | C₃H₅(cyclo) | |
| 12.0013 | H | OCF₃ | CH₃ | C₃H₇(iso) | C₃H₅(cyclo) | |
| 12.0014 | H | OCF₂CHFCF₃ | CH₃ | C₃H₇(iso) | C₃H₅(cyclo) | |
| 12.0015 | H | OC₆H₅ | CH₃ | C₃H₇(iso) | C₃H₅(cyclo) | |
| 12.0016 | H | CF₃ | CH₃ | C₃H₇(iso) | C₃H₅(cyclo) | |
| 12.0017 | H | Br | CH₃ | C₃H₇(iso) | C₃H₅(cyclo) | |
| 12.0018 | H | Cl | CH₃ | C₃H₇(iso) | C₃H₅(cyclo) | |
| 12.0019 | H | F | CH₃ | C₃H₇(iso) | C₃H₅(cyclo) | |
| 12.0020 | H | SCH₃ | CH₃ | C₃H₇(iso) | C₃H₅(cyclo) | |
| 12.0021 | H | SCH₃ | CH₃ | C₃H₇(iso) | C₃H₅(cyclo) | |
| 12.0022 | H | SC₃H₇-n | CH₃ | C₃H₇(iso) | C₃H₅(cyclo) | |
| 12.0023 | H | SO₂CH₃ | CH₃ | C₃H₇(iso) | C₃H₅(cyclo) | |
| 12.0024 | H | SO₂CH₃ | CH₃ | C₃H₇(iso) | C₃H₅(cyclo) | |
| 12.0025 | H | NO₂ | CH₃ | C₃H₇(iso) | C₃H₅(cyclo) | |
| 12.0026 | H | CN | CH₃ | C₃H₇(iso) | C₃H₅(cyclo) | |
| 12.0027 | H | CH₂OH | CH₃ | C₃H₇(iso) | C₃H₅(cyclo) | |
| 12.0028 | H | CH₂CH₂OH | CH₃ | C₃H₇(iso) | C₃H₅(cyclo) | |
| 12.0029 | H | CH₂CH₂CH₂OH | CH₃ | C₃H₇(iso) | C₃H₅(cyclo) | |
| 12.0030 | H | C₆H₅ | CH₃ | C₃H₇(iso) | C₃H₅(cyclo) | |
| 12.0031 | H | CH₂Cl | CH₃ | C₃H₇(iso) | C₃H₅(cyclo) | |
| 12.0032 | H | CH₂CH₂Cl | CH₃ | C₃H₇(iso) | C₃H₅(cyclo) | |
| 12.0033 | H | CH₂CH₂CH₂Cl | CH₃ | C₃H₇(iso) | C₃H₅(cyclo) | |

TABLE 12.01

| No. | X | Y | R₂ | R₃ | Z | phys. data |
|---|---|---|---|---|---|---|
| 12.0101 | H | H | CH₃ | C₃H₇(iso) | CH₂OC₂H₅ | |
| 12.0102 | H | CH₃ | CH₃ | C₃H₇(iso) | CH₂OC₂H₅ | |
| 12.0103 | H | C₂H₅ | CH₃ | C₃H₇(iso) | CH₂OC₂H₅ | |
| 12.0104 | H | C₃H₇ | CH₃ | C₃H₇(iso) | CH₂OC₂H₅ | |
| 12.0105 | H | OCH₃ | CH₃ | C₃H₇(iso) | CH₂OC₂H₅ | |
| 12.0106 | H | OC₂H₅ | CH₃ | C₃H₇(iso) | CH₂OC₂H₅ | |
| 12.0107 | H | OCH₂CH=CH₂ | CH₃ | C₃H₇(iso) | CH₂OC₂H₅ | |
| 12.0108 | H | OCH₂CH=CHCH₃ | CH₃ | C₃H₇(iso) | CH₂OC₂H₅ | |
| 12.0109 | H | OCH₂C(Cl)=CH₂ | CH₃ | C₃H₇(iso) | CH₂OC₂H₅ | |
| 12.0110 | H | OCH₂CH=CHCl | CH₃ | C₃H₇(iso) | CH₂OC₂H₅ | |
| 12.0111 | H | OCH₂C≡CH | CH₃ | C₃H₇(iso) | CH₂OC₂H₅ | |
| 12.0112 | H | OCHF₂ | CH₃ | C₃H₇(iso) | CH₂OC₂H₅ | |
| 12.0113 | H | OCF₃ | CH₃ | C₃H₇(iso) | CH₂OC₂H₅ | |
| 12.0114 | H | OCF₂CHFCF₃ | CH₃ | C₃H₇(iso) | CH₂OC₂H₅ | |
| 12.0115 | H | OC₆H₅ | CH₃ | C₃H₇(iso) | CH₂OC₂H₅ | |
| 12.0116 | H | CF₃ | CH₃ | C₃H₇(iso) | CH₂OC₂H₅ | |
| 12.0117 | H | Br | CH₃ | C₃H₇(iso) | CH₂OC₂H₅ | |
| 12.0118 | H | Cl | CH₃ | C₃H₇(iso) | CH₂OC₂H₅ | |
| 12.0119 | H | F | CH₃ | C₃H₇(iso) | CH₂OC₂H₅ | |
| 12.0120 | H | SCH₃ | CH₃ | C₃H₇(iso) | CH₂OC₂H₅ | |
| 12.0121 | H | SCH₃ | CH₃ | C₃H₇(iso) | CH₂OC₂H₅ | |
| 12.0122 | H | SC₃H₇-n | CH₃ | C₃H₇(iso) | CH₂OC₂H₅ | |
| 12.0123 | H | SO₂CH₃ | CH₃ | C₃H₇(iso) | CH₂OC₂H₅ | |
| 12.0124 | H | SO₂CH₃ | CH₃ | C₃H₇(iso) | CH₂OC₂H₅ | |
| 12.0125 | H | NO₂ | CH₃ | C₃H₇(iso) | CH₂OC₂H₅ | |
| 12.0126 | H | CN | CH₃ | C₃H₇(iso) | CH₂OC₂H₅ | |
| 12.0127 | H | CH₂OH | CH₃ | C₃H₇(iso) | CH₂OC₂H₅ | |
| 12.0128 | H | CH₂CH₂OH | CH₃ | C₃H₇(iso) | CH₂OC₂H₅ | |
| 12.0129 | H | CH₂CH₂CH₂OH | CH₃ | C₃H₇(iso) | CH₂OC₂H₅ | |
| 12.0130 | H | C₆H₅ | CH₃ | C₃H₇(iso) | CH₂OC₂H₅ | |
| 12.0131 | H | CH₂Cl | CH₃ | C₃H₇(iso) | CH₂OC₂H₅ | |
| 12.0132 | H | CH₂CH₂Cl | CH₃ | C₃H₇(iso) | CH₂OC₂H₅ | |
| 12.0133 | H | CH₂CH₂CH₂Cl | CH₃ | C₃H₇(iso) | CH₂OC₂H₅ | |

TABLE 12.02

| No. | X | Y | R₂ | R₃ | Z | phys. data |
|---|---|---|---|---|---|---|
| 12.0201 | H | H | CH₃ | C₃H₇(iso) | CH₂OC₆H₅ | |
| 12.0202 | H | CH₃ | CH₃ | C₃H₇(iso) | CH₂OC₆H₅ | |
| 12.0203 | H | C₂H₅ | CH₃ | C₃H₇(iso) | CH₂OC₆H₅ | |
| 12.0204 | H | C₃H₇ | CH₃ | C₃H₇(iso) | CH₂OC₆H₅ | |
| 12.0205 | H | OCH₃ | CH₃ | C₃H₇(iso) | CH₂OC₆H₅ | |
| 12.0206 | H | OC₂H₅ | CH₃ | C₃H₇(iso) | CH₂OC₆H₅ | |
| 12.0207 | H | OCH₂CH=CH₂ | CH₃ | C₃H₇(iso) | CH₂OC₆H₅ | |
| 12.0208 | H | OCH₂CH=CHCH₃ | CH₃ | C₃H₇(iso) | CH₂OC₆H₅ | |
| 12.0209 | H | OCH₂C(Cl)=CH₂ | CH₃ | C₃H₇(iso) | CH₂OC₆H₅ | |
| 12.0210 | H | OCH₂CH=CHCl | CH₃ | C₃H₇(iso) | CH₂OC₆H₅ | |
| 12.0211 | H | OCH₂C≡CH | CH₃ | C₃H₇(iso) | CH₂OC₆H₅ | |
| 12.0212 | H | OCHF₂ | CH₃ | C₃H₇(iso) | CH₂OC₆H₅ | |
| 12.0213 | H | OCF₃ | CH₃ | C₃H₇(iso) | CH₂OC₆H₅ | |
| 12.0214 | H | OCF₂CHFCF₃ | CH₃ | C₃H₇(iso) | CH₂OC₆H₅ | |

TABLE 12.02-continued

| No. | X | Y | $R_2$ | $R_3$ | Z | phys. data |
|---|---|---|---|---|---|---|
| 12.0215 | H | $OC_6H_5$ | $CH_3$ | $C_3H_7$(iso) | $CH_2OC_6H_5$ | |
| 12.0216 | H | $CF_3$ | $CH_3$ | $C_3H_7$(iso) | $CH_2OC_6H_5$ | |
| 12.0217 | H | Br | $CH_3$ | $C_3H_7$(iso) | $CH_2OC_6H_5$ | |
| 12.0218 | H | Cl | $CH_3$ | $C_3H_7$(iso) | $CH_2OC_6H_5$ | |
| 12.0219 | H | F | $CH_3$ | $C_3H_7$(iso) | $CH_2OC_6H_5$ | |
| 12.0220 | H | $SCH_3$ | $CH_3$ | $C_3H_7$(iso) | $CH_2OC_6H_5$ | |
| 12.0221 | H | $SCH_3$ | $CH_3$ | $C_3H_7$(iso) | $CH_2OC_6H_5$ | |
| 12.0222 | H | $SC_3H_7$-n | $CH_3$ | $C_3H_7$(iso) | $CH_2OC_6H_5$ | |
| 12.0223 | H | $SO_2CH_3$ | $CH_3$ | $C_3H_7$(iso) | $CH_2OC_6H_5$ | |
| 12.0224 | H | $SO_2CH_3$ | $CH_3$ | $C_3H_7$(iso) | $CH_2OC_6H_5$ | |
| 12.0225 | H | $NO_2$ | $CH_3$ | $C_3H_7$(iso) | $CH_2OC_6H_5$ | |
| 12.0226 | H | CN | $CH_3$ | $C_3H_7$(iso) | $CH_2OC_6H_5$ | |
| 12.0227 | H | $CH_2OH$ | $CH_3$ | $C_3H_7$(iso) | $CH_2OC_6H_5$ | |
| 12.0228 | H | $CH_2CH_2OH$ | $CH_3$ | $C_3H_7$(iso) | $CH_2OC_6H_5$ | |
| 12.0229 | H | $CH_2CH_2CH_2OH$ | $CH_3$ | $C_3H_7$(iso) | $CH_2OC_6H_5$ | |
| 12.0230 | H | $C_6H_5$ | $CH_3$ | $C_3H_7$(iso) | $CH_2OC_6H_5$ | |
| 12.0231 | H | $CH_2Cl$ | $CH_3$ | $C_3H_7$(iso) | $CH_2OC_6H_5$ | |
| 12.0232 | H | $CH_2CH_2Cl$ | $CH_3$ | $C_3H_7$(iso) | $CH_2OC_6H_5$ | |
| 12.0233 | H | $CH_2CH_2CH_2Cl$ | $CH_3$ | $C_3H_7$(iso) | $CH_2OC_6H_5$ | |

Formulation Examples

EXAMPLE 21

Formulation Examples for the active ingredients of formula I (%=percent by weight)

| (a) Wettable powders | (a) | (b) | (c) |
|---|---|---|---|
| an active ingredient according to Tables 1 to 4 | 20% | 60% | 0.5% |
| sodium lignosulphonate | 5% | 5% | 5% |
| sodium laurylsulphate | 3% | — | — |
| sodium diisobutylnaph-thalenesulphonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| an active ingredient according to Tables 1 to 4 | 10% | 1% |
| octylphenol polyethylene glycol ether (4-5 moles of ethylene oxide) | 3% | 3% |
| calcium dodecylbenzene-sulphonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this by dilution with water.

| (c) Dusts | (a) | (b) |
|---|---|---|
| an active ingredient according to Tables 1 to 4 | 0.1% | 1% |
| talcum | 99.9% | — |
| kaolin | — | 99% |

Ready-for-use dusts are obtained by mixing the active ingredient with the carrier and grinding the mixture in a suitable mill.

| (d) Extruder granulate | (a) | (b) |
|---|---|---|
| an active ingredient according to Tables 1 to 4 | 10% | 1% |
| sodium lignosulphonate | 2% | 2% |
| carboxymethylcellulose | 1% | 1% |
| kaolin | 87% | 96% |

The active ingredient is mixed and ground with the adjuvants, and the mixture is moistened with water. The mixture is extruded and then dried in a stream of air.

| (e) Coated granulate | |
|---|---|
| an active ingredient according to Tables 1 to 4 | 3% |
| polyethylene glycol (MW 200) | 3% |
| kaolin | 94% |

The finely ground active ingredient is uniformly applied, in a mixer, to the kaolin moistened with polyethylene glycol. Dust-free coated granulates are obtained in this manner.

| (f) Suspension concentrate | (a) | (b) |
|---|---|---|
| an active ingredient according to Tables 1 to 4 | 40% | 5% |
| ethylene glycol | 10% | 10% |
| nonylphenol polyethylene glycol ether (15 moles of ethylene oxide) | 6% | 1% |
| sodium lignosulphonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is homogeneously mixed with the adjuvants, giving a suspension concentrate from which suspensions of any desired concentration can be obtained by dilution with water.

Biological Examples

EXAMPLE 22

Pre-emergence herbicidal action

Directly after the test plants have been sown in seed trays in a greenhouse the surface of the soil is treated with an aqueous dispersion of the active ingredients, obtained from a 25% emulsifiable concentrate. Concentrations of 4 kg of active ingredient/hectare are used. The seed trays are kept in the greenhouse at 22° to 25° C. and 50 to 70% relative humidity and the test is assessed after three weeks, the results being evaluated in accordance with the following scale:

| | |
|---|---|
| 1 | plant has not germinated or has withered |
| 2–3 | very pronounced damage |
| 4 | pronounced damage |
| 5 | moderate damage, the plants are stunted |
| 6 | damage which the plant can regenerate |
| 8–8 | slight damage |
| 9 | normal growth, like the untreated plant |

In this test the compounds of Tables 1 to 4 exhibited a strong herbicidal action.

EXAMPLE 23

Post-emergence herbicidal action (contact herbicide)

A number of weeds, both monocotyledonous and dicotyledonous, were sprayed post-emergence (in the 4- to 6-leaf stage) with an aqueous dispersion of active ingredient at a rate of 4 kg of active ingredient per hectare, and maintained at 24° to 26° C. and 45 to 60% relative humidity. 15 days after the treatment the test is evaluated in accordance with the above scale. In this test too, the compounds of Tables 1 to 4 exhibit a strong to very strong herbicidal action.

EXAMPLE 24

Pre-emergence herbicidal action

Plastics pots are filled with expanded vermiculite (density: 0.135 g/cm³, water-absorbing capacity: 0.565 l/l). After the non-adsorptive vermiculite has been saturated with an aqueous emulsion of the active ingredient, seeds of the following plants are sown on the surface: Nasturtium officinalis, Agrostis tenuis, Stellaria media and Digitaria sanguinalis. The pots are then kept in a climatic chamber at 20° C., an illumination of about 20 klux and a relative humidity of 70%. During the germination phase of from 4 to 6 days, the pots are covered with light-permeable material in order to increase the local humidity and watered with deionised water. After the 5th day 0.5% of a commercial liquid fertilizer (®Greenzit) is added to the water. The test is evaluated 12 days after sowing and the action on the test plants is assessed according to the scale given in Example 3.

The results are compiled in Table 13:

TABLE 13

| Comp. No. | rate of application ppm | Nasturtium officinalis | Agrostis tenuis | Stellaria media | Digitaria sang. |
|---|---|---|---|---|---|
| 1.000.3 | 100 | 2 | 2 | 2 | 2 |
| 1.0402 | 100 | 2 | 1 | 2 | 2 |
| 2.0001 | 100 | 2 | 2 | 2 | 2 |
| 2.0002 | 100 | 2 | 2 | 2 | 2 |
| 2.0003 | 100 | 2 | 2 | 2 | 2 |
| 2.0017 | 100 | 1 | 1 | 1 | 1 |
| 2.0034 | 100 | 2 | 3 | 4 | 4 |
| 2.0301 | 100 | 2 | 2 | 2 | 2 |
| 2.0401 | 100 | 2 | 2 | 2 | 2 |
| 2.0402 | 100 | 2 | 2 | 2 | 2 |
| 2.0403 | 100 | 2 | 2 | 2 | 2 |
| 2.0434 | 100 | 8 | 8 | 8 | 8 |
| 2.0601 | 100 | 2 | 2 | 2 | 2 |
| 2.0602 | 100 | 2 | 2 | 2 | 2 |
| 2.0603 | 100 | 2 | 2 | 2 | 2 |
| 2.1001 | 100 | 2 | 2 | 2 | 2 |
| 2.1201 | 100 | 4 | 4 | 3 | 4 |
| 2.1301 | 100 | 2 | 2 | 2 | 2 |
| 2.1401 | 100 | 3 | 3 | 3 | 3 |
| 2.1601 | 100 | 6 | 6 | 6 | 7 |
| 3.0002 | 100 | 1 | 1 | 2 | 2 |
| 3.0403 | 100 | 2 | 2 | 2 | 2 |
| 4.0002 | 100 | 3 | 3 | 3 | 3 |
| 4.0003 | 100 | 2 | 2 | 2 | 2 |
| 4.0403 | 100 | 2 | 2 | 2 | 2 |
| 4.1001 | 100 | 2 | 2 | 2 | 2 |

EXAMPLE 25

Herbicidal action for paddy rice

The water weeds Echinochloa crus galli and Monochari vag. are sown in plastics beakers (surface area 60 cm², volume 500 ml). After sowing, the beakers are filled with water up to the surface of the soil. 3 days after sowing, the water level is raised to slightly above (3–5 mm) the surface of the soil. Application is effected 3 days after sowing by spraying the beakers with an aqueous emulsion of the test substances. The dose corresponds to an amount of active ingredient of 4 kg per hectare (quantity of spray mixture: 550 l/ha). The beakers are then kept in the greenhouse under optimum growth conditions for rice weeds, i.e. at 25° to 30° C. and at high humidity. The evaluation of the tests takes place 3 weeks after application.

The assessment is carried out in accordance with the linear scale given in Example 22.

The tested compounds of Tables 1 to 4 exhibit a good action against these weeds with the rice plantlets to a large extent being preserved.

EXAMPLE 26

Growth inhibition of tropical cover crops

The test plants (Centrosema plumieri and Centrosema pubescens) are reared until fully grown and then cut back to a height of 60 cm. The plants are sprayed 7 days later with an aqueous emulsion of the active ingredient. The test plants are kept at 70% relative humidity and 6000 lux artifical light for 14 hours per day at day temperatures of 27° C. and night temperatures of 21° C. The test is evaluated 4 weeks after application by assessing and weighing the new growth compared with controls and by determining the phytotoxicity. In this test a marked reduction in new growth (less than 20% of the new growth of untreated control plants) of the plants treated with the active ingredients of Table 1 at application rates of 50–3000 g/ha is observed without at the same time the test plants being damaged.

EXAMPLE 27

Growth regulation of soybeans

Soybeans of the "Hark" variety are sown in plastics containers containing an earth/peat/sand mixture in a ratio of 6:3:1 and placed in a climatic chamber. As a result of optimum choice of temperature, illumination, addition of fertilizer and watering, the plants have developed to the 5 to 6 trefoil leaf stage after about 5 weeks. The plants are then sprayed with an aqueous mixture of an active ingredient of formula I until thoroughly wet. The concentration of active ingredient is up to 100 g a.i./ha. The evaluation is carried out about 5 weeks after application of the active ingredient. Compared with untreated control plants, active ingredients according to the invention of Table 1 cause a marked increase in the number and weight of the siliques on the leading shoot.

EXAMPLE 28

Growth inhibition of cereals

*Hordeum vulgare* (summer barley) and Secale (summer rye) are sown according to cereal type in a greenhouse in plastics pots containing sterilised soil and watered as required. The shoots are sprayed about 21 days after sowing with an aqueous spray mixture of an active ingredient of Table 1. The amount of active ingredient is up to 100 g per hectare. 21 days after the application the growth of the cereal is assessed. Compared with untreated controls, the treated plants exhibit a reduction in new growth (60-90% of the control) and also, in some cases, an increase in the stalk diameter.

EXAMPLE 29

Growth inhibition of grasses

The grasses *Lolium perenne, Poa pratensis, Festuca ovina, Dactylis glomerate* and *Cynodon dactylon* are sown in a greenhouse in plastics trays containing an earth-/peat/sand mixture (6:3:1) and watered as required. The grasses are cut back weekly to a height of 4 cm and, about 50 days after sowing and one day after the last cut, sprayed with an aqueous spray mixture of an active ingredient of Tables 3 to 8. The amount of active ingredient corresponds to up to 500 g of active ingredient per hectare. 21 days after application the growth of the grasses is assessed.

The tested compounds of Table 1 cause a reduction in new growth of about 10 to 30% in comparison with untreated controls.

EXAMPLE 30

Dessication and defoliation activity

Cotton plants of the Deltapine variety were sown in clay pots in a greenhouse. When capsule formation was complete they were sprayed with aqueous preparations of the active ingredients at a rate of application that would correspond to 1.2, 0.6 and 0.3 kg/ha in the field. Untreated plants were used as controls. The evaluation of the test was carried out 3, 7 and 14 days after application of the active substance by determining the degree of defoliation (% of leaves that had fallen) and of dessication (% drying out of the leaves left on the plants).

In this test, at rates of application of 0.6 and 1.2 kg/ha, the tested compounds of Table 1 left only few dried leaves on the plants (>80% leaf fall and dessication).

We claim:

1. A process for the preparation of a 6-substituted 2-(imidazolin-2-yl)-nicotinic acid of the formula III

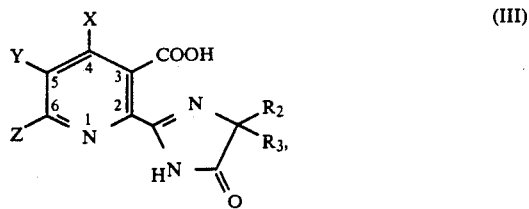

(III)

in which $R_2$ is $C_1$-$C_4$-alkyl;

$R_3$ is $C_1$-$C_4$-alkyl or $C_3$-$C_6$-cycloalkyl; or $R_2$ and $R_3$, together with the carbon atom to which they are bonded, also represent a $C_3$-$C_6$-cycloalkyl radical which may be substituted by methyl radicals;

X is hydrogen or methyl;

Y is hydrogen; halogen; $C_1$-$C_6$-alkyl; $C_1$-$C_6$-haloalkyl; $C_1$-$C_6$-hydroxyalkyl; $C_1$-$C_6$-alkoxy; $C_1$-$C_6$-alkylthio; phenoxy; nitro; cyano; $C_1$-$C_4$-alkylamino; di-$C_1$-$C_4$-alkylamino; $C_1$-$C_4$-alkylsulphonyl; phenyl; halophenyl; lower alkylphenyl; lower alkoxyphenyl; $C_3$-$C_8$-alkenyloxy; $C_3$-$C_8$-haloalkenyloxy; $C_3$-$C_8$-alkynyloxy or $C_3$-$C_8$-haloalkynyloxy; and Z is a $-CQ_1Q_2Q_3$ or $-CQ_1Q_4Q_5$ radical in which $Q_1$ is hydrogen or $C_1$-$C_4$-alkyl;

$Q_2$ is hydrogen or $C_1$-$C_4$-alkyl;

$Q_3$ is $C_1$-$C_6$-alkoxy that is unsubstituted or is substituted by $C_1$-$C_4$-alkyl, $C_1$-$C_4$-alkoxy, $C_4$-$C_9$-alkoxyalkoxy, cyano or by carbamoyl; phenoxy that is unsubstituted or is substituted by halogen, $C_1$-$C_4$-alkyl, $C_1$-$C_4$-alkoxy, $C_1$-$C_4$-haloalkyl or by nitro; or $C_3$-$C_6$-alkenyloxy or $C_3$-$C_6$-alkynyloxy;

$Q_4$ and $Q_5$, together with the carbon atom to which they are bonded, represent $C_3$-$C_6$-cycloalkyl; or a 5- or 6-membered ring containing one oxygen atom or two oxygen atoms that are not vicinal, each of which radicals may be substituted by $C_1$-$C_4$-alkyl; or Z is a 5- or 6-membered, saturated or unsaturated, heterocyclic radical that is bonded by way of carbon and is unsubstituted or is substituted by lower alkyl;

which consists in reacting a pyridine-2,3-dicarboxylic acid diester of the formula V

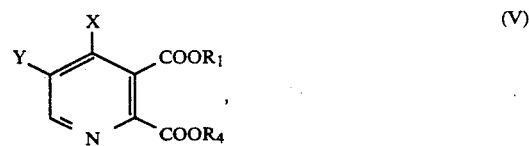

(V)

in which X and Y are as defined above; $R_1$ is hydrogen; the cation equivalent of an alkali metal, alkaline earth metal, magnesium, copper, iron, zinc, cobalt, lead, silver, nickel or quaternary ammonium or alkylammonium salt; $C_1$-$C_6$-alkyl unsubstituted or substituted by halogen, hydroxy, $C_1$-$C_3$-alkoxy, $C_3$-$C_6$-cycloalkyl, benzyloxy, furyl, phenyl, halophenyl, lower alkylphenyl, lower alkoxyphenyl, nitrophenyl, carboxy, $C_1$-$C_4$-alkoxycarbonyl or by cyano; $C_3$-$C_6$-cycloalkyl unsubstituted or mono- or di-substituted by $C_1$–$C_3$-alkyl; $C_3$–$C_6$-alkenyl unsubstituted or substituted by halogen, $C_1$–$C_3$-alkoxy, phenyl or by $C_1$–$C_4$-alkoxycarbonyl; or $C_3$–$C_6$-alkynyl unsubstituted or mono- or di-substituted by $C_1$–$C_3$-alkyl and $R_4$ is a $C_1$–$C_3$alkyl radical; a $C_1$–$C_8$-alkylphenyl radical or a phenyl-$C_1$–$C_4$-alkyl radical; in aqueous solution at a temperature of between room temperature and the boiling point of the reaction mixture, under atmospheric pressure, in the presence of a catalytic amount of silver (II) ions and a peroxysulphate salt, with a carboxylic acid of the formula XVII $$Z\text{—COOH} \qquad (XVII),$$

in which Z is as defined above, and reacting the resulting 6-substituted pyridine-2,3-dicarboxylic acid diester of the formula IV

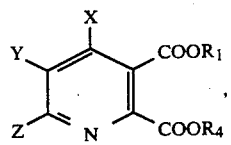

(IV)

in an inert organic solvent, in the presence of a strong base at temperature of between room temperature and the boiling point of the reaction mixture under atomospheric pressure, with a 2-aminoalkanecarboxylic acid amide of formula XV

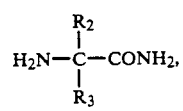

(XV)

in which $R_2$ and $R_3$ are as defined above, and the resulting salt of the 2-(imidazolin-2-yl)-nicotinic acid of formula III is taken up in aqueous acidic solution to form the free 6-substituted-2-(imidazolin-2-yl)-nicotinic acid of formula III.

2. A process of claim 1 in which $R_1$ is hydrogen or $C_1$–$C_6$-alkyl; Y is hydrogen, $C_1$–$C_6$-alkyl or halogen; Z is a heterocyclic radical or, if it is —$CQ_1Q_2Q_2Q_3$, is a $C_1$–$C_6$-alkoxy-$C_1$–$C_4$-alkyl-, phenoxy-$C_1$–$C_4$-alkyl or carbamoyl-$C_1$–$C_4$-alkoxy-$C_1$–$C_4$-alkyl radical or, if it is —$CQ_1Q_4Q_5$, is a $C_3$–$C_6$-cycloalkyl radical or a $C_3$–$C_6$-cycloalkyl radical that may be substituted by $C_1$–$C_4$-alkyl.

* * * * *